(12) United States Patent
Desir et al.

(10) Patent No.: US 12,234,500 B2
(45) Date of Patent: Feb. 25, 2025

(54) METHODS FOR MEASURING RENALASE

(71) Applicant: Yale University, New Haven, CT (US)

(72) Inventors: Gary Desir, Woodbridge, CT (US);
Jeffrey Testani, Guilford, CT (US);
Veena Rao, Derby, CT (US)

(73) Assignee: Yale University, New Haven, CT (US)

( * ) Notice: Subject to any disclaimer, the term of this patent is extended or adjusted under 35 U.S.C. 154(b) by 725 days.

(21) Appl. No.: 16/958,945

(22) PCT Filed: Dec. 27, 2018

(86) PCT No.: PCT/US2018/067608
§ 371 (c)(1),
(2) Date: Jun. 29, 2020

(87) PCT Pub. No.: WO2019/133665
PCT Pub. Date: Jul. 4, 2019

(65) Prior Publication Data
US 2020/0340031 A1    Oct. 29, 2020

Related U.S. Application Data

(60) Provisional application No. 62/611,602, filed on Dec. 29, 2017.

(51) Int. Cl.
| | | |
|---|---|---|
| C12Q 1/26 | (2006.01) | |
| C07K 16/40 | (2006.01) | |
| A61K 45/06 | (2006.01) | |

(52) U.S. Cl.
CPC .............. *C12Q 1/26* (2013.01); *C07K 16/40* (2013.01); *A61K 45/06* (2013.01); *C07K 2317/24* (2013.01); *C07K 2317/31* (2013.01); *C07K 2317/41* (2013.01); *C07K 2317/565* (2013.01); *C07K 2317/622* (2013.01); *G01N 2333/90209* (2013.01)

(58) Field of Classification Search
None
See application file for complete search history.

(56) References Cited

U.S. PATENT DOCUMENTS

2017/0226228 A1    8/2017    Desir

FOREIGN PATENT DOCUMENTS

| CN | 106659772 | 5/2017 |
|---|---|---|
| JP | 2017521401 A | 8/2017 |
| TW | 200738255 | 10/2007 |
| WO | 2013056352 | 4/2013 |
| WO | 2014014899 A1 | 1/2014 |
| WO | 2015058861 | 4/2015 |
| WO | 2015200790 A2 | 12/2015 |
| WO | 2016015162 | 2/2016 |

OTHER PUBLICATIONS

Desir et al. (J Am Heart Assoc. 2012;1(4):e002634. doi: 10.1161/JAHA.112.002634).*
Baca et al., Journal of Biological Chemistry, American Society for Biochemistry and Molecular Biology, 272:10678-10684.
Beaupre et al., 2015, "Metabolic function for human renalase: oxidation of isomeric forms of β-NAD(P)H that are inhibitory to primary metabolism", Biochemistry., 54(3):795-806.
Chinese Office Action (including English translation) issued in App. No. CN20188084379, dated Oct. 28, 2022, 10 pages.
Dankort et al., 2009, "BRAF(V600E) cooperates with Pten silencing to elicit metastatic melanoma." Nature genetics. 41:544-52.
Desir et al, 'Renalase Lowers Ambulatory Blood Pressure by Metabolizing Circulating Adrenaline,' 2012, J. of the Am. Heart Assn, 1(4):e002634. 11 pages.
Desir et al., 2012 J Am Soc Hypertens. 6(6):417-26.
European Patent Office Communication issued in Appln. No. 1 8897086.7 (Extended European Search Report dated Dec. 20, 2021).
European Patent Office Communication issued in Appln. No. 1 8897086.7 (Office Action dated Mar. 11, 2023).
European Patent Office Communication issued in Appln. No. 1 8897086.7 (Partial Supplementary European Search Report dated Sep. 17, 2021).
Farzaneh-Far et al., 2010, "Telomere Length Trajectory and Its Determinants in Persons with Coronary Artery Disease: Longitudinal Findings from the Heart and Soul Study", PLoS One., 5(10):e13496.
Farzaneh-Far et al., A Functional Polymorphism in Renalase (Glu37Asp) Is Associated with Cardiac Hypertrophy, Dysfunction, and Ischemia: Data from the Heart and Soul Study, 2010 PLoS One. 5(10):e13496.
Fedchenko et al., 2016, "Renalase Secreted by Human Kidney HEK293T Cells Lacks its N-Terminal Peptide: Implications for Putative Mechanisms of Renalase Action", Kidney Blood Press. Res., 41:593-603.
Gray-Schopfer et al., 2007 Nature. 445:851-7.
Gray-Schopfer et al., 2007, "Melanoma biology and new targeted therapy." Nature. 445:851-7.
Hidalgo et al., 2012, "New insights into pancreatic cancer biology." Annals of Oncology. 23(suppl 10):x135-x8.
Hidalgo, 2010, "Pancreatic Cancer", New England Journal of Medicine., 362(17):1605-17.
Hollander et al, 2016, Cancer Research, 76: 3884-3894.
Japanese Office Action (including English translation) issued in App. No. JP2020-536124, dated Jun. 6, 2023, 5 pages.
Japanese Office Action (including English translation) issued in App. No. JP2020-536124, dated Oct. 18, 2022, 16 pages.

(Continued)

*Primary Examiner* — Sharon X Wen
(74) *Attorney, Agent, or Firm* — Riverside Law LLP

(57) ABSTRACT

The present invention relates to compositions and methods for binding and detecting or measuring renalase. In one embodiment, the renalase binding molecule measures renalase amount or activity. Thus, in diseases and conditions where a measurement of renalase is beneficial, such renalase binding molecules may act as diagnostics.

1 Claim, 39 Drawing Sheets
Specification includes a Sequence Listing.

(56) References Cited

OTHER PUBLICATIONS

Jones et al., 2008, "Core Signaling Pathways in Human Pancreatic Cancers Revealed by Global Genomic Analyses." Science. 321(5897):1801-6.

Kolodecik et al. 2017; The serum protein renalase reduces injury in experimental pancreatitis. J. Bio. Chem. 292(51):21047-21059.

Kussie et al., A Single Engineered Amino Acid Substitution Changes Antibody Fine Specificity, 1994, Journal of Immunology, pp. 146-152 (Year: 1994).

Lee et al., 'Renalase Protects against Ischemic AKI,' 2013, J Am Soc Nephrol, 24:445-455.

Lesinski et al., 2013, "The potential for targeting the STAT3 pathway as a novel therapy for melanoma." Future Oncology. 9:925-7.

Li et al., 2008, "Catecholamines Regulate the Activity, Secretion, and Synthesis of Renalase", Circulation., 117(10):1277-82.

Li et al., Catecholamines Regulate the Activity, Secretion, and Synthesis of Renalase, 2008 Circulation. 117(10):1277-82.

Lowe et al., 2014, "Increasing Incidence of Melanoma among Middle-Aged Adults: An Epidemiologic Study in Olmsted County, Minnesota" Mayo Clinic Proceedings., 89:52-9.

Nolen et al., 2014, "Prediagnostic Serum Biomarkers as Early Detection Tools for Pancreatic Cancer in a Large Prospective Cohort Study." PLoS ONE. 9(4):e94928.

Nolen et al., Prediagnostic Serum Biomarkers as Early Detection Tools for Pancreatic Cancer in a Large Prospective Cohort Study, 2014 PLoS ONE. 9(4):e94928.

Office Action (Non-Final Rejection) dated Feb. 13, 2024 for U.S. Appl. No. 16/958,960 (pp. 1-14).

Sela-Culang et al., The structural basis of antibody-antigen recognition, 2013, Frontiers in Immunology, vol. 4, Article 302, pp. 1-13 (Year: 2013).

Wang et al., 2008, "Identification, expression and tissue distribution of a renalase homologue from mouse." Mol Biol Rep. 35(4):613-20.

Wang et al., 2014 Journal of the American Society of Nephrology., DOI:10.1681/asn.2013060665.

Wang et al., Renalase-Specific Polyclonal Antibody and Its Application in the Detection of Renalase's Expression, 2012, Hybridoma vol. 31, No. 5, pp. 378-381 (Year: 2012).

Wang Feng et al., PLOS ONE, vol. 7, p. e46442, XP055826003.

World Cancer Report 2014. WHO Press; 2014.

Xu et al., 2005, Renalase is a novel, soluble monoamine oxidase that regulates cardiac function and blood pressure, J Clin Invest. 115 (5):1275-80.

Yajima et al., 2012, "RAS/RAF/MEK/ERK and PI3K/PTEN/AKT Signaling in Malignant Melanoma Progression and Therapy." Dermatology research and practice. 2012:354191.

\* cited by examiner

Peptide antigens used to immunize rabbits

| SEQ ID NO | Antigen Code | Antigen Sequence | Specificity | Polyclonal | Monoclonal | Monoclonal Name |
|---|---|---|---|---|---|---|
| 1 | 1A | AVWDKADDSGGRMTTAC | R1, R2 | Yes | | |
| 2 | 1B | AVWDKAEDSGGRMTTAC | R1, R2 | Yes | | |
| 3 | 1C | CTPHYAKKHQRFYDEL | R1, R2 | Yes | Yes | 1C-22-1 |
| 4 | 1D | CIRFVSIDNKKRNIESSEIGP | R1, R2 | Yes | Yes | 1D-28-4, 1D-37-10 |
| 5 | 1E | PGQMTLHHKPFLAC | R1, R2 | Yes | | |
| 6 | 1F | CVLEALKNYI | R1 | Yes | Yes | 1F-26-1, 1F-42-7 |
| 7 | 3A | PSAGVILGC | R2 | Yes | Yes | 3A-5-2 |
| | Whole Protein | See FIG. 2 | R1, R2 | Yes (E2930) | | |

FIG. 1

SEQ ID NO: 8

Full-length renalase-1 protein sequence

1---MAQVLIVGAGMTGSLCAALIRRQTSGPLYLAVWDKAEDSGGRMTTACSPHNPQCTADLGA

61---QYITCTPHYAKKHQRFYDELLAYGVLRPLSSPIEGMVMKEGDCNFVAPQGISSIIKHYLK

121---ESGAEVYFRHRVTQINLRDDKWEVSKQTGSPEQFDLIVLTMPVPEILQLQGDITTLISEC

181---QRQQLEAVSYSSRYALGLFYEAGTKIDVPWAGQYITSNPCIRFVSIDNKKRNIESSEIGP

241---SLVIHTTVPFGVTYLEHSIEDVQELVFQQLENILPGLPQPIATKCQKWRHSQVTNAANC

301---PGQMTLHHKPFLACGGDGFTQSNFDGCITSALCVLEALKNYI

FIG. 2

Antigen positions within the renalase protein

| SEQ ID NO | | | | |
|---|---|---|---|---|
| 8 | Hu Ren 1 | MAQVLIVGAG&MTGSLCAALLRRQTSGPLYLY | 1A/1B AVNEKAESGSGRMTTAG | SPHNPQCTADLGAQYII | 1C CTPHYAKKHQRFYDKLAIYGVLRP |
| 50 | Hu Ren 2 | MAQVLIVGAG&MTGSLCAALLRRQTSGPLY | 1A/1B AVNEKAESGSGRMTTAG | SPHNPQCTADLGAQYII | 1C CTPHYAKKHQRFYDKLAIYGVLRP |
| 8 | Hu Ren 1 | LSSPIEGNVMKEGDCNFVAPQGISSIIKHYLKESGAEVYFRHRVTQINLRQMKWEVSKQTGSPKQFDLIVLTMPVPKIIQLQGDITTL |
| 50 | Hu Ren 2 | LSSPIEGNVMKEGDCNFVAPQGISSIIKHYLKESGAEVYFRHRVTQINLRQMKWEVSKQTGSPKQFDLIVLTMPVPKIIQLQGDITTL |
| 8 | Hu Ren 1 | ISECQRQQLEAVSTSSRYALGLFYTAGTKIDVPRAGQIITSM | 1D CIRFVSIHHHREKKFTKSSKIGH | SLVIHTTVPFGVTTLKHSIEKDVQE |
| 50 | Hu Ren 2 | ISECQRQQLEAVSYSSRYALGLFYKAGTKIDVPNAGQIITSND | 1D CIREVYSIIHHRKKKKFTKSSKIGH | SLVIHTTVPFGVTTLKHSIEKDVQE |
| 8 | Hu Ren 1 | LVFQQLKNILPGLRQPIAFKCQ | 1E KMWRHSQVTNAAANG | PCQMTLHHKPFTLADSSDGFTYQSNFDGCIITSA | 1F CVLFALKNYI |
| 50 | Hu Ren 2 | LVFQQLKNILPGLRQPIAFKCQ | KMWRHSQVTSAGVILGCAKGFNMMAIGFPI 3A5 | | |

FIG. 3

| SEQ ID NO | Anti-1D epitope Monoclonal 1D-28-4 heavy chain coding sequence: |
|---|---|
| 529 | atggagactgggctgcgctggcttctcctggtcgctgtgctcaaaggtgtccagtgtcag |
| 529 | M E T G L R W L L L V A V L K G V Q C Q |
| 529 | tcggtggaggagtccggggtcgcctggtcacgcctgggacacccctgacactcacctgc |
| 529 | S V E E S G G R L V T P G T P L T L T C |
| 529 | acagtctctggattctccctcagtagttttgcagtgggctgggtccgccaggctccaggg |
| 529 | T V S G F S <u>L S S F A V G</u> W V R Q A P G |
| 529 | aaggggctggaatacatcggaatcattagtagtgttggtattacacgctacgcgagctgg |
| 529 | K G L E Y I G <u>I I S S V G I T R Y A S W</u> |
| 529 | gcggccggccgattcaccatctccaaaacctcgaccacggtggatctgaaaatcaccagt |
| 529 | <u>A A G</u> R F T I S K T S T T V D L K I T S |
| 529 | ccgacaaccgaggacacggccacctatttttgtgccagatatggttatagtggtgatgtt |
| 529 | P T T E D T A T Y F C A R <u>Y G Y S G D V</u> |
| 529 | aatcggttggatctctggggccagggcaccctggtcaccgtctcctcaggcaacctaag |
| 529 | <u>N R L D</u> L W G Q G T L V T V S S G Q P K |
| 529 | gctccatcagtcttcccactggcccctgctgcggggacacaccagctccacggtgacc |
| 529 | A P S V F P L A P C C G D T P S S T V T |
| 529 | ctgggctgcctggtcaaagggtacctcccggagccagtgaccgtgacctggaactcgggc |
| 529 | L G C L V K G Y L P E P V T V T W N S G |
| 529 | acctcaccaatggggtacgcaccttcccgtccgtccggcagtcctcaggcctctactcg |
| 529 | T L T N G V R T F P S V R Q S S G L Y S |
| 529 | ctgagcagcgtggtgagcgtgacctcaagcagccagccgtcacctgcaacgtggcccac |
| 529 | L S S V V S V T S S S Q P V T C N V A H |
| 529 | ccagcaaccaacaccaaagtggacaagaccgttgcgcctcgacatgcagcaagcccacg |
| 529 | P A T N T K V D K T V A P S T C S K P T |
| 529 | tgcccaccccctgaactcctgggggacgtctgtcttcatcttccccaaaacccaag |
| 529 | C P P P E L L G G P S V F I F P P K P K |
| 529 | gacacccctcatgatctcacgcaccccgaggtcacatgcgtggtggtggacgtgagccag |

FIG. 4

| SEQ ID NO | |
|---|---|
| 9 | D T L M I S R T P E V T C V V V D V S Q |
| 52 | gatgacccgaggtgcagttcacatggtacataaacaacgagcaggtgcgcaccgcccgg |
| 9 | D D P E V Q F T W Y I N N E Q V R T A R |
| 52 | ccgccgctacgggagcagcagttcaacagcacgatccgcgtggtcagcaccctccccatc |
| 9 | P P L R E Q Q F N S T I R V V S T L P I |
| 52 | gcgcaccaggactggctgaggggcaaggagttcaagtgcaaagtccacaacaaggcactc |
| 9 | A H Q D W L R G K E F K C K V H N K A L |
| 52 | ccggcccccatcgagaaaaccatctccaaagccagagggcagcccctggagccgaaggtc |
| 9 | P A P I E K T I S K A R G Q P L E P K V |
| 52 | tacaccatgggccctcccggggaggagctgagcagcaggtcggtcagcctgacctgcatg |
| 9 | Y T M G P P R E E L S S R V S L T C M |
| 52 | atcaacggcttctaccttccgacatctcggtggagtgggagaagaacgggaaggcagag |
| 9 | I N G F Y P S D I S V E W E K N G K A E |
| 52 | gacaactacaagaccacgccggccgtgctggacagcgacggctcctacttcctctacagc |
| 9 | D N Y K T T P A V L D S D G S Y F L Y S |
| 52 | aagctctcagtgcccacgagtgagtggcagcggggcgacgtcttcacctgctccgtgatg |
| 9 | K L S V P T S E W Q R G D V F T C S V M |
| 52 | cacgaggccttgcacaaccactacacgcagaagtccatctcccgctctccgggtaaatga |
| 9 | H E A L H N H Y T Q K S I S R S P G K - |

FIG. 4 (CONTINUED)

| SEQ ID NO | Anti-1D epitope Monoclonal 1D-28-4 Light chain coding sequence: |
|---|---|
| 53 | atggacacgagggcccccactcagctgctggggctcctgctgctctggctcccaggtgcc |
| 10 | M D T R A P T Q L G L L L L W L P G A |
| 53 | acatttgcccaagtgctgacccagactgcatcgccgtgtctgcagctgtgggaggcaca |
| 10 | T F A Q V L T Q T A S P V S A A V G G T |
| 53 | gtcaccatcaattgccaggccagtcagagtgtttatgataacaacaacttagcctggtat |
| 10 | V T I N C Q A <u>S Q S V Y D N N N L A</u> W Y |
| 53 | cagcagaaaccagggcagcctcccaagcaactgatctatggtgcatccactctggcatct |
| 10 | Q Q K P G Q P P K Q L I Y <u>G A S T L A S</u> |
| 53 | ggggtctcatcgcggttcaaaggcagtggatctgggacacagttcactctcaccatcagc |

FIG. 5

| SEQ ID NO | |
|---|---|
| 10 | G V S S R F K G S G S G T Q F T L T I S |
| 53 | ggcgtgcagtgtgacgatgctgccacttactactgtctaggcgaatttagttgtagtagt |
| 10 | G V Q C D D A A T Y Y C <u>L G E F S C S S</u> |
| 53 | gctgattgttttgctttcggcggagggaccgaggtggtcgtcaaaggtgatccagttgca |
| 10 | <u>A D C F A</u> F G G G T E V V V K G D P V A |
| 53 | cctactgtcctcatcttccaccatctgctgatcttgtggcaactggaacagtcaccatc |
| 10 | P T V L I F P P S A D L V A T G T V T I |
| 53 | gtgtgtgtggcaataaatactttccgatgtcaccgtcacctgggaggtggatggcacc |
| 10 | V C V A N K Y F P D V T V T W E V D G T |
| 53 | acccaaacaactggcatcgagaacagtaaaacaccgcagaattctgcagattgtacctac |
| 10 | T Q T T G I E N S K T P Q N S A D C T Y |
| 53 | aacctcagcagcactctgacactgaccagcacacagtacaacagccacaaagagtacacc |
| 10 | N L S S T L T L T S T Q Y N S H K E Y T |
| 53 | tgcaaggtgacccagggcacgacctcagtcgtccagagcttcaatagggggtgactgttag |
| 10 | C K V T Q G T T S V V Q S F N R G D - |

FIG. 5 (CONTINUED)

| SEQ ID NO | Anti-1D epitope Monoclonal 1D-37-10 heavy chain coding sequence: |
|---|---|
| 60 | atggagactgggctgcgctggcttctcctggtcgctgtgctcaaaggtgtccagtgtcag |
| 17 | M E T G L R W L L L V A V L K G V Q C Q |
| 60 | tcggtggaggagtccggggtcgcctggtcacgcctggaggatccctgacactcacctgc |
| 17 | S V E E S G G R L V T P G G S L T L T C |
| 60 | acagtctctggattctcctcagtgactatgcaataatctgggtccgccaggctccaggg |
| 17 | T V S G F S <u>L S D Y A I I</u> W V R Q A P G |
| 60 | aaggggctggaatacatcgcaattattggtagtagtggtgacacattctacgcgacctgg |
| 17 | K G L E Y I A <u>I I G S S G D T F Y A T W</u> |
| 60 | gcgaaaggccgattcaccatctccaaaacctcgaccacggtggatctgaaaatgaccagt |
| 17 | <u>A K G</u> R F T I S K T S T T V D L K M T S |
| 60 | ctgacagccgcggacacggccacctatttctgtgcccacgttatgctggtactactgat |
| 17 | L T A A D T A T Y F C A P <u>R Y A G T T D</u> |
| 60 | tatcatgatgcttttgatccctggggcccaggcactttggtcaccgtctcctcagggcaa |

FIG. 6

| SEQ ID NO | |
|---|---|
| 17 | Y H D A F D P W G P G T L V T V S S G Q |
| 60 | cctaaggctccatcagtcttcccactggccccctgctgcggggacacacccagctccacg |
| 17 | P K A P S V F P L A P C C G D T P S S T |
| 60 | gtgaccctgggctgcctggtcaaagggtacctcccggagccagtgaccgtgacctggaac |
| 17 | V T L G C L V K G Y L P E P V T V T W N |
| 60 | tcgggcaccctcaccaatggggtacgcaccttcccgtccgtccggcagtcctcaggcctc |
| 17 | S G T L T N G V R T F P S V R Q S S G L |
| 60 | tactcgctgagcagcgtggtgagcgtgacctcaagcagccagcccgtcacctgcaacgtg |
| 17 | Y S L S S V V S V T S S Q P V T C N V |
| 60 | gccacccagccaccaacaccaaagtggacaagaccgttgcgccctcgacatgcagcaag |
| 17 | A H P A T N T K V D K T V A P S T C S K |
| 60 | cccacgtgcccacccctgaactcctgggggacgtctgtcttcatcttccccccaaaa |
| 17 | P T C P P P E L L G G P S V F I F P P K |
| 60 | cccaaggacaccctcatgatctcacgcacccccgaggtcacatgcgtggtggtggacgtg |
| 17 | P K D T L M I S R T P E V T C V V V D V |
| 60 | agccaggatgaccccgaggtgcagttcacatggtacataaacaacgagcaggtgcgcacc |
| 17 | S Q D D P E V Q F T W Y I N N E Q V R T |
| 60 | gcccggccgccgctacgggagcagcagttcaacagcacgatccgcgtggtcagcaccctc |
| 17 | A R P P L R E Q Q F N S T I R V V S T L |
| 60 | cccatcgcgcaccaggactggctgaggggcaaggagttcaagtgcaaagtccacaacaag |

FIG. 6 (CONTINUED)

| SEQ ID NO | |
|---|---|
| 17 | P I A H Q D W L R G K E F K C K V H N K |
| 60 | gcactcccggccccatcgagaaaaccatctccaaagccagagggcagcccctggagccg |
| 17 | A L P A P I E K T I S K A R G Q P L E P |
| 60 | aaggtctacaccatgggcctccccggaggagctgagcagcaggtcggtcagcctgacc |
| 17 | K V Y T M G P P R E E L S S R S V S L T |
| 60 | tgcatgatcaacggcttctacccttcgacatctcggtggagtgggagaagaacgggaag |
| 17 | C M I N G F Y P S D I S V E W E K N G K |
| 60 | gcagaggacaactacaagaccacgccggccgtgctggacagcgacggctcctacttcctc |
| 17 | A E D N Y K T T P A V L D S D G S Y F L |
| 60 | tacagcaagctctcagtgcccacgagtgagtggcagcggggcgacgtcttcacctgctcc |
| 17 | Y S K L S V P T S E W Q R G D V F T C S |
| 60 | gtgatgcacgaggccttgcacaaccactacacgcagaagtccatctcccgctctccgggt |
| 17 | V M H E A L H N H Y T Q K S I S R S P G |
| 60 | aaatga |
| 17 | K - |

FIG. 6 (CONTINUED)

| SEQ ID NO | Anti-1D epitope Monoclonal 1D-37-10 light-chain coding sequence: |
|---|---|
| 61 | atggacacgagggcccccactcagctgctggggctcctgctgctctggctcccaggtgcc |
| 18 | M D T R A P T Q L L G L L L L W L P G A |
| 61 | agatgtgccgaagtagtgatgacccagactccagcctccatggaggcacctatgggaggc |
| 18 | R C A E V V M T Q T P A S M E A P M G G |
| 61 | acagtcaccatcaagtgccaggccagtcagaacatttacaactacttatcctggtatcag |
| 18 | T V T I K C Q A <u>S Q N I Y N Y L S</u> W Y Q |
| 61 | cagaaaccagggcagcctcccaagctcctagtctacaaggcctccactctgacttctggg |
| 18 | Q K P G Q P P K L L V Y <u>K A S T L T S</u> G |
| 61 | gtcccgtcgcgcttcaaaggcagtggatctgggacacagttcactctcaccatcagcgac |
| 18 | V P S R F K G S G S G T Q F T L T I S D |
| 61 | ctggagtgtgccgatgctgccacttactactgtcaaatcaattactctatttataatcat |
| 18 | L E C A D A A T Y Y C <u>Q I N Y S I Y N H</u> |
| 61 | tataatattattttggcggagggaccgaggtggtcgtcaagggtgatccagttgcacct |
| 18 | <u>Y N I I</u> F G G G T E V V V K G D P V A P |
| 61 | actgtcctcatcttcccaccatctgctgatcttgtggcaactggaacagtcaccatcgtg |
| 18 | T V L I F P P S A D L V A T G T V T I V |
| 61 | tgtgtggcgaataaatactttccgatgtcaccgtcacctggaggtggatggcaccacc |
| 18 | C V A N K Y F P D V T V T W E V D G T T |
| 61 | caaacaactggcatcgagaacagtaaaacaccgcagaattctgcagattgtacctacaac |
| 18 | Q T T G I E N S K T P Q N S A D C T Y N |
| 61 | ctcagcagcactctgacactgaccagcacacagtacaacagccacaaagagtacacctgc |
| 18 | L S S T L T L T S T Q Y N S H K E Y T C |
| 61 | aaggtgacccagggcacgacctcagtcgtccagagcttcaatagggtgactgttag |
| 18 | K V T Q G T T S V V Q S F N R G D C - |

FIG. 7

| SEQ ID NO | Anti-1F epitope Monoclonal    1F-26-1 heavy chain coding sequence: |
|---|---|
| 68 | atggagactgggctgcgctggcttctcctggtcgctgtgctcaaaggtgtccagtgtcag |
| 25 | M E T G L R W L L L V A V L K G V Q C Q |
| 68 | tcggtgaaggagtccgagggaggtctcttcaagccaacggatatcctgacactcacctgc |
| 25 | S V K E S E G G L F K P T D I L T L T C |
| 68 | acagtctctggattctccctcagtagctatggagtgacctgggtccgccaggctccaggg |
| 25 | T V S G F S <u>L S S Y G V T</u> W V R Q A P G |
| 68 | aacgggctggagtggatcggattgattggtgatcgtggtactacgttctacgcgagctgg |
| 25 | N G L E W I G <u>L I G D R G T T F Y A S W</u> |
| 68 | gcgaaaagccgatccaccatcaccagaaacaccaacctgaacacggtgactctgaaaatg |
| 25 | <u>A K S</u> R S T I T R N T N L N T V T L K M |
| 68 | accaggctgacagccgcggacacggccacctatttctgtgcgagggggagtgggtatggt |
| 25 | T R L T A A D T A T Y F C A R <u>G S G Y G</u> |
| 68 | gctcgcatctggggcccaggcaccctggtcaccgtctcctcatggcaacctaaggctcca |
| 25 | <u>A R I</u> W G P G T L V T V S S W Q P K A P |
| 68 | tcagtcttcccactggccccctgctgcgggacacacccagctccacggtgaccctgggc |
| 25 | S V F P L A P C C G D T P S S T V T L G |
| 68 | tgcctggtcaaagggtacctcccggagccagtgaccgtgacctggaactcgggcacctc |
| 25 | C L V K G Y L P E P V T V T W N S G T L |
| 68 | accaatggggtacgcaccttcccgtccgtccggcagtcctcaggctctactcgctgagc |
| 25 | T N G V R T F P S V R Q S S G L Y S L S |
| 68 | agcgtggtgagcgtgacctcaagcagccagcccgtcacctgcaacgtggcccacccagcc |
| 25 | S V V S V T S S Q P V T C N V A H P A |

FIG. 8

| SEQ ID NO | |
|---|---|
| 68 | accaacaccaaagtggacaagaccgttgcgccctcgacatgcagcaagcccacgtgccca |
| 25 | I N T K V D K T V A P S T C S K P T C P |
| 68 | cccctgaactcctgggggaccgtctgtcttcatcttccccccaaaacccaaggacacc |
| 25 | P P E L L G G P S V F I F P P K P K D T |
| 68 | ctcatgatctcacgcaccccgaggtcacatgcgtggtggtggacgtgagccaggatgac |
| 25 | L M I S R T P E V T C V V V D V S Q D D |
| 68 | cccgaggtgcagttcacatggtacataaacaacgagcaggtgcgcaccgcccggccgcg |
| 25 | P E V Q F T W Y I N N E Q V R T A R P P |
| 68 | ctacgggagcagcagttcaacagcacgatccgcgtggtcagcaccctccccatcgctcac |
| 25 | L R E Q Q F N S T I R V V S T L P I A H |
| 68 | caggactggctgaggggcaaggagttcaagtgcaaagtccacaacaaggcactcccggcc |
| 25 | Q D W L R G K E F K C K V H N K A L P A |
| 68 | cccatcgagaaaaccatctccaaagccagagggcagcccctggagccgaaggtctacacc |
| 25 | P I E K T I S K A R G Q P L E P K V Y T |
| 68 | atgggccctccccgggaggagctgagcagcaggtcggtcagcctgacctgcatgatcaac |
| 25 | M G P P R E E L S S R S V S L T C M I N |
| 68 | ggcttctaccttccgacatctcggtggagtgggagaagaacgggaaggcagaggacaac |
| 25 | G F Y P S D I S V E W E K N G K A E D N |
| 68 | tacaagaccacgccggccgtgctggacagcgacggctcctacttcctctacagcaagctc |
| 25 | Y K T T P A V L D S D G S Y F L Y S K L |
| 68 | tcagtgcccacgagtgagtggcagcgggggacgtcttcacctgctccgtgatgcacgag |
| 25 | S V P T S E W Q R G D V F T C S V M H E |
| 68 | gccttgcacaaccactacacgcagaagtccatctcccgctctccgggtaaatga |
| 25 | A L H N H Y T Q K S I S R S P G K - |

FIG. 8 (CONTINUED)

| SEQ ID NO | Anti-1F epitope Monoclonal 1F-26-1 light-chain coding sequence: |
|---|---|
| 69 | atggacacgagggcccccactcagctcctggggctcctgctgctctggctcccaggtgcc |
| 26 | M D T R A P T Q L L G L L L W L P G A |
| 69 | acatttgcccaagtgctgacccagactccatcgcctgtgtctgcagctgtgggaggcaca |
| 26 | T F A Q V L T Q T P S P V S A A V G G T |
| 69 | gtcaccatcaattgccagtccagtcagagtgtttataagaacaactacttagcctggtat |
| 26 | V T I N C Q S <u>S Q S V Y K N N Y L A</u> W Y |
| 69 | cagcagaaaccagggcagcctcccaagctcctttatctacgaaacatccaaactggcatct |
| 26 | Q Q K P G Q P P K L L I Y <u>E T S K L A S</u> |
| 69 | ggggtcccaccgcggttcagcggcagtgggtctgggacacagttcactctcaccatcagc |
| 26 | G V P P R F S G S G S G T Q F T L T I S |
| 69 | agcgtgcagtgtgacgatgctgccacttactactgtcaaggcggttatagtggtgttgat |
| 26 | S V Q C D D A A T Y Y C <u>Q G G Y S G V D</u> |
| 69 | tttatggctttcggcggagggacgaggtggtcgtcaaaggtgatccagttgcacctact |
| 26 | <u>F M A</u> F G G G T E V V V K G D P V A P T |
| 69 | gtcctcatcttcccaccatctgctgatcttgtggcaactggaacagtcaccatcgtgtgt |
| 26 | V L I F P P S A D L V A T G T V T I V C |
| 69 | gtggcgaataaatactttccgatgtcaccgtcacctgggaggtggatggcaccacccaa |
| 26 | V A N K Y F P M S P S P G G G M A P P Q |
| 26 | V A N K Y F P D V T V T W E V D G T T Q |
| 69 | acaactggcatcgagaacagtaaaacaccgcagaattctgcagattgtacctacaacctc |
| 26 | T T G I E N S K T P Q N S A D C T Y N L |
| 69 | agcagcactctgacactgaccagcacacagtacaacagccacaaagagtacacctgcaag |
| 26 | S S T L T L T S T Q Y N S H K E Y T C K |
| 69 | gtgacccagggcacgacctcagtcgtccagagcttcaatagggggtgactgttag |
| 26 | V T Q G T T S V V Q S F N R G D - |

FIG. 9

| SEQ ID NO | Anti-1F epitope Monoclonal 1F-42-7 heavy-chain coding sequence: |
|---|---|
| 76 | atggagactgggctgcgctggcttctcctggtcgctgtgctcaaaggtgtccagtgtcag |
| 33 | M E T G L R W L L L V A V L K G V Q C Q |
| 76 | tcggtgaaggagtccgagggaggtctcttcaagccaacggataccctgacactcacctgc |
| 33 | S V K E S E G G L F K P T D T L T L C |
| 76 | acagtctctggattctccctcactacctatggagtgacctgggtccgccaggctccaggg |
| 33 | T V S G F S <u>L T T Y G V T</u> W V R Q A P G |
| 76 | aatggctggagtggatcggattgattggtgatcgcggtaccacttactacgcgagctgg |
| 33 | N G L E W I G <u>L I G D R G T T Y Y A S W</u> |
| 76 | gtgaatggccgatccaccatcaccagaaacaccaacctgaacacggtgactctgaaaatg |
| 33 | <u>V N G</u> R S T I T R N T N L N T V T L K M |
| 76 | accaggctgacagccgcggacacggccacctatttctgtgcgagggggagtggatatggt |
| 33 | T R L T A A D T A T Y F C A R <u>G S G Y G</u> |
| 76 | gctcgcatctggggcccaggcaccctggtcaccgtcgcctcatggcaacctaaggctcca |
| 33 | <u>A R I</u> W G P G T L V T V A S W Q P K A P |
| 76 | tcagtcttcccactggccccctgctgcggggacacacccagctccacggtgaccctgggc |
| 33 | S V F P L A P C C G D T P S S T V T L G |
| 76 | tgcctggtcaaagggtacctcccggagccagtgaccgtgacctggaactcgggcaccctc |
| 33 | C L V K G Y L P E P V T V T W N S G T L |
| 76 | accaatggggtacgcaccttcccgtccgtccggcagtcctcaggcctctactcgctgagc |
| 33 | T N G V R T F P S V R Q S S G L Y S L |
| 76 | agcgtggtgagcgtgacctcaagcagccagcccgtcacctgcaacgtggcccacccagcc |
| 33 | S V V S V T S S Q P V T C N V A H P A |
| 76 | accaacaccaaagtggacaagaccgttgcgccctcgacatgcagcaagccacgtgccca |
| 33 | T N T K V D K T V A P S T C S K P T C P |

FIG. 10

| SEQ ID NO | |
|---|---|
| 76 | cccctgaactcctggggggacgtctgtcttcatcttccccccaaaacccaaggacacc |
| 33 | P P E L L G G P S V F I F P P K P K D T |
| 76 | ctcatgatctcacgcacccccgaggtcacatgcgtggtggtggacgtgagccaggatgac |
| 33 | L M I S R T P E V T C V V V D V S Q D D |
| 76 | cccgaggtgcagttcacatggtacataaacaacgagcaggtgcgcaccgcccggccgcg |
| 33 | P E V Q F T W Y I N N E Q V R T A R P P |
| 76 | ctacgggagcagcagttcaacagcacgatccgcgtggtcagcaccctccccatcgcgcac |
| 33 | L R E Q Q F N S T I R V V S T L P I A H |
| 76 | caggactggctgaggggcaaggagttcaagtgcaaagtccacaacaaggcactcccggcc |
| 33 | Q D W L R G K E F K C K V H N K A L P A |
| 76 | cccatcgagaaaaccatctccaaagccagagggcagcccctggagccgaaggtctacacc |
| 33 | P I E K T I S K A R G Q P L E P K V Y T |
| 76 | atgggccctcccggggaggagctgagcagcaggtcggtcagcctgacctgcatgatcaac |
| 33 | M G P P R E E L S S R S V S L T C M I N |
| 76 | ggcttctaccttccgacatctcggtggagtgggagaagaacgggaaggcagaggacaac |
| 33 | G F Y P S D I S V E W E K N G K A E D N |
| 76 | tacaagaccacgccggccgtgctggacagcgacggctcctacttcctctacagcaagctc |
| 33 | Y K T T P A V L D S D G S Y F L Y S K L |
| 76 | tcagtgcccacgagtgagtggcagcggggcgacgtcttcacctgctccgtgatgcacgag |
| 33 | S V P T S E W Q R G D V F T C S V M H E |
| 76 | gccttgcacaaccactacacgcagaagtccatctcccgctctccgggtaaatga |
| 33 | A L H N H Y T Q K S I S R S P G K - |

FIG. 10 (CONTINUED)

| SEQ ID NO | Anti-1F epitope Monoclonal 1F-42-7 light-chain coding sequence: |
|---|---|
| 77 | atggacacgagggcccccactcagctcctggggctcctgctgctctggctcccaggtgcc |
| 34 | M D T R A P T Q L L G L L L W L P G A |
| 77 | acatttgcccaagtgctgacccagactccatcccccatgtctgcagctctgggaggcaca |
| 34 | T F A Q V L T Q T P S P M S A A L G G T |
| 77 | gtcaccatcaattgccagtccagtcagactgtttataacaataactacttatcctggtat |
| 34 | V T I N C Q S <u>S Q T V Y N N N Y L S</u> W Y |
| 77 | cagcagaaaccagggcagcctcccaagctccttatctacgaaacatccaaactgtcatct |
| 34 | Q Q K P G Q P P K L L I Y <u>E T S K L S S</u> |
| 77 | ggggtcccaccgcggttcagcggcagtgggtctggacacagttcactctcaccatcagc |
| 34 | G V P P R F S G S G S G T Q F T L T I S |
| 77 | agcgtgcagtgtgacgatgctgccacttactactgtcaaggcggttatagtggtgttgat |
| 34 | S V Q C D D A A T Y Y C Q <u>G G Y S G V D</u> |
| 77 | tttatggctttcggcggagggaccgaggtggtcgtcaaaggtgatccagttgcacctact |
| 34 | <u>F M A</u> F G G G T E V V V K G D P V A P T |
| 77 | gtcctcatcttcccaccatctgctgatcttgtggcaactggaacagtcaccatcgtgtgt |
| 34 | V L I F P P S A D L V A T G T V T I V C |
| 77 | gtggcgaataaatactttccgatgtcaccgtcacctgggaggtggatggcaccacccaa |
| 34 | V A N K Y F P D V T V T W E V D G T T Q |
| 77 | acaactggcatcgagaacagtaaaacaccgcagaattctgcagattgtacctacaacctc |
| 34 | T T G I E N S K T P Q N S A D C T Y N L |
| 77 | agcagcactctgacactgaccagcacacagtacaacagccacaaagagtacacctgcaag |
| 34 | S S T L T L T S T Q Y N S H K E Y T C K |
| 77 | gtgacccagggcacgacctcagtcgtccagagcttcaataggggtgactgttag |
| 34 | V T Q G T T S V V Q S F N R G D C - |

FIG. 11

| SEQ ID NO | Anti-renalase-2 epitope Monoclonal 3A-5-2 heavy-chain coding sequence: |
|---|---|
| 84 | atggagactgggctgcgctggcttctcctggtcgctgtgctcaaaggtgtccagtgtcag |
| 41 | M E T G L R W L L L V A V L K G V Q C Q |
| 84 | tcgctggaggagtccggggggtcgcctggtcacgcctgggacacccctgacactcacctgc |
| 41 | S L E E S G G R L V T P G T P L T L T C |
| 84 | acagtctctggattctccctcaataactaccacatatactgggtccgccaggctccagga |
| 41 | T V S G F S <u>L N N Y H I Y</u> W V R Q A P G |
| 84 | aaggggctggaatacatcggaatcattttcaatggtggcacatattacgcgagatggaca |
| 41 | K G L E Y I G <u>I I F N G G T Y Y A R W T</u> |
| 84 | aaaggccgattcaccatctccaaaacctcgaccacggtggatctgaaaatgaccagtctg |
| 41 | <u>K G</u> R F T I S K T S T T V D L K M T S L |
| 84 | acaaccgaggacacggccacctatttctgtgccagaggggacggcatctggggcccaggc |
| 41 | T T E D T A T Y F C A R <u>G D G I</u> W G P G |
| 84 | accctggtcaccgtctccttagggcaacctaaggctccatcagtcttcccactggcccc |
| 41 | T L V T V S L G Q P K A P S V F P L A P |
| 84 | tgctgcggggacacacccagctccacggtgaccctgggctgcctggtcaaagggtacctc |
| 41 | C C G D T P S S T V T L G C L V K G Y L |

FIG. 12

| SEQ ID NO | |
|---|---|
| 84 | cggagccagtgaccgtgacctggaactcgggcaccctcaccaatggggtacgcacttc |
| 41 | P E P V T V T W N S G T L T N G V R T F |
| 84 | ccgtccgtccggcagtcctcaggcctctactcgctgagcagcgtggtgagcgtgacctca |
| 41 | P S V R Q S S G L Y S L S S V V S V T S |
| 84 | agcagccagccgtcacctgcaacgtggcccacccagccaccaacaccaaagtggacaag |
| 41 | S S Q P V T C N V A H P A T N T K V D K |
| 84 | accgttgcgccctcgacatgcagcaagccgacgtgccaccccctgaactcctgggggga |
| 41 | T V A P S C S K P T C P P P E L L G G |
| 84 | ccgtctgtcttcatcttccccccaaaacccaaggacaccctcatgatctcacgcacccc |
| 41 | P S V F I F P P K P K D T L M I S R T P |
| 84 | gaggtcacatgcgtggtggtggacgtgagccaggatgaccccgaggtgcagttcacatgg |
| 41 | E V T C V V V D V S Q D D P E V Q F T W |
| 84 | tacataaacaacgagcaggtgcgcaccgccggccgcgctacgggagcagcagttcaac |
| 41 | Y I N N E Q V R T A R P P L R E Q Q F N |
| 84 | agcacgatccgcgtggtcagcaccctccccatcgcgcaccaggactggctgaggggcaag |
| 41 | S T I R V V S T L P I A H Q D W L R G K |
| 84 | gagttcaagtgcaaagtccacaacaaggcactcccggcccccatcgagaaaaccatctcc |
| 41 | E F K C K V H N K A L P A P I E K T I S |
| 84 | aaagccagagggcagcccctggagccgaaggtctacaccatgggccctccccggggaggag |
| 41 | K A R G Q P L E P K V Y T M G P P R E E |
| 84 | ctgagcagcaggtcggtcagcctgacctgcatgatcaacggcttctacccttccgacatc |
| 41 | L S S R S V S L T C M I N G F Y P S D I |
| 84 | tcggtggagtgggagaagaacggggaaggcagaggacaactacaagaccacgcggccgtg |
| 41 | S V E W E K N G E A E D N Y K T T P A V |
| 84 | ctggacagcgacggctcctacttcctctacagcaagctctcagtgcccacgagtgagtgg |
| 41 | L D S D G S Y F L Y S K L S V P T S E W |
| 84 | cagcggggcgacgtcttcacctgctccgtgatgcacgaggccttgcacaaccactacacg |
| 41 | Q R G D V F T C S V M H E A L H N H Y T |
| 84 | cagaagtccatctcccgctctccgggtaaatga |
| 41 | Q K S I S R S P G K - |

FIG. 12 (CONTINUED)

| SEQ ID NO | Anti-renalase-2 epitope Monoclonal 3A-5-2 light-chain coding sequence: |
|---|---|
| 85 | atggacacgagggcccccactcagctgctggggctcctgctgctctggctcccaggtgcc |
| 42 | M D T R A P T Q L L G L L L L W L P G A |
| 85 | acatttgcccaagtgctgacccagactccagcctccgtgtctgcagctgtgggaggcaca |
| 42 | T F A Q V L T Q T P A S V S A A V G G T |
| 85 | gtcaccatcaattgccaggccagtcagagtgttttaataacaactatttagcctggtat |
| 42 | V T I N C Q A <u>S Q S V F N N N Y L A</u> W Y |
| 85 | cagcagaaaccagggcagcctcccaagcgcctgatctattctgcatccactctggcgtct |
| 42 | Q Q K P G Q P P K R L I Y <u>S A S T L A S</u> |
| 85 | gggtctcatcgcggttcaaaggcagtggatctgggacagaattcactctgaccatgagt |
| 42 | G V S R F K G S G S G T E F T L T M S |
| 85 | ggcgtggagtgtgacgatgctgccacttactactgtcaggcagttttgattgtaatagt |
| 42 | G V E C D D A A T Y Y C <u>A G S F D C N S</u> |
| 85 | ggtgattgtgttgcttcggcggagggaccgaggtggtggtcaagggtgatccagttgca |
| 42 | <u>G D C V A</u> F G G G T E V V V K G D P V A |
| 85 | cctactgtcctcatcttcccaccagctgctgatcaggtggcaactggaacagtcaccatc |
| 42 | P T V L I F P P A A D Q V A T G T V T I |
| 85 | gtgtgtgtggcgaataaatactttcccgatgtcaccgtcacctgggaggtggatggcacc |
| 42 | V C V A N K Y F P D V T V T W E V D G T |
| 85 | acccaaacaactggcatcgagaacagtaaaacaccgcagaattctgcagattgtacctac |
| 42 | T Q T T G I E N S K T P Q N S A D C T Y |
| 85 | aacctcagcagcactctgacactgaccagcacagtacaacagccacaaagagtacacc |
| 42 | N L S S T L T L T S T Q Y N S H K E Y T |
| 85 | tgcaaggtgacccagggcacgacctcagtcgtccagagcttcaataggggtgactgttag |
| 42 | C K V T Q G T T S V V Q S F N R G D C - |

FIG. 13

Use of Anti-renalase antibodies to detect renalase in tissue lysates

The capture and detection of bacterially expressed recombinant renalase using a sandwich-ELISA format

A.

B.

The use of a sandwich-ELISA for the capture and detection of renalase in serum

B.

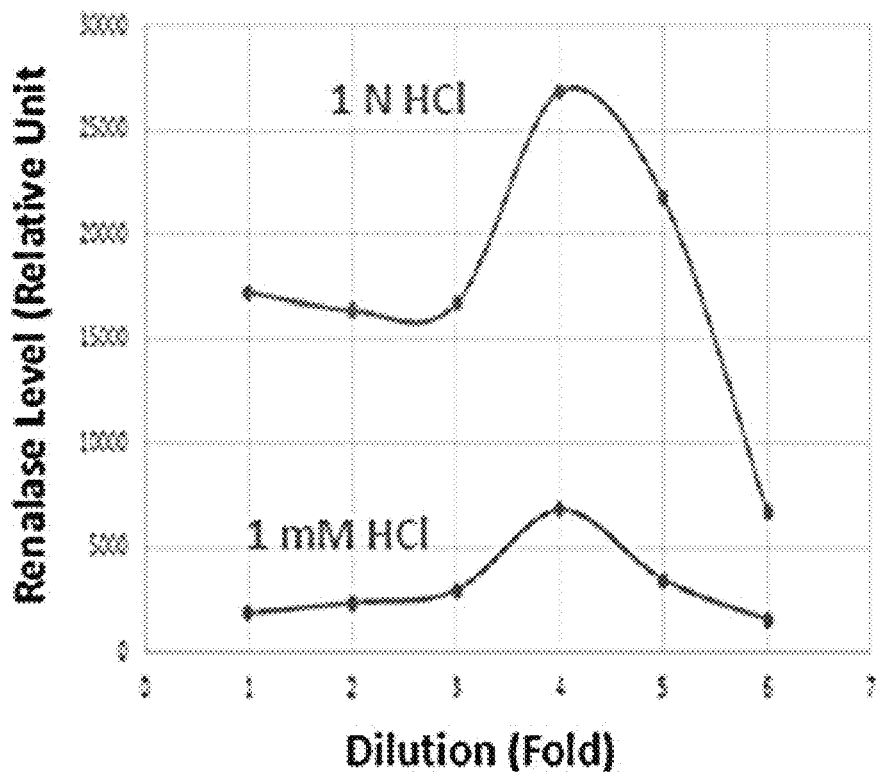
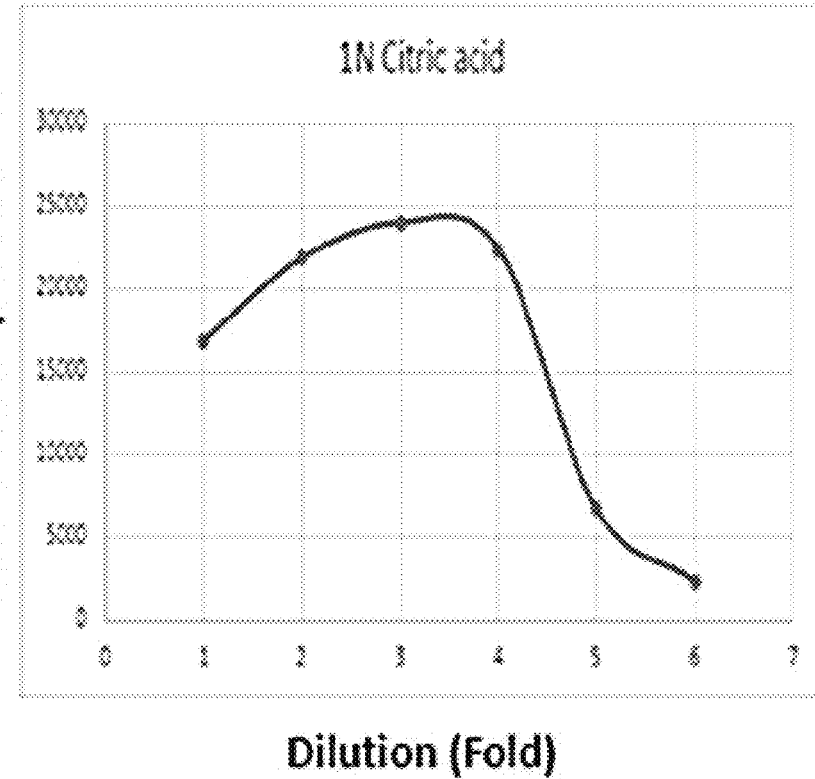
FIG. 27

| RNLS Levels in Human Plasma (mean ± SD) | | | |
|---|---|---|---|
|  | Total (µg/ml) | Free (µg/ml) | % Free |
| Normal (n = 15) | 4.319 ± 0.183 | 0.541 ± 0.229 | 12.06 ± 4.72 |
| Chest Pain (n = 45) | 5.916 ± 2.931 | 0.973 ± 1.305 | 17.91 ± 15.80 |
| Heart Failure (n=78) | 3.270 ± 1.822 | 0.056 ± 0.105 | 1.46 ± 2.33 |

FIG. 29

SEQUENCE LISTING

<160> NUMBER OF SEQ ID NOS: 234

<210> SEQ ID NO 1
<211> LENGTH: 17
<212> TYPE: PRT
<213> ORGANISM: Artificial Sequence
<220> FEATURE:
<223> OTHER INFORMATION: Chemically Synthesized, antigen seq 1a

<400> SEQUENCE: 1

Ala Val Trp Asp Lys Ala Asp Asp Ser Gly Gly Arg Met Thr Thr Ala

Cys

<210> SEQ ID NO 2
<211> LENGTH: 17
<212> TYPE: PRT
<213> ORGANISM: Artificial Sequence
<220> FEATURE:
<223> OTHER INFORMATION: Chemically Synthesized, antigen seq 1b

<400> SEQUENCE: 2

Ala Val Trp Asp Lys Ala Glu Asp Ser Gly Gly Arg Met Thr Thr Ala
1               5                   10                  15

Cys

<210> SEQ ID NO 3
<211> LENGTH: 16
<212> TYPE: PRT
<213> ORGANISM: Artificial Sequence
<220> FEATURE:
<223> OTHER INFORMATION: Chemically Synthesized, antigen seq 1c

<400> SEQUENCE: 3

Cys Thr Pro His Tyr Ala Lys Lys His Gln Arg Phe Tyr Asp Glu Leu
1               5                   10                  15

<210> SEQ ID NO 4
<211> LENGTH: 21
<212> TYPE: PRT
<213> ORGANISM: Artificial Sequence
<220> FEATURE:
<223> OTHER INFORMATION: Chemically Synthesized, antigen seq 1d

<400> SEQUENCE: 4

Cys Ile Arg Phe Val Ser Ile Asp Asn Lys Lys Arg Asn Ile Glu Ser
1               5                   10                  15

Ser Glu Ile Gly Pro
            20

<210> SEQ ID NO 5
<211> LENGTH: 14
<212> TYPE: PRT
<213> ORGANISM: Artificial Sequence
<220> FEATURE:
<223> OTHER INFORMATION: Chemically Synthesized, antigen seq 1e

<400> SEQUENCE: 5

Pro Gly Gln Met Thr Leu His His Lys Pro Phe Leu Ala Cys
1               5                   10

<210> SEQ ID NO 6
<211> LENGTH: 10
<212> TYPE: PRT
<213> ORGANISM: Artificial Sequence
<220> FEATURE:
<223> OTHER INFORMATION: Chemically Synthesized, antigen seq 1f

<400> SEQUENCE: 6

Cys Val Leu Glu Ala Leu Lys Asn Tyr Ile
1               5                   10

<210> SEQ ID NO 7
<211> LENGTH: 9
<212> TYPE: PRT
<213> ORGANISM: Artificial Sequence

```
<220> FEATURE:
<223> OTHER INFORMATION: Chemically Synthesized, antigen seq 3a

<400> SEQUENCE: 7

Pro Ser Ala Gly Val Ile Leu Gly Cys
1               5

<210> SEQ ID NO 8
<211> LENGTH: 342
<212> TYPE: PRT
<213> ORGANISM: Artificial Sequence
<220> FEATURE:
<223> OTHER INFORMATION: Hu Renalase-1 protein, polymorphism resulting
      in the highlighted glutamate amino acid at position 37

<400> SEQUENCE: 8

Met Ala Gln Val Leu Ile Val Gly Ala Gly Met Thr Gly Ser Leu Cys
1               5                   10                  15

Ala Ala Leu Leu Arg Arg Gln Thr Ser Gly Pro Leu Tyr Leu Ala Val
            20                  25                  30

Trp Asp Lys Ala Glu Asp Ser Gly Arg Met Thr Thr Ala Cys Ser
        35                  40                  45

Pro His Asn Pro Gln Cys Thr Ala Asp Leu Gly Ala Gln Tyr Ile Thr
    50                  55                  60

Cys Thr Pro His Tyr Ala Lys Lys His Gln Arg Phe Tyr Asp Glu Leu
65                  70                  75                  80

Leu Ala Tyr Gly Val Leu Arg Pro Leu Ser Ser Pro Ile Glu Gly Met
                85                  90                  95

Val Met Lys Glu Gly Asp Cys Asn Phe Val Ala Pro Gln Gly Ile Ser
            100                 105                 110

Ser Ile Ile Lys His Tyr Leu Lys Glu Ser Gly Ala Glu Val Tyr Phe
        115                 120                 125

Arg His Arg Val Thr Gln Ile Asn Leu Arg Asp Asp Lys Trp Glu Val
    130                 135                 140

Ser Lys Gln Thr Gly Ser Pro Glu Gln Phe Asp Leu Ile Val Leu Thr
145                 150                 155                 160

Met Pro Val Pro Glu Ile Leu Gln Leu Gln Gly Asp Ile Thr Thr Leu
                165                 170                 175

Ile Ser Glu Cys Gln Arg Gln Gln Leu Glu Ala Val Ser Tyr Ser Ser
            180                 185                 190

Arg Tyr Ala Leu Gly Leu Phe Tyr Glu Ala Gly Thr Lys Ile Asp Val
        195                 200                 205

Pro Trp Ala Gly Gln Tyr Ile Thr Ser Asn Pro Cys Ile Arg Phe Val
    210                 215                 220

Ser Ile Asp Asn Lys Lys Arg Asn Ile Glu Ser Ser Glu Ile Gly Pro
225                 230                 235                 240

Ser Leu Val Ile His Thr Thr Val Pro Phe Gly Val Thr Tyr Leu Glu
                245                 250                 255

His Ser Ile Glu Asp Val Gln Glu Leu Val Phe Gln Gln Leu Glu Asn
            260                 265                 270

Ile Leu Pro Gly Leu Pro Gln Pro Ile Ala Thr Lys Cys Gln Lys Trp
        275                 280                 285

Arg His Ser Gln Val Thr Asn Ala Ala Ala Asn Cys Pro Gly Gln Met
    290                 295                 300

Thr Leu His His Lys Pro Phe Leu Ala Cys Gly Gly Asp Gly Phe Thr
305                 310                 315                 320
```

Gln Ser Asn Phe Asp Gly Cys Ile Thr Ser Ala Leu Cys Val Leu Glu
                    325                 330                 335

Ala Leu Lys Asn Tyr Ile
            340

<210> SEQ ID NO 9
<211> LENGTH: 459
<212> TYPE: PRT
<213> ORGANISM: Artificial Sequence
<220> FEATURE:
<223> OTHER INFORMATION: Chemically Synthesized, mAb 1D-28-4 full length
      heavy chain amino acid

<400> SEQUENCE: 9

Met Glu Thr Gly Leu Arg Trp Leu Leu Leu Val Ala Val Leu Lys Gly
1               5                   10                  15

Val Gln Cys Gln Ser Val Glu Glu Ser Gly Gly Arg Leu Val Thr Pro
            20                  25                  30

Gly Thr Pro Leu Thr Leu Thr Cys Thr Val Ser Gly Phe Ser Leu Ser
        35                  40                  45

Ser Phe Ala Val Gly Trp Val Arg Gln Ala Pro Gly Lys Gly Leu Glu
    50                  55                  60

Tyr Ile Gly Ile Ile Ser Ser Val Gly Ile Thr Arg Tyr Ala Ser Trp
65                  70                  75                  80

Ala Ala Gly Arg Phe Thr Ile Ser Lys Thr Ser Thr Thr Val Asp Leu
                85                  90                  95

Lys Ile Thr Ser Pro Thr Thr Glu Asp Thr Ala Thr Tyr Phe Cys Ala
            100                 105                 110

Arg Tyr Gly Tyr Ser Gly Asp Val Asn Arg Leu Asp Leu Trp Gly Gln
        115                 120                 125

Gly Thr Leu Val Thr Val Ser Ser Gly Gln Pro Lys Ala Pro Ser Val
    130                 135                 140

Phe Pro Leu Ala Pro Cys Cys Gly Asp Thr Pro Ser Ser Thr Val Thr
145                 150                 155                 160

Leu Gly Cys Leu Val Lys Gly Tyr Leu Pro Glu Pro Val Thr Val Thr
                165                 170                 175

Trp Asn Ser Gly Thr Leu Thr Asn Gly Val Arg Thr Phe Pro Ser Val
            180                 185                 190

Arg Gln Ser Ser Gly Leu Tyr Ser Leu Ser Ser Val Val Ser Val Thr
        195                 200                 205

Ser Ser Ser Gln Pro Val Thr Cys Asn Val Ala His Pro Ala Thr Asn
    210                 215                 220

Thr Lys Val Asp Lys Thr Val Ala Pro Ser Thr Cys Ser Lys Pro Thr
225                 230                 235                 240

Cys Pro Pro Pro Glu Leu Leu Gly Gly Pro Ser Val Phe Ile Phe Pro
                245                 250                 255

Pro Lys Pro Lys Asp Thr Leu Met Ile Ser Arg Thr Pro Glu Val Thr
            260                 265                 270

Cys Val Val Val Asp Val Ser Gln Asp Asp Pro Glu Val Gln Phe Thr
        275                 280                 285

Trp Tyr Ile Asn Asn Glu Gln Val Arg Thr Ala Arg Pro Pro Leu Arg
    290                 295                 300

Glu Gln Gln Phe Asn Ser Thr Ile Arg Val Val Ser Thr Leu Pro Ile
305                 310                 315                 320

Ala His Gln Asp Trp Leu Arg Gly Lys Glu Phe Lys Cys Lys Val His
                325                 330                 335

Asn Lys Ala Leu Pro Ala Pro Ile Glu Lys Thr Ile Ser Lys Ala Arg
                340                 345                 350

Gly Gln Pro Leu Glu Pro Lys Val Tyr Thr Met Gly Pro Arg Glu
            355                 360                 365

Glu Leu Ser Ser Arg Ser Val Ser Leu Thr Cys Met Ile Asn Gly Phe
370                 375                 380

Tyr Pro Ser Asp Ile Ser Val Glu Trp Glu Lys Asn Gly Lys Ala Glu
385                 390                 395                 400

Asp Asn Tyr Lys Thr Thr Pro Ala Val Leu Asp Ser Asp Gly Ser Tyr
                405                 410                 415

Phe Leu Tyr Ser Lys Leu Ser Val Pro Thr Ser Glu Trp Gln Arg Gly
            420                 425                 430

Asp Val Phe Thr Cys Ser Val Met His Glu Ala Leu His Asn His Tyr
            435                 440                 445

Thr Gln Lys Ser Ile Ser Arg Ser Pro Gly Lys
    450                 455

<210> SEQ ID NO 10
<211> LENGTH: 239
<212> TYPE: PRT
<213> ORGANISM: Artificial Sequence
<220> FEATURE:
<223> OTHER INFORMATION: Chemically Synthesized, mAb 1D-28-4 full length
      light chain amino acid

<400> SEQUENCE: 10

Met Asp Thr Arg Ala Pro Thr Gln Leu Leu Gly Leu Leu Leu Leu Trp
1               5                   10                  15

Leu Pro Gly Ala Thr Phe Ala Gln Val Leu Thr Gln Thr Ala Ser Pro
            20                  25                  30

Val Ser Ala Ala Val Gly Gly Thr Val Thr Ile Asn Cys Gln Ala Ser
        35                  40                  45

Gln Ser Val Tyr Asp Asn Asn Leu Ala Trp Tyr Gln Gln Lys Pro
    50                  55                  60

Gly Gln Pro Pro Lys Gln Leu Ile Tyr Gly Ala Ser Thr Leu Ala Ser
65                  70                  75                  80

Gly Val Ser Ser Arg Phe Lys Gly Ser Gly Ser Gly Thr Gln Phe Thr
                85                  90                  95

Leu Thr Ile Ser Gly Val Gln Cys Asp Asp Ala Ala Thr Tyr Tyr Cys
                100                 105                 110

Leu Gly Glu Phe Ser Cys Ser Ser Ala Asp Cys Phe Ala Phe Gly Gly
            115                 120                 125

Gly Thr Glu Val Val Val Lys Gly Asp Pro Val Ala Pro Thr Val Leu
        130                 135                 140

Ile Phe Pro Pro Ser Ala Asp Leu Val Ala Thr Gly Thr Val Thr Ile
145                 150                 155                 160

Val Cys Val Ala Asn Lys Tyr Phe Pro Asp Val Thr Val Thr Trp Glu
                165                 170                 175

Val Asp Gly Thr Thr Gln Thr Thr Gly Ile Glu Asn Ser Lys Thr Pro
            180                 185                 190

Gln Asn Ser Ala Asp Cys Thr Tyr Asn Leu Ser Ser Thr Leu Thr Leu
        195                 200                 205

Thr Ser Thr Gln Tyr Asn Ser His Lys Glu Tyr Thr Cys Lys Val Thr
210                 215                 220

Gln Gly Thr Thr Ser Val Val Gln Ser Phe Asn Arg Gly Asp Cys

-continued

<210> SEQ ID NO 11
<211> LENGTH: 7
<212> TYPE: PRT
<213> ORGANISM: Artificial Sequence
<220> FEATURE:
<223> OTHER INFORMATION: Chemically Synthesized, 1D-28-4 heavy chain
      CDR1 amino acid

<400> SEQUENCE: 11

Leu Ser Ser Phe Ala Val Gly
1               5

<210> SEQ ID NO 12
<211> LENGTH: 16
<212> TYPE: PRT
<213> ORGANISM: Artificial Sequence
<220> FEATURE:
<223> OTHER INFORMATION: Chemically Synthesized, 1D-28-4 heavy chain
      CDR2 amino acid

<400> SEQUENCE: 12

Ile Ile Ser Ser Val Gly Ile Thr Arg Tyr Ala Ser Trp Ala Ala Gly
1               5                   10                  15

<210> SEQ ID NO 13
<211> LENGTH: 12
<212> TYPE: PRT
<213> ORGANISM: Artificial Sequence
<220> FEATURE:
<223> OTHER INFORMATION: Chemically Synthesized, 1D-28-4 heavy chain
      CDR3 amino acid

<400> SEQUENCE: 13

Tyr Gly Tyr Ser Gly Asp Val Asn Arg Leu Asp Leu
1               5                   10

<210> SEQ ID NO 14
<211> LENGTH: 11
<212> TYPE: PRT
<213> ORGANISM: Artificial Sequence
<220> FEATURE:
<223> OTHER INFORMATION: Chemically Synthesized, 1D-28-4 light chain
      CDR1 amino acid

<400> SEQUENCE: 14

Ser Gln Ser Val Tyr Asp Asn Asn Asn Leu Ala
1               5                   10

<210> SEQ ID NO 15
<211> LENGTH: 7
<212> TYPE: PRT
<213> ORGANISM: Artificial Sequence
<220> FEATURE:
<223> OTHER INFORMATION: Chemically Synthesized, 1D-28-4 light chain
      CDR2 amino acid

<400> SEQUENCE: 15

Gly Ala Ser Thr Leu Ala Ser
1               5

<210> SEQ ID NO 16
<211> LENGTH: 13
<212> TYPE: PRT
<213> ORGANISM: Artificial Sequence
<220> FEATURE:
<223> OTHER INFORMATION: Chemically Synthesized, 1D-28-4 light chain -continued CDR3 amino acid

<400> SEQUENCE: 16

Leu Gly Glu Phe Ser Cys Ser Ser Ala Asp Cys Phe Ala
1               5                   10

<210> SEQ ID NO 17
<211> LENGTH: 461
<212> TYPE: PRT
<213> ORGANISM: Artificial Sequence
<220> FEATURE:
<223> OTHER INFORMATION: Chemically Synthesized, mAb 1D-37-10 full
      length heavy chain amino acid

<400> SEQUENCE: 17

Met Glu Thr Gly Leu Arg Trp Leu Leu Leu Val Ala Val Leu Lys Gly
1               5                   10                  15

Val Gln Cys Gln Ser Val Glu Glu Ser Gly Gly Arg Leu Val Thr Pro
            20                  25                  30

Gly Gly Ser Leu Thr Leu Thr Cys Thr Val Ser Gly Phe Ser Leu Ser
        35                  40                  45

Asp Tyr Ala Ile Ile Trp Val Arg Gln Ala Pro Gly Lys Gly Leu Glu
    50                  55                  60

Tyr Ile Ala Ile Ile Gly Ser Ser Gly Asp Thr Phe Tyr Ala Thr Trp
65                  70                  75                  80

Ala Lys Gly Arg Phe Thr Ile Ser Lys Thr Ser Thr Thr Val Asp Leu
                85                  90                  95

Lys Met Thr Ser Leu Thr Ala Ala Asp Thr Ala Thr Tyr Phe Cys Ala
            100                 105                 110

Pro Arg Tyr Ala Gly Thr Thr Asp Tyr His Asp Ala Phe Asp Pro Trp
        115                 120                 125

Gly Pro Gly Thr Leu Val Thr Val Ser Ser Gly Gln Pro Lys Ala Pro
    130                 135                 140

Ser Val Phe Pro Leu Ala Pro Cys Cys Gly Asp Thr Pro Ser Ser Thr
145                 150                 155                 160

Val Thr Leu Gly Cys Leu Val Lys Gly Tyr Leu Pro Glu Pro Val Thr
                165                 170                 175

Val Thr Trp Asn Ser Gly Thr Leu Thr Asn Gly Val Arg Thr Phe Pro
            180                 185                 190

Ser Val Arg Gln Ser Ser Gly Leu Tyr Ser Leu Ser Ser Val Val Ser
        195                 200                 205

Val Thr Ser Ser Ser Gln Pro Val Thr Cys Asn Val Ala His Pro Ala
    210                 215                 220

Thr Asn Thr Lys Val Asp Lys Thr Val Ala Pro Ser Thr Cys Ser Lys
225                 230                 235                 240

Pro Thr Cys Pro Pro Pro Glu Leu Leu Gly Gly Pro Ser Val Phe Ile
                245                 250                 255

Phe Pro Pro Lys Pro Lys Asp Thr Leu Met Ile Ser Arg Thr Pro Glu
            260                 265                 270

Val Thr Cys Val Val Val Asp Val Ser Gln Asp Asp Pro Glu Val Gln
        275                 280                 285

Phe Thr Trp Tyr Ile Asn Asn Glu Gln Val Arg Thr Ala Arg Pro Pro
    290                 295                 300

Leu Arg Glu Gln Gln Phe Asn Ser Thr Ile Arg Val Val Ser Thr Leu
305                 310                 315                 320

Pro Ile Ala His Gln Asp Trp Leu Arg Gly Lys Glu Phe Lys Cys Lys

```
                      325                 330                 335
Val His Asn Lys Ala Leu Pro Ala Pro Ile Glu Lys Thr Ile Ser Lys
            340                 345                 350
Ala Arg Gly Gln Pro Leu Glu Pro Lys Val Tyr Thr Met Gly Pro Pro
            355                 360                 365
Arg Glu Glu Leu Ser Ser Arg Ser Val Ser Leu Thr Cys Met Ile Asn
            370                 375                 380
Gly Phe Tyr Pro Ser Asp Ile Ser Val Glu Trp Glu Lys Asn Gly Lys
385                 390                 395                 400
Ala Glu Asp Asn Tyr Lys Thr Thr Pro Ala Val Leu Asp Ser Asp Gly
            405                 410                 415
Ser Tyr Phe Leu Tyr Ser Lys Leu Ser Val Pro Thr Ser Glu Trp Gln
            420                 425                 430
Arg Gly Asp Val Phe Thr Cys Ser Val Met His Glu Ala Leu His Asn
            435                 440                 445
His Tyr Thr Gln Lys Ser Ile Ser Arg Ser Pro Gly Lys
            450                 455                 460

<210> SEQ ID NO 18
<211> LENGTH: 238
<212> TYPE: PRT
<213> ORGANISM: Artificial Sequence
<220> FEATURE:
<223> OTHER INFORMATION: Chemically Synthesized, mAb 1D-37-10 full
      length light chain amino acid

<400> SEQUENCE: 18

Met Asp Thr Arg Ala Pro Thr Gln Leu Leu Gly Leu Leu Leu Leu Trp
1               5                   10                  15
Leu Pro Gly Ala Arg Cys Ala Glu Val Val Met Thr Gln Thr Pro Ala
            20                  25                  30
Ser Met Glu Ala Pro Met Gly Gly Thr Val Thr Ile Lys Cys Gln Ala
            35                  40                  45
Ser Gln Asn Ile Tyr Asn Tyr Leu Ser Trp Tyr Gln Gln Lys Pro Gly
            50                  55                  60
Gln Pro Pro Lys Leu Leu Val Tyr Lys Ala Ser Thr Leu Thr Ser Gly
65                  70                  75                  80
Val Pro Ser Arg Phe Lys Gly Ser Gly Ser Gly Thr Gln Phe Thr Leu
            85                  90                  95
Thr Ile Ser Asp Leu Glu Cys Ala Asp Ala Ala Thr Tyr Tyr Cys Gln
            100                 105                 110
Ile Asn Tyr Ser Ile Tyr Asn His Tyr Asn Ile Ile Phe Gly Gly Gly
            115                 120                 125
Thr Glu Val Val Val Lys Gly Asp Pro Val Ala Pro Thr Val Leu Ile
            130                 135                 140
Phe Pro Pro Ser Ala Asp Leu Val Ala Thr Gly Thr Val Thr Ile Val
145                 150                 155                 160
Cys Val Ala Asn Lys Tyr Phe Pro Asp Val Thr Val Thr Trp Glu Val
            165                 170                 175
Asp Gly Thr Thr Gln Thr Thr Gly Ile Glu Asn Ser Lys Thr Pro Gln
            180                 185                 190
Asn Ser Ala Asp Cys Thr Tyr Asn Leu Ser Ser Thr Leu Thr Leu Thr
            195                 200                 205
Ser Thr Gln Tyr Asn Ser His Lys Glu Tyr Thr Cys Lys Val Thr Gln
            210                 215                 220
```

```
Gly Thr Thr Ser Val Val Gln Ser Phe Asn Arg Gly Asp Cys
225                 230                 235
```

<210> SEQ ID NO 19
<211> LENGTH: 7
<212> TYPE: PRT
<213> ORGANISM: Artificial Sequence
<220> FEATURE:
<223> OTHER INFORMATION: Chemically Synthesized, 1D-37-10 heavy chain
      CDR1 amino acid

<400> SEQUENCE: 19

```
Leu Ser Asp Tyr Ala Ile Ile
1               5
```

<210> SEQ ID NO 20
<211> LENGTH: 16
<212> TYPE: PRT
<213> ORGANISM: Artificial Sequence
<220> FEATURE:
<223> OTHER INFORMATION: Chemically Synthesized, 1D-37-10 heavy chain
      CDR2 amino acid

<400> SEQUENCE: 20

```
Ile Ile Gly Ser Ser Gly Asp Thr Phe Tyr Ala Thr Trp Ala Lys Gly
1               5                   10                  15
```

<210> SEQ ID NO 21
<211> LENGTH: 14
<212> TYPE: PRT
<213> ORGANISM: Artificial Sequence
<220> FEATURE:
<223> OTHER INFORMATION: Chemically Synthesized, 1D-37-10 heavy chain
      CDR3 amino acid

<400> SEQUENCE: 21

```
Arg Tyr Ala Gly Thr Thr Asp Tyr His Asp Ala Phe Asp Pro
1               5                   10
```

<210> SEQ ID NO 22
<211> LENGTH: 9
<212> TYPE: PRT
<213> ORGANISM: Artificial Sequence
<220> FEATURE:
<223> OTHER INFORMATION: Chemically Synthesized, 1D-37-10 light chain
      CDR1 amino acid

<400> SEQUENCE: 22

```
Ser Gln Asn Ile Tyr Asn Tyr Leu Ser
1               5
```

<210> SEQ ID NO 23
<211> LENGTH: 7
<212> TYPE: PRT
<213> ORGANISM: Artificial Sequence
<220> FEATURE:
<223> OTHER INFORMATION: Chemically Synthesized, 1D-37-10 light chain
      CDR2 amino acid

<400> SEQUENCE: 23

```
Lys Ala Ser Thr Leu Thr Ser
1               5
```

<210> SEQ ID NO 24
<211> LENGTH: 13
<212> TYPE: PRT
<213> ORGANISM: Artificial Sequence
<220> FEATURE:

-continued

<223> OTHER INFORMATION: Chemically Synthesized, 1D-37-10 light chain
      CDR3 amino acid

<400> SEQUENCE: 24

Gln Ile Asn Tyr Ser Ile Tyr Asn His Tyr Asn Ile Ile
1               5                   10

<210> SEQ ID NO 25
<211> LENGTH: 457
<212> TYPE: PRT
<213> ORGANISM: Artificial Sequence
<220> FEATURE:
<223> OTHER INFORMATION: Chemically Synthesized, mAb 1F-26-1 full length
      heavy chain amino acid

<400> SEQUENCE: 25

Met Glu Thr Gly Leu Arg Trp Leu Leu Leu Val Ala Val Leu Lys Gly
1               5                   10                  15

Val Gln Cys Gln Ser Val Lys Glu Ser Glu Gly Gly Leu Phe Lys Pro
                20                  25                  30

Thr Asp Thr Leu Thr Leu Thr Cys Thr Val Ser Gly Phe Ser Leu Ser
            35                  40                  45

Ser Tyr Gly Val Thr Trp Val Arg Gln Ala Pro Gly Asn Gly Leu Glu
    50                  55                  60

Trp Ile Gly Leu Ile Gly Asp Arg Gly Thr Thr Phe Tyr Ala Ser Trp
65                  70                  75                  80

Ala Lys Ser Arg Ser Thr Ile Thr Arg Asn Thr Asn Leu Asn Thr Val
                85                  90                  95

Thr Leu Lys Met Thr Arg Leu Thr Ala Ala Asp Thr Ala Thr Tyr Phe
            100                 105                 110

Cys Ala Arg Gly Ser Gly Tyr Gly Ala Arg Ile Trp Gly Pro Gly Thr
        115                 120                 125

Leu Val Thr Val Ser Ser Trp Gln Pro Lys Ala Pro Ser Val Phe Pro
130                 135                 140

Leu Ala Pro Cys Cys Gly Asp Thr Pro Ser Ser Thr Val Thr Leu Gly
145                 150                 155                 160

Cys Leu Val Lys Gly Tyr Leu Pro Glu Pro Val Thr Val Thr Trp Asn
                165                 170                 175

Ser Gly Thr Leu Thr Asn Gly Val Arg Thr Phe Pro Ser Val Arg Gln
            180                 185                 190

Ser Ser Gly Leu Tyr Ser Leu Ser Ser Val Val Ser Val Thr Ser Ser
        195                 200                 205

Ser Gln Pro Val Thr Cys Asn Val Ala His Pro Ala Thr Asn Thr Lys
    210                 215                 220

Val Asp Lys Thr Val Ala Pro Ser Thr Cys Ser Lys Pro Thr Cys Pro
225                 230                 235                 240

Pro Pro Glu Leu Leu Gly Gly Pro Ser Val Phe Ile Phe Pro Pro Lys
                245                 250                 255

Pro Lys Asp Thr Leu Met Ile Ser Arg Thr Pro Glu Val Thr Cys Val
            260                 265                 270

Val Val Asp Val Ser Gln Asp Asp Pro Glu Val Gln Phe Thr Trp Tyr
        275                 280                 285

Ile Asn Asn Glu Gln Val Arg Thr Ala Arg Pro Pro Leu Arg Glu Gln
    290                 295                 300

Gln Phe Asn Ser Thr Ile Arg Val Val Ser Thr Leu Pro Ile Ala His
305                 310                 315                 320

```
Gln Asp Trp Leu Arg Gly Lys Glu Phe Lys Cys Lys Val His Asn Lys
                325                 330                 335

Ala Leu Pro Ala Pro Ile Glu Lys Thr Ile Ser Lys Ala Arg Gly Gln
            340                 345                 350

Pro Leu Glu Pro Lys Val Tyr Thr Met Gly Pro Pro Arg Glu Glu Leu
        355                 360                 365

Ser Ser Arg Ser Val Ser Leu Thr Cys Met Ile Asn Gly Phe Tyr Pro
    370                 375                 380

Ser Asp Ile Ser Val Glu Trp Glu Lys Asn Gly Lys Ala Glu Asp Asn
385                 390                 395                 400

Tyr Lys Thr Thr Pro Ala Val Leu Asp Ser Asp Gly Ser Tyr Phe Leu
                405                 410                 415

Tyr Ser Lys Leu Ser Val Pro Thr Ser Glu Trp Gln Arg Gly Asp Val
            420                 425                 430

Phe Thr Cys Ser Val Met His Glu Ala Leu His Asn His Tyr Thr Gln
        435                 440                 445

Lys Ser Ile Ser Arg Ser Pro Gly Lys
    450                 455

<210> SEQ ID NO 26
<211> LENGTH: 237
<212> TYPE: PRT
<213> ORGANISM: Artificial Sequence
<220> FEATURE:
<223> OTHER INFORMATION: Chemically Synthesized, mAb 1F-26-1 full length
      light chain amino acid

<400> SEQUENCE: 26

Met Asp Thr Arg Ala Pro Thr Gln Leu Leu Gly Leu Leu Leu Leu Trp
1               5                   10                  15

Leu Pro Gly Ala Thr Phe Ala Gln Val Leu Thr Gln Thr Pro Ser Pro
            20                  25                  30

Val Ser Ala Ala Val Gly Gly Thr Val Thr Ile Asn Cys Gln Ser Ser
        35                  40                  45

Gln Ser Val Tyr Lys Asn Asn Tyr Leu Ala Trp Tyr Gln Gln Lys Pro
    50                  55                  60

Gly Gln Pro Pro Lys Leu Leu Ile Tyr Glu Thr Ser Lys Leu Ala Ser
65                  70                  75                  80

Gly Val Pro Pro Arg Phe Ser Gly Ser Gly Ser Gly Thr Gln Phe Thr
                85                  90                  95

Leu Thr Ile Ser Ser Val Gln Cys Asp Asp Ala Ala Thr Tyr Tyr Cys
            100                 105                 110

Gln Gly Gly Tyr Ser Gly Val Asp Phe Met Ala Phe Gly Gly Gly Thr
        115                 120                 125

Glu Val Val Val Lys Gly Asp Pro Val Ala Pro Thr Val Leu Ile Phe
    130                 135                 140

Pro Pro Ser Ala Asp Leu Val Ala Thr Gly Thr Val Thr Ile Val Cys
145                 150                 155                 160

Val Ala Asn Lys Tyr Phe Pro Asp Val Thr Val Thr Trp Glu Val Asp
                165                 170                 175

Gly Thr Thr Gln Thr Thr Gly Ile Glu Asn Ser Lys Thr Pro Gln Asn
            180                 185                 190

Ser Ala Asp Cys Thr Tyr Asn Leu Ser Ser Thr Leu Thr Leu Thr Ser
        195                 200                 205

Thr Gln Tyr Asn Ser His Lys Glu Tyr Thr Cys Lys Val Thr Gln Gly
    210                 215                 220
```

```
Thr Thr Ser Val Val Gln Ser Phe Asn Arg Gly Asp Cys
225                 230                 235

<210> SEQ ID NO 27
<211> LENGTH: 7
<212> TYPE: PRT
<213> ORGANISM: Artificial Sequence
<220> FEATURE:
<223> OTHER INFORMATION: Chemically Synthesized, 1F-26-1 heavy chain
      CDR1 amino acid

<400> SEQUENCE: 27

Leu Ser Ser Tyr Gly Val Thr
1               5

<210> SEQ ID NO 28
<211> LENGTH: 16
<212> TYPE: PRT
<213> ORGANISM: Artificial Sequence
<220> FEATURE:
<223> OTHER INFORMATION: Chemically Synthesized, 1F-26-1 heavy chain
      CDR2 amino acid

<400> SEQUENCE: 28

Leu Ile Gly Asp Arg Gly Thr Thr Phe Tyr Ala Ser Trp Ala Lys Ser
1               5                   10                  15

<210> SEQ ID NO 29
<211> LENGTH: 8
<212> TYPE: PRT
<213> ORGANISM: Artificial Sequence
<220> FEATURE:
<223> OTHER INFORMATION: Chemically Synthesized, 1F-26-1 heavy chain
      CDR3 amino acid

<400> SEQUENCE: 29

Gly Ser Gly Tyr Gly Ala Arg Ile
1               5

<210> SEQ ID NO 30
<211> LENGTH: 11
<212> TYPE: PRT
<213> ORGANISM: Artificial Sequence
<220> FEATURE:
<223> OTHER INFORMATION: Chemically Synthesized, 1F-26-1 light chain
      CDR1 amino acid

<400> SEQUENCE: 30

Ser Gln Ser Val Tyr Lys Asn Asn Tyr Leu Ala
1               5                   10

<210> SEQ ID NO 31
<211> LENGTH: 7
<212> TYPE: PRT
<213> ORGANISM: Artificial Sequence
<220> FEATURE:
<223> OTHER INFORMATION: Chemically Synthesized, 1F-26-1 light chain
      CDR2 amino acid

<400> SEQUENCE: 31

Glu Thr Ser Lys Leu Ala Ser
1               5

<210> SEQ ID NO 32
<211> LENGTH: 11
<212> TYPE: PRT
<213> ORGANISM: Artificial Sequence
```

<220> FEATURE:
<223> OTHER INFORMATION: Chemically Synthesized, 1F-26-1 light chain
      CDR3 amino acid

<400> SEQUENCE: 32

Gln Gly Gly Tyr Ser Gly Val Asp Phe Met Ala
1               5                   10

<210> SEQ ID NO 33
<211> LENGTH: 457
<212> TYPE: PRT
<213> ORGANISM: Artificial Sequence
<220> FEATURE:
<223> OTHER INFORMATION: Chemically Synthesized, mAb 1F-42-7 full length
      heavy chain amino acid

<400> SEQUENCE: 33

Met Glu Thr Gly Leu Arg Trp Leu Leu Leu Val Ala Val Leu Lys Gly
1               5                   10                  15

Val Gln Cys Gln Ser Val Lys Glu Ser Glu Gly Gly Leu Phe Lys Pro
            20                  25                  30

Thr Asp Thr Leu Thr Leu Thr Cys Thr Val Ser Gly Phe Ser Leu Thr
        35                  40                  45

Thr Tyr Gly Val Thr Trp Val Arg Gln Ala Pro Gly Asn Gly Leu Glu
    50                  55                  60

Trp Ile Gly Leu Ile Gly Asp Arg Gly Thr Thr Tyr Tyr Ala Ser Trp
65                  70                  75                  80

Val Asn Gly Arg Ser Thr Ile Thr Arg Asn Thr Asn Leu Asn Thr Val
                85                  90                  95

Thr Leu Lys Met Thr Arg Leu Thr Ala Ala Asp Thr Ala Thr Tyr Phe
            100                 105                 110

Cys Ala Arg Gly Ser Gly Tyr Gly Ala Arg Ile Trp Gly Pro Gly Thr
        115                 120                 125

Leu Val Thr Val Ala Ser Trp Gln Pro Lys Ala Pro Ser Val Phe Pro
    130                 135                 140

Leu Ala Pro Cys Cys Gly Asp Thr Pro Ser Ser Thr Val Thr Leu Gly
145                 150                 155                 160

Cys Leu Val Lys Gly Tyr Leu Pro Glu Pro Val Thr Val Thr Trp Asn
                165                 170                 175

Ser Gly Thr Leu Thr Asn Gly Val Arg Thr Phe Pro Ser Val Arg Gln
            180                 185                 190

Ser Ser Gly Leu Tyr Ser Leu Ser Ser Val Val Ser Val Thr Ser Ser
        195                 200                 205

Ser Gln Pro Val Thr Cys Asn Val Ala His Pro Ala Thr Asn Thr Lys
    210                 215                 220

Val Asp Lys Thr Val Ala Pro Ser Thr Cys Ser Lys Pro Thr Cys Pro
225                 230                 235                 240

Pro Pro Glu Leu Leu Gly Gly Pro Ser Val Phe Ile Phe Pro Pro Lys
                245                 250                 255

Pro Lys Asp Thr Leu Met Ile Ser Arg Thr Pro Glu Val Thr Cys Val
            260                 265                 270

Val Val Asp Val Ser Gln Asp Asp Pro Glu Val Gln Phe Thr Trp Tyr
        275                 280                 285

Ile Asn Asn Glu Gln Val Arg Thr Ala Arg Pro Pro Leu Arg Glu Gln
    290                 295                 300

Gln Phe Asn Ser Thr Ile Arg Val Val Ser Thr Leu Pro Ile Ala His
305                 310                 315                 320

```
Gln Asp Trp Leu Arg Gly Lys Glu Phe Lys Cys Lys Val His Asn Lys
                325                 330                 335

Ala Leu Pro Ala Pro Ile Glu Lys Thr Ile Ser Lys Ala Arg Gly Gln
                340                 345                 350

Pro Leu Glu Pro Lys Val Tyr Thr Met Gly Pro Pro Arg Glu Glu Leu
                355                 360                 365

Ser Ser Arg Ser Val Ser Leu Thr Cys Met Ile Asn Gly Phe Tyr Pro
                370                 375                 380

Ser Asp Ile Ser Val Glu Trp Glu Lys Asn Gly Lys Ala Glu Asp Asn
385                 390                 395                 400

Tyr Lys Thr Thr Pro Ala Val Leu Asp Ser Asp Gly Ser Tyr Phe Leu
                405                 410                 415

Tyr Ser Lys Leu Ser Val Pro Thr Ser Glu Trp Gln Arg Gly Asp Val
                420                 425                 430

Phe Thr Cys Ser Val Met His Glu Ala Leu His Asn His Tyr Thr Gln
                435                 440                 445

Lys Ser Ile Ser Arg Ser Pro Gly Lys
                450                 455

<210> SEQ ID NO 34
<211> LENGTH: 237
<212> TYPE: PRT
<213> ORGANISM: Artificial Sequence
<220> FEATURE:
<223> OTHER INFORMATION: Chemically Synthesized, mAb 1F-42-7 full length
      light chain amino acid

<400> SEQUENCE: 34

Met Asp Thr Arg Ala Pro Thr Gln Leu Leu Gly Leu Leu Leu Leu Trp
1               5                   10                  15

Leu Pro Gly Ala Thr Phe Ala Gln Val Leu Thr Gln Thr Pro Ser Pro
                20                  25                  30

Met Ser Ala Ala Leu Gly Gly Thr Val Thr Ile Asn Cys Gln Ser Ser
                35                  40                  45

Gln Thr Val Tyr Asn Asn Asn Tyr Leu Ser Trp Tyr Gln Gln Lys Pro
            50                  55                  60

Gly Gln Pro Pro Lys Leu Leu Ile Tyr Glu Thr Ser Lys Leu Ser Ser
65              70                  75                  80

Gly Val Pro Pro Arg Phe Ser Gly Ser Gly Ser Gly Thr Gln Phe Thr
                85                  90                  95

Leu Thr Ile Ser Ser Val Gln Cys Asp Asp Ala Ala Thr Tyr Tyr Cys
                100                 105                 110

Gln Gly Gly Tyr Ser Gly Val Asp Phe Met Ala Phe Gly Gly Gly Thr
                115                 120                 125

Glu Val Val Val Lys Gly Asp Pro Val Ala Pro Thr Val Leu Ile Phe
                130                 135                 140

Pro Pro Ser Ala Asp Leu Val Ala Thr Gly Thr Val Thr Ile Val Cys
145                 150                 155                 160

Val Ala Asn Lys Tyr Phe Pro Asp Val Thr Val Thr Trp Glu Val Asp
                165                 170                 175

Gly Thr Thr Gln Thr Thr Gly Ile Glu Asn Ser Lys Thr Pro Gln Asn
                180                 185                 190

Ser Ala Asp Cys Thr Tyr Asn Leu Ser Ser Thr Leu Thr Leu Thr Ser
                195                 200                 205

Thr Gln Tyr Asn Ser His Lys Glu Tyr Thr Cys Lys Val Thr Gln Gly
```

```
            210                 215                 220
Thr Thr Ser Val Val Gln Ser Phe Asn Arg Gly Asp Cys
225                 230                 235

<210> SEQ ID NO 35
<211> LENGTH: 7
<212> TYPE: PRT
<213> ORGANISM: Artificial Sequence
<220> FEATURE:
<223> OTHER INFORMATION: Chemically Synthesized, 1F-42-7 heavy chain
      CDR1 amino acid

<400> SEQUENCE: 35

Leu Thr Thr Tyr Gly Val Thr
1               5

<210> SEQ ID NO 36
<211> LENGTH: 16
<212> TYPE: PRT
<213> ORGANISM: Artificial Sequence
<220> FEATURE:
<223> OTHER INFORMATION: Chemically Synthesized, 1F-42-7 heavy chain
      CDR2 amino acid

<400> SEQUENCE: 36

Leu Ile Gly Asp Arg Gly Thr Thr Tyr Tyr Ala Ser Trp Val Asn Gly
1               5                   10                  15

<210> SEQ ID NO 37
<211> LENGTH: 8
<212> TYPE: PRT
<213> ORGANISM: Artificial Sequence
<220> FEATURE:
<223> OTHER INFORMATION: Chemically Synthesized, 1F-42-7 heavy chain
      CDR3 amino acid

<400> SEQUENCE: 37

Gly Ser Gly Tyr Gly Ala Arg Ile
1               5

<210> SEQ ID NO 38
<211> LENGTH: 11
<212> TYPE: PRT
<213> ORGANISM: Artificial Sequence
<220> FEATURE:
<223> OTHER INFORMATION: Chemically Synthesized, 1F-42-7 light chain
      CDR1 amino acid

<400> SEQUENCE: 38

Ser Gln Thr Val Tyr Asn Asn Asn Tyr Leu Ser
1               5                   10

<210> SEQ ID NO 39
<211> LENGTH: 7
<212> TYPE: PRT
<213> ORGANISM: Artificial Sequence
<220> FEATURE:
<223> OTHER INFORMATION: Chemically Synthesized, 1F-42-7 light chain
      CDR2 amino acid

<400> SEQUENCE: 39

Glu Thr Ser Lys Leu Ser Ser
1               5

<210> SEQ ID NO 40
<211> LENGTH: 10
<212> TYPE: PRT
```

<213> ORGANISM: Artificial Sequence
<220> FEATURE:
<223> OTHER INFORMATION: Chemically Synthesized, 1F-42-7 light chain
    CDR3 amino acid

<400> SEQUENCE: 40

```
Gln Gly Gly Tyr Ser Gly Val Asp Phe Met
1               5                   10
```

<210> SEQ ID NO 41
<211> LENGTH: 450
<212> TYPE: PRT
<213> ORGANISM: Artificial Sequence
<220> FEATURE:
<223> OTHER INFORMATION: Chemically Synthesized, mAb 3A-5-2 full length
    heavy chain amino acid

<400> SEQUENCE: 41

```
Met Glu Thr Gly Leu Arg Trp Leu Leu Leu Val Ala Val Leu Lys Gly
1               5                   10                  15

Val Gln Cys Gln Ser Leu Glu Glu Ser Gly Gly Arg Leu Val Thr Pro
            20                  25                  30

Gly Thr Pro Leu Thr Leu Thr Cys Thr Val Ser Gly Phe Ser Leu Asn
        35                  40                  45

Asn Tyr His Ile Tyr Trp Val Arg Gln Ala Pro Gly Lys Gly Leu Glu
    50                  55                  60

Tyr Ile Gly Ile Ile Phe Asn Gly Gly Thr Tyr Tyr Ala Arg Trp Thr
65                  70                  75                  80

Lys Gly Arg Phe Thr Ile Ser Lys Thr Ser Thr Val Asp Leu Lys
                85                  90                  95

Met Thr Ser Leu Thr Thr Glu Asp Thr Ala Thr Tyr Phe Cys Ala Arg
            100                 105                 110

Gly Asp Gly Ile Trp Gly Pro Gly Thr Leu Val Thr Val Ser Leu Gly
        115                 120                 125

Gln Pro Lys Ala Pro Ser Val Phe Pro Leu Ala Pro Cys Cys Gly Asp
    130                 135                 140

Thr Pro Ser Ser Thr Val Thr Leu Gly Cys Leu Val Lys Gly Tyr Leu
145                 150                 155                 160

Pro Glu Pro Val Thr Val Thr Trp Asn Ser Gly Thr Leu Thr Asn Gly
                165                 170                 175

Val Arg Thr Phe Pro Ser Val Arg Gln Ser Ser Gly Leu Tyr Ser Leu
            180                 185                 190

Ser Ser Val Val Ser Val Thr Ser Ser Gln Pro Val Thr Cys Asn
        195                 200                 205

Val Ala His Pro Ala Thr Asn Thr Lys Val Asp Lys Thr Val Ala Pro
    210                 215                 220

Ser Thr Cys Ser Lys Pro Thr Cys Pro Pro Glu Leu Leu Gly Gly
225                 230                 235                 240

Pro Ser Val Phe Ile Phe Pro Pro Lys Pro Lys Asp Thr Leu Met Ile
                245                 250                 255

Ser Arg Thr Pro Glu Val Thr Cys Val Val Val Asp Val Ser Gln Asp
            260                 265                 270

Asp Pro Glu Val Gln Phe Thr Trp Tyr Ile Asn Asn Glu Gln Val Arg
        275                 280                 285

Thr Ala Arg Pro Pro Leu Arg Glu Gln Gln Phe Asn Ser Thr Ile Arg
    290                 295                 300

Val Val Ser Thr Leu Pro Ile Ala His Gln Asp Trp Leu Arg Gly Lys
```

```
                305                 310                 315                 320
        Glu Phe Lys Cys Lys Val His Asn Lys Ala Leu Pro Ala Pro Ile Glu
                        325                 330                 335

Lys Thr Ile Ser Lys Ala Arg Gly Gln Pro Leu Glu Pro Lys Val Tyr
                        340                 345                 350

Thr Met Gly Pro Pro Arg Glu Glu Leu Ser Ser Arg Ser Val Ser Leu
                        355                 360                 365

Thr Cys Met Ile Asn Gly Phe Tyr Pro Ser Asp Ile Ser Val Glu Trp
                        370                 375                 380

Glu Lys Asn Gly Lys Ala Glu Asp Asn Tyr Lys Thr Thr Pro Ala Val
        385                 390                 395                 400

Leu Asp Ser Asp Gly Ser Tyr Phe Leu Tyr Ser Lys Leu Ser Val Pro
                        405                 410                 415

Thr Ser Glu Trp Gln Arg Gly Asp Val Phe Thr Cys Ser Val Met His
                        420                 425                 430

Glu Ala Leu His Asn His Tyr Thr Gln Lys Ser Ile Ser Arg Ser Pro
                        435                 440                 445

Gly Lys
            450

<210> SEQ ID NO 42
<211> LENGTH: 239
<212> TYPE: PRT
<213> ORGANISM: Artificial Sequence
<220> FEATURE:
<223> OTHER INFORMATION: Chemically Synthesized, mAb 3A-5-2 full length
      light chain amino acid

<400> SEQUENCE: 42

Met Asp Thr Arg Ala Pro Thr Gln Leu Leu Gly Leu Leu Leu Leu Trp
        1               5                   10                  15

Leu Pro Gly Ala Thr Phe Ala Gln Val Leu Thr Gln Thr Pro Ala Ser
                        20                  25                  30

Val Ser Ala Ala Val Gly Gly Thr Val Thr Ile Asn Cys Gln Ala Ser
                        35                  40                  45

Gln Ser Val Phe Asn Asn Tyr Leu Ala Trp Tyr Gln Gln Lys Pro
            50                  55                  60

Gly Gln Pro Pro Lys Arg Leu Ile Tyr Ser Ala Ser Thr Leu Ala Ser
        65                  70                  75                  80

Gly Val Ser Ser Arg Phe Lys Gly Ser Gly Ser Gly Thr Glu Phe Thr
                        85                  90                  95

Leu Thr Met Ser Gly Val Glu Cys Asp Asp Ala Ala Thr Tyr Tyr Cys
                        100                 105                 110

Ala Gly Ser Phe Asp Cys Asn Ser Gly Asp Cys Val Ala Phe Gly Gly
                        115                 120                 125

Gly Thr Glu Val Val Lys Gly Asp Pro Val Ala Pro Thr Val Leu
        130                 135                 140

Ile Phe Pro Pro Ala Ala Asp Gln Val Ala Thr Gly Thr Val Thr Ile
        145                 150                 155                 160

Val Cys Val Ala Asn Lys Tyr Phe Pro Asp Val Thr Val Thr Trp Glu
                        165                 170                 175

Val Asp Gly Thr Thr Gln Thr Thr Gly Ile Glu Asn Ser Lys Thr Pro
                        180                 185                 190

Gln Asn Ser Ala Asp Cys Thr Tyr Asn Leu Ser Ser Thr Leu Thr Leu
                        195                 200                 205
```

```
Thr Ser Thr Gln Tyr Asn Ser His Lys Glu Tyr Thr Cys Lys Val Thr
    210                 215                 220

Gln Gly Thr Thr Ser Val Val Gln Ser Phe Asn Arg Gly Asp Cys
225                 230                 235

<210> SEQ ID NO 43
<211> LENGTH: 7
<212> TYPE: PRT
<213> ORGANISM: Artificial Sequence
<220> FEATURE:
<223> OTHER INFORMATION: Chemically Synthesized, 3A-5-2 heavy chain CDR1
      amino acid

<400> SEQUENCE: 43

Leu Asn Asn Tyr His Ile Tyr
1               5

<210> SEQ ID NO 44
<211> LENGTH: 15
<212> TYPE: PRT
<213> ORGANISM: Artificial Sequence
<220> FEATURE:
<223> OTHER INFORMATION: Chemically Synthesized, 3A-5-2 heavy chain CDR2
      amino acid

<400> SEQUENCE: 44

Ile Ile Phe Asn Gly Gly Thr Tyr Tyr Ala Arg Trp Thr Lys Gly
1               5                   10                  15

<210> SEQ ID NO 45
<211> LENGTH: 4
<212> TYPE: PRT
<213> ORGANISM: Artificial Sequence
<220> FEATURE:
<223> OTHER INFORMATION: Chemically Synthesized, 3A-5-2 heavy chain CDR3
      amino acid

<400> SEQUENCE: 45

Gly Asp Gly Ile
1

<210> SEQ ID NO 46
<211> LENGTH: 11
<212> TYPE: PRT
<213> ORGANISM: Artificial Sequence
<220> FEATURE:
<223> OTHER INFORMATION: Chemically Synthesized, 3A-5-2 light chain CDR1
      amino acid

<400> SEQUENCE: 46

Ser Gln Ser Val Phe Asn Asn Asn Tyr Leu Ala
1               5                   10

<210> SEQ ID NO 47
<211> LENGTH: 7
<212> TYPE: PRT
<213> ORGANISM: Artificial Sequence
<220> FEATURE:
<223> OTHER INFORMATION: Chemically Synthesized, 3A-5-2 light chain CDR2
      amino acid

<400> SEQUENCE: 47

Ser Ala Ser Thr Leu Ala Ser
1               5

<210> SEQ ID NO 48
<211> LENGTH: 13
```

```
<212> TYPE: PRT
<213> ORGANISM: Artificial Sequence
<220> FEATURE:
<223> OTHER INFORMATION: Chemically Synthesized, 3A-5-2 light chain CDR3
      amino acid

<400> SEQUENCE: 48

Ala Gly Ser Phe Asp Cys Asn Ser Gly Asp Cys Val Ala
1               5                   10

<210> SEQ ID NO 49
<211> LENGTH: 1029
<212> TYPE: DNA
<213> ORGANISM: Artificial Sequence
<220> FEATURE:
<223> OTHER INFORMATION: Chemically Synthesized, Human Renalase-1
      nucleic acid sequence, Note potential polymorphism at nucleotide
      position 111

<400> SEQUENCE: 49
atggcgcagg tgctgatcgt gggcgccggg atgacaggaa gcttgtgcgc tgcgctgctg      60
aggaggcaga cgtccggtcc cttgtacctt gctgtgtggg acaaggctga ggactcaggg     120
ggaagaatga ctacagcctg cagtcctcat aatcctcagt gcacagctga cttgggtgct     180
cagtacatca cctgcactcc tcattatgcc aaaaaacacc aacgttttta tgatgaactg     240
ttagcctatg gcgttttgag gcctctaagc tcgcctattg aaggaatggt gatgaaagaa     300
ggagactgta actttgtggc acctcaagga atttcttcaa ttattaagca ttacttgaaa     360
gaatcaggtg cagaagtcta cttcagacat cgtgtgacac agatcaacct aagagatgac     420
aaatgggaag tatccaaaca acaggctccc ctgagcagtt tgatcttat tgttctcaca      480 atgccagttc ctgagattct gcagcttcaa ggtgacatca ccaccttaat tagtgaatgc     540
caaaggcagc aactggaggc tgtgagctac tcctctcgat atgctctggg cctcttttat     600
gaagctggta cgaagattga tgtcccttgg gctgggcagt acatcaccag taatccctgc     660
atacgcttcg tctccattga taataagaag cgcaatatag agtcatcaga aattgggcct     720
tccctcgtga ttcacaccac tgtcccattt ggagttacat acttggaaca cagcattgag     780
gatgtgcaag agttagtctt ccagcagctg gaaaacattt tgccgggttt gcctcagcca     840
attgctacca atgccaaaaa atggagacat tcacaggtta caaatgctgc tgccaactgt     900
cctggccaaa tgactctgca tcacaaacct ttccttgcat gtggagggga tggatttact     960
cagtccaact tgatggctg catcacttct gccctatgtg ttctggaagc tttaaagaat    1020
tatatttaa                                                           1029

<210> SEQ ID NO 50
<211> LENGTH: 315
<212> TYPE: PRT
<213> ORGANISM: Artificial Sequence
<220> FEATURE:
<223> OTHER INFORMATION: Chemically Synthesized, Human Renalase-2 amino
      acid sequence, polymorphism resulting in the highlighted glutamate
      amino acid at position 37

<400> SEQUENCE: 50

Met Ala Gln Val Leu Ile Val Gly Ala Gly Met Thr Gly Ser Leu Cys
1               5                   10                  15

Ala Ala Leu Leu Arg Arg Gln Thr Ser Gly Pro Leu Tyr Leu Ala Val
                20                  25                  30

Trp Asp Lys Ala Glu Asp Ser Gly Gly Arg Met Thr Thr Ala Cys Ser
            35                  40                  45
```

Pro His Asn Pro Gln Cys Thr Ala Asp Leu Gly Ala Gln Tyr Ile Thr
    50                  55                  60

Cys Thr Pro His Tyr Ala Lys Lys His Gln Arg Phe Tyr Asp Glu Leu
65                  70                  75                  80

Leu Ala Tyr Gly Val Leu Arg Pro Leu Ser Ser Pro Ile Glu Gly Met
                85                  90                  95

Val Met Lys Glu Gly Asp Cys Asn Phe Val Ala Pro Gln Gly Ile Ser
            100                 105                 110

Ser Ile Ile Lys His Tyr Leu Lys Glu Ser Gly Ala Glu Val Tyr Phe
                115                 120                 125

Arg His Arg Val Thr Gln Ile Asn Leu Arg Asp Asp Lys Trp Glu Val
            130                 135                 140

Ser Lys Gln Thr Gly Ser Pro Glu Gln Phe Asp Leu Ile Val Leu Thr
145                 150                 155                 160

Met Pro Val Pro Glu Ile Leu Gln Leu Gln Gly Asp Ile Thr Thr Leu
                165                 170                 175

Ile Ser Glu Cys Gln Arg Gln Leu Glu Ala Val Ser Tyr Ser Ser
                180                 185                 190

Arg Tyr Ala Leu Gly Leu Phe Tyr Glu Ala Gly Thr Lys Ile Asp Val
                195                 200                 205

Pro Trp Ala Gly Gln Tyr Ile Thr Ser Asn Pro Cys Ile Arg Phe Val
    210                 215                 220

Ser Ile Asp Asn Lys Lys Arg Asn Ile Glu Ser Ser Glu Ile Gly Pro
225                 230                 235                 240

Ser Leu Val Ile His Thr Thr Val Pro Phe Gly Val Thr Tyr Leu Glu
                245                 250                 255

His Ser Ile Glu Asp Val Gln Glu Leu Val Phe Gln Gln Leu Glu Asn
                260                 265                 270

Ile Leu Pro Gly Leu Pro Gln Pro Ile Ala Thr Lys Cys Gln Lys Trp
                275                 280                 285

Arg His Ser Gln Val Pro Ser Ala Gly Val Ile Leu Gly Cys Ala Lys
    290                 295                 300

Ser Pro Trp Met Met Ala Ile Gly Phe Pro Ile
305                 310                 315

<210> SEQ ID NO 51
<211> LENGTH: 945
<212> TYPE: DNA
<213> ORGANISM: Artificial Sequence
<220> FEATURE:
<223> OTHER INFORMATION: Chemically Synthesized, Human Ren 2 nucleic
      acid sequence, Note potential polymorphism at nucleotide position
      111

<400> SEQUENCE: 51
atggcgcagg tgctgatcgt gggcgccggg atgacaggaa gcttgtgcgc tgcgctgctg     60
aggaggcaga cgtccggtcc cttgtacctt gctgtgtggg acaaggctga ggactcaggg    120
ggaagaatga ctacagcctg cagtcctcat aatcctcagt gcacagctga cttgggtgct    180
cagtacatca cctgcactcc tcattatgcc aaaaaacacc aacgttttta tgatgaactg    240
ttagcctatg gcgttttgag gcctctaagc tcgcctattg aaggaatggt gatgaaagaa    300
ggagactgta actttgtggc acctcaagga atttcttcaa ttattaagca ttacttgaaa    360
gaatcaggtg cagaagtcta cttcagacat cgtgtgacac agatcaacct aagagatgac    420
aaatgggaag tatccaaaca aacaggctcc cctgagcagt ttgatcttat tgttctcaca    480

```
atgccagttc ctgagattct gcagcttcaa ggtgacatca ccaccttaat tagtgaatgc    540
caaaggcagc aactggaggc tgtgagctac tcctctcgat atgctctggg cctcttttat    600
gaagctggta cgaagattga tgtcccttgg gctgggcagt acatcaccag taatccctgc    660
atacgcttcg tctccattga taataagaag cgcaatatag agtcatcaga aattgggcct    720
tccctcgtga ttcacaccac tgtcccattt ggagttacat acttggaaca cagcattgag    780
gatgtgcaag agttagtctt ccagcagctg aaaacattt gccgggttt gcctcagcca    840 attgctacca aatgccaaaa atggagacat tcacaggtac caagtgctgg tgtgattcta    900
ggatgtgcga agagcccctg gatgatggcg attggatttc ccatc                   945

<210> SEQ ID NO 52
<211> LENGTH: 1380
<212> TYPE: DNA
<213> ORGANISM: Artificial Sequence
<220> FEATURE:
<223> OTHER INFORMATION: Chemically Synthesized, mAb 1D-28-4 full length
      heavy chain nucleic acid

<400> SEQUENCE: 52
atggagactg ggctgcgctg gcttctcctg gtcgctgtgc tcaaaggtgt ccagtgtcag     60
tcggtggagg agtccggggg tcgcctggtc acgcctggga cacccctgac actcacctgc    120
acagtctctg gattctccct cagtagtttt gcagtgggct gggtccgcca ggctccaggg    180
aaggggctgg aatacatcgg aatcattagt agtgttggta ttacacgcta cgcgagctgg    240
gcggccggcc gattcaccat ctccaaaacc tcgaccacgg tggatctgaa aatcaccagt    300
ccgacaaccg aggacacggc cacctatttt tgtgccagat atggttatag tggtgatgtt    360
aatcggttgg atctctgggg ccagggcacc ctggtcaccg tctcctcagg caacctaag     420 gctccatcag tcttcccact ggccccctgc tgcgggaca cccagctc cacggtgacc       480 ctgggctgcc tggtcaaagg gtacctcccg agccagtga ccgtgacctg gaactcgggc    540
accctcacca atgggtacg caccttcccg tccgtccggc agtcctcagg cctctactcg    600
ctgagcagcg tggtgagcgt gacctcaagc agccagcccg tcacctgcaa cgtggcccac    660
ccagccacca acaccaagt ggacaagacc gttgcgccct cgacatgcag caagcccacg    720
tgcccacccc ctgaactcct gggggaccg tctgtcttca tcttccccc aaaacccaag    780 gacaccctca tgatctcacg cacccccgag gtcacatgcg tggtggtgga cgtgagccag    840
gatgaccccg aggtgcagtt cacatggtac ataaacaacg agcaggtgcg caccgcccgg    900
ccgccgctac gggagcagca gttcaacagc acgatccgcg tggtcagcac cctccccatc    960
gcgcaccagg actggctgag gggcaaggag ttcaagtgca agtccacaa caaggcactc   1020 ccggccccca tcgagaaaac catctccaaa gccagagggc agccctgga gccgaaggtc   1080 tacaccatgg ccctcccg ggaggagctg agcagcaggt cggtcagcct gacctgcatg    1140
atcaacggct ctaccccttc cgacatctcg gtggagtggg agaagaacgg gaaggcagag    1200
gacaactaca agaccacgcc ggccgtgctg gacagcgacg gctcctactt cctctacagc    1260
aagctctcag tgcccacgag tgagtggcag cggggcgacg tcttcacctg ctccgtgatg    1320
cacgaggcct tgcacaacca ctacacgcag aagtccatct cccgctctcc gggtaaatga    1380

<210> SEQ ID NO 53
<211> LENGTH: 720
<212> TYPE: DNA
<213> ORGANISM: Artificial Sequence
```

<220> FEATURE:
<223> OTHER INFORMATION: Chemically Synthesized, mAb 1D-28-4 full length
      light chain nucleic acid

<400> SEQUENCE: 53

| | | | | | |
|---|---|---|---|---|---|
| atggacacga | gggcccccac | tcagctgctg | gggctcctgc | tgctctggct | cccaggtgcc | 60 |
| acatttgccc | aagtgctgac | ccagactgca | tcgcccgtgt | ctgcagctgt | gggaggcaca | 120 |
| gtcaccatca | attgccaggc | cagtcagagt | gtttatgata | caacaacttt | agcctggtat | 180 |
| cagcagaaac | cagggcagcc | tcccaagcaa | ctgatctatg | gtgcatccac | tctggcatct | 240 |
| ggggtctcat | cgcggttcaa | aggcagtgga | tctgggacac | agttcactct | caccatcagc | 300 |
| ggcgtgcagt | gtgacgatgc | tgccacttac | tactgtctag | gcgaatttag | ttgtagtagt | 360 |
| gctgattgtt | ttgctttcgg | cggagggacc | gaggtggtcg | tcaaaggtga | tccagttgca | 420 |
| cctactgtcc | tcatcttccc | accatctgct | gatcttgtgg | caactggaac | agtcaccatc | 480 |
| gtgtgtgtgg | cgaataaata | ctttcccgat | gtcaccgtca | cctgggaggt | ggatggcacc | 540 |
| acccaaacaa | ctggcatcga | gaacagtaaa | acaccgcaga | attctgcaga | ttgtacctac | 600 |
| aacctcagca | gcactctgac | actgaccagc | acacagtaca | cagccacaa | agagtacacc | 660 |
| tgcaaggtga | cccagggcac | gacctcagtc | gtccagagct | tcaatagggg | tgactgttag | 720 |

<210> SEQ ID NO 54
<211> LENGTH: 21
<212> TYPE: DNA
<213> ORGANISM: Artificial Sequence
<220> FEATURE:
<223> OTHER INFORMATION: Chemically Synthesized, 1D-28-4 heavy chain
      CDR1 nucleic acid

<400> SEQUENCE: 54
ctcagtagtt ttgcagtggg c                                              21

<210> SEQ ID NO 55
<211> LENGTH: 48
<212> TYPE: DNA
<213> ORGANISM: Artificial Sequence
<220> FEATURE:
<223> OTHER INFORMATION: Chemically Synthesized, 1D-28-4 heavy chain
      CDR2 nucleic acid

<400> SEQUENCE: 55
atcattagta gtgttggtat tacacgctac gcgagctggg cggccggc                 48

<210> SEQ ID NO 56
<211> LENGTH: 36
<212> TYPE: DNA
<213> ORGANISM: Artificial Sequence
<220> FEATURE:
<223> OTHER INFORMATION: Chemically Synthesized, 1D-28-4 heavy chain
      CDR3 nucleic acid

<400> SEQUENCE: 56
tatggttata gtggtgatgt taatcggttg gatctc                              36

<210> SEQ ID NO 57
<211> LENGTH: 33
<212> TYPE: DNA
<213> ORGANISM: Artificial Sequence
<220> FEATURE:
<223> OTHER INFORMATION: Chemically Synthesized, 1D-28-4 light chain
      CDR1 nucleic acid

<400> SEQUENCE: 57
agtcagagtg tttatgataa caacaactta gcc						33

<210> SEQ ID NO 58
<211> LENGTH: 21
<212> TYPE: DNA
<213> ORGANISM: Artificial Sequence
<220> FEATURE:
<223> OTHER INFORMATION: Chemically Synthesized, 1D-28-4 light chain
      CDR2 nucleic acid

<400> SEQUENCE: 58
ggtgcatcca ctctggcatc t						21

<210> SEQ ID NO 59
<211> LENGTH: 39
<212> TYPE: DNA
<213> ORGANISM: Artificial Sequence
<220> FEATURE:
<223> OTHER INFORMATION: Chemically Synthesized, 1D-28-4 light chain
      CDR3 nucleic acid

<400> SEQUENCE: 59
ctaggcgaat ttagttgtag tagtgctgat tgttttgct						39

<210> SEQ ID NO 60
<211> LENGTH: 1386
<212> TYPE: DNA
<213> ORGANISM: Artificial Sequence
<220> FEATURE:
<223> OTHER INFORMATION: Chemically Synthesized, mAb 1D-37-10 full
      length heavy chain nucleic acid

<400> SEQUENCE: 60
atggagactg ggctgcgctg gcttctcctg gtcgctgtgc tcaaaggtgt ccagtgtcag						60
tcggtggagg agtccggggg tcgcctggtc acgcctggag gatccctgac actcacctgc						120
acagtctctg gattctccct cagtgactat gcaataatct gggtccgcca ggctccaggg						180
aaggggctgg aatacatcgc aattattggt agtagtggtg acacattcta cgcgacctgg						240
gcgaaaggcc gattcaccat ctccaaaacc tcgaccacgg tggatctgaa aatgaccagt						300
ctgacagccg cggacacggc cacctatttc tgtgcccac gttatgctgg tactactgat						360
tatcatgatg cttttgatcc ctggggccca ggcactttgg tcaccgtctc ctcagggcaa						420
cctaaggctc catcagtctt cccactggcc cctgctgcg gggacacacc cagctccacg						480
gtgaccctgg gctgcctggt caaagggtac ctcccggagc cagtgaccgt gacctggaac						540
tcgggcaccc tcaccaatgg ggtacgcacc ttcccgtccg tcggcagtc ctcaggcctc						600
tactcgctga gcagcgtggt gagcgtgacc tcaagcagcc agcccgtcac ctgcaacgtg						660
gcccacccag ccaccaacac caaagtggac aagaccgttg cgcctcgac atgcagcaag						720
cccacgtgcc cacccctga actcctgggg ggaccgtctg tcttcatctt ccccccaaaa						780
cccaaggaca cctcatgat ctcacgcacc cccgaggtca catgcgtggt ggtggacgtg						840
agccaggatg accccgaggt gcagttcaca tggtacataa acaacgagca ggtgcgcacc						900
gcccggccgc cgctacggga gcagcagttc aacagcacga tccgcgtggt cagcaccctc						960
cccatcgcgc accaggactg gctgaggggc aaggagttca gtgcaaagt ccacaacaag						1020
gcactcccgg cccccatcga gaaaccatc tccaaagcca gagggcagcc cctggagccg						1080
aaggtctaca ccatgggccc tcccggagg gagctgagca gcaggtcggt cagcctgacc						1140
tgcatgatca acggcttcta cccttccgac atctcggtgg agtgggagaa gaacgggaag						1200

```
gcagaggaca actacaagac cacgccggcc gtgctggaca gcgacggctc ctacttcctc    1260
tacagcaagc tctcagtgcc cacgagtgag tggcagcggg gcgacgtctt cacctgctcc    1320
gtgatgcacg aggccttgca caaccactac acgcagaagt ccatctcccg ctctccgggt    1380
aaatga                                                               1386
```

<210> SEQ ID NO 61
<211> LENGTH: 717
<212> TYPE: DNA
<213> ORGANISM: Artificial Sequence
<220> FEATURE:
<223> OTHER INFORMATION: Chemically Synthesized, mAb 1D-37-10 full
      length light chain nucleic acid

<400> SEQUENCE: 61

```
atggacacga gggcccccac tcagctgctg gggctcctgc tgctctggct cccaggtgcc     60
agatgtgccg aagtagtgat gacccagact ccagcctcca tggaggcacc tatgggaggc    120
acagtcacca tcaagtgcca ggccagtcag aacatttaca ctacttatc ctggtatcag    180 cagaaaccag gcagcctcc caagctccta gtctacaagg cctccactct gacttctggg    240
gtcccgtcgc gcttcaaagg cagtggatct gggacacagt tcactctcac catcagcgac    300
ctggagtgtg ccgatgctgc cacttactac tgtcaaatca attactctat ttataatcat    360
tataatatta ttttggcgg agggaccgag gtggtcgtca agggtgatcc agttgcacct    420
actgtcctca tcttcccacc atctgctgat cttgtggcaa ctggaacagt caccatcgtg    480
tgtgtggcga ataaatactt tcccgatgtc accgtcacct gggaggtgga tggcaccacc    540
caaacaactg gcatcgagaa cagtaaaaca ccgcagaatt ctgcagattg tacctacaac    600
ctcagcagca ctctgacact gaccagcaca cagtacaaca gccacaaaga gtacacctgc    660
aaggtgaccc agggcacgac ctcagtcgtc cagagcttca taggggtga ctgttag        717
```

<210> SEQ ID NO 62
<211> LENGTH: 21
<212> TYPE: DNA
<213> ORGANISM: Artificial Sequence
<220> FEATURE:
<223> OTHER INFORMATION: Chemically Synthesized, 1D-37-10 heavy chain
      CDR1 nucleic acid

<400> SEQUENCE: 62

```
ctcagtgact atgcaataat c                                               21
```

<210> SEQ ID NO 63
<211> LENGTH: 48
<212> TYPE: DNA
<213> ORGANISM: Artificial Sequence
<220> FEATURE:
<223> OTHER INFORMATION: Chemically Synthesized, 1D-37-10 heavy chain
      CDR2 nucleic acid

<400> SEQUENCE: 63

```
attattggta gtagtggtga cacattctac gcgacctggg cgaaaggc                  48
```

<210> SEQ ID NO 64
<211> LENGTH: 42
<212> TYPE: DNA
<213> ORGANISM: Artificial Sequence
<220> FEATURE:
<223> OTHER INFORMATION: Chemically Synthesized, 1D-37-10 heavy chain
      CDR3 nucleic acid

<400> SEQUENCE: 64
cgttatgctg gtactactga ttatcatgat gcttttgatc cc    42

<210> SEQ ID NO 65
<211> LENGTH: 27
<212> TYPE: DNA
<213> ORGANISM: Artificial Sequence
<220> FEATURE:
<223> OTHER INFORMATION: Chemically Synthesized, 1D-37-10 light chain
      CDR1 nucleic acid

<400> SEQUENCE: 65
agtcagaaca tttacaacta cttatcc    27

<210> SEQ ID NO 66
<211> LENGTH: 21
<212> TYPE: DNA
<213> ORGANISM: Artificial Sequence
<220> FEATURE:
<223> OTHER INFORMATION: Chemically Synthesized, 1D-37-10 light chain
      CDR2 nucleic acid

<400> SEQUENCE: 66
aaggcctcca ctctgacttc t    21

<210> SEQ ID NO 67
<211> LENGTH: 39
<212> TYPE: DNA
<213> ORGANISM: Artificial Sequence
<220> FEATURE:
<223> OTHER INFORMATION: Chemically Synthesized, 1D-37-10 light chain
      CDR3 nucleic acid

<400> SEQUENCE: 67
caaatcaatt actctattta taatcattat aatattatt    39

<210> SEQ ID NO 68
<211> LENGTH: 1374
<212> TYPE: DNA
<213> ORGANISM: Artificial Sequence
<220> FEATURE:
<223> OTHER INFORMATION: Chemically Synthesized, mAb 1F-26-1 full length
      heavy chain nucleic acid

<400> SEQUENCE: 68
atggagactg ggctgcgctg gcttctcctg gtcgctgtgc tcaaaggtgt ccagtgtcag    60
tcggtgaagg agtccgaggg aggtctcttc aagccaacgg ataccctgac actcacctgc    120
acagtctctg gattctccct cagtagctat ggagtgacct gggtccgcca ggctccaggg    180
aacgggctgg agtggatcgg attgattggt gatcgtggta ctacgttcta cgcgagctgg    240
gcgaaaagcc gatccaccat caccagaaac accaacctga cacggtgac tctgaaaatg    300 accaggctga cagccgcgga cacggccacc tatttctgtg cgaggggag tgggtatggt    360 gctcgcatct ggggcccagg caccctggtc accgtctcct catggcaacc taaggctcca    420
tcagtcttcc cactggcccc ctgctgcggg gacacaccca gctccacggt gaccctgggc    480
tgcctggtca agggtacct cccggagcca gtgaccgtga cctggaactc gggcaccctc    540
accaatgggg tacgcacctt cccgtccgtc cggcagtcct caggcctcta ctcgctgagc    600
agcgtggtga gcgtgacctc aagcagccag cccgtcacct gcaacgtggc cacccagcc    660 accaacacca agtggacaa gaccgttgcg ccctcgacat gcagcaagcc cacgtgccca    720 cccctgaac tcctgggggg accgtctgtc ttcatcttcc cccaaaaacc caaggacacc    780

-continued

```
ctcatgatct cacgcacccc cgaggtcaca tgcgtggtgg tggacgtgag ccaggatgac    840
cccgaggtgc agttcacatg gtacataaac aacgagcagg tgcgcaccgc ccggccgccg    900
ctacgggagc agcagttcaa cagcacgatc cgcgtggtca gcaccctccc catcgcgcac    960
caggactggc tgaggggcaa ggagttcaag tgcaaagtcc acaacaaggc actcccggcc   1020
cccatcgaga aaaccatctc caaagccaga gggcagcccc tggagccgaa ggtctacacc   1080
atgggccctc cccggagga gctgagcagc aggtcggtca gcctgacctg catgatcaac   1140
ggcttctacc cttccgacat ctcggtggag tgggagaaga cgggaaggc agaggacaac   1200 tacaagacca cgccggccgt gctggacagc gacggctcct acttcctcta cagcaagctc   1260
tcagtgccca cgagtgagtg gcagcggggc gacgtcttca cctgctccgt gatgcacgag   1320
gccttgcaca accactacac gcagaagtcc atctcccgct ccgggtaa atga          1374
```

<210> SEQ ID NO 69
<211> LENGTH: 714
<212> TYPE: DNA
<213> ORGANISM: Artificial Sequence
<220> FEATURE:
<223> OTHER INFORMATION: Chemically Synthesized, mAb 1F-26-1 full length light chain nucleic acid

<400> SEQUENCE: 69

```
atggacacga gggcccccac tcagctcctg gggctcctgc tgctctggct cccaggtgcc     60
acatttgccc aagtgctgac ccagactcca tcgcctgtgt ctgcagctgt gggaggcaca    120
gtcaccatca attgccagtc cagtcagagt gtttataaga caactactt agcctggtat    180 cagcagaaac cagggcagcc tcccaagctc cttatctacg aaacatccaa actggcatct    240
ggggtcccac gcggttcag cggcagtggg tctgggacac agttcactct caccatcagc    300
agcgtgcagt gtgacgatgc tgccacttac tactgtcaag gcggttatag tggtgttgat    360
tttatggctt tcggcggagg gaccgaggtg gtcgtcaaag tgatccagt tgcacctact    420 gtcctcatct tcccaccatc tgctgatctt gtggcaactg aacagtcac atcgtgtgt    480 gtggcgaata atactttcc cgatgtcacc gtcacctggg aggtggatgg caccacccaa    540
acaactggca tcgagaacag taaaacaccg cagaattctg cagattgtac ctacaacctc    600
agcagcactc tgacactgac cagcacacag tacaacagcc acaaagagta cacctgcaag    660
gtgacccagg gcacgacctc agtcgtccag agcttcaata ggggtgactg ttag        714
```

<210> SEQ ID NO 70
<211> LENGTH: 21
<212> TYPE: DNA
<213> ORGANISM: Artificial Sequence
<220> FEATURE:
<223> OTHER INFORMATION: Chemically Synthesized, 1F-26-1 heavy chain CDR1 nucleic acid

<400> SEQUENCE: 70

```
ctcagtagct atggagtgac c                                              21
```

<210> SEQ ID NO 71
<211> LENGTH: 48
<212> TYPE: DNA
<213> ORGANISM: Artificial Sequence
<220> FEATURE:
<223> OTHER INFORMATION: Chemically Synthesized, 1F-26-1 heavy chain CDR2 nucleic acid

<400> SEQUENCE: 71
ttgattggtg atcgtggtac tacgttctac gcgagctggg cgaaaagc 48

<210> SEQ ID NO 72
<211> LENGTH: 24
<212> TYPE: DNA
<213> ORGANISM: Artificial Sequence
<220> FEATURE:
<223> OTHER INFORMATION: Chemically Synthesized, 1F-26-1 heavy chain
      CDR3 nucleic acid

<400> SEQUENCE: 72
gggagtgggt atggtgctcg catc 24

<210> SEQ ID NO 73
<211> LENGTH: 33
<212> TYPE: DNA
<213> ORGANISM: Artificial Sequence
<220> FEATURE:
<223> OTHER INFORMATION: Chemically Synthesized, 1F-26-1 light chain
      CDR1 nucleic acid

<400> SEQUENCE: 73
agtcagagtg tttataagaa caactactta gcc 33

<210> SEQ ID NO 74
<211> LENGTH: 21
<212> TYPE: DNA
<213> ORGANISM: Artificial Sequence
<220> FEATURE:
<223> OTHER INFORMATION: Chemically Synthesized, 1F-26-1 light chain
      CDR2 nucleic acid

<400> SEQUENCE: 74
gaaacatcca aactggcatc t 21

<210> SEQ ID NO 75
<211> LENGTH: 33
<212> TYPE: DNA
<213> ORGANISM: Artificial Sequence
<220> FEATURE:
<223> OTHER INFORMATION: Chemically Synthesized, 1F-26-1 light chain
      CDR3 nucleic acid

<400> SEQUENCE: 75
caaggcggtt atagtggtgt tgattttatg gct 33

<210> SEQ ID NO 76
<211> LENGTH: 1374
<212> TYPE: DNA
<213> ORGANISM: Artificial Sequence
<220> FEATURE:
<223> OTHER INFORMATION: Chemically Synthesized, mAb 1F-42-7 full length
      heavy chain nucleic acid

<400> SEQUENCE: 76
atggagactg ggctgcgctg gcttctcctg gtcgctgtgc tcaaaggtgt ccagtgtcag 60
tcggtgaagg agtccgaggg aggtctcttc aagccaacgg ataccctgac actcacctgc 120
acagtctctg gattctccct cactacctat ggagtgacct gggtccgcca ggctccaggg 180
aatgggctgg agtggatcgg attgattggt gatcgcggta ccacttacta cgcgagctgg 240
gtgaatggcc gatccaccat caccagaaac accaacctga acacggtgac tctgaaaatg 300
accaggctga cagccgcgga cacggccacc tatttctgtg cgaggggag tggatatggt 360 gctcgcatct ggggcccagg caccctggtc accgtcgcct catggcaacc taaggctcca 420

```
tcagtcttcc cactggcccc ctgctgcggg gacacaccca gctccacggt gaccctgggc    480
tgcctggtca aagggtacct cccggagcca gtgaccgtga cctggaactc gggcaccctc    540
accaatgggg tacgcacctt cccgtccgtc cggcagtcct caggcctcta ctcgctgagc    600
agcgtggtga gcgtgacctc aagcagcag cccgtcacct gcaacgtggc ccacccagcc    660
accaacacca agtggacaa gaccgttgcg ccctcgacat gcagcaagcc cacgtgccca    720
ccccctgaac tcctgggggg accgtctgtc ttcatcttcc ccccaaaacc caaggacacc    780
ctcatgatct cacgcacccc cgaggtcaca tgcgtggtgg tggacgtgag ccaggatgac    840
cccgaggtgc agttcacatg gtacataaac aacgagcagg tgcgcaccgc cggccgccg    900 ctacgggagc agcagttcaa cagcacgatc cgcgtggtca gcaccctccc catcgcgcac    960
caggactggc tgaggggcaa ggagttcaag tgcaaagtcc acaacaaggc actcccggcc    1020
cccatcgaga aaccatctc caaagccaga gggcagcccc tggagccgaa ggtctacacc    1080
atgggccctc ccggggagga gctgagcagc aggtcggtca gcctgacctg catgatcaac    1140
ggcttctacc cttccgacat ctcggtggag tgggagaaga cgggaaggc agaggacaac    1200 tacaagacca cgccggccgt gctggacagc gacggctcct acttcctcta cagcaagctc    1260
tcagtgccca cgagtgagtg cagcgggc gacgtcttca cctgctccgt gatgcacgag    1320
gccttgcaca accactacac gcagaagtcc atctcccgct ctccgggtaa atga    1374
```

<210> SEQ ID NO 77
<211> LENGTH: 714
<212> TYPE: DNA
<213> ORGANISM: Artificial Sequence
<220> FEATURE:
<223> OTHER INFORMATION: Chemically Synthesized, mAb 1F-42-7 full length
     light chain nucleic acid

<400> SEQUENCE: 77

```
atggacacga gggcccccac tcagctcctg gggctcctgc tgctctggct cccaggtgcc     60
acatttgccc aagtgctgac ccagactcca tcccccatgt ctgcagctct gggaggcaca    120
gtcaccatca attgccagtc cagtcagact gtttataaca ataactactt atcctggtat    180
cagcagaaac cagggcagcc tcccaagctc cttatctacg aaacatccaa actgtcatct    240
ggggtcccac cgcggttcag cggcagtggg tctgggacac agttcactct caccatcagc    300
agcgtgcagt gtgacgatgc tgccacttac tactgtcaag cggttatag tggtgttgat    360 tttatggctt cggcggagg gaccgaggtg gtcgtcaaag tgatccagt tgcacctact    420 gtcctcatct tcccaccatc tgctgatctt gtggcaactg aacagtcac catcgtgtgt    480 gtggcgaata atactttcc cgatgtcacc gtcacctggg aggtggatgg caccaccaa    540 acaactggca tcgagaacag taaaacaccg cagaattctg cagattgtac ctacaacctc    600
agcagcactc tgacactgac cagcacacag tacaacagcc acaaagagta cacctgcaag    660
gtgacccagg gcacgacctc agtcgtccag agcttcaata ggggtgactg ttag           714
```

<210> SEQ ID NO 78
<211> LENGTH: 21
<212> TYPE: DNA
<213> ORGANISM: Artificial Sequence
<220> FEATURE:
<223> OTHER INFORMATION: Chemically Synthesized, 1F-42-7 heavy chain
     CDR1 nucleic acid

<400> SEQUENCE: 78
ctcactacct atggagtgac c                                              21

<210> SEQ ID NO 79
<211> LENGTH: 48
<212> TYPE: DNA
<213> ORGANISM: Artificial Sequence
<220> FEATURE:
<223> OTHER INFORMATION: Chemically Synthesized, 1F-42-7 heavy chain
      CDR2 nucleic acid

<400> SEQUENCE: 79
ttgattggtg atcgcggtac cacttactac gcgagctggg tgaatggc                 48

<210> SEQ ID NO 80
<211> LENGTH: 24
<212> TYPE: DNA
<213> ORGANISM: Artificial Sequence
<220> FEATURE:
<223> OTHER INFORMATION: Chemically Synthesized, 1F-42-7 heavy chain
      CDR3 nucleic acid

<400> SEQUENCE: 80
gggagtggat atggtgctcg catc                                           24

<210> SEQ ID NO 81
<211> LENGTH: 33
<212> TYPE: DNA
<213> ORGANISM: Artificial Sequence
<220> FEATURE:
<223> OTHER INFORMATION: Chemically Synthesized, 1F-42-7 light chain
      CDR1 nucleic acid

<400> SEQUENCE: 81
agtcagactg tttataacaa taactactta tcc                                 33

<210> SEQ ID NO 82
<211> LENGTH: 21
<212> TYPE: DNA
<213> ORGANISM: Artificial Sequence
<220> FEATURE:
<223> OTHER INFORMATION: Chemically Synthesized, 1F-42-7 light chain
      CDR2 nucleic acid

<400> SEQUENCE: 82
gaaacatcca aactgtcatc t                                              21

<210> SEQ ID NO 83
<211> LENGTH: 30
<212> TYPE: DNA
<213> ORGANISM: Artificial Sequence
<220> FEATURE:
<223> OTHER INFORMATION: Chemically Synthesized, 1F-42-7 light chain
      CDR3 nucleic acid

<400> SEQUENCE: 83
ggcggttata gtggtgttga ttttatggct                                     30

<210> SEQ ID NO 84
<211> LENGTH: 1353
<212> TYPE: DNA
<213> ORGANISM: Artificial Sequence
<220> FEATURE:
<223> OTHER INFORMATION: Chemically Synthesized, mAb 3A-5-2 full length
      heavy chain nucleic acid

<400> SEQUENCE: 84
atggagactg ggctgcgctg gcttctcctg gtcgctgtgc tcaaaggtgt ccagtgtcag    60

```
tcgctggagg agtccggggg tcgcctggtc acgcctggga cacccctgac actcacctgc    120
acagtctctg gattctccct caataactac cacatatact gggtccgcca ggctccagga    180
aaggggctgg aatacatcgg aatcattttc aatggtggca catattacgc gagatggaca    240
aaaggccgat tcaccatctc caaaacctcg accacggtgg atctgaaaat gaccagtctg    300
acaaccgagg acacggccac ctatttctgt gccagagggg acggcatctg gggcccaggc    360
accctggtca ccgtctcctt agggcaacct aaggctccat cagtcttccc actgccccc    420 tgctgcgggg acacacccag ctccacggtg accctgggct gcctggtcaa agggtacctc    480
ccggagccag tgaccgtgac ctggaactcg ggcaccctca ccaatggggt acgcaccttc    540
ccgtccgtcc ggcagtcctc aggcctctac tcgctgagca gcgtggtgag cgtgacctca    600
agcagccagc ccgtcacctg caacgtggcc cacccagcca ccaacaccaa agtggacaag    660
accgttgcgc cctcgacatg cagcaagccc acgtgcccac cccctgaact cctgggggga    720
ccgtctgtct tcatcttccc cccaaaaccc aaggacaccc tcatgatctc acgcaccccc    780
gaggtcacat gcgtggtggt ggacgtgagc caggatgacc ccgaggtgca gttcacatgg    840
tacataaaca acgagcaggt gcgcaccgcc cggccgccgc tacggagca gcagttcaac    900 agcacgatcc gcgtggtcag caccctcccc atcgcgcacc aggactggct gagggcaag    960 gagttcaagt gcaaagtcca caacaaggca ctcccggccc ccatcgagaa aaccatctcc   1020
aaagccagag ggcagcccct ggagccgaag gtctacacca tgggccctcc ccgggaggag   1080
ctgagcagca ggtcggtcag cctgacctgc atgatcaacg gcttctaccc ttccgacatc   1140
tcggtggagt gggagaagaa cgggaaggca gaggacaact acaagaccac gccggccgtg   1200
ctggacagcg acggctccta cttcctctac agcaagctct cagtgcccac gagtgagtgg   1260
cagcggggcg acgtcttcac ctgctccgtg atgcacgagg ccttgcacaa ccactacacg   1320
cagaagtcca tctcccgctc tccgggtaaa tga                                 1353

<210> SEQ ID NO 85
<211> LENGTH: 720
<212> TYPE: DNA
<213> ORGANISM: Artificial Sequence
<220> FEATURE:
<223> OTHER INFORMATION: Chemically Synthesized, mAb 3A-5-2 full length
      light chain nucleic acid

<400> SEQUENCE: 85
atggacacga gggcccccac tcagctgctg ggctcctgc tgctctggct cccaggtgcc      60
acatttgccc aagtgctgac ccagactcca gcctccgtgt ctgcagctgt gggaggcaca    120
gtcaccatca attgccaggc cagtcagagt gttttaata caactatttt agcctggtat    180
cagcagaaac cagggcagcc tcccaagcgc ctgatctatt ctgcatccac tctggcgtct    240
ggggtctcat cgcggttcaa aggcagtgga tctgggacag aattcactct gaccatgagt    300
ggcgtggagt gtgacgatgc tgccacttac tactgtcag gcagttttga ttgtaatagt    360
ggtgattgtg ttgctttcgg cggagggacc gaggtggtgg tcaagggtga tccagttgca    420
cctactgtcc tcatcttccc accagctgct gatcaggtgg caactggaac agtcaccatc    480
gtgtgtgtgg cgaataaata ctttcccgat gtcaccgtca cctgggaggt ggatggcacc    540
acccaaacaa ctggcatcga gaacagtaaa acaccgcaga attctgcaga ttgtacctac    600
aacctcagca gcactctgac actgaccagc acacagtaca cagccacaa agagtacacc    660 tgcaaggtga cccagggcac gacctcagtc gtccagagct tcaataggg tgactgttag    720
```

<210> SEQ ID NO 86
<211> LENGTH: 21
<212> TYPE: DNA
<213> ORGANISM: Artificial Sequence
<220> FEATURE:
<223> OTHER INFORMATION: Chemically Synthesized, 3A-5-2 heavy chain CDR1
      nucleic acid

<400> SEQUENCE: 86
ctcaataact accacatata c                                              21

<210> SEQ ID NO 87
<211> LENGTH: 45
<212> TYPE: DNA
<213> ORGANISM: Artificial Sequence
<220> FEATURE:
<223> OTHER INFORMATION: Chemically Synthesized, 3A-5-2 heavy chain CDR2
      nucleic acid

<400> SEQUENCE: 87
atcattttca atggtggcac atattacgcg agatggacaa aaggc                    45

<210> SEQ ID NO 88
<211> LENGTH: 12
<212> TYPE: DNA
<213> ORGANISM: Artificial Sequence
<220> FEATURE:
<223> OTHER INFORMATION: Chemically Synthesized, 3A-5-2 heavy chain CDR3
      nucleic acid

<400> SEQUENCE: 88
ggggacggca tc                                                        12

<210> SEQ ID NO 89
<211> LENGTH: 33
<212> TYPE: DNA
<213> ORGANISM: Artificial Sequence
<220> FEATURE:
<223> OTHER INFORMATION: Chemically Synthesized, 3A-5-2 light chain CDR1
      nucleic acid

<400> SEQUENCE: 89
agtcagagtg tttttaataa caactattta gcc                                 33

<210> SEQ ID NO 90
<211> LENGTH: 21
<212> TYPE: DNA
<213> ORGANISM: Artificial Sequence
<220> FEATURE:
<223> OTHER INFORMATION: Chemically Synthesized, 3A-5-2 light chain CDR2
      nucleic acid

<400> SEQUENCE: 90
tctgcatcca ctctggcgtc t                                              21

<210> SEQ ID NO 91
<211> LENGTH: 39
<212> TYPE: DNA
<213> ORGANISM: Artificial Sequence
<220> FEATURE:
<223> OTHER INFORMATION: Chemically Synthesized, 3A-5-2 light chain CDR3
      nucleic acid

<400> SEQUENCE: 91
gcaggcagtt ttgattgtaa tagtggtgat tgtgttgct                           39

<210> SEQ ID NO 92
<211> LENGTH: 342
<212> TYPE: PRT
<213> ORGANISM: Artificial Sequence
<220> FEATURE:
<223> OTHER INFORMATION: Chemically Synthesized, Alternative Human
      Renalase-1 protein, polymorphism resulting in the highlighted
      aspartate amino acid at position 37

<400> SEQUENCE: 92

Met Ala Gln Val Leu Ile Val Gly Ala Gly Met Thr Gly Ser Leu Cys
1               5                   10                  15

Ala Ala Leu Leu Arg Arg Gln Thr Ser Gly Pro Leu Tyr Leu Ala Val
            20                  25                  30

Trp Asp Lys Ala Asp Asp Ser Gly Gly Arg Met Thr Thr Ala Cys Ser
        35                  40                  45

Pro His Asn Pro Gln Cys Thr Ala Asp Leu Gly Ala Gln Tyr Ile Thr
    50                  55                  60

Cys Thr Pro His Tyr Ala Lys Lys His Gln Arg Phe Tyr Asp Glu Leu
65                  70                  75                  80

Leu Ala Tyr Gly Val Leu Arg Pro Leu Ser Ser Pro Ile Glu Gly Met
                85                  90                  95

Val Met Lys Glu Gly Asp Cys Asn Phe Val Ala Pro Gln Gly Ile Ser
            100                 105                 110

Ser Ile Ile Lys His Tyr Leu Lys Glu Ser Gly Ala Glu Val Tyr Phe
        115                 120                 125

Arg His Arg Val Thr Gln Ile Asn Leu Arg Asp Asp Lys Trp Glu Val
    130                 135                 140

Ser Lys Gln Thr Gly Ser Pro Glu Gln Phe Asp Leu Ile Val Leu Thr
145                 150                 155                 160

Met Pro Val Pro Glu Ile Leu Gln Leu Gln Gly Asp Ile Thr Thr Leu
                165                 170                 175

Ile Ser Glu Cys Gln Arg Gln Gln Leu Glu Ala Val Ser Tyr Ser Ser
            180                 185                 190

Arg Tyr Ala Leu Gly Leu Phe Tyr Glu Ala Gly Thr Lys Ile Asp Val
        195                 200                 205

Pro Trp Ala Gly Gln Tyr Ile Thr Ser Asn Pro Cys Ile Arg Phe Val
    210                 215                 220

Ser Ile Asp Asn Lys Lys Arg Asn Ile Glu Ser Ser Glu Ile Gly Pro
225                 230                 235                 240

Ser Leu Val Ile His Thr Thr Val Pro Phe Gly Val Thr Tyr Leu Glu
                245                 250                 255

His Ser Ile Glu Asp Val Gln Glu Leu Val Phe Gln Gln Leu Glu Asn
            260                 265                 270

Ile Leu Pro Gly Leu Pro Gln Pro Ile Ala Thr Lys Cys Gln Lys Trp
        275                 280                 285

Arg His Ser Gln Val Thr Asn Ala Ala Asn Cys Pro Gly Gln Met
    290                 295                 300

Thr Leu His His Lys Pro Phe Leu Ala Cys Gly Gly Asp Gly Phe Thr
305                 310                 315                 320

Gln Ser Asn Phe Asp Gly Cys Ile Thr Ser Ala Leu Cys Val Leu Glu
                325                 330                 335

Ala Leu Lys Asn Tyr Ile
            340

<210> SEQ ID NO 93
<211> LENGTH: 1029
<212> TYPE: DNA
<213> ORGANISM: Artificial Sequence
<220> FEATURE:
<223> OTHER INFORMATION: Chemically Synthesized, Alternative Human
      Renalase-1 nucleic acid sequence, Note potential polymorphism at
      nucleotide position 111

<400> SEQUENCE: 93

| | | | | | |
|---|---|---|---|---|---|
| atggcgcagg | tgctgatcgt | gggcgccggg | atgacaggaa | gcttgtgcgc | tgcgctgctg | 60 |
| acgaggcaga | cgtccggtcc | cttgtacctt | gctgtgtggg | acaaggctga | ggactcaggg | 120 |
| ggaagaatga | ctacagcctg | cagtcctcat | aatcctcagt | gcacagctga | cttgggtgct | 180 |
| cagtacatca | cctgcactcc | tcattatgcc | aaaaaacacc | aacgttttta | tgatgaactg | 240 |
| ttagcctatg | gcgttttgag | gcctctaagc | tcgcctattg | aaggaatggt | gatgaaagaa | 300 |
| ggagactgta | actttgtggc | acctcaagga | atttcttcaa | ttattaagca | ttacttgaaa | 360 |
| gaatcaggtg | cagaagtcta | cttcagacat | cgtgtgacac | agatcaacct | aagagatgac | 420 |
| aaatgggaag | tatccaaaca | aacaggctcc | cctgagcagt | ttgatcttat | tgttctcaca | 480 |
| atgccagttc | ctgagattct | gcagcttcaa | ggtgacatca | ccaccttaat | tagtgaatgc | 540 |
| caaaggcagc | aactggaggc | tgtgagctac | tcctctcgat | atgctctggg | cctcttttat | 600 |
| gaagctggta | cgaagattga | tgtcccttgg | gctgggcagt | acatcaccag | taatccctgc | 660 |
| atacgcttcg | tctccattga | taataagaag | cgcaatatag | agtcatcaga | aattgggcct | 720 |
| tccctcgtga | ttcacaccac | tgtcccattt | ggagttacat | acttggaaca | cagcattgag | 780 |
| gatgtgcaag | agttagtctt | ccagcagctg | gaaaacattt | tgccgggttt | gcctcagcca | 840 |
| attgctacca | aatgccaaaa | atggagacat | tcacaggtta | caaatgctgc | tgccaactgt | 900 |
| cctggccaaa | tgactctgca | tcacaaacct | ttccttgcat | gtggagggga | tggatttact | 960 |
| cagtccaact | tgatggctg | catcacttct | gccctatgtg | ttctggaagc | tttaaagaat | 1020 |
| tatatttaa | | | | | | 1029 |

<210> SEQ ID NO 94
<211> LENGTH: 315
<212> TYPE: PRT
<213> ORGANISM: Artificial Sequence
<220> FEATURE:
<223> OTHER INFORMATION: Chemically Synthesized, Alternative Human
      Renalase-2 amino acid sequence, polymorphism resulting in the
      highlighted aspartate amino acid at position 37

<400> SEQUENCE: 94

Met Ala Gln Val Leu Ile Val Gly Ala Gly Met Thr Gly Ser Leu Cys
1               5                   10                  15

Ala Ala Leu Leu Arg Arg Gln Thr Ser Gly Pro Leu Tyr Leu Ala Val
            20                  25                  30

Trp Asp Lys Ala Asp Asp Ser Gly Gly Arg Met Thr Thr Ala Cys Ser
        35                  40                  45

Pro His Asn Pro Gln Cys Thr Ala Asp Leu Gly Ala Gln Tyr Ile Thr
    50                  55                  60

Cys Thr Pro His Tyr Ala Lys Lys His Gln Arg Phe Tyr Asp Glu Leu
65                  70                  75                  80

Leu Ala Tyr Gly Val Leu Arg Pro Leu Ser Ser Pro Ile Glu Gly Met
                85                  90                  95

Val Met Lys Glu Gly Asp Cys Asn Phe Val Ala Pro Gln Gly Ile Ser
            100                 105                 110

Ser Ile Ile Lys His Tyr Leu Lys Glu Ser Gly Ala Glu Val Tyr Phe
        115                 120                 125

Arg His Arg Val Thr Gln Ile Asn Leu Arg Asp Asp Lys Trp Glu Val
        130                 135                 140

Ser Lys Gln Thr Gly Ser Pro Glu Gln Phe Asp Leu Ile Val Leu Thr
145                 150                 155                 160

Met Pro Val Pro Glu Ile Leu Gln Leu Gln Gly Asp Ile Thr Thr Leu
                165                 170                 175

Ile Ser Glu Cys Gln Arg Gln Leu Glu Ala Val Ser Tyr Ser Ser
                180                 185                 190

Arg Tyr Ala Leu Gly Leu Phe Tyr Glu Ala Gly Thr Lys Ile Asp Val
        195                 200                 205

Pro Trp Ala Gly Gln Tyr Ile Thr Ser Asn Pro Cys Ile Arg Phe Val
        210                 215                 220

Ser Ile Asp Asn Lys Lys Arg Asn Ile Glu Ser Ser Glu Ile Gly Pro
225                 230                 235                 240

Ser Leu Val Ile His Thr Thr Val Pro Phe Gly Val Thr Tyr Leu Glu
                245                 250                 255

His Ser Ile Glu Asp Val Gln Glu Leu Val Phe Gln Gln Leu Glu Asn
                260                 265                 270

Ile Leu Pro Gly Leu Pro Gln Pro Ile Ala Thr Lys Cys Gln Lys Trp
        275                 280                 285

Arg His Ser Gln Val Pro Ser Ala Gly Val Ile Leu Gly Cys Ala Lys
        290                 295                 300

Ser Pro Trp Met Met Ala Ile Gly Phe Pro Ile
305                 310                 315

<210> SEQ ID NO 95
<211> LENGTH: 945
<212> TYPE: DNA
<213> ORGANISM: Artificial Sequence
<220> FEATURE:
<223> OTHER INFORMATION: Chemically Synthesized, Alternative Human
      Renalase-2 nucleic acid sequence (Note potential polymorphism at
      nucleotide position 111)

<400> SEQUENCE: 95
atggcgcagg tgctgatcgt gggcgccggg atgacaggaa gcttgtgcgc tgcgctgctg      60
acgaggcaga cgtccggtcc cttgtacctt gctgtgtggg acaaggctga ggactcaggg     120
ggaagaatga ctacagcctg cagtcctcat aatcctcagt gcacagctga cttgggtgct     180
cagtacatca cctgcactcc tcattatgcc aaaaaacacc aacgttttta tgatgaactg     240
ttagcctatg gcgttttgag gcctctaagc tcgcctattg aaggaatggt gatgaaagaa     300
ggagactgta actttgtggc acctcaagga atttcttcaa ttattaagca ttacttgaaa     360
gaatcaggtg cagaagtcta cttcagacat cgtgtgacac agatcaacct aagagatgac     420
aaatgggaag tatccaaaca aacaggctcc cctgagcagt ttgatcttat tgttctcaca     480
atgccagttc ctgagattct gcagcttcaa ggtgacatca ccaccttaat tagtgaatgc     540
caaaggcagc aactggaggc tgtgagctac tcctctcgat atgctctggg cctctttttat     600 gaagctggta cgaagattga tgtcccttgg gctgggcagt acatcaccag taatccctgc     660
atacgcttcg tctccattga taataagaag cgcaatatag agtcatcaga aattgggcct     720
tccctcgtga ttcacaccac tgtcccattt ggagttacat cttggaaca cagcattgag     780 gatgtgcaag agttagtctt ccagcagctg gaaaacattt tgccgggttt gcctcagcca     840
attgctacca aatgccaaaa atggagacat tcacaggtac caagtgctgg tgtgattcta    900
ggatgtgcga agagcccctg gatgatggcg attggatttc ccatc                   945

<210> SEQ ID NO 96
<211> LENGTH: 51
<212> TYPE: DNA
<213> ORGANISM: Artificial Sequence
<220> FEATURE:
<223> OTHER INFORMATION: Chemically Synthesized, BN452 M28 L1

<400> SEQUENCE: 96
tgccgtgcca gtcagagcgt gtatgacaac aacaacgtag cctggtatca a            51

<210> SEQ ID NO 97
<211> LENGTH: 17
<212> TYPE: PRT
<213> ORGANISM: Artificial Sequence
<220> FEATURE:
<223> OTHER INFORMATION: Chemically Synthesized, BN452 M28 L1

<400> SEQUENCE: 97

Cys Arg Ala Ser Gln Ser Val Tyr Asp Asn Asn Asn Val Ala Trp Tyr
1               5                   10                  15

Gln

<210> SEQ ID NO 98
<211> LENGTH: 51
<212> TYPE: DNA
<213> ORGANISM: Artificial Sequence
<220> FEATURE:
<223> OTHER INFORMATION: Chemically Synthesized, BN453 M42 L1

<400> SEQUENCE: 98
tgccgtgcca gtcagaccgt gtataacaac aactacgtag cctggtatca a            51

<210> SEQ ID NO 99
<211> LENGTH: 17
<212> TYPE: PRT
<213> ORGANISM: Artificial Sequence
<220> FEATURE:
<223> OTHER INFORMATION: Chemically Synthesized, BN453 M42 L1

<400> SEQUENCE: 99

Cys Arg Ala Ser Gln Thr Val Tyr Asn Asn Asn Tyr Val Ala Trp Tyr
1               5                   10                  15

Gln

<210> SEQ ID NO 100
<211> LENGTH: 42
<212> TYPE: DNA
<213> ORGANISM: Artificial Sequence
<220> FEATURE:
<223> OTHER INFORMATION: Chemically Synthesized, BN454 M28 L2

<400> SEQUENCE: 100
aagcttctga tttacggcgc cagcaccctc tactctggag tc                      42

<210> SEQ ID NO 101
<211> LENGTH: 14
<212> TYPE: PRT
<213> ORGANISM: Artificial Sequence
<220> FEATURE:
<223> OTHER INFORMATION: Chemically Synthesized, BN454 M28 L2

<400> SEQUENCE: 101

Lys Leu Leu Ile Tyr Gly Ala Ser Thr Leu Tyr Ser Gly Val
1               5                   10

<210> SEQ ID NO 102
<211> LENGTH: 42
<212> TYPE: DNA
<213> ORGANISM: Artificial Sequence
<220> FEATURE:
<223> OTHER INFORMATION: Chemically Synthesized, BN455 M42 L2

<400> SEQUENCE: 102
aagcttctga tttacgaaac cagcaaactc tactctggag tc                42

<210> SEQ ID NO 103
<211> LENGTH: 14
<212> TYPE: PRT
<213> ORGANISM: Artificial Sequence
<220> FEATURE:
<223> OTHER INFORMATION: Chemically Synthesized, BN455 M42 L2

<400> SEQUENCE: 103

Lys Leu Leu Ile Tyr Glu Thr Ser Lys Leu Tyr Ser Gly Val
1               5                   10

<210> SEQ ID NO 104
<211> LENGTH: 69
<212> TYPE: DNA
<213> ORGANISM: Artificial Sequence
<220> FEATURE:
<223> OTHER INFORMATION: Chemically Synthesized, BN456 M28 L3

<400> SEQUENCE: 104
gcaacttatt actgtctggg cgaattcagc tgcagcagcg ctgactgctt cgccttcgga    60
cagggtacc                                                           69

<210> SEQ ID NO 105
<211> LENGTH: 23
<212> TYPE: PRT
<213> ORGANISM: Artificial Sequence
<220> FEATURE:
<223> OTHER INFORMATION: Chemically Synthesized, BN456 M28 L3

<400> SEQUENCE: 105

Ala Thr Tyr Tyr Cys Leu Gly Glu Phe Ser Cys Ser Ser Ala Asp Cys
1               5                   10                  15

Phe Ala Phe Gly Gln Gly Thr
            20

<210> SEQ ID NO 106
<211> LENGTH: 63
<212> TYPE: DNA
<213> ORGANISM: Artificial Sequence
<220> FEATURE:
<223> OTHER INFORMATION: Chemically Synthesized, BN457 M42 L3

<400> SEQUENCE: 106
gcaacttatt actgtcaggg cggctacagc ggcgtggact tcatggcttt cggacagggt    60
acc                                                                 63

<210> SEQ ID NO 107
<211> LENGTH: 21
<212> TYPE: PRT
<213> ORGANISM: Artificial Sequence
<220> FEATURE:
<223> OTHER INFORMATION: Chemically Synthesized, BN457 M42 L3

<400> SEQUENCE: 107

Ala Thr Tyr Tyr Cys Gln Gly Gly Tyr Ser Gly Val Asp Phe Met Ala
1               5                   10                  15

Phe Gly Gln Gly Thr
            20

<210> SEQ ID NO 108
<211> LENGTH: 48
<212> TYPE: DNA
<213> ORGANISM: Artificial Sequence
<220> FEATURE:
<223> OTHER INFORMATION: Chemically Synthesized, BN458 M28 H1

<400> SEQUENCE: 108
gcttctggct tcaacctgag cagcttcgcc gttcactggg tgcgtcag                48

<210> SEQ ID NO 109
<211> LENGTH: 16
<212> TYPE: PRT
<213> ORGANISM: Artificial Sequence
<220> FEATURE:
<223> OTHER INFORMATION: Chemically Synthesized, BN458 M28 H1

<400> SEQUENCE: 109

Ala Ser Gly Phe Asn Leu Ser Ser Phe Ala Val His Trp Val Arg Gln
1               5                   10                  15

<210> SEQ ID NO 110
<211> LENGTH: 48
<212> TYPE: DNA
<213> ORGANISM: Artificial Sequence
<220> FEATURE:
<223> OTHER INFORMATION: Chemically Synthesized, BN459 M42 H1

<400> SEQUENCE: 110
gcttctggct tcaacctgac cacctacggc gttcactggg tgcgtcag                48

<210> SEQ ID NO 111
<211> LENGTH: 16
<212> TYPE: PRT
<213> ORGANISM: Artificial Sequence
<220> FEATURE:
<223> OTHER INFORMATION: Chemically Synthesized, BN459 M42 H1

<400> SEQUENCE: 111

Ala Ser Gly Phe Asn Leu Thr Thr Tyr Gly Val His Trp Val Arg Gln
1               5                   10                  15

<210> SEQ ID NO 112
<211> LENGTH: 57
<212> TYPE: DNA
<213> ORGANISM: Artificial Sequence
<220> FEATURE:
<223> OTHER INFORMATION: Chemically Synthesized, BN460 M28 H2

<400> SEQUENCE: 112
ctggaatggg ttgcaatcat cagcagcgtt ggcatcaccc gctatgccga tagcgtc     57

<210> SEQ ID NO 113
<211> LENGTH: 19
<212> TYPE: PRT
<213> ORGANISM: Artificial Sequence
<220> FEATURE:

<223> OTHER INFORMATION: Chemically Synthesized, BN460 M28 H2

<400> SEQUENCE: 113

Leu Glu Trp Val Ala Ile Ile Ser Ser Val Gly Ile Thr Arg Tyr Ala
1               5                   10                  15

Asp Ser Val

<210> SEQ ID NO 114
<211> LENGTH: 57
<212> TYPE: DNA
<213> ORGANISM: Artificial Sequence
<220> FEATURE:
<223> OTHER INFORMATION: Chemically Synthesized, BN461 M42 H2

<400> SEQUENCE: 114
ctggaatggg ttgcactgat cggcgatcgc ggcaccacct attatgccga tagcgtc      57

<210> SEQ ID NO 115
<211> LENGTH: 19
<212> TYPE: PRT
<213> ORGANISM: Artificial Sequence
<220> FEATURE:
<223> OTHER INFORMATION: Chemically Synthesized, BN461 M42 H2

<400> SEQUENCE: 115

Leu Glu Trp Val Ala Leu Ile Gly Asp Arg Gly Thr Thr Tyr Tyr Ala
1               5                   10                  15

Asp Ser Val

<210> SEQ ID NO 116
<211> LENGTH: 66
<212> TYPE: DNA
<213> ORGANISM: Artificial Sequence
<220> FEATURE:
<223> OTHER INFORMATION: Chemically Synthesized, BN462 M28 H3

<400> SEQUENCE: 116
tattattgtg ctcgctatgg ctatagcggc gacgtgaacc gcctggacct gtggggtcaa      60
ggaacc                                                                66

<210> SEQ ID NO 117
<211> LENGTH: 22
<212> TYPE: PRT
<213> ORGANISM: Artificial Sequence
<220> FEATURE:
<223> OTHER INFORMATION: Chemically Synthesized, BN462 M28 H3

<400> SEQUENCE: 117

Tyr Tyr Cys Ala Arg Tyr Gly Tyr Ser Gly Asp Val Asn Arg Leu Asp
1               5                   10                  15

Leu Trp Gly Gln Gly Thr
            20

<210> SEQ ID NO 118
<211> LENGTH: 54
<212> TYPE: DNA
<213> ORGANISM: Artificial Sequence
<220> FEATURE:
<223> OTHER INFORMATION: Chemically Synthesized, BN463 M42 H3

<400> SEQUENCE: 118
tattattgtg ctcgcggcag cggctatggc gctcgcatct ggggtcaagg aacc      54

```
<210> SEQ ID NO 119
<211> LENGTH: 18
<212> TYPE: PRT
<213> ORGANISM: Artificial Sequence
<220> FEATURE:
<223> OTHER INFORMATION: Chemically Synthesized, BN463 M42 H3

<400> SEQUENCE: 119

Tyr Tyr Cys Ala Arg Gly Ser Gly Tyr Gly Ala Arg Ile Trp Gly Gln
1               5                   10                  15
Gly Thr

<210> SEQ ID NO 120
<211> LENGTH: 33
<212> TYPE: DNA
<213> ORGANISM: Artificial Sequence
<220> FEATURE:
<223> OTHER INFORMATION: Chemically Synthesized, BN464 M28 HC71

<400> SEQUENCE: 120
cgtttcacta taagcaaaga cacatccaaa aac                              33

<210> SEQ ID NO 121
<211> LENGTH: 11
<212> TYPE: PRT
<213> ORGANISM: Artificial Sequence
<220> FEATURE:
<223> OTHER INFORMATION: Chemically Synthesized, BN464 M28 HC71

<400> SEQUENCE: 121

Arg Phe Thr Ile Ser Lys Asp Thr Ser Lys Asn
1               5                   10

<210> SEQ ID NO 122
<211> LENGTH: 33
<212> TYPE: DNA
<213> ORGANISM: Artificial Sequence
<220> FEATURE:
<223> OTHER INFORMATION: Chemically Synthesized, BN465 M42 HC71

<400> SEQUENCE: 122
cgtttcacta taagccgcga cacatccaaa aac                              33

<210> SEQ ID NO 123
<211> LENGTH: 11
<212> TYPE: PRT
<213> ORGANISM: Artificial Sequence
<220> FEATURE:
<223> OTHER INFORMATION: Chemically Synthesized, BN465 M42 HC71

<400> SEQUENCE: 123

Arg Phe Thr Ile Ser Arg Asp Thr Ser Lys Asn
1               5                   10

<210> SEQ ID NO 124
<211> LENGTH: 39
<212> TYPE: DNA
<213> ORGANISM: Artificial Sequence
<220> FEATURE:
<223> OTHER INFORMATION: Chemically Synthesized, BN498 M28 L3 STOP

<400> SEQUENCE: 124
gcaacttatt actgttaatg ataattcgga cagggtacc                        39

<210> SEQ ID NO 125
<211> LENGTH: 5
```

```
<212> TYPE: PRT
<213> ORGANISM: Artificial Sequence
<220> FEATURE:
<223> OTHER INFORMATION: Chemically Synthesized, BN498 M28 L3, sequence
      prior to triple STOP

<400> SEQUENCE: 125

Ala Thr Tyr Tyr Cys
1               5

<210> SEQ ID NO 126
<211> LENGTH: 39
<212> TYPE: DNA
<213> ORGANISM: Artificial Sequence
<220> FEATURE:
<223> OTHER INFORMATION: Chemically Synthesized, BN484 M28 H1 STOP

<400> SEQUENCE: 126
gcttctggct tcaattaatg ataacactgg gtgcgtcag                              39

<210> SEQ ID NO 127
<211> LENGTH: 5
<212> TYPE: PRT
<213> ORGANISM: Artificial Sequence
<220> FEATURE:
<223> OTHER INFORMATION: Chemically Synthesized, BN484 M28 H1, sequence
      prior to triple STOP

<400> SEQUENCE: 127

Ala Ser Gly Phe Asn
1               5

<210> SEQ ID NO 128
<211> LENGTH: 39
<212> TYPE: DNA
<213> ORGANISM: Artificial Sequence
<220> FEATURE:
<223> OTHER INFORMATION: Chemically Synthesized, BN467 M28 and M42 H2
      STOP

<400> SEQUENCE: 128
ctggaatggg ttgcatgata atgatatgcc gatagcgtc                              39

<210> SEQ ID NO 129
<211> LENGTH: 5
<212> TYPE: PRT
<213> ORGANISM: Artificial Sequence
<220> FEATURE:
<223> OTHER INFORMATION: Chemically Synthesized, BN467 M28 and M42 H2,
      sequence prior to triple STOP

<400> SEQUENCE: 129

Leu Glu Trp Val Ala
1               5

<210> SEQ ID NO 130
<211> LENGTH: 39
<212> TYPE: DNA
<213> ORGANISM: Artificial Sequence
<220> FEATURE:
<223> OTHER INFORMATION: Chemically Synthesized, BN485 M28 and M42 H3
      STOP

<400> SEQUENCE: 130
tattattgtg ctcgctaatg ataatgggt caaggaacc                               39

<210> SEQ ID NO 131
```

```
<211> LENGTH: 5
<212> TYPE: PRT
<213> ORGANISM: Artificial Sequence
<220> FEATURE:
<223> OTHER INFORMATION: Chemically Synthesized, BN485 M28 and M42 H3,
      sequence prior to triple STOP

<400> SEQUENCE: 131

Tyr Tyr Cys Ala Arg
1               5

<210> SEQ ID NO 132
<211> LENGTH: 39
<212> TYPE: DNA
<213> ORGANISM: Artificial Sequence
<220> FEATURE:
<223> OTHER INFORMATION: Chemically Synthesized, BN469 M42 L1 STOP

<400> SEQUENCE: 132
tgccgtgcca gtcagtgata atgagtagcc tggtatcaa                          39

<210> SEQ ID NO 133
<211> LENGTH: 5
<212> TYPE: PRT
<213> ORGANISM: Artificial Sequence
<220> FEATURE:
<223> OTHER INFORMATION: Chemically Synthesized, BN469 M42 L1, sequence
      prior to triple STOP

<400> SEQUENCE: 133

Cys Arg Ala Ser Gln
1               5

<210> SEQ ID NO 134
<211> LENGTH: 39
<212> TYPE: DNA
<213> ORGANISM: Artificial Sequence
<220> FEATURE:
<223> OTHER INFORMATION: Chemically Synthesized, BN466 M42 H1 STOP

<400> SEQUENCE: 134
gcttctggct tcaactgata atgacactgg gtgcgtcag                          39

<210> SEQ ID NO 135
<211> LENGTH: 5
<212> TYPE: PRT
<213> ORGANISM: Artificial Sequence
<220> FEATURE:
<223> OTHER INFORMATION: Chemically Synthesized, BN466 M42 H1, sequence
      prior to triple STOP

<400> SEQUENCE: 135

Ala Ser Gly Phe Asn
1               5

<210> SEQ ID NO 136
<211> LENGTH: 69
<212> TYPE: DNA
<213> ORGANISM: Artificial Sequence
<220> FEATURE:
<223> OTHER INFORMATION: Chemically Synthesized, BN492 M28 L3
      randomization

<400> SEQUENCE: 136
gcaacttatt actgtctggg cgaattcagc tgcagcagcg ctgactgctt cgccttcgga   60
cagggtacc                                                          69
```

<210> SEQ ID NO 137
<211> LENGTH: 23
<212> TYPE: PRT
<213> ORGANISM: Artificial Sequence
<220> FEATURE:
<223> OTHER INFORMATION: Chemically Synthesized, BN492 M28 L3
      randomization

<400> SEQUENCE: 137

Ala Thr Tyr Tyr Cys Leu Gly Glu Phe Ser Cys Ser Ser Ala Asp Cys
1               5                   10                  15

Phe Ala Phe Gly Gln Gly Thr
            20

<210> SEQ ID NO 138
<211> LENGTH: 48
<212> TYPE: DNA
<213> ORGANISM: Artificial Sequence
<220> FEATURE:
<223> OTHER INFORMATION: Chemically Synthesized, BN488 M28 H1
      randomization

<400> SEQUENCE: 138
gcttctggct tcaacctgag cagcttcgcc gttcactggg tgcgtcag            48

<210> SEQ ID NO 139
<211> LENGTH: 16
<212> TYPE: PRT
<213> ORGANISM: Artificial Sequence
<220> FEATURE:
<223> OTHER INFORMATION: Chemically Synthesized, BN488 M28 H1
      randomization

<400> SEQUENCE: 139

Ala Ser Gly Phe Asn Leu Ser Ser Phe Ala Val His Trp Val Arg Gln
1               5                   10                  15

<210> SEQ ID NO 140
<211> LENGTH: 57
<212> TYPE: DNA
<213> ORGANISM: Artificial Sequence
<220> FEATURE:
<223> OTHER INFORMATION: Chemically Synthesized, BN489 M28 H2
      randomization

<400> SEQUENCE: 140
ctggaatggg ttgcaatcat cagcagcgtt ggcatcaccc gctatgccga tagcgtc         57

<210> SEQ ID NO 141
<211> LENGTH: 19
<212> TYPE: PRT
<213> ORGANISM: Artificial Sequence
<220> FEATURE:
<223> OTHER INFORMATION: Chemically Synthesized, BN489 M28 H2
      randomization

<400> SEQUENCE: 141

Leu Glu Trp Val Ala Ile Ile Ser Ser Val Gly Ile Thr Arg Tyr Ala
1               5                   10                  15

Asp Ser Val

<210> SEQ ID NO 142
<211> LENGTH: 66
<212> TYPE: DNA
<213> ORGANISM: Artificial Sequence
<220> FEATURE:

<223> OTHER INFORMATION: Chemically Synthesized, BN490 M28 H3
      randomization

<400> SEQUENCE: 142
tattattgtg ctcgctatgg ctatagcggc gacgtgaacc gcctggacct gtggggtcaa    60
ggaacc    66

<210> SEQ ID NO 143
<211> LENGTH: 22
<212> TYPE: PRT
<213> ORGANISM: Artificial Sequence
<220> FEATURE:
<223> OTHER INFORMATION: Chemically Synthesized, BN490 M28 H3
      randomization

<400> SEQUENCE: 143

Tyr Tyr Cys Ala Arg Tyr Gly Tyr Ser Gly Asp Val Asn Arg Leu Asp
1               5                   10                  15

Leu Trp Gly Gln Gly Thr
            20

<210> SEQ ID NO 144
<211> LENGTH: 51
<212> TYPE: DNA
<213> ORGANISM: Artificial Sequence
<220> FEATURE:
<223> OTHER INFORMATION: Chemically Synthesized, BN496 M42 L1
      randomization

<400> SEQUENCE: 144
tgccgtgcca gtcagaccgt gtataacaac aactacgtag cctggtatca a    51

<210> SEQ ID NO 145
<211> LENGTH: 17
<212> TYPE: PRT
<213> ORGANISM: Artificial Sequence
<220> FEATURE:
<223> OTHER INFORMATION: Chemically Synthesized, BN496 M42 L1
      randomization

<400> SEQUENCE: 145

Cys Arg Ala Ser Gln Thr Val Tyr Asn Asn Asn Tyr Val Ala Trp Tyr
1               5                   10                  15

Gln

<210> SEQ ID NO 146
<211> LENGTH: 48
<212> TYPE: DNA
<213> ORGANISM: Artificial Sequence
<220> FEATURE:
<223> OTHER INFORMATION: Chemically Synthesized, BN493 M42 H1
      randomization

<400> SEQUENCE: 146
gcttctggct tcaacctgac cacctacggc gttcactggg tgcgtcag    48

<210> SEQ ID NO 147
<211> LENGTH: 16
<212> TYPE: PRT
<213> ORGANISM: Artificial Sequence
<220> FEATURE:
<223> OTHER INFORMATION: Chemically Synthesized, BN493 M42 H1
      randomization

<400> SEQUENCE: 147

Ala Ser Gly Phe Asn Leu Thr Thr Tyr Gly Val His Trp Val Arg Gln
1               5                   10                  15

<210> SEQ ID NO 148
<211> LENGTH: 57
<212> TYPE: DNA
<213> ORGANISM: Artificial Sequence
<220> FEATURE:
<223> OTHER INFORMATION: Chemically Synthesized, BN494 M42 H2
      randomization

<400> SEQUENCE: 148
ctggaatggg ttgcactgat cggcgatcgc ggcaccacct attatgccga tagcgtc        57

<210> SEQ ID NO 149
<211> LENGTH: 19
<212> TYPE: PRT
<213> ORGANISM: Artificial Sequence
<220> FEATURE:
<223> OTHER INFORMATION: Chemically Synthesized, BN494 M42 H2
      randomization

<400> SEQUENCE: 149

Leu Glu Trp Val Ala Leu Ile Gly Asp Arg Gly Thr Thr Tyr Tyr Ala
1               5                   10                  15

Asp Ser Val

<210> SEQ ID NO 150
<211> LENGTH: 54
<212> TYPE: DNA
<213> ORGANISM: Artificial Sequence
<220> FEATURE:
<223> OTHER INFORMATION: Chemically Synthesized, BN495 M42 H3
      randomization

<400> SEQUENCE: 150
tattattgtg ctcgcggcag cggctatggc gctcgcatct ggggtcaagg aacc           54

<210> SEQ ID NO 151
<211> LENGTH: 18
<212> TYPE: PRT
<213> ORGANISM: Artificial Sequence
<220> FEATURE:
<223> OTHER INFORMATION: Chemically Synthesized, BN495 M42 H3
      randomization

<400> SEQUENCE: 151

Tyr Tyr Cys Ala Arg Gly Ser Gly Tyr Gly Ala Arg Ile Trp Gly Gln
1               5                   10                  15

Gly Thr

<210> SEQ ID NO 152
<211> LENGTH: 7
<212> TYPE: PRT
<213> ORGANISM: Artificial Sequence
<220> FEATURE:
<223> OTHER INFORMATION: Chemically Synthesized, M28 Parental CDR-L1

<400> SEQUENCE: 152

Ser Val Tyr Asp Asn Asn Asn
1               5

<210> SEQ ID NO 153
<211> LENGTH: 4
<212> TYPE: PRT
<213> ORGANISM: Artificial Sequence

```
<220> FEATURE:
<223> OTHER INFORMATION: Chemically Synthesized, M28 Parental CDR-L2

<400> SEQUENCE: 153

Gly Ala Ser Thr
1

<210> SEQ ID NO 154
<211> LENGTH: 13
<212> TYPE: PRT
<213> ORGANISM: Artificial Sequence
<220> FEATURE:
<223> OTHER INFORMATION: Chemically Synthesized, M28 Parental CDR-L3

<400> SEQUENCE: 154

Leu Gly Glu Phe Ser Cys Ser Ser Ala Asp Cys Phe Ala
1               5                   10

<210> SEQ ID NO 155
<211> LENGTH: 6
<212> TYPE: PRT
<213> ORGANISM: Artificial Sequence
<220> FEATURE:
<223> OTHER INFORMATION: Chemically Synthesized, M28 Parental CDR-H1

<400> SEQUENCE: 155

Leu Ser Ser Phe Ala Val
1               5

<210> SEQ ID NO 156
<211> LENGTH: 9
<212> TYPE: PRT
<213> ORGANISM: Artificial Sequence
<220> FEATURE:
<223> OTHER INFORMATION: Chemically Synthesized, M28 Parental CDR-H2

<400> SEQUENCE: 156

Ile Ile Ser Ser Val Gly Ile Thr Arg
1               5

<210> SEQ ID NO 157
<211> LENGTH: 12
<212> TYPE: PRT
<213> ORGANISM: Artificial Sequence
<220> FEATURE:
<223> OTHER INFORMATION: Chemically Synthesized, M28 Parental CDR-H3

<400> SEQUENCE: 157

Tyr Gly Tyr Ser Gly Asp Val Asn Arg Leu Asp Leu
1               5                   10

<210> SEQ ID NO 158
<211> LENGTH: 7
<212> TYPE: PRT
<213> ORGANISM: Artificial Sequence
<220> FEATURE:
<223> OTHER INFORMATION: Chemically Synthesized, M28-K2 CDR-L1

<400> SEQUENCE: 158

Ser Val Tyr Asp Asn Asn Asn
1               5

<210> SEQ ID NO 159
<211> LENGTH: 4
<212> TYPE: PRT
<213> ORGANISM: Artificial Sequence
<220> FEATURE:
```

```
<223> OTHER INFORMATION: Chemically Synthesized, M28-K2 CDR-L2

<400> SEQUENCE: 159

Gly Ala Ser Thr
1

<210> SEQ ID NO 160
<211> LENGTH: 13
<212> TYPE: PRT
<213> ORGANISM: Artificial Sequence
<220> FEATURE:
<223> OTHER INFORMATION: Chemically Synthesized, M28-K2 CDR-L3

<400> SEQUENCE: 160

Leu Gly Glu Gly Pro Cys Ser Val Thr Asp Cys Leu Ile
1               5                   10

<210> SEQ ID NO 161
<211> LENGTH: 6
<212> TYPE: PRT
<213> ORGANISM: Artificial Sequence
<220> FEATURE:
<223> OTHER INFORMATION: Chemically Synthesized, M28-K2 CDR-H1

<400> SEQUENCE: 161

Leu Ser Ser Phe Ala Val
1               5

<210> SEQ ID NO 162
<211> LENGTH: 9
<212> TYPE: PRT
<213> ORGANISM: Artificial Sequence
<220> FEATURE:
<223> OTHER INFORMATION: Chemically Synthesized, M28-K2 CDR-H2

<400> SEQUENCE: 162

Leu Ile Gly Val Arg Gly Ser Leu Tyr
1               5

<210> SEQ ID NO 163
<211> LENGTH: 12
<212> TYPE: PRT
<213> ORGANISM: Artificial Sequence
<220> FEATURE:
<223> OTHER INFORMATION: Chemically Synthesized, M28-K2 CDR-H3

<400> SEQUENCE: 163

His Trp Tyr Ser Gly Gly Val Val Arg Leu Asp Ala
1               5                   10

<210> SEQ ID NO 164
<211> LENGTH: 7
<212> TYPE: PRT
<213> ORGANISM: Artificial Sequence
<220> FEATURE:
<223> OTHER INFORMATION: Chemically Synthesized, M28-K5 CDR-L1

<400> SEQUENCE: 164

Ser Val Tyr Asp Asn Asn Asn
1               5

<210> SEQ ID NO 165
<211> LENGTH: 4
<212> TYPE: PRT
<213> ORGANISM: Artificial Sequence
<220> FEATURE:
<223> OTHER INFORMATION: Chemically Synthesized, M28-K5 CDR-L2
```

```
<400> SEQUENCE: 165

Gly Ala Ser Thr
1

<210> SEQ ID NO 166
<211> LENGTH: 13
<212> TYPE: PRT
<213> ORGANISM: Artificial Sequence
<220> FEATURE:
<223> OTHER INFORMATION: Chemically Synthesized, M28-K5 CDR-L3

<400> SEQUENCE: 166

Leu Gly Glu Gly Pro Cys Ser Val Thr Asp Cys Leu Ile
1               5                   10

<210> SEQ ID NO 167
<211> LENGTH: 6
<212> TYPE: PRT
<213> ORGANISM: Artificial Sequence
<220> FEATURE:
<223> OTHER INFORMATION: Chemically Synthesized, M28-K5 CDR-H1

<400> SEQUENCE: 167

Leu Ser Ser Phe Ala Val
1               5

<210> SEQ ID NO 168
<211> LENGTH: 9
<212> TYPE: PRT
<213> ORGANISM: Artificial Sequence
<220> FEATURE:
<223> OTHER INFORMATION: Chemically Synthesized, M28-K5 CDR-H2

<400> SEQUENCE: 168

Leu Ile Ser Gly Arg Gly Thr Arg Phe
1               5

<210> SEQ ID NO 169
<211> LENGTH: 12
<212> TYPE: PRT
<213> ORGANISM: Artificial Sequence
<220> FEATURE:
<223> OTHER INFORMATION: Chemically Synthesized, M28-K5 CDR-H3

<400> SEQUENCE: 169

His Trp Tyr Ser Gly Gly Val Val Arg Leu Asp Ala
1               5                   10

<210> SEQ ID NO 170
<211> LENGTH: 7
<212> TYPE: PRT
<213> ORGANISM: Artificial Sequence
<220> FEATURE:
<223> OTHER INFORMATION: Chemically Synthesized, M28-K9 CDR-L1

<400> SEQUENCE: 170

Ser Val Tyr Asp Asn Asn Asn
1               5

<210> SEQ ID NO 171
<211> LENGTH: 4
<212> TYPE: PRT
<213> ORGANISM: Artificial Sequence
<220> FEATURE:
<223> OTHER INFORMATION: Chemically Synthesized, M28-K9 CDR-L2
```

```
<400> SEQUENCE: 171

Gly Ala Ser Thr
1

<210> SEQ ID NO 172
<211> LENGTH: 13
<212> TYPE: PRT
<213> ORGANISM: Artificial Sequence
<220> FEATURE:
<223> OTHER INFORMATION: Chemically Synthesized, M28-K9 CDR-L3

<400> SEQUENCE: 172

Leu Gly Glu Gly Pro Cys Ser Val Thr Asp Cys Leu Ile
1               5                   10

<210> SEQ ID NO 173
<211> LENGTH: 6
<212> TYPE: PRT
<213> ORGANISM: Artificial Sequence
<220> FEATURE:
<223> OTHER INFORMATION: Chemically Synthesized, M28-K9 CDR-H1

<400> SEQUENCE: 173

Leu Ser Ser Phe Ala Val
1               5

<210> SEQ ID NO 174
<211> LENGTH: 9
<212> TYPE: PRT
<213> ORGANISM: Artificial Sequence
<220> FEATURE:
<223> OTHER INFORMATION: Chemically Synthesized, M28-K9 CDR-H2

<400> SEQUENCE: 174

Ile Ile Ser Ser Val Gly Ile Thr Arg
1               5

<210> SEQ ID NO 175
<211> LENGTH: 12
<212> TYPE: PRT
<213> ORGANISM: Artificial Sequence
<220> FEATURE:
<223> OTHER INFORMATION: Chemically Synthesized, M28-K9 CDR-H3

<400> SEQUENCE: 175

His Trp Tyr Ser Gly Gly Val Val Arg Leu Asp Ala
1               5                   10

<210> SEQ ID NO 176
<211> LENGTH: 7
<212> TYPE: PRT
<213> ORGANISM: Artificial Sequence
<220> FEATURE:
<223> OTHER INFORMATION: Chemically Synthesized, M28-K13 CDR-L1

<400> SEQUENCE: 176

Ser Val Tyr Asp Asn Asn Asn
1               5

<210> SEQ ID NO 177
<211> LENGTH: 4
<212> TYPE: PRT
<213> ORGANISM: Artificial Sequence
<220> FEATURE:
<223> OTHER INFORMATION: Chemically Synthesized, M28-K13 CDR-L2

<400> SEQUENCE: 177
```

Gly Ala Ser Thr
1

<210> SEQ ID NO 178
<211> LENGTH: 13
<212> TYPE: PRT
<213> ORGANISM: Artificial Sequence
<220> FEATURE:
<223> OTHER INFORMATION: Chemically Synthesized, M28-K13 CDR-L3

<400> SEQUENCE: 178

Leu Gly Glu Phe Ser Cys Ser Ser Ala Asp Cys Phe Ala
1               5                   10

<210> SEQ ID NO 179
<211> LENGTH: 6
<212> TYPE: PRT
<213> ORGANISM: Artificial Sequence
<220> FEATURE:
<223> OTHER INFORMATION: Chemically Synthesized, M28-K13 CDR-H1

<400> SEQUENCE: 179

Leu Ser Ser Phe Ala Val
1               5

<210> SEQ ID NO 180
<211> LENGTH: 9
<212> TYPE: PRT
<213> ORGANISM: Artificial Sequence
<220> FEATURE:
<223> OTHER INFORMATION: Chemically Synthesized, M28-K13 CDR-H2

<400> SEQUENCE: 180

Leu Ile Gly Val Arg Gly Ser Leu Tyr
1               5

<210> SEQ ID NO 181
<211> LENGTH: 12
<212> TYPE: PRT
<213> ORGANISM: Artificial Sequence
<220> FEATURE:
<223> OTHER INFORMATION: Chemically Synthesized, M28-K13 CDR-H3

<400> SEQUENCE: 181

His Trp Tyr Ser Gly Gly Val Val Arg Leu Asp Ala
1               5                   10

<210> SEQ ID NO 182
<211> LENGTH: 7
<212> TYPE: PRT
<213> ORGANISM: Artificial Sequence
<220> FEATURE:
<223> OTHER INFORMATION: Chemically Synthesized, M28-K14 CDR-L1

<400> SEQUENCE: 182

Ser Val Tyr Asp Asn Asn Asn
1               5

<210> SEQ ID NO 183
<211> LENGTH: 4
<212> TYPE: PRT
<213> ORGANISM: Artificial Sequence
<220> FEATURE:
<223> OTHER INFORMATION: Chemically Synthesized, M28-K14 CDR-L2

<400> SEQUENCE: 183

Gly Ala Ser Thr
1

<210> SEQ ID NO 184
<211> LENGTH: 13
<212> TYPE: PRT
<213> ORGANISM: Artificial Sequence
<220> FEATURE:
<223> OTHER INFORMATION: Chemically Synthesized, M28-K14 CDR-L3

<400> SEQUENCE: 184

Leu Gly Glu Gly Pro Cys Ser Val Thr Asp Cys Leu Ile
1               5                   10

<210> SEQ ID NO 185
<211> LENGTH: 6
<212> TYPE: PRT
<213> ORGANISM: Artificial Sequence
<220> FEATURE:
<223> OTHER INFORMATION: Chemically Synthesized, M28-K14 CDR-H1

<400> SEQUENCE: 185

Leu Ser Ser Phe Ala Val
1               5

<210> SEQ ID NO 186
<211> LENGTH: 9
<212> TYPE: PRT
<213> ORGANISM: Artificial Sequence
<220> FEATURE:
<223> OTHER INFORMATION: Chemically Synthesized, M28-K14 CDR-H2

<400> SEQUENCE: 186

Leu Ile Ser Gly Arg Gly Thr Arg Phe
1               5

<210> SEQ ID NO 187
<211> LENGTH: 12
<212> TYPE: PRT
<213> ORGANISM: Artificial Sequence
<220> FEATURE:
<223> OTHER INFORMATION: Chemically Synthesized, M28-K14 CDR-H3

<400> SEQUENCE: 187

Tyr Gly Tyr Ser Gly Asp Val Asn Arg Leu Asp Leu
1               5                   10

<210> SEQ ID NO 188
<211> LENGTH: 7
<212> TYPE: PRT
<213> ORGANISM: Artificial Sequence
<220> FEATURE:
<223> OTHER INFORMATION: Chemically Synthesized, M28-K16 CDR-L1

<400> SEQUENCE: 188

Ser Val Tyr Asp Asn Asn Asn
1               5

<210> SEQ ID NO 189
<211> LENGTH: 4
<212> TYPE: PRT
<213> ORGANISM: Artificial Sequence
<220> FEATURE:
<223> OTHER INFORMATION: Chemically Synthesized, M28-K16 CDR-L2

<400> SEQUENCE: 189

Gly Ala Ser Thr

-continued

```
<210> SEQ ID NO 190
<211> LENGTH: 13
<212> TYPE: PRT
<213> ORGANISM: Artificial Sequence
<220> FEATURE:
<223> OTHER INFORMATION: Chemically Synthesized, M28-K16 CDR-L3

<400> SEQUENCE: 190

Leu Gly Glu Phe Ser Cys Ser Ser Ala Asp Cys Phe Ala
1               5                   10

<210> SEQ ID NO 191
<211> LENGTH: 6
<212> TYPE: PRT
<213> ORGANISM: Artificial Sequence
<220> FEATURE:
<223> OTHER INFORMATION: Chemically Synthesized, M28-K16 CDR-H1

<400> SEQUENCE: 191

Leu Ser Ser Phe Ala Val
1               5

<210> SEQ ID NO 192
<211> LENGTH: 9
<212> TYPE: PRT
<213> ORGANISM: Artificial Sequence
<220> FEATURE:
<223> OTHER INFORMATION: Chemically Synthesized, M28-K16 CDR-H2

<400> SEQUENCE: 192

Leu Ile Ser Gly Arg Gly Thr Arg Phe
1               5

<210> SEQ ID NO 193
<211> LENGTH: 12
<212> TYPE: PRT
<213> ORGANISM: Artificial Sequence
<220> FEATURE:
<223> OTHER INFORMATION: Chemically Synthesized, M28-K16 CDR-H3

<400> SEQUENCE: 193

His Trp Tyr Ser Gly Gly Val Val Arg Leu Asp Ala
1               5                   10

<210> SEQ ID NO 194
<211> LENGTH: 7
<212> TYPE: PRT
<213> ORGANISM: Artificial Sequence
<220> FEATURE:
<223> OTHER INFORMATION: Chemically Synthesized, M42 Parental CDR-L1

<400> SEQUENCE: 194

Thr Val Tyr Asn Asn Asn Tyr
1               5

<210> SEQ ID NO 195
<211> LENGTH: 4
<212> TYPE: PRT
<213> ORGANISM: Artificial Sequence
<220> FEATURE:
<223> OTHER INFORMATION: Chemically Synthesized, M42 Parental CDR-L2

<400> SEQUENCE: 195

Glu Thr Ser Lys
1
```

```
<210> SEQ ID NO 196
<211> LENGTH: 11
<212> TYPE: PRT
<213> ORGANISM: Artificial Sequence
<220> FEATURE:
<223> OTHER INFORMATION: Chemically Synthesized, M42 Parental CDR-L3

<400> SEQUENCE: 196

Gln Gly Gly Tyr Ser Gly Val Asp Phe Met Ala
1               5                   10

<210> SEQ ID NO 197
<211> LENGTH: 6
<212> TYPE: PRT
<213> ORGANISM: Artificial Sequence
<220> FEATURE:
<223> OTHER INFORMATION: Chemically Synthesized, M42 Parental CDR-H1

<400> SEQUENCE: 197

Leu Thr Thr Tyr Gly Val
1               5

<210> SEQ ID NO 198
<211> LENGTH: 9
<212> TYPE: PRT
<213> ORGANISM: Artificial Sequence
<220> FEATURE:
<223> OTHER INFORMATION: Chemically Synthesized, M42 Parental CDR-H2

<400> SEQUENCE: 198

Leu Ile Gly Asp Arg Gly Thr Thr Tyr
1               5

<210> SEQ ID NO 199
<211> LENGTH: 8
<212> TYPE: PRT
<213> ORGANISM: Artificial Sequence
<220> FEATURE:
<223> OTHER INFORMATION: Chemically Synthesized, M42 Parental CDR-H3

<400> SEQUENCE: 199

Gly Ser Gly Tyr Gly Ala Arg Ile
1               5

<210> SEQ ID NO 200
<211> LENGTH: 7
<212> TYPE: PRT
<213> ORGANISM: Artificial Sequence
<220> FEATURE:
<223> OTHER INFORMATION: Chemically Synthesized, M42-K31 CDR-L1

<400> SEQUENCE: 200

Ser Val Tyr Arg Asn Asn Tyr
1               5

<210> SEQ ID NO 201
<211> LENGTH: 4
<212> TYPE: PRT
<213> ORGANISM: Artificial Sequence
<220> FEATURE:
<223> OTHER INFORMATION: Chemically Synthesized, M42-K31 CDR-L2

<400> SEQUENCE: 201

Glu Thr Ser Lys
1
```

<210> SEQ ID NO 202
<211> LENGTH: 11
<212> TYPE: PRT
<213> ORGANISM: Artificial Sequence
<220> FEATURE:
<223> OTHER INFORMATION: Chemically Synthesized, M42-K31 CDR-L3

<400> SEQUENCE: 202

Gln Gly Gly Tyr Ser Gly Val Asp Phe Met Ala
1               5                   10

<210> SEQ ID NO 203
<211> LENGTH: 6
<212> TYPE: PRT
<213> ORGANISM: Artificial Sequence
<220> FEATURE:
<223> OTHER INFORMATION: Chemically Synthesized, M42-K31 CDR-H1

<400> SEQUENCE: 203

Met Ser Ser Glu Arg Arg
1               5

<210> SEQ ID NO 204
<211> LENGTH: 9
<212> TYPE: PRT
<213> ORGANISM: Artificial Sequence
<220> FEATURE:
<223> OTHER INFORMATION: Chemically Synthesized, M42-K31 CDR-H2

<400> SEQUENCE: 204

Leu Ile Arg Asp Arg Gly Trp Asn Tyr
1               5

<210> SEQ ID NO 205
<211> LENGTH: 8
<212> TYPE: PRT
<213> ORGANISM: Artificial Sequence
<220> FEATURE:
<223> OTHER INFORMATION: Chemically Synthesized, M42-K31 CDR-H3

<400> SEQUENCE: 205

Gly Ile Cys Tyr Cys Ala Arg Ser
1               5

<210> SEQ ID NO 206
<211> LENGTH: 7
<212> TYPE: PRT
<213> ORGANISM: Artificial Sequence
<220> FEATURE:
<223> OTHER INFORMATION: Chemically Synthesized, M42-K34 CDR-L1

<400> SEQUENCE: 206

Ser Val Tyr Arg Asn Asn Tyr
1               5

<210> SEQ ID NO 207
<211> LENGTH: 4
<212> TYPE: PRT
<213> ORGANISM: Artificial Sequence
<220> FEATURE:
<223> OTHER INFORMATION: Chemically Synthesized, M42-K34 CDR-L2

<400> SEQUENCE: 207

Glu Thr Ser Lys
1

```
<210> SEQ ID NO 208
<211> LENGTH: 11
<212> TYPE: PRT
<213> ORGANISM: Artificial Sequence
<220> FEATURE:
<223> OTHER INFORMATION: Chemically Synthesized, M42-K34 CDR-L3

<400> SEQUENCE: 208

Gln Gly Gly Tyr Ser Gly Val Asp Phe Met Ala
1               5                   10

<210> SEQ ID NO 209
<211> LENGTH: 6
<212> TYPE: PRT
<213> ORGANISM: Artificial Sequence
<220> FEATURE:
<223> OTHER INFORMATION: Chemically Synthesized, M42-K34 CDR-H1

<400> SEQUENCE: 209

Leu Thr Thr Tyr Gly Val
1               5

<210> SEQ ID NO 210
<211> LENGTH: 9
<212> TYPE: PRT
<213> ORGANISM: Artificial Sequence
<220> FEATURE:
<223> OTHER INFORMATION: Chemically Synthesized, M42-K34 CDR-H2

<400> SEQUENCE: 210

Leu Ile Arg Asp Arg Gly Trp Asn Tyr
1               5

<210> SEQ ID NO 211
<211> LENGTH: 8
<212> TYPE: PRT
<213> ORGANISM: Artificial Sequence
<220> FEATURE:
<223> OTHER INFORMATION: Chemically Synthesized, M42-K34 CDR-H3

<400> SEQUENCE: 211

Gly Ile Cys Tyr Cys Ala Arg Ser
1               5

<210> SEQ ID NO 212
<211> LENGTH: 7
<212> TYPE: PRT
<213> ORGANISM: Artificial Sequence
<220> FEATURE:
<223> OTHER INFORMATION: Chemically Synthesized, M42-K35 CDR-L1

<400> SEQUENCE: 212

Thr Val Tyr Asn Asn Asn Tyr
1               5

<210> SEQ ID NO 213
<211> LENGTH: 4
<212> TYPE: PRT
<213> ORGANISM: Artificial Sequence
<220> FEATURE:
<223> OTHER INFORMATION: Chemically Synthesized, M42-K35 L2

<400> SEQUENCE: 213

Glu Thr Ser Lys
1

<210> SEQ ID NO 214
```

<210> SEQ ID NO 214
<211> LENGTH: 11
<212> TYPE: PRT
<213> ORGANISM: Artificial Sequence
<220> FEATURE:
<223> OTHER INFORMATION: Chemically Synthesized, M42-K35 L3

<400> SEQUENCE: 214

Gln Gly Gly Tyr Ser Gly Val Asp Phe Met Ala
1               5                   10

<210> SEQ ID NO 215
<211> LENGTH: 6
<212> TYPE: PRT
<213> ORGANISM: Artificial Sequence
<220> FEATURE:
<223> OTHER INFORMATION: Chemically Synthesized, M42-K35 H1

<400> SEQUENCE: 215

Met Ser Ser Glu Arg Arg
1               5

<210> SEQ ID NO 216
<211> LENGTH: 9
<212> TYPE: PRT
<213> ORGANISM: Artificial Sequence
<220> FEATURE:
<223> OTHER INFORMATION: Chemically Synthesized, M42-K35 H2

<400> SEQUENCE: 216

Leu Ile Arg Asp Arg Gly Trp Asn Tyr
1               5

<210> SEQ ID NO 217
<211> LENGTH: 8
<212> TYPE: PRT
<213> ORGANISM: Artificial Sequence
<220> FEATURE:
<223> OTHER INFORMATION: Chemically Synthesized, M42-K35 H3

<400> SEQUENCE: 217

Gly Ile Cys Tyr Cys Ala Arg Ser
1               5

<210> SEQ ID NO 218
<211> LENGTH: 360
<212> TYPE: DNA
<213> ORGANISM: Artificial Sequence
<220> FEATURE:
<223> OTHER INFORMATION: Chemically Synthesized, M28-humanized Fv
      sequence Heavy chain

<400> SEQUENCE: 218
gaggttcagc tggtggagtc tggcggtggc ctggtgcagc caggggcctc actccgtttg      60
tcctgtgcag cttctggctt caatctgagc agcttcgccg ttcactgggt gcgtcaggcc     120
ccgggtaagg gcctggaatg ggttgcaatc atcagcagcg ttggcatcac ccgctatgcc     180
gatagcgtca agggccgttt cactataagc aaagacacat ccaaaaacac agcctaccta     240
caaatgaaca gcttaagagc tgaggacact gccgtctatt attgtgctcg ctatggctat     300
agcggcgacg tgaaccgcct ggacctgtgg ggtcaaggaa ccctggtcac cgtctcctcg     360

<210> SEQ ID NO 219
<211> LENGTH: 120
<212> TYPE: PRT
<213> ORGANISM: Artificial Sequence
<220> FEATURE:

<223> OTHER INFORMATION: Chemically Synthesized, M28-humanized Fv
      sequence Heavy chain

<400> SEQUENCE: 219

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Leu Ser Ser Phe
            20                  25                  30

Ala Val His Trp Val Arg Gln Ala Pro Gly Lys Gly Leu Glu Trp Val
        35                  40                  45

Ala Ile Ile Ser Ser Val Gly Ile Thr Arg Tyr Ala Asp Ser Val Lys
    50                  55                  60

Gly Arg Phe Thr Ile Ser Lys Asp Thr Ser Lys Asn Thr Ala Tyr Leu
65                  70                  75                  80

Gln Met Asn Ser Leu Arg Ala Glu Asp Thr Ala Val Tyr Tyr Cys Ala
                85                  90                  95

Arg Tyr Gly Tyr Ser Gly Asp Val Asn Arg Leu Asp Leu Trp Gly Gln
            100                 105                 110

Gly Thr Leu Val Thr Val Ser Ser
        115                 120

<210> SEQ ID NO 220
<211> LENGTH: 342
<212> TYPE: DNA
<213> ORGANISM: Artificial Sequence
<220> FEATURE:
<223> OTHER INFORMATION: Chemically Synthesized, M28-humanized Fv
      sequence Light chain

<400> SEQUENCE: 220
gatatccaga tgacccagtc cccgagctcc ctgtccgcct ctgtgggcga tagggtcacc      60
atcacctgcc gtgccagtca gagcgtgtat gacaacaaca acgtagcctg gtatcaacag     120
aaaccaggaa aagctccgaa gcttctgatt tacggcgcca gcaccctcta ctctggagtc     180
ccttctcgct tctctggtag ccgttccggg acggatttca ctctgaccat cagcagtctg     240
cagccggaag acttcgcaac ttattactgt ctgggcgaat cagctgcag cagcgctgac      300 tgcttcgcct tcggacaggg taccaaggtg gagatcaaac ga                        342

<210> SEQ ID NO 221
<211> LENGTH: 114
<212> TYPE: PRT
<213> ORGANISM: Artificial Sequence
<220> FEATURE:
<223> OTHER INFORMATION: Chemically Synthesized, M28-humanized Fv
      sequence Light chain

<400> SEQUENCE: 221

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Tyr Asp Asn
            20                  25                  30

Asn Asn Val Ala Trp Tyr Gln Gln Lys Pro Gly Lys Ala Pro Lys Leu
        35                  40                  45

Leu Ile Tyr Gly Ala Ser Thr Leu Tyr Ser Gly Val Pro Ser Arg Phe
    50                  55                  60

Ser Gly Ser Arg Ser Gly Thr Asp Phe Thr Leu Thr Ile Ser Ser Leu
65                  70                  75                  80

Gln Pro Glu Asp Phe Ala Thr Tyr Tyr Cys Leu Gly Glu Phe Ser Cys

```
                    85                  90                  95
Ser Ser Ala Asp Cys Phe Ala Phe Gly Gln Gly Thr Lys Val Glu Ile
                100                 105                 110

Lys Arg

<210> SEQ ID NO 222
<211> LENGTH: 348
<212> TYPE: DNA
<213> ORGANISM: Artificial Sequence
<220> FEATURE:
<223> OTHER INFORMATION: Chemically Synthesized, M42 humanized Fv
      sequence Heavy chain

<400> SEQUENCE: 222
gaggttcagc tggtggagtc tggcggtggc ctggtgcagc caggggctc actccgtttg      60 tcctgtgcag cttctggctt caacctgacc acctacggcg ttcactgggt gcgtcaggcc    120
ccgggtaagg gcctggaatg ggttgcactg atcggcgatc gcggcaccac ctattatgcc    180
gatagcgtca agggccgttt cactataagc cgcgacacat ccaaaaacac agcctaccta    240
caaatgaaca gcttaagagc tgaggacact gccgtctatt attgtgctcg cggcagcggc    300
tatggcgctc gcatctgggg tcaaggaacc ctggtcaccg tctcctcg                 348

<210> SEQ ID NO 223
<211> LENGTH: 116
<212> TYPE: PRT
<213> ORGANISM: Artificial Sequence
<220> FEATURE:
<223> OTHER INFORMATION: Chemically Synthesized, M42 humanized Fv
      sequence Heavy chain

<400> SEQUENCE: 223

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Leu Thr Thr Tyr
            20                  25                  30

Gly Val His Trp Val Arg Gln Ala Pro Gly Lys Gly Leu Glu Trp Val
        35                  40                  45

Ala Leu Ile Gly Asp Arg Gly Thr Thr Tyr Tyr Ala Asp Ser Val Lys
    50                  55                  60

Gly Arg Phe Thr Ile Ser Arg Asp Thr Ser Lys Asn Thr Ala Tyr Leu
65                  70                  75                  80

Gln Met Asn Ser Leu Arg Ala Glu Asp Thr Ala Val Tyr Tyr Cys Ala
                85                  90                  95

Arg Gly Ser Gly Tyr Gly Ala Arg Ile Trp Gly Gln Gly Thr Leu Val
            100                 105                 110

Thr Val Ser Ser
```

<210> SEQ ID NO 224
<211> LENGTH: 336
<212> TYPE: DNA
<213> ORGANISM: Artificial Sequence
<220> FEATURE:
<223> OTHER INFORMATION: Chemically Synthesized, M42 humanized Fv
      sequence Light chain

<400> SEQUENCE: 224

```
gatatccaga tgacccagtc cccgagctcc ctgtccgcct ctgtgggcga tagggtcacc      60
atcacctgcc gtgccagtca gaccgtgtat aacaacaact acgtagcctg gtatcaacag     120
aaaccaggaa aagctccgaa gcttctgatt tacgaaacca gcaaactcta ctctggagtc     180
ccttctcgct tctctggtag ccgttccggg acggatttca ctctgaccat cagcagtctg     240
cagccggaag acttcgcaac ttattactgt cagggcggct acagcggcgt ggacttcatg     300
gctttcggac agggtaccaa ggtggagatc aaacga                                336
```

<210> SEQ ID NO 225
<211> LENGTH: 112
<212> TYPE: PRT
<213> ORGANISM: Artificial Sequence
<220> FEATURE:
<223> OTHER INFORMATION: Chemically Synthesized, M42 humanized Fv
      sequence Light chain

<400> SEQUENCE: 225

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Thr Val Tyr Asn Asn
            20                  25                  30

Asn Tyr Val Ala Trp Tyr Gln Gln Lys Pro Gly Lys Ala Pro Lys Leu
        35                  40                  45

Leu Ile Tyr Glu Thr Ser Lys Leu Tyr Ser Gly Val Pro Ser Arg Phe
    50                  55                  60

Ser Gly Ser Arg Ser Gly Thr Asp Phe Thr Leu Thr Ile Ser Ser Leu
65                  70                  75                  80

Gln Pro Glu Asp Phe Ala Thr Tyr Tyr Cys Gln Gly Gly Tyr Ser Gly
                85                  90                  95

Val Asp Phe Met Ala Phe Gly Gln Gly Thr Lys Val Glu Ile Lys Arg
            100                 105                 110
```

<210> SEQ ID NO 226
<211> LENGTH: 45
<212> TYPE: PRT
<213> ORGANISM: Artificial Sequence
<220> FEATURE:
<223> OTHER INFORMATION: Chemically Synthesized, RPC1

<400> SEQUENCE: 226

Val Leu Glu Ala Leu Lys Asn Tyr Ile Lys Ile Asp Val Pro Trp Ala
1               5                   10                  15

Gly Gln Tyr Ile Thr Ser Asn Pro Cys Ile Arg Phe Val Ser Ile Asp
                20                  25                  30

Asn Lys Lys Arg Asn Ile Glu Ser Ser Glu Ile Gly Pro
            35                  40                  45

<210> SEQ ID NO 227
<211> LENGTH: 41
<212> TYPE: PRT
<213> ORGANISM: Artificial Sequence
<220> FEATURE:
<223> OTHER INFORMATION: Chemically Synthesized, RPC2

<400> SEQUENCE: 227

Val Leu Glu Ala Leu Lys Asn Tyr Ile Pro Trp Ala Gly Gln Tyr Ile
1               5                   10                  15

Thr Ser Asn Pro Cys Ile Arg Phe Val Ser Ile Asp Asn Lys Lys Arg
                20                  25                  30

Asn Ile Glu Ser Ser Glu Ile Gly Pro
            35                  40

<210> SEQ ID NO 228
<211> LENGTH: 28
<212> TYPE: PRT
<213> ORGANISM: Artificial Sequence
<220> FEATURE:
<223> OTHER INFORMATION: Chemically Synthesized, RPC3

<400> SEQUENCE: 228

Val Leu Glu Ala Leu Lys Asn Tyr Ile Arg Phe Val Ser Ile Asp Asn
1               5                   10                  15

Lys Lys Arg Asn Ile Glu Ser Ser Glu Ile Gly Pro
                20                  25

<210> SEQ ID NO 229
<211> LENGTH: 5
<212> TYPE: PRT
<213> ORGANISM: Artificial Sequence
<220> FEATURE:
<223> OTHER INFORMATION: Chemically Synthesized, BN498 M28 L3, sequence
      following triple STOP of SEQ ID NO:125

<400> SEQUENCE: 229

Phe Gly Gln Gly Thr
1               5

<210> SEQ ID NO 230
<211> LENGTH: 5
<212> TYPE: PRT
<213> ORGANISM: Artificial Sequence
<220> FEATURE:
<223> OTHER INFORMATION: Chemically Synthesized, BN484 M28 H1, sequence
      following triple STOP of SEQ ID NO:127

<400> SEQUENCE: 230

His Trp Val Arg Gln
1               5

<210> SEQ ID NO 231
<211> LENGTH: 5
<212> TYPE: PRT
<213> ORGANISM: Artificial Sequence
<220> FEATURE:
<223> OTHER INFORMATION: Chemically Synthesized, BN467 M28 and M42 H2,
      sequence following triple STOP of SEQ ID NO:129

<400> SEQUENCE: 231

Tyr Ala Asp Ser Val
1               5

<210> SEQ ID NO 232
<211> LENGTH: 5
<212> TYPE: PRT
<213> ORGANISM: Artificial Sequence
<220> FEATURE:
<223> OTHER INFORMATION: Chemically Synthesized, BN485 M28 and M42 H3,
      sequence following triple STOP of SEQ ID NO:131

<400> SEQUENCE: 232

Trp Gly Gln Gly Thr
1               5

<210> SEQ ID NO 233
<211> LENGTH: 5
<212> TYPE: PRT
<213> ORGANISM: Artificial Sequence
<220> FEATURE:
<223> OTHER INFORMATION: Chemically Synthesized, BN469 M42 L1, sequence
      following triple STOP of SEQ ID NO:133

<400> SEQUENCE: 233

Val Ala Trp Tyr Gln
1               5

<210> SEQ ID NO 234
<211> LENGTH: 5
<212> TYPE: PRT
<213> ORGANISM: Artificial Sequence
<220> FEATURE:
<223> OTHER INFORMATION: Chemically Synthesized, BN466 M42 H1, sequence
      following triple STOP of SEQ ID NO:135

<400> SEQUENCE: 234

His Trp Val Arg Gln
1               5

METHODS FOR MEASURING RENALASE

CROSS REFERENCE TO RELATED APPLICATIONS

This application is a U.S. national phase application filed under 35 U.S.C. § 371 claiming benefit to International Patent Application No. PCT/US2018/067608, filed Dec. 27, 2018, which is entitled to priority under 35 U.S.C. § 119 (e) to U.S. Provisional Patent Application No. 62/611,602, filed Dec. 29, 2017, each of which applications is hereby incorporated herein by reference in its entirety.

BACKGROUND OF THE INVENTION

Renalase (RNLS) is a protein produced predominantly in the kidney, heart, skeletal muscle, testes and to a lesser extent in other tissues (Xu et al., 2005 J Clin Invest. 115 (5):1275-80 and Wang et al., 2008 Mol Biol Rep. 35(4): 613-20). Two isoform variants of renalase have been described, Renalase-1 and Renalase-2. These two forms of renalase differ due to differential splicing of the final exon. Renalase has been described as a novel flavin adenine dinucleotide-containing monoamine oxidase with an activity that selectively deaminates the catecholamines epinephrine, norepinephrine and dopamine. A deficiency of renalase in the plasma of patients with end-stage renal disease, in comparison to healthy individuals, has been described. Catecholamines play a major role in the maintenance and modulation of blood pressure, including in disease, through effects on cardiac output and vascular resistance. The infusion of a recombinant form of renalase into rats caused a decrease in cardiac contractility, heart rate, and blood pressure. Patients with renal failure have been characterized with heightened levels of circulating catecholamines which correlate with hypertension and greater mortality through cardiovascular complications. Thus the protein renalase may play a role in the control and maintenance of catecholamine-induced changes in blood pressure and the deficiency of renalase observed in renal disease patients may be detrimental to outcomes.

A deficiency of renalase in the plasma of patients with end-stage renal disease, in comparison to healthy individuals, has been described. Patients with renal failure have been characterized with heightened levels of circulating catecholamines which correlate with hypertension and greater mortality through cardiovascular complications. Thus the protein renalase may play a role in the control and maintenance of catecholamine-induced changes in blood pressure and the deficiency of renalase observed in renal disease patients may be detrimental to outcomes. However, little is known about the role of renalase in cancer.

An essential feature of cancer is dysregulation of cell senescence and death. Renalase (RNLS) is a secreted flavoprotein that protects against ischemic and toxic cellular injury by signaling through the plasma membrane calcium ATPase PMCA4b to activate the PI3K/AKT, and MAPK pathways.

Skin cancer is a common human malignancy, and its incidence has been increasing in developed countries (Gray-Schopfer et al., 2007 Nature. 445:851-7; Lowe et al., 2014 Mayo Clinic Proceedings. 89:52-9; Lesinski et al., 2013 Future oncology. 9:925-7). Melanoma is the deadliest form of skin cancer, with low survival rates once it becomes unresectable (Lowe et al., 2014 Mayo Clinic Proceedings. 89:52-9). It is a molecularly heterogeneous disease and some of the key alterations in signaling pathways that participate in disease development and progression have been identified. The Ras/Raf/MEK/ERK and the PI3K/AKT signaling pathways play key roles in the pathogenesis of melanoma (Gray-Schopfer et al., 2007 Nature. 445:851-7; Lesinski et al., 2013 Future oncology. 9:925-7; Yajima et al., 2012 Dermatology research and practice. 2012:354191). Mutations in Ras, Raf, PI3K or PTEN (PI3K inhibitor) can lead to the sustained activation of ERK and AKT, which in turn promote cell survival and proliferation. Dankort et al. demonstrated this well with conditional melanocyte-specific expression of BRaf$^{V600E}$ in mice, none of whom developed melanoma, however, revealed 100% penetrance of melanoma development when combined with silencing of the Pten tumor suppressor gene (Dankort et al., 2009 Nature genetics. 41:544-52). The elucidation of these pathogenic pathways has facilitated the development of specific inhibitors that target hyper-activated kinases. While these agents have proven effective in the treatment of selective groups of patients with metastatic melanoma, their beneficial actions are often short lived, hence the pressing need for the identification of additional therapeutic targets.

RNLS expression is markedly increased in melanoma tumors, and specifically in CD163+ tumor associated macrophages (TAMs). In a cohort of patients with primary melanoma, disease-specific survival was inversely correlated with RNLS expression in the tumor mass, suggesting a pathogenic role for RNLS. Inhibition of RNLS signaling using siRNA, anti-RNLS antibodies, or a RNLS derived inhibitory peptide significantly decreases melanoma cells survival in vitro. Anti-RNLS therapy with a monoclonal antibody markedly inhibits melanoma tumor growth in a xenograft mouse model. Treatment with m28-RNLS (also previously known as 1D-28-4), caused a marked reduction in endogenous RNLS expression, and in total and phosphorylated STAT3 in CD163$^{+}$ TAMs. Increased apoptosis in tumor cells was temporally related to p38 MAPK mediated activation of the B-cell lymphoma 2 related protein Bax. Expression of the cell cycle inhibitor p21 increased and cell cycle arrest was documented. These results indicate that increased RNLS production by CD163$^{+}$ TAMs facilitates melanoma growth by activating STAT3, and that inhibition of RNLS signaling has potential therapeutic application in the management of melanoma.

Improved methods for the detection of renalase in bodily fluids and tissues may aid in the diagnosis and prognosis of renal disease, cardiovascular disease and/or cancer. However, the validation of renalase as a relevant biomarker requires highly selective reagents for its detection. Antibody-based technologies are widely used for the detection of biomarkers. To date there have been only a small number of reagent antibodies raised against renalase with no to minimal characterization.

Pancreatic cancer is one of the most lethal neoplasms, causing approximately 330,000 death globally and 40,000 in the US (World Cancer Report 2014. WHO Press; 2014). Pancreas cancer is difficult to detect, and most cases are diagnosed at a late stage (Nolen et al., 2014 PLoS ONE. 9(4):e94928). Although there has been some progress in the use of chemotherapy of this cancer, the disease remains extremely resistant to all drug therapies (Hidalgo et al., 2010 New England Journal of Medicine. 362(17):1605-17). The overall 5-year survival for individuals with pancreatic cancer is <5% (Hidalgo et al., 2010 New England Journal of Medicine. 362(17):1605-17), and additional therapeutic targets are needed.

The development of pancreatic cancer relies on the stepwise accumulation of gene mutations (Jones et al., 2008

Science. 321(5897):1801-6), some of which cause abnormal MAPK, PI3K and JAK-STAT signaling. Progression from minimally dysplastic epithelium to dysplasia to invasive carcinoma reflects the stepwise accumulation of gene mutations that either activate oncogenes (e.g. KRAS2), or inactivate tumor suppressor genes 9 e.g. CDKN2a/NK4a, TP53 and DPC4/SMaD4) (Hidalgo et al., 2012 Annals of Oncology. 23(suppl 10):x135-x8). Ninety-five, 90 and 75% of pancreatic tumors carry mutations in KRAS2, CDKN2a, and TP53, respectively. These mutations result in sustained and dysregulated proliferation that characterizes cancer growth. The mutational landscape and core signaling pathways in pancreatic ductal adenocarcinoma (PDAC) have been defined through a comprehensive genetic analysis of 24 advanced PDACs (Jones et al., 2008 Science. 321(5897): 1801-6). These data indicate that most PDACs contain a large number of genetic changes that are primarily point mutations, and which affect approximately 12 cell signaling pathways.

That study also identified five hundred and forty-one genes overexpressed in PDAC by at least 10-fold in 90% of the tumors. This included a 2 to 4-fold increase in the recently characterized protein, renalase (RNLS), in tumors or in tumor derived cell lines. RNLS, a novel secreted flavo-protein (Xu et al., 2005 J Clin Invest. 115(5):1275-80; Desir et al., 2012 J Am Heart Assoc. 1(e002634; Desir et al., 2012 J Am Soc Hypertens. 6(6):417-26; Li et al., 2008 Circulation. 117(10):1277-82) with NADH oxidase activity, (Farzaneh-Far et al., 2010 PLoS One. 5(10):e13496; Beaupre et al., 2015 Biochemistry. 54(3):795-806) promotes cell and organ survival (Lee et al., 2013 J Am Soc Nephrol. 24(3):445-55) through a receptor-mediated process that is independent of its intrinsic enzymatic activities (Wang et al., 2014 Journal of the American Society of Nephrology. DOI: 10.1681/asn.2013060665). RNLS rapidly activates protein kinase B (AKT), the extracellular signal-regulated kinase (ERK), and the mitogen activated protein kinase (p38). Chemical inhibition of either ERK or AKT abrogated the protective effect of RNLS (Wang et al., 2014 Journal of the American Society of Nephrology. DOI:10.1681/asn.2013060665).

Accordingly, there exists a need for improved methods and compositions that bind renalase, such as antibodies, for the detection, diagnosis, and prevention of diseases or disorders including inflammatory disease, renal disease, cardiovascular disease, and cancer. The present invention addresses this need.

SUMMARY OF THE INVENTION

In one embodiment, the invention relates to a method of measuring the amount of a renalase polypeptide or a renalase polypeptide fragment in a sample, comprising contacting the renalase polypeptide or the renalase polypeptide fragment of the sample with a composition comprising an antibody or binding portion thereof that specifically binds to renalase or a fragment thereof.

In one embodiment, the renalase is human renalase.

In one embodiment, the antibody or binding portion thereof is a monoclonal antibody, a polyclonal antibody, a single chain antibody, an immunoconjugate, a defuicosylated antibody, or a bispecific antibody.

In one embodiment, the immunoconjugate comprises a therapeutic agent or a detection moiety.

In one embodiment, the antibody or binding portion thereof is a humanized antibody, a chimeric antibody, a fully human antibody, or an antibody mimetic.

In one embodiment, the antibody or binding portion thereof comprises at least one selected from the group consisting of: a) a heavy chain (H) CDR1 comprising an amino acid sequence of SEQ ID NO: 155, b) a HC CDR2 comprising an amino acid sequence selected from the group consisting of SEQ ID NO: 156, SEQ ID NO: 162, and SEQ ID NO: 168, c) a HC CDR3 comprising an amino acid sequence selected from the group consisting of SEQ ID NO: 157, and SEQ ID NO: 163, d) a light chain (LC) CDR1 comprising the amino acid sequence of SEQ ID NO: 152, e) a LC CDR2 comprising the amino acid sequence of SEQ ID NO: 153, and f) a LC CDR3 comprising an amino acid sequence selected from the group consisting of SEQ ID NO: 154, and SEQ ID NO: 160.

In one embodiment, the antibody or binding portion thereof comprises a HC CDR1 comprising the amino acid sequence of SEQ ID NO: 155, a HC CDR2 comprising the amino acid sequence of SEQ ID NO: 156, a HC CDR3 comprising the amino acid sequence of SEQ ID NO: 157, a LC CDR1 comprising the amino acid sequence of SEQ ID NO: 152, a LC CDR2 comprising the amino acid sequence of SEQ ID NO: 153, and a LC CDR3 comprising the amino acid sequence of SEQ ID NO: 154.

In one embodiment, the antibody or binding portion thereof comprises a VH comprising the amino acid sequence of SEQ ID NO: 219 and a VL comprising the amino acid sequence of SEQ ID NO: 221.

In one embodiment, the antibody or binding portion thereof comprises at least one selected from the group consisting of: a) a HC CDR1 comprising an amino acid sequence selected from the group consisting of SEQ ID NO: 197 and SEQ ID NO: 203, b) a HC CDR2 comprising an amino acid sequence selected from the group consisting of SEQ ID NO: 198 and SEQ ID NO: 204, c) a HC CDR3 comprising an amino acid sequence selected from the group consisting of SEQ ID NO: 199 and SEQ ID NO: 205, d) a LC CDR1 comprising an amino acid sequence selected from the group consisting of SEQ ID NO: 194 and SEQ ID NO: 200, e) a LC CDR2 comprising the amino acid sequence of SEQ ID NO: 195, f) and a LC CDR3 comprising the amino acid sequence of SEQ ID NO: 196.

In one embodiment, the antibody or binding portion thereof comprises a HC CDR1 comprising the amino acid sequence of SEQ ID NO: 197, a HC CDR2 comprising the amino acid sequence of SEQ ID NO: 198, a HC CDR3 comprising the amino acid sequence of SEQ ID NO: 199, a LC CDR1 comprising the amino acid sequence of SEQ ID NO: 194, a LC CDR2 comprising the amino acid sequence of SEQ ID NO: 195, and a LC CDR3 comprising the amino acid sequence of SEQ ID NO: 196.

In one embodiment, the antibody or binding portion thereof comprises a $V_H$ comprising the amino acid sequence of SEQ ID NO: 223 and $V_L$ comprising the amino acid sequence of SEQ ID NO: 225.

In one embodiment, the invention relates to a method of treating or preventing a disease or disorder in a subject, the method comprising measuring the amount of a renalase polypeptide or a renalase polypeptide fragment in a sample, comprising contacting the renalase polypeptide or the renalase polypeptide fragment of the sample with a composition comprising an antibody or binding portion thereof that specifically binds to renalase or a fragment thereof, and further comprising administering to the subject a composition comprising antibody or binding portion thereof that specifically binds to renalase.

In one embodiment, the method further comprises the step of administering to the subject at least one additional therapeutic or prophylactic agent.

In one embodiment, the disease or disorder is at least one selected from the group consisting of renal disease, cardiovascular disease, and cancer.

In one embodiment, the disease or disorder is cancer, and the cancer is pancreatic cancer or melanoma.

In one embodiment, the invention relates to a method of diagnosing a disease or disorder in a subject in need thereof, the method comprising: measuring the level of renalase in a biological sample of the subject according to the method of measuring the amount of a renalase polypeptide or a renalase polypeptide fragment in a sample, comprising contacting the renalase polypeptide or the renalase polypeptide fragment of the sample with a composition comprising an antibody or binding portion thereof that specifically binds to renalase or a fragment thereof, comparing the level of renalase in the biological sample of the subject with the level of renalase in a comparator control, and diagnosing the subject with a disease or disorder when the level of renalase in the biological sample of the subject is altered compared to the level of renalase in the comparator control.

In one embodiment, the level of renalase in the biological sample is determined to be altered when the level of renalase is altered by at least 10%, by at least 20%, by at least 30%, by at least 40%, by at least 50%, by at least 60%, by at least 70%, by at least 80%, by at least 90%, by at least 100%, by at least 200%, by at least 300%, by at least 400%, by at least 500%, by at least 600%, by at least 700%, by at least 800%, by at least 900%, or by at least 1000%, compared to the level of renalase in a comparator control.

In one embodiment, the comparator control is a positive control, a negative control, a reference standard, a historical control, a historical norm, or the level of a reference molecule in the biological sample.

In one embodiment, the comparator control is an acid-treated recombinant renalase, an acid-treated recombinant renalase fragment, RPC1, or RPC2 reference standard.

In one embodiment, the disease or disorder is inflammatory disease, renal disease, cardiovascular disease, or cancer.

In one embodiment, the disease or disorder is cancer, and the cancer is pancreatic cancer or melanoma.

In one embodiment, the method further comprises the step of administering a treatment to the subject that was diagnosed as having a disease or disorder.

In one embodiment, the subject is human.

In one embodiment, the invention relates to a reference standard comprising an acid-treated recombinant renalase, an acid-treated recombinant renalase fragment, RPC1, and RPC2.

BRIEF DESCRIPTION OF THE DRAWINGS

The following detailed description of embodiments of the invention will be better understood when read in conjunction with the appended drawings. It should be understood that the invention is not limited to the precise arrangements and instrumentalities of the embodiments shown in the drawings.

FIG. 1 depicts peptide antigens used to immunize rabbits (SEQ ID NOs: 1-7).

FIG. 2 depicts full-length renalase-1 protein sequence (SEQ ID NO: 8).

FIG. 3 depicts antigen positions within the renalase proteins (SEQ ID NO: 8 and SEQ ID NO: 50). Antigens 1A/1B, 1C, 1D, 1E, 1F, and 3A5 are depicted.

FIG. 4 depicts anti-1D epitope monoclonal 1D-28-4 heavy chain coding sequence (SEQ ID NO: 52) and amino acid sequence (SEQ ID NO: 9).

FIG. 5 depicts anti-1D epitope monoclonal 1D-28-4 light chain coding sequence (SEQ ID NO: 53) and amino acid sequence (SEQ ID NO: 10).

FIG. 6 depicts anti-1D epitope monoclonal 1D-37-10 heavy chain coding sequence (SEQ ID NO: 60) and amino acid sequence (SEQ ID NO: 17).

FIG. 7 depicts anti-1D epitope monoclonal 1D-37-10 light chain coding sequence (SEQ ID NO: 61) and amino acid sequence (SEQ ID NO: 18).

FIG. 8 depicts anti-1F epitope monoclonal 1F-26-1 heavy chain coding sequence (SEQ ID NO: 68) and amino acid sequence (SEQ ID NO: 25).

FIG. 9 depicts anti-1F epitope monoclonal 1F-26-1 light chain coding sequence (SEQ ID NO: 69) and amino acid sequence (SEQ ID NO: 26).

FIG. 10 depicts anti-1F epitope monoclonal 1F-42-7 heavy chain coding sequence (SEQ ID NO: 76) and amino acid sequence (SEQ ID NO: 33).

FIG. 11 depicts anti-1F epitope monoclonal 1F-42-7 light chain coding sequence (SEQ ID NO: 77) and amino acid sequence (SEQ ID NO: 34).

FIG. 12 depicts anti-renalase-2 epitope monoclonal 3A-5-2 heavy chain coding sequence (SEQ ID NO: 84) and amino acid sequence (SEQ ID NO: 41).

FIG. 13 depicts anti-renalase-2 epitope monoclonal 3A-5-2 light chain coding sequence (SEQ ID NO: 85) and amino acid sequence (SEQ ID NO: 42).

FIG. 15, comprising (FIG. 15A) 1D-28-4 monoclonal showing renalase from kidney and brain, as well as recombinant renalase. (FIG. 15B) 1D-28-4 monoclonal showing renalase from human testis, heart and adrenal gland. (FIG. 15C) Western blots with Ren1D polyclonal, Ren1F polyclonal, Ren 1F 42-7 monoclonal and the whole protein polyclonal E2930 are shown. (FIG. 15D) Detection of rat, mouse or pig kidney renalase with the whole protein polyclonal antibody E2930 is shown.

FIG. 20, comprising (FIG. 20A) The capture and detection of purified recombinant renalase expressed from bacterial cells. (FIG. 20B) In a second example using the same protocol, the polyclonal antibody #3018, raised against the id epitope was used as the capture antibody and the biotinylated monoclonal antibody Ren 1C 22-1 was used as the detection antibody.

FIG. 22, comprising

FIG. 27 depicts that different methods were tested to disrupt the renalase complex in human plasma, and it was found that acidification of the plasma samples for 10 minutes with either HCl or citric acid unmasked the antigenic site, thus enabling m42-RNLS to serve as the capture antibody in a sandwich ELISA assay using electro-chemiluminescence detection.

FIG. 29 depicts renalase levels in human plasma. Total and free plasma renalase levels were measured (mean±standard deviation) in 15 control subjects, 45 with acute chest pain, and 78 with heart failure.

DETAILED DESCRIPTION

Figure 14:
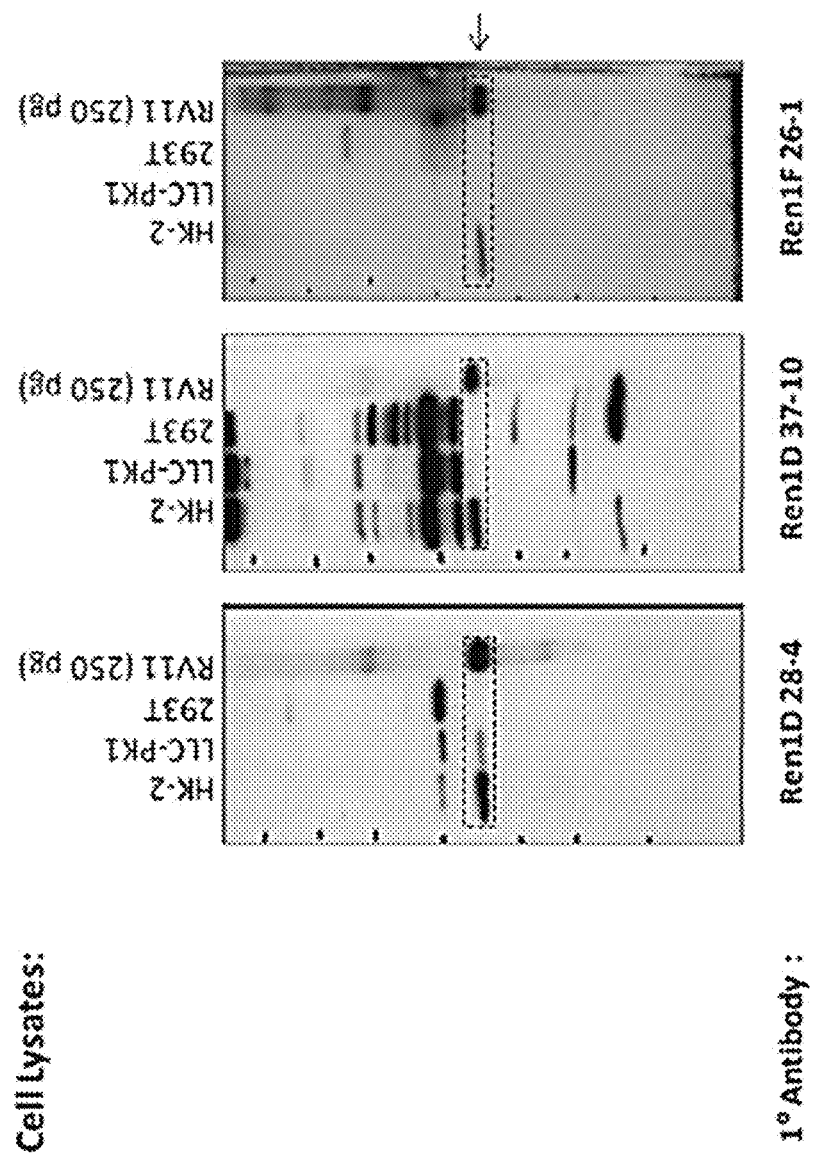
FIG. 14 depicts the use of renalase antibodies to detect renalase in cell lysates by western blotting. Significant renalase protein could be detected in HK-2 cells, with all of the antibodies tested. Renalase was also detected in LLC-PK1 cells by the Ren 1D 28-4 antibody, but not with the Ren 1D 37-10 or Ren 1F 26-1 antibodies, most likely reflecting both lower expression levels and differences in amino acid sequence between human and porcine renalase.

This invention relates to the measurement of renalase using an agent that binds to renalase. In various embodiments, the invention is directed to compositions and methods for diagnosing, preventing, or treating a renalase-associated pathology or renalase-associated condition in an individual by performing an assay that measures renalase in a biological sample. In various embodiments, the diseases and disorders diagnosable, preventable and treatable using the compositions and methods of the invention include acute renal failure (i.e., acute tubular necrosis, or ATN, an ischemic condition in the kidney), inflammatory disease, cardiovascular disease, and cancer.

In one embodiment, the invention broadly relates to the treatment, prevention, and diagnosis of a renalase-associated condition, such as cancer. In one embodiment, the present invention is directed to methods and compositions for diagnosis, treatment, inhibition, prevention, or reduction of a renalase-associated condition. In one embodiment, the invention provides compositions and methods for measuring one or more of the level, production, and activity of renalase. In the context of renalase-associated conditions and related diseases and disorders, the invention provides compositions and methods for measuring one or more of the level, production, and activity of renalase. Some aspects of the invention provide methods and compositions for the treatment, prevention, diagnosis or prognosis of a renalase-associated condition.

DEFINITIONS

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

Generally, the nomenclature used herein and the laboratory procedures in cell culture, molecular genetics, organic chemistry, and nucleic acid chemistry and hybridization are those well-known and commonly employed in the art.

Standard techniques are used for nucleic acid and peptide synthesis. The techniques and procedures are generally performed according to conventional methods in the art and various general references (e.g., Sambrook and Russell, 2012, Molecular Cloning, A Laboratory Approach, Cold Spring Harbor Press, Cold Spring Harbor, NY, and Ausubel et al., 2012, Current Protocols in Molecular Biology, John Wiley & Sons, NY), which are provided throughout this document.

The nomenclature used herein and the laboratory procedures used in analytical chemistry and organic syntheses described below are those well-known and commonly employed in the art. Standard techniques or modifications thereof are used for chemical syntheses and chemical analyses.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, or +0.1% from the specified value, as such variations are appropriate to perform the disclosed methods.

The term "abnormal" when used in the context of organisms, tissues, cells or components thereof, refers to those organisms, tissues, cells or components thereof that differ in at least one observable or detectable characteristic (e.g., age, treatment, time of day, etc.) from those organisms, tissues, cells or components thereof that display the "normal" (expected/homeostatic) respective characteristic. Characteristics which are normal or expected for one cell, tissue type, or subject, might be abnormal for a different cell or tissue type.

The term "analog" as used herein generally refers to compounds that are generally structurally similar to the compound of which they are an analog, or "parent" compound. Generally analogs will retain certain characteristics of the parent compound, e.g., a biological or pharmacological activity. An analog may lack other, less desirable characteristics, e.g., antigenicity, proteolytic instability, toxicity, and the like. An analog includes compounds in which a particular biological activity of the parent is reduced, while one or more distinct biological activities of the parent are unaffected in the "analog." As applied to polypeptides, the term "analog" may have varying ranges of amino acid sequence identity to the parent compound, for example at least about 70%, more preferably at least about 80%-85% or about 86%-89%, and still more preferably at least about 90', about 92%, about 94%, about 96%, about 98% or about 99% of the amino acids in a given amino acid sequence the parent or a selected portion or domain of the parent. As applied to polypeptides, the term "analog" generally refers to polypeptides which are comprised of a segment of about at least 3 amino acids that has substantial identity to at least a portion of a binding domain fusion protein. Analogs typically are at least 5 amino acids long, at least 20 amino acids long or longer, at least 50 amino acids long or longer, at least 100 amino acids long or longer, at least 150 amino acids long or longer, at least 200 amino acids long or longer, and more typically at least 250 amino acids long or longer. Some analogs may lack substantial biological activity but may still be employed for various uses, such as for raising antibodies to predetermined epitopes, as an immunological reagent to detect and/or purify reactive antibodies by affinity chromatography, or as a competitive or noncompetitive agonist, antagonist, or partial agonist of a binding domain fusion protein function.

The term "antibody," as used herein, refers to an immunoglobulin molecule which is able to specifically bind to a specific epitope of a binding partner molecule. Antibodies can be intact immunoglobulins derived from natural sources, or from recombinant sources and can be immunoreactive portions of intact immunoglobulins. The antibodies in the present invention may exist in a variety of forms including, for example, polyclonal antibodies, monoclonal antibodies, intracellular antibodies ("intrabodies"), Fv, Fab, Fab', F(ab)$_2$ and F(ab')$_2$, as well as single chain antibodies (scFv), heavy chain antibodies, such as camelid antibodies, and humanized antibodies (Harlow et al., 1999, Using Antibodies: A Laboratory Manual, Cold Spring Harbor Laboratory Press, NY; Harlow et al., 1989, Antibodies: A Laboratory Manual, Cold Spring Harbor, New York; Houston et al., 1988, Proc. Natl. Acad. Sci. USA 85:5879-5883; Bird et al., 1988, Science 242:423-426).

The term "antibody fragment" refers to at least one portion of an intact antibody and refers to the antigenic determining variable regions of an intact antibody. Examples of antibody fragments include, but are not limited to, Fab, Fab', F(ab')2, and Fv fragments, linear antibodies, sdAb (either $V_L$ or $V_H$), camelid $V_{HH}$ domains, scFv antibodies, and multi-specific antibodies formed from antibody fragments. The term "scFv" refers to a fusion protein comprising at least one antibody fragment comprising a variable region of a light chain and at least one antibody fragment comprising a variable region of a heavy chain, wherein the light and heavy chain variable regions are contiguously linked via a short flexible polypeptide linker, and capable of being expressed as a single chain polypeptide, and wherein the scFv retains the specificity of the intact antibody from which it was derived. Unless specified, as used herein an scFv may have the $V_L$ and $V_H$ variable regions in either order, e.g., with respect to the N-terminal and C-terminal ends of the polypeptide, the scFv may comprise $V_L$-linker-$V_H$ or may comprise $V_H$-linker-$V_L$.

An "antibody heavy chain," as used herein, refers to the larger of the two types of polypeptide chains present in antibody molecules in their naturally occurring conformations, and which normally determines the class to which the antibody belongs.

An "antibody light chain," as used herein, refers to the smaller of the two types of polypeptide chains present in antibody molecules in their naturally occurring conformations. Kappa (κ) and lambda (λ) light chains refer to the two major antibody light chain isotypes.

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

A "chimeric antibody" refers to a type of engineered antibody which contains a naturally-occurring variable region (light chain and heavy chains) derived from a donor antibody in association with light and heavy chain constant regions derived from an acceptor antibody.

A "humanized antibody" refers to a type of engineered antibody having its CDRs derived from a non-human donor immunoglobulin, the remaining immunoglobulin-derived parts of the molecule being derived from one (or more) human immunoglobulin(s). In addition, framework support residues may be altered to preserve binding affinity (see, e.g., 1989, Queen et al., Proc. Nat. Acad Sci USA, 86:10029-10032; 1991, Hodgson et al., Bio/Technology, 9:421). A suitable human acceptor antibody may be one selected from a conventional database, e.g., the KABAT database, Los Alamos database, and Swiss Protein database, by homology to the nucleotide and amino acid sequences of the donor antibody. A human antibody characterized by a homology to the framework regions of the donor antibody (on an amino acid basis) may be suitable to provide a heavy chain constant region and/or a heavy chain variable framework region for insertion of the donor CDRs. A suitable acceptor antibody capable of donating light chain constant or variable framework regions may be selected in a similar manner. It should be noted that the acceptor antibody heavy and light chains are not required to originate from the same acceptor antibody. The prior art describes several ways of producing such humanized antibodies (see for example EP-A-0239400 and EP-A-054951).

The term "donor antibody" refers to an antibody (monoclonal, and/or recombinant) which contributes the amino acid sequences of its variable regions, CDRs, or other functional fragments or analogs thereof to a first immunoglobulin partner, so as to provide the altered immunoglobulin coding region and resulting expressed altered antibody with the binding specificity and neutralizing activity characteristic of the donor antibody.

The term "acceptor antibody" refers to an antibody (monoclonal and/or recombinant) heterologous to the donor antibody, which contributes all (or any portion, but in some embodiments all) of the amino acid sequences encoding its heavy and/or light chain framework regions and/or its heavy and/or light chain constant regions to the first immunoglobulin partner. In certain embodiments a human antibody is the acceptor antibody.

"CDRs" are defined as the complementarity determining region amino acid sequences of an antibody which are the hypervariable regions of immunoglobulin heavy and light chains. See, e.g., Kabat et al., Sequences of Proteins of Immunological Interest, 4th Ed., U.S. Department of Health and Human Services, National Institutes of Health (1987). There are three heavy chain and three light chain CDRs (or CDR regions) in the variable portion of an immunoglobulin. Thus, "CDRs" as used herein refers to all three heavy chain CDRs, or all three light chain CDRs (or both all heavy and all light chain CDRs, if appropriate). The structure and protein folding of the antibody may mean that other residues are considered part of the binding region and would be understood to be so by a skilled person. See for example Chothia et al., (1989) Conformations of immunoglobulin hypervariable regions; Nature 342, p 877-883.

The term "framework" or "framework sequence" refers to the remaining sequences of a variable region minus the CDRs. Because the exact definition of a CDR sequence may be determined by different systems, the meaning of a framework sequence is subject to correspondingly different interpretations. The six CDRs (CDR-L1, -L2, and -L3 of light chain and CDR-H1, —H2, and —H3 of heavy chain) also divide the framework regions on the light chain and the heavy chain into four sub-regions (FR1, FR2, FR3 and FR4) on each chain, in which CDR1 is positioned between FR1 and FR2, CDR2 between FR2 and FR3, and CDR3 between FR3 and FR4. Without specifying the particular sub-regions as FR1, FR2, FR3 or FR4, a framework region, as referred by others, represents the combined FR's within the variable region of a single, naturally occurring immunoglobulin chain. An FR represents one of the four sub-regions, and FRs represents two or more of the four sub-regions constituting a framework region.

As used herein, an "immunoassay" refers to any binding assay that uses an antibody capable of binding specifically to a target molecule to detect and quantify the target molecule.

By the term "specifically binds," as used herein with respect to an antibody, is meant an antibody which recognizes a specific binding partner molecule, but does not substantially recognize or bind other molecules in a sample. For example, an antibody that specifically binds to a binding partner molecule from one species may also bind to that binding partner molecule from one or more species. But, such cross-species reactivity does not itself alter the classification of an antibody as specific. In another example, an antibody that specifically binds to binding partner molecule may also bind to different allelic forms of the binding partner molecule. However, such cross reactivity does not itself alter the classification of an antibody as specific.

In some instances, the terms "specific binding" or "specifically binding", can be used in reference to the interaction of an antibody, a protein, or a peptide with a second binding partner molecule, to mean that the interaction is dependent upon the presence of a particular structure (e.g., an antigenic determinant or epitope) on the binding partner molecule; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody. In some instances, the terms "specific binding" and "specifically binding" refers to selective binding, wherein the antibody recognizes a sequence or conformational epitope important for the enhanced affinity of binding to the binding partner molecule.

The term "epitope" has its ordinary meaning of a site on binding partner molecule recognized by an antibody or a binding portion thereof or other binding molecule, such as, for example, an scFv. Epitopes may be molecules or segments of amino acids, including segments that represent a small portion of a whole protein or polypeptide. Epitopes may be conformational (i.e., discontinuous). That is, they may be formed from amino acids encoded by noncontiguous parts of a primary sequence that have been juxtaposed by protein folding.

The phrase "biological sample" as used herein, is intended to include any sample comprising a cell, a tissue, or a bodily fluid in which expression of a nucleic acid or polypeptide can be detected. Examples of such biological samples include but are not limited to blood, lymph, bone marrow, biopsies and smears. Samples that are liquid in nature are referred to herein as "bodily fluids." Biological samples may be obtained from a patient by a variety of techniques including, for example, by scraping or swabbing an area or by using a needle to obtain bodily fluids. Methods for collecting various body samples are well known in the art.

The term "cancer" as used herein is defined as disease characterized by the abnormal growth of aberrant cells. Cancer cells can spread locally or through the bloodstream and lymphatic system to other parts of the body. Examples of various cancers include but are not limited to, breast cancer, prostate cancer, ovarian cancer, cervical cancer, skin cancer (e.g., melanoma), pancreatic cancer, colorectal cancer, renal cancer, liver cancer, brain cancer, lymphoma, leukemia, lung cancer, sarcoma and the like.

As used herein, "conjugated" refers to covalent attachment of one molecule to a second molecule.

A "coding region" of a gene consists of the nucleotide residues of the coding strand of the gene and the nucleotides of the non-coding strand of the gene which are homologous with or complementary to, respectively, the coding region of an mRNA molecule which is produced by transcription of the gene.

A "coding region" of a mRNA molecule also consists of the nucleotide residues of the mRNA molecule which are matched with an anti-codon region of a transfer RNA molecule during translation of the mRNA molecule or which encode a stop codon. The coding region may thus include nucleotide residues comprising codons for amino acid residues which are not present in the mature protein encoded by the mRNA molecule (e.g., amino acid residues in a protein export signal sequence).

"Complementary" as used herein to refer to a nucleic acid, refers to the broad concept of sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. Preferably, the first region comprises a first portion and the second region comprises a second portion, whereby, when the first and second portions are arranged in an antiparallel fashion, at least about 50%, and preferably at least about 75%, at least about 90%, or at least about 95% of the nucleotide residues of the first portion are capable of base pairing with nucleotide residues in the second portion. More preferably, all nucleotide residues of the first portion are capable of base pairing with nucleotide residues in the second portion.

As used herein, the term "derivative" includes a chemical modification of a polypeptide, polynucleotide, or other molecule. In the context of this invention, a "derivative polypeptide," for example, one modified by glycosylation, pegylation, or any similar process, retains binding activity. For example, the term "derivative" of binding domain includes binding domain fusion proteins, variants, or fragments that have been chemically modified, as, for example, by addition of one or more polyethylene glycol molecules, sugars, phosphates, and/or other such molecules, where the molecule or molecules are not naturally attached to wild-type binding domain fusion proteins. A "derivative" of a polypeptide further includes those polypeptides that are "derived" from a reference polypeptide by having, for example, amino acid substitutions, deletions, or insertions relative to a reference polypeptide. Thus, a polypeptide may be "derived" from a wild-type polypeptide or from any other polypeptide. As used herein, a compound, including polypeptides, may also be "derived" from a particular source, for example from a particular organism, tissue type, or from a particular polypeptide, nucleic acid, or other compound that is present in a particular organism or a particular tissue type.

The term "DNA" as used herein is defined as deoxyribonucleic acid.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting there from. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

A disease or disorder is "alleviated" if the severity of a sign or symptom of the disease or disorder, the frequency with which such a sign or symptom is experienced by a patient, or both, is reduced.

An "effective amount" or "therapeutically effective amount" of a compound is that amount of compound which is sufficient to provide a beneficial effect to the subject to which the compound is administered.

The term "high affinity" for binding domain polypeptides described herein refers to a dissociation constant (Kd) of at least about $10^{-6}$M, preferably at least about $10^{-7}$M, more preferably at least about $10^{-8}$M or stronger, more preferably at least about $10^{-9}$M or stronger, more preferably at least about $10^{-10}$M or stronger, for example, up to $10^{-12}$ M or stronger. However, "high affinity" binding can vary for other binding domain polypeptides.

The term "inhibit," as used herein, means to suppress or block an activity or function, for example, about ten percent relative to a control value. Preferably, the activity is suppressed or blocked by 50% compared to a control value, more preferably by 75%, and even more preferably by 95%. "Inhibit," as used herein, also means to reduce the level of a molecule, a reaction, an interaction, a gene, an mRNA, and/or a protein's expression, stability, function or activity by a measurable amount or to prevent entirely. Inhibitors are compounds that, e.g., bind to, partially or totally block activity, decrease, prevent, delay activation, inactivate, desensitize, or down regulate a protein, a gene, and an mRNA stability, expression, function and activity, e.g., antagonists.

The terms "modulator" and "modulation" of a molecule of interest, as used herein in its various forms, is intended to encompass antagonism, agonism, partial antagonism and/or partial agonism of an activity associated the protease of interest. In various embodiments, "modulators" may inhibit or stimulate protease expression or activity. Such modulators include small molecules agonists and antagonists of a protease molecule, antisense molecules, ribozymes, triplex molecules, and RNAi polynucleotides, and others.

As used herein, an "instructional material" includes a publication, a recording, a diagram, or any other medium of expression which can be used to communicate the usefulness of a compound, composition, vector, or delivery system of the invention in the kit for effecting alleviation of the various diseases or disorders recited herein. Optionally, or alternately, the instructional material can describe one or more methods of alleviating the diseases or disorders in a cell or a tissue of a mammal. The instructional material of the kit of the invention can, for example, be affixed to a container which contains the identified compound, composition, vector, or delivery system of the invention or be shipped together with a container which contains the identified compound, composition, vector, or delivery system. Alternatively, the instructional material can be shipped separately from the container with the intention that the instructional material and the compound be used cooperatively by the recipient.

"Isolated" means altered or removed from the natural state. For example, a nucleic acid or a peptide naturally present in its normal context in a living animal is not "isolated," but the same nucleic acid or peptide partially or completely separated from the coexisting materials of its natural context is "isolated." An isolated nucleic acid or protein can exist in substantially purified form, or can exist in a non-native environment such as, for example, a host cell.

An "isolated nucleic acid" refers to a nucleic acid segment or fragment which has been separated from sequences which flank it in a naturally occurring state, i.e., a DNA fragment which has been removed from the sequences which are normally adjacent to the fragment, i.e., the sequences adjacent to the fragment in a genome in which it naturally occurs. The term also applies to nucleic acids which have been substantially purified from other components which naturally accompany the nucleic acid, i.e., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (i.e., as a cDNA or a genomic or cDNA fragment produced by PCR or restriction enzyme digestion) independent of other sequences. It also includes a recombinant DNA which is part of a hybrid gene encoding additional polypeptide sequence.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine. The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR, and the like, and by synthetic means.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

The term "conservative substitution," when describing a polypeptide, refers to a change in the amino acid composition of the polypeptide that does not substantially alter the activity of the polypeptide, i.e., substitution of amino acids with other amino acids having similar properties. Conservative substitution tables providing functionally similar amino acids are well known in the art. The following six groups each contain amino acids that are generally understood to represent conservative substitutions for one another: (1) Alanine (A), Serine (S), Threonine (T); (2) Aspartic acid (D), Glutamic acid (E); (3) Asparagine (N), Glutamine (Q); (4) Arginine (R), Lysine (K); (5) Isoleucine (I), Leucine (L), Methionine (M), Valine (V); and (6) Phenylalanine (F), Tyrosine (Y), Tryptophan (W) (see also, Creighton, 1984, Proteins, W.H. Freeman and Company). In addition to the above-defined conservative substitutions, other modifications of amino acid residues can also result in "conservatively modified variants." For example, one may regard all charged amino acids as substitutions for each other whether they are positive or negative. In addition, conservatively modified variants can also result from individual substitutions, deletions or additions which alter, add or delete a single amino acid or a small percentage of amino acids, for example, often less than 5%, in an encoded sequence. Further, a conservatively modified variant can be made from a recombinant polypeptide by substituting a codon for an amino acid employed by the native or wild-type gene with a different codon for the same amino acid.

The term "RNA" as used herein is defined as ribonucleic acid.

The term "recombinant DNA" as used herein is defined as DNA produced by joining pieces of DNA from different sources.

The term "recombinant polypeptide" as used herein is defined as a polypeptide produced by using recombinant DNA methods.

By "pharmaceutically acceptable" or "analytically acceptable" it is meant, for example, a carrier, diluent or excipient that is compatible with the other ingredients of the formulation and generally appropriate for use in an assay, or for administration to a subject. As used herein, "carrier"

includes any material, which when combined with the conjugate retains the conjugates' activity and is non-reactive with the subject's immune systems. Examples include, but are not limited to, any of the standard pharmaceutical carriers such as a phosphate buffered saline solution, water, emulsions such as oil/water emulsion, and various types of wetting agents. Other carriers may also include sterile solutions, tablets including coated tablets and capsules. Typically such carriers contain excipients such as starch, milk, sugar, certain types of clay, gelatin, stearic acid or salts thereof, magnesium or calcium stearate, talc, vegetable fats or oils, gums, glycols, or other known excipients. Such carriers may also include flavor and color additives or other ingredients. Compositions comprising such carriers are formulated by well-known conventional methods.

The terms "patient," "subject," "individual," and the like are used interchangeably herein, and refer to any animal, preferably a mammal, and most preferably a human, having a complement system, including a human in need of therapy for, or susceptible to, a condition or its sequelae. Thus, the individual may include, for example, dogs, cats, pigs, cows, sheep, goats, horses, rats, monkeys, and mice and humans.

"Identical" or "identity" as used herein in the context of two or more nucleic acids or polypeptide sequences, means that the sequences have a specified percentage of residues that are the same over a specified region. The percentage can be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) can be considered equivalent. Identity can be performed manually or by using a computer sequence algorithm such as BLAST or BLAST 2.0.

The phrase "percent (%) identity" or "percent identical" refers to the percentage of sequence similarity found in a comparison of two or more amino acid sequences. Percent identity can be determined electronically using any suitable software. Likewise, "similarity" between two polypeptides (or one or more portions of either or both of them) is determined by comparing the amino acid sequence of one polypeptide to the amino acid sequence of a second polypeptide. Any suitable algorithm useful for such comparisons can be adapted for application in the context of the invention.

A "therapeutic" treatment is a treatment administered to a subject who exhibits signs of pathology, for the purpose of diminishing or eliminating those signs.

"Therapeutically effective amount" is an amount of a compound of the invention, that when administered to a patient, ameliorates a symptom of the disease. The amount of a compound of the invention which constitutes a "therapeutically effective amount" will vary depending on the compound, the disease state and its severity, the age of the patient to be treated, and the like. The therapeutically effective amount can be determined routinely by one of ordinary skill in the art having regard to his own knowledge and to this disclosure.

The terms "treat," "treating," and "treatment," refer to therapeutic or preventative measures described herein. The methods of "treatment" employ administration to a subject, in need of such treatment, a composition of the present invention, for example, a subject afflicted a disease or disorder, or a subject who ultimately may acquire such a disease or disorder, in order to prevent, cure, delay, reduce the severity of, or ameliorate one or more symptoms of the disorder or recurring disorder, or in order to prolong the survival of a subject beyond that expected in the absence of such treatment.

"Variant" as the term is used herein, is a nucleic acid sequence or a peptide sequence that differs in sequence from a reference nucleic acid sequence or peptide sequence respectively, but retains essential biological properties of the reference molecule. Changes in the sequence of a nucleic acid variant may not alter the amino acid sequence of a peptide encoded by the reference nucleic acid, or may result in amino acid substitutions, additions, deletions, fusions and truncations. Changes in the sequence of peptide variants are typically limited or conservative, so that the sequences of the reference peptide and the variant are closely similar overall and, in many regions, identical. A variant and reference peptide can differ in amino acid sequence by one or more substitutions, additions, deletions in any combination. A variant of a nucleic acid or peptide can be a naturally occurring such as an allelic variant, or can be a variant that is not known to occur naturally. Non-naturally occurring variants of nucleic acids and peptides may be made by mutagenesis techniques or by direct synthesis.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

DESCRIPTION

This invention relates to the measurement of renalase using an agent that specifically binds renalase. In various embodiments, the invention is directed to compositions and methods for diagnosing, preventing, or treating a renalase-associated disease or disorder in an individual by measuring renalase in a biological sample from the individual. In some embodiments, the renalase binding molecule is an antibody. In various embodiments, the diseases and disorders diagnosable, preventable and treatable using the compositions and methods of the invention include acute renal failure (i.e., acute tubular necrosis, or ATN, an ischemic condition in the kidney), inflammatory disease, cardiovascular disease, and cancer.

Renalase Measurement Compositions and Methods of Use

In various embodiments, the present invention includes renalase measurement compositions and methods of treating or preventing a disease or disorder associated with renalase. In various embodiments, the renalase measurement compositions and methods of treatment or prevention of the invention measure the amount of active renalase polypeptide, the amount of active renalase peptide fragment, the amount of renalase enzymatic activity, the amount of renalase substrate binding activity, the amount of renalase receptor binding activity, or a combination thereof.

In some embodiments, the renalase measurement compositions and methods comprise a comparator control. In some embodiments, the comparator control is a reference standard. In various embodiments, the reference standard comprises one selected from the group consisting of an acid-treated recombinant renalase, an acid-treated recombinant renalase fragment, RPC1, and RPC2.

It will be understood by one skilled in the art, based upon the disclosure provided herein, that a measurement of the level of active renalase encompasses measurement of renalase at the protein level. The skilled artisan will also appreciate, once armed with the teachings of the present invention, that a measurement of the level of active renalase includes a measurement of a renalase activity (e.g., enzymatic activity, substrate binding activity, receptor binding activity, etc.). Thus, measuring the level or activity of renalase includes, but is not limited to, measuring transcription, translation, or both, of a nucleic acid encoding renalase; and it also includes measuring any activity of a renalase polypeptide, or peptide fragment thereof, as well. The renalase measurement compositions and methods of the invention can selectively measure renalase, or can measure both renalase and another molecule.

Measurement of renalase can be performed using a wide variety of methods, including those disclosed herein, as well as methods known in the art or to be developed in the future. That is, the routineer would appreciate, based upon the disclosure provided herein, that measuring the level or activity of renalase can be readily performed using methods that assess the level of a nucleic acid encoding renalase (e.g., mRNA), the level of a renalase polypeptide, or peptide fragment thereof, present in a biological sample, the level of renalase activity (e.g., enzymatic activity, substrate binding activity, receptor binding activity, etc.), or combinations thereof.

One skilled in the art, based upon the disclosure provided herein, would understand that the invention is useful in treating or preventing a disease or disorder in a subject in need thereof, whether or not the subject is also being treated with other medication or therapy. Further, the skilled artisan would further appreciate, based upon the teachings provided herein, that the diseases or disorders treatable by the compositions and methods described herein encompass any disease or disorder where renalase plays a role. In various embodiments, the disease or disorder treatable or preventable using the compounds and methods of the invention include acute renal failure (i.e., acute tubular necrosis, or ATN, an ischemic condition in the kidney), a cardiovascular disease or disorder (e.g., hypertension, pulmonary hypertension, systolic hypertension, diabetic hypertension, asymptomatic left ventricular dysfunction, chronic congestive heart failure, myocardial infarction, cardiac rhythm disturbance, atherosclerosis, etc.), cancer, heart disease or disorder, a kidney disease or disorder, a gastrointestinal disease or disorder, a liver disease or disorder, a lung disease or disorder, a pancreas disease or disorder (e.g., pancreatitis), mental disease or disorder (e.g., depression, anxiety, etc.), or a neurological disease or disorder.

The renalase measurement compositions and methods of the invention that measure the level or activity (e.g., enzymatic activity, substrate binding activity, receptor binding activity, etc.) of renalase, or a renalase fragment, include, but should not be construed as being limited to, a chemical compound, a protein, a peptide, a peptidomemetic, an antibody, an antibody fragment, an antibody mimetic, a nucleic acid sequence encoding a protein, a renalase receptor, a renalase receptor fragment, or combinations thereof. One of skill in the art would readily appreciate, based on the disclosure provided herein, that a renalase measuring composition encompasses any chemical compound that is used to measure the level or activity of renalase, or a fragment thereof. Additionally, a renalase measurement composition encompasses a chemically modified compound, and derivatives, as is well known to one of skill in the chemical arts.

The renalase measurement compositions and methods of the invention that measure the level or activity (e.g., enzymatic activity, substrate binding activity, receptor binding activity, etc.) of renalase, or a renalase fragment, include antibodies, and fragments thereof. The antibodies of the invention include a variety of forms of antibodies including, for example, polyclonal antibodies, monoclonal antibodies, intracellular antibodies ("intrabodies"), Fv, Fab and F(ab)2, single chain antibodies (scFv), heavy chain antibodies (such as camelid antibodies), synthetic antibodies, chimeric antibodies, and humanized antibodies. In one embodiment, the antibody of the invention is an antibody that specifically binds to renalase. In some embodiments, the antibodies of the invention are bispecific antibodies, where the first specificity is to renalase and the second specificity is to a second molecule.

Further, one of skill in the art, when equipped with this disclosure and the methods exemplified herein, would appreciate that a renalase measurement composition includes such compounds as discovered in the future, as can be identified by well-known criteria in the art of biochemistry. Therefore, the present invention is not limited in any way to any particular renalase measurement composition as exemplified or disclosed herein; rather, the invention encompasses those measurement compositions that would be understood by the routineer to be useful as are known in the art and as are discovered in the future.

Further methods of identifying and producing renalase measurement compositions are well known to those of ordinary skill in the art, including, but not limited, obtaining a composition from a naturally occurring source (e.g., *Streptomyces* sp., *Pseudomonas* sp., *Stylotella aurantium*, etc.). Alternatively, a renalase measurement composition can be synthesized chemically. Further, the routineer would appreciate, based upon the teachings provided herein, that a renalase measurement composition can be obtained from a recombinant organism. Compositions and methods for chemically synthesizing renalase measurement compositions and for obtaining them from natural sources are well known in the art and are described in the art.

One of skill in the art will appreciate that a renalase measurement composition can be encoded by a nucleic acid sequence encoding a protein. Numerous vectors and other compositions and methods are well known for administering a nucleic acid construct encoding a protein to cells or tissues. Therefore, the invention includes a method of using a nucleic acid encoding a protein that binds to renalase. (Sambrook et al., 2012, Molecular Cloning: A Laboratory Manual, Cold Spring Harbor Laboratory, New York; Ausubel et al., 1997, Current Protocols in Molecular Biology, John Wiley & Sons, New York).

One of skill in the art will appreciate that compositions that measure renalase, or a renalase fragment, can be utilized acutely (e.g., over a short period of time, such as a day, a week or a month) or chronically (e.g., over a long period of time, such as several months or a year or more). One of skill in the art will appreciate that the compositions and methods disclosed herein can be utilized singly or in any combination with other compositions and methods. Further, renalase measurement can be performed singly or in any combination with another assay in a temporal sense, in that they may be performed concurrently, or before, and/or after each other. One of ordinary skill in the art will appreciate, based on the disclosure provided herein, that renalase measurement compositions can be used in methods to treat or prevent a disease or disorder in a subject in need thereof, and that a renalase measurement composition can be used alone or in any combination with another composition to effect a diagnostic or therapeutic result.

It will be appreciated by one of skill in the art, when armed with the present disclosure including the methods detailed herein, that the invention is not limited to treatment of a disease or disorder, such as cancer. Particularly, the disease or disorder need not have manifested to the point of detriment to the subject; indeed, the disease or disorder need not be detected in a subject before renalase, or a fragment thereof, is measured. That is, significant disease or disorder does not have to occur before the present invention may provide benefit. Therefore, the present invention includes a method for preventing a disease or disorder in a subject, in that a renalase measurement composition, as discussed previously elsewhere herein, can be used prior to the onset of the disease or disorder, as part of a method of preventing the disease or disorder from developing. The preventive methods described herein also include the treatment of a subject that is in remission for the prevention of a recurrence of a disease or disorder.

Additionally, as disclosed elsewhere herein, one skilled in the art would understand, once armed with the teaching provided herein, that the present invention encompasses a method of preventing a wide variety of diseases, disorders and pathologies where a change in expression and/or activity of renalase is characteristic of the disease, disorder or pathology. Methods for assessing whether a disease relates to the levels or activity of renalase are known in the art. Further, the invention encompasses treatment or prevention of such diseases discovered in the future.

The invention encompasses use of a composition that measures renalase to practice the methods of the invention; the skilled artisan would understand, based on the disclosure provided herein, how to formulate the appropriate renalase measurement composition. However, the present invention is not limited to any particular method of formulation.

In some instances, renalase can be used as a diagnostic marker for diseases or disorders including, but not limited to, acute renal failure (i.e., acute tubular necrosis, or ATN, an ischemic condition in the kidney), inflammatory disease, cardiovascular disease, and cancer. Patients without a properly functioning kidney possess lower levels of renalase. Accordingly, also included in the invention are methods of diagnosing susceptibility to cardiovascular, heart, kidney, gastrointestinal, liver, lung, pancreas and mental and neurological related conditions, disorders and diseases, including cancer, based on the detection and/or quantitation of renalase using the renalase binding agents of the present invention. For example, cardiovascular conditions, disorders and diseases such as hypertension, asymptomatic left ventricular dysfunction, chronic congestive heart failure, myocardial infarction, cardiac rhythm disturbance, and atherosclerosis; mental conditions, disorders and diseases such as depression and anxiety; and heart conditions, disorders and diseases, such as pulmonary hypertension, can all be diagnosed, evaluated and monitored by determining renalase levels, such as renalase protein levels. For example, reduced levels of the renalase protein would be a diagnostic marker for a disorder associated with an increased sympathetic output. The compositions and methods of the present invention can be used to treat, prevent, reduce or ameliorate hypertension, including systolic hypertension, isolated systolic hypertension and diabetic hypertension. Moreover, the same benefit is anticipated for the rare hypertensive disorder, pulmonary hypertension, as well as pancreatitis. Pulmonary hypertension is a rare blood vessel disorder of the lung in which the pressure in the pulmonary artery (the blood vessel that leads from the heart to the lungs) rises above normal levels and may become life threatening. The similarity in development of elevated blood pressure in the pulmonary bed with the increase in systemic blood pressure in diabetic hypertension and in isolated systolic hypertension suggests similar mechanisms are involved.

The renalase measurement compositions of the invention include, but should not be construed as being limited to, a chemical compound, a protein, a peptide, a peptidomemetic, an antibody, an antibody fragment, an antibody mimetic, a nucleic acid sequence encoding a protein, or combinations thereof. One of skill in the art would readily appreciate, based on the disclosure provided herein, that a renalase measurement composition encompasses a chemical compound that measures the level or activity of renalase. Additionally, a renalase measurement composition encompasses a chemically modified compound, and derivatives, as is well known to one of skill in the chemical arts.

The renalase measurement compositions of the invention include antibodies, and fragments thereof. The antibodies of the invention include a variety of forms of antibodies including, for example, polyclonal antibodies, monoclonal antibodies, intracellular antibodies ("intrabodies"), Fv, Fab and F(ab)2, single chain antibodies (scFv), heavy chain antibodies (such as camelid antibodies), synthetic antibodies, chimeric antibodies, and humanized antibodies. In one embodiment, the antibody of the invention is an antibody that specifically binds to renalase. In some embodiments, the antibodies of the invention are bispecific antibodies, where the first specificity is to renalase and the second specificity is to a second molecule.

Antibodies, including a renalase binding fragment thereof, of the present invention include, in certain embodiments, antibody amino acid sequences disclosed herein encoded by any suitable polynucleotide, or any isolated or formulated antibody. Further, antibodies of the present disclosure comprise antibodies having the structural and/or functional features of anti-renalase antibodies described herein. In one embodiment, the anti-renalase antibody binds renalase and, thereby partially or substantially alters at least one biological activity of renalase (e.g., enzymatic activity, substrate binding activity, receptor binding activity, etc.). In some embodiments, the renalase is human renalase.

In one embodiment, anti-renalase antibodies of the invention immunospecifically bind at least one specified epitope specific to the renalase protein, peptide, subunit, fragment, portion or any combination thereof and do not specifically bind to other polypeptides, other than renalase from other species. The at least one epitope can comprise at least one antibody binding region that comprises at least one portion of the renalase protein. The term "epitope" as used herein refers to a protein determinant capable of binding to an antibody. Epitopes usually consist of chemically active surface groupings of molecules such as amino acids or sugar side chains and usually have specific three dimensional structural characteristics, as well as specific charge characteristics. Conformational and non-conformational epitopes are distinguished in that the binding to the former but not the latter is lost in the presence of denaturing solvents.

In some embodiments, the invention includes compositions comprising an antibody that specifically binds to renalase (e.g., binding portion of an antibody). In one embodiment, the anti-renalase antibody is a polyclonal antibody. In another embodiment, the anti-renalase antibody is a monoclonal antibody. In some embodiments, the anti-renalase antibody is a chimeric antibody. In further embodiments, the anti-renalase antibody is a humanized antibody. In some embodiments, the renalase is human renalase. In some embodiments, the antibodies of the invention specifically bind to at least one of SEQ ID NOs: 1-7, 8, 50, 92, 94, and fragments thereof.

The binding portion of an antibody comprises one or more fragments of an antibody that retain the ability to specifically bind to binding partner molecule (e.g., renalase). It has been shown that the binding function of an antibody can be performed by fragments of a full-length antibody. Examples of binding fragments encompassed within the term "binding portion" of an antibody include (i) a Fab fragment, a monovalent fragment consisting of the $V_L$, $V_H$, $C_L$ and $C_H1$ domains; (ii) a F(ab')2 fragment, a bivalent fragment comprising two Fab fragments linked by a disulfide bridge at the hinge region; (iii) a Fd fragment consisting of the $V_H$ and $C_H1$ domains; (iv) a Fv fragment consisting of the $V_L$ and $V_H$ domains of a single arm of an antibody, (v) a dAb fragment (Ward et al., (1989) Nature 341:544-546), which consists of a $V_H$ domain; and (vi) an isolated complementarity determining region (CDR). Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. (1988) Science 242:423-426; and Huston et al. (1988) Proc. Nat. Acad. Sci. USA 85:5879-5883). Such single chain antibodies are also intended to be encompassed within the term "binding portion" of an antibody. These antibody fragments are obtained using conventional techniques known to those with skill in the art, and the fragments are screened for utility in the same manner as are intact antibodies. Binding portions can be produced by recombinant DNA techniques, or by enzymatic or chemical cleavage of intact immunoglobulins.

An antibody that binds to renalase of the invention may be an antibody that measures at least one renalase property (e.g., amount, enzymatic activity, substrate binding activity, receptor binding activity, etc.), in vitro, in situ and/or in vivo. A suitable anti-renalase antibody, specified portion, or variant can also optionally affect at least one renalase activity or function, such as but not limited to, RNA, DNA or protein synthesis, protein release, renalase signaling, renalase cleavage, renalase activity, renalase receptor binding, renalase production and/or synthesis.

In one embodiment, antibodies of the invention bind renalase. In one embodiment, the antibodies specifically bind to renalase-1. In another embodiment, the antibodies specifically bind to renalase-2. In yet another embodiment, the antibodies specifically bind to both renalase-1 and renalase-2. In addition, epitope specific antibodies have been generated. Preferred antibodies of the invention include monoclonal antibodies 1C-22-1, 1D-28-4, 1D-37-10, 1F-26-1, 1F-42-7 and 3A-5-2. Examples of dual specificity antibodies, e.g. antibodies that recognize renalase-1 and renalase-2 include antibodies 1C-22-1, 1D-28-4, 1D-37-10, and polyclonal antibodies as described herein. Examples of renalase-type specific antibodies include 1F-26-1, 1F-42-7, which are specific for renalase-1. 3A-5-2 is specific for renalase-2. Preferred antibody fragments of the invention include humanized heavy chain and light chain Fv regions, as set forth in SEQ ID NOs: 219, 221, 223, and 225. In various embodiments of the invention, an anti-renalase antibody or antibody fragment comprises humanized heavy chain and light chain Fv regions, as set forth in SEQ ID NOs: 219, 221, 223, and 225, or a fragment or portion thereof. Sequences encoding anti-renalase monoclonal antibodies are set forth in FIG. 4 through FIG. 13, and in Example 2.

The nucleic acid (SEQ ID NO: 52) and amino acid sequence (SEQ ID NO: 9) of the heavy chain coding sequence of monoclonal antibody 1D-28-4 are found in FIG. 4. The nucleic acid (SEQ ID NO: 53) and amino acid sequence (SEQ ID NO: 10) of the light chain coding sequence of monoclonal antibody 1D-28-4 are found in FIG. 5.

The nucleic acid (SEQ ID NO: 60) and amino acid sequence (SEQ ID NO: 17) of the heavy chain coding sequence of monoclonal antibody 1D-37-10 are found in FIG. 6. The nucleic acid (SEQ ID NO: 61) and amino acid sequence (SEQ ID NO: 18) of the light chain coding sequence of monoclonal antibody 1D-37-10 are found in FIG. 7.

The nucleic acid (SEQ ID NO: 68) and amino acid sequence (SEQ ID NO: 25) of the heavy chain coding sequence of monoclonal antibody 1F-26-1 are found in FIG. 8. The nucleic acid (SEQ ID NO: 69) and amino acid sequence (SEQ ID NO: 26) of the light chain coding sequence of monoclonal antibody 1F-26-1 are found in FIG. 9.

The nucleic acid (SEQ ID NO: 76) and amino acid sequence (SEQ ID NO: 33) of the heavy chain coding sequence of monoclonal antibody 1F-42-7 are found in FIG. 10. The nucleic acid (SEQ ID NO: 77) and amino acid sequence (SEQ ID NO: 34) of the light chain coding sequence of monoclonal antibody 1F-42-7 are found in FIG. 11.

The nucleic acid (SEQ ID NO: 84) and amino acid sequence (SEQ ID NO: 41) of the heavy chain coding sequence of monoclonal antibody 3A-5-2 are found in FIG. 12. The nucleic acid (SEQ ID NO: 85) and amino acid sequence (SEQ ID NO: 42) of the light chain coding sequence of monoclonal antibody 3A-5-2 are found in FIG. 13.

Given that certain embodiments of the monoclonal antibodies can bind to the renalase protein, the $V_H$ and $V_L$ sequences can be "mixed and matched" to create other anti-renalase binding molecules of this disclosure. Renalase binding of such "mixed and matched" antibodies can be tested using the binding assays described above and in the Examples (e.g., immunoblot, Bia-Core, etc.). Preferably, when $V_H$ and $V_L$ chains are mixed and matched, a $V_H$ sequence from a particular $V_H/V_L$ pairing is replaced with a structurally similar $V_H$ sequence. Likewise, preferably a $V_L$ sequence from a particular $V_H/V_L$ pairing is replaced with a structurally similar $V_L$ sequence.

Therefore, in one aspect, this disclosure provides an antibody or antibody fragment, wherein the antibody or antibody fragment comprises at least one polypeptide sequence encoding a novel heavy chain variable sequence. In another aspect, this disclosure provides an antibody or antibody fragment, wherein the antibody or antibody fragment comprises at least one polypeptide sequence encoding a novel light chain variable sequence.

In one embodiment, the first $V_H$ complementarity determining region (HC CDR1) comprises the amino acid sequence as set forth in SEQ ID NO: 155; the second $V_H$ complementarity determining region (HC CDR2) comprises the amino acid sequence selected from the group: SEQ ID NO: 156, SEQ ID NO: 162, and SEQ ID NO: 168; the third $V_H$ complementarity determining region (HC CDR3) comprises the amino acid sequence selected from the group: SEQ ID NO: 157, and SEQ ID NO: 163; the first $V_L$ complementarity determining region (LC CDR1) comprises the amino acid sequence as set forth in SEQ ID NO: 152; the second $V_L$ complementarity determining region (LC CDR2) comprises the amino acid sequence as set forth in SEQ ID NO: 153; the third $V_L$ complementarity determining region (LC CDR3) comprises the amino acid sequence selected from the group: SEQ ID NO: 154, and SEQ ID NO: 160. In one embodiment, the HC CDR1 comprises SEQ ID NO: 155; the HC CDR2 comprises SEQ ID NO: 156; the HC CDR3 comprises SEQ ID NO: 157; the LC CDR1 comprises SEQ ID NO: 152; the LC CDR2 comprises SEQ ID NO: 153; the LC CDR3 comprises SEQ ID NO: 154. In one embodiment, $V_H$ comprises SEQ ID NO: 219; $V_L$ comprises SEQ ID NO: 221. In one embodiment, the two polypeptides are linked by a linker to form a single chain variable fragment (scFv), wherein the arrangement of the polypeptides relative to the linker is selected from the group consisting of: $V_H$-linker-$V_L$, and $V_L$-linker-$V_H$.

In one embodiment, the first $V_H$ complementarity determining region (HC CDR1) comprises the amino acid sequence selected from the group: SEQ ID NO: 197, and SEQ ID NO: 203; the second $V_H$ complementarity determining region (HC CDR2) comprises the amino acid sequence selected from the group: SEQ ID NO: 198, and SEQ ID NO: 204; the third $V_H$ complementarity determining region (HC CDR3) comprises the amino acid sequence selected from the group: SEQ ID NO: 199, and SEQ ID NO: 205; the first $V_L$ complementarity determining region (LC CDR1) comprises the amino acid sequence selected from the group: SEQ ID NO: 194, and SEQ ID NO: 200; the second $V_L$ complementarity determining region (LC CDR2) comprises the amino acid sequence as set forth in SEQ ID NO: 195; the third $V_L$ complementarity determining region (LC CDR3) comprises the amino acid sequence as set forth in SEQ ID NO: 196. In one embodiment, the HC CDR1 comprises SEQ ID NO: 197; wherein the HC CDR2 comprises SEQ ID NO: 198; wherein the HC CDR3 comprises SEQ ID NO: 199; wherein the LC CDR1 comprises SEQ ID NO: 194; wherein the LC CDR2 comprises SEQ ID NO: 195; wherein the LC CDR3 comprises SEQ ID NO: 196. In one embodiment, $V_H$ comprises SEQ ID NO: 223; $V_L$ comprises SEQ ID NO: 225. In one embodiment, the two polypeptides are linked by a linker to form a single chain variable fragment (scFv), wherein the arrangement of the polypeptides relative to the linker is selected from the group: $V_H$-linker-$V_L$, and $V_L$-linker-$V_H$.

In various embodiments, the novel heavy chain variable sequence further comprises at least one additional polypeptide sequence. In various embodiments, the novel light chain variable sequence further comprises at least one additional polypeptide sequence. In one embodiment, the $V_H$ polypeptide further comprises a heavy chain $C_H 1$ domain; the $V_L$ polypeptide further comprises a light chain $C_L$ domain. In one embodiment, the $V_H$ polypeptide further comprises a heavy chain $C_H 1$ domain, a heavy chain $C_H^2$ domain, and a heavy chain $C_H^3$ domain to form an antibody heavy chain; the $V_L$ polypeptide further comprises a light chain $C_L$ domain to form an antibody light chain. In one embodiment, the antibody heavy chain and the antibody light chain are linked to form a half antibody. In one embodiment, the half antibody is linked to another half antibody to form an antibody. In various embodiments, the linking of the heavy chain to the light chain to form the half antibody, and the linking of the two half antibodies, is achieved using a disulfide bond. In other embodiments, the linking of the heavy chain to the light chain to form the half antibody, and the linking of the two half antibodies, is achieved using a bond or linkage that is not a disulfide bond.

In another aspect, this disclosure provides an isolated monoclonal antibody, or binding portion thereof comprising: (a) a heavy chain variable region comprising an amino acid sequence selected from the group consisting of SEQ ID NOs: 9, 17, 25, 33 and 41; and (b) a light chain variable region comprising an amino acid sequence selected from the group consisting of SEQ ID NOs: 10, 18, 26, 34 and 42, wherein the antibody specifically binds a renalase protein.

Preferred heavy and light chain combinations include: (a) a heavy chain variable region comprising the amino acid sequence of SEQ ID NO: 9 and a light chain variable region comprising the amino acid sequence of SEQ ID NO: 10; or (b) a heavy chain variable region comprising the amino acid sequence of SEQ ID NO: 17 and a light chain variable region comprising the amino acid sequence of SEQ ID NO: 18; or (c) a heavy chain variable region comprising the amino acid sequence of SEQ ID NO: 25 and a light chain variable region comprising the amino acid sequence of SEQ ID NO: 26; or (d) a heavy chain variable region comprising the amino acid sequence of SEQ ID NO: 33 and a light chain variable region comprising the amino acid sequence of SEQ ID NO: 34; or (e) a heavy chain variable region comprising the amino acid sequence of SEQ ID NO: 41 and a light chain variable region comprising the amino acid sequence of SEQ ID NO: 42.

In another aspect, this disclosure provides antibodies that comprise the heavy chain and light chain CDR1s, CDR2s and CDR3s of D-28-4, 1D-37-10, 1F-26-1, 1F-42-7 or 3A-5-2, or combinations thereof. The amino acid sequences of the $V_H$ CDR Is of 1D-28-4, 1D-37-10, 1F-26-1, 1F-42-7 and 3A-5-2 incorporate the sequences shown in SEQ ID NOs: 11, 19, 27, 35, and 43, respectively. The amino acid sequences of the $V_H$ CDR2s 1D-28-4, 1D-37-10, 1F-26-1, 1F-42-7 and 3A-5-2 incorporate the sequences shown in SEQ ID NOs: 12, 20, 28, 36, and 44, respectively. The amino acid sequences of the $V_H$ CDR3s of 1D-28-4, 1D-37-10, 1F-26-1, 1F-42-7 and 3A-5-2 incorporate the sequences shown in SEQ ID NOs: 13, 21, 29, 37, and 45, respectively. The amino acid sequences of the VK CDR1s of 1D-28-4, 1D-37-10, 1F-26-1, 1F-42-7 and 3A-5-2 incorporate the sequences shown in SEQ ID NOs: 14, 22, 30, 38, and 46, respectively. The amino acid sequences of the VK CDR2s of 1D-28-4, 1D-37-10, 1F-26-1, 1F-42-7 and 3A-5-2 incorporate the sequences shown in SEQ ID NOs: 15, 23, 31, 39 and 47. The amino acid sequences of the VK CDR3s of 1D-28-4, 1D-37-10, 1F-26-1, 1F-42-7 and 3A-5-2 incorporate the sequences shown in SEQ ID NOs: 16, 24, 32, 40 and 48, respectively. The CDR regions are delineated using the Kabat system (Kabat, E. A., et al. (1991) Sequences of Proteins of Immunological Interest, Fifth Edition, U.S. Department of Health and Human Services, NIH Publication No. 91-3242).

Given that each of these antibodies can bind to renalase family members and that binding specificity is provided primarily by the CDR1, CDR2, and CDR3 regions, the $V_H$ CDR1, CDR2, and CDR3 sequences and $V_L$ CDR1, CDR2, and CDR3 sequences can be "mixed and matched" (i.e., CDRs from different antibodies can be mixed and match, although each antibody must contain a $V_H$ CDR, CDR2, and CDR3 and a $V_L$ CDR1, CDR2, and CDR3) to create other anti-renalase binding molecules of this disclosure. renalase binding of such "mixed and matched" antibodies can be tested using the binding assays described above and in the Examples (e.g., immunoblot, Biacore® analysis, etc). Preferably, when $V_H$ CDR sequences are mixed and matched, the CDR1, CDR2 and/or CDR3 sequence from a particular $V_H$ sequence is replaced with a structurally similar CDR sequence(s). Likewise, when $V_L$ CDR sequences are mixed and matched, the CDR1, CDR2 and/or CDR3 sequence from a particular $V_L$ sequence preferably is replaced with a structurally similar CDR sequence(s). It will be readily apparent to the ordinarily skilled artisan that novel $V_H$ and $V_L$ sequences can be created by substituting one or more $V_H$ and/or $V_L$ CDR region sequences with structurally similar sequences from the CDR sequences disclosed herein for monoclonal antibodies 1D-28-4, 1D-37-10, 1F-26-1, 1F42-7 or 3A-5-2.

Accordingly, in another aspect, the invention provides an isolated monoclonal antibody, or binding portion thereof comprising at least one selected from: (a) a heavy chain variable region CDR1 comprising an amino acid sequence selected from the group consisting of SEQ ID NOs: 11, 19, 27, 35, and 43; (b) a heavy chain variable region CDR2 comprising an amino acid sequence selected from the group consisting of SEQ ID NOs: 12, 20, 28, 36, and 44: (c) a heavy chain variable region CDR3 comprising an amino acid sequence selected from the group consisting of SEQ ID NOs: 13, 21, 29, 37, and 45; (d) a light chain variable region CDR1 comprising an amino acid sequence selected from the group consisting of SEQ ID NOs: 14, 22, 30, 38, and 46; (e) a light chain variable region CDR2 comprising an amino acid sequence selected from the group consisting of SEQ ID NOs: 15, 23, 31, 39 and 47; and (f) a light chain variable region CDR3 comprising an amino acid sequence selected from the group consisting of SEQ ID NOs: 16, 24, 32, 40 and 48; wherein the antibody specifically binds an renalase.

In another embodiment, the antibody comprises at least one of the CDRs selected from: (a) a heavy chain variable region CDR1 comprising SEQ ID NO: 11; (b) a heavy chain variable region CDR2 comprising SEQ ID NO: 12; (c) a heavy chain variable region CDR3 comprising SEQ ID NO: 13; (d) a light chain variable region CDR1 comprising SEQ ID NO: 14; (e) a light chain variable region CDR2 comprising SEQ ID NO: 15; and (f) a light chain variable region CDR3 comprising SEQ ID NO: 16.

In another embodiment, the antibody comprises at least one of the CDRs selected from: (a) a heavy chain variable region CDR1 comprising SEQ ID NO: 19; (b) a heavy chain variable region CDR2 comprising SEQ ID NO: 20: (c) a heavy chain variable region CDR3 comprising SEQ ID NO: 21; (d) a light chain variable region CDR1 comprising SEQ ID NO: 22; (e) a light chain variable region CDR2 comprising SEQ ID NO: 23. and (f) a light chain variable region CDR3 comprising SEQ ID NO: 24.

In another embodiment, the antibody comprises at least one of the CDRs selected from: (a) a heavy chain variable region CDR1 comprising SEQ ID NO: 27; (b) a heavy chain variable region CDR2 comprising SEQ ID NO: 28; (c) a heavy chain variable region CDR3 comprising SEQ ID NO: 29; (d) a light chain variable region CDR1 comprising SEQ ID NO: 30; (e) a light chain variable region CDR2 comprising SEQ ID NO:31; and (f) a light chain variable region CDR3 comprising SEQ ID NO: 32.

In another other embodiment, the antibody comprises at least one of the CDRs selected from: (a) a heavy chain variable region CDR1 comprising SEQ ID NO: 35, (b) a heavy chain variable region CDR2 comprising SEQ ID NO: 36; (c) a heavy chain variable region CDR3 comprising SEQ ID NO: 37; (d) a light chain variable region CDR1 comprising SEQ ID NO: 38, (e) a light chain variable region CDR2 comprising SEQ ID NO: 39; and (f) a light chain variable region CDR3 comprising SEQ ID NO: 40.

In another embodiment, the antibody comprises at least one of the CDRs selected from: (a) a heavy chain variable region CDR1 comprising SEQ ID NO: 43; (b) a heavy chain variable region CDR2 comprising SEQ ID NO: 44; (c) a heavy chain variable region CDR3 comprising SEQ ID NO: 45; (d) a light chain variable region CDR1 comprising SEQ ID NO: 46; (e) a light chain variable region CDR2 comprising SEQ ID NO: 47; and (f) a light chain variable region CDR3 comprising SEQ ID NO: 48.

The foregoing isolated anti-renalase antibody CDR sequences establish a novel family of renalase binding proteins, isolated in accordance with this invention, and comprising polypeptides that include the CDR sequences listed. To generate and to select CDR's of the invention having renalase binding and/or renalase detection and/or renalase neutralization activity, standard methods known in the art for generating binding proteins of the present invention and assessing the renalase and/or renalase binding and/or detection and/or neutralizing characteristics of those binding protein may be used, including but not limited to those specifically described herein.

Preferably, renalase binding molecules (e.g., antibodies, etc.) of the present invention, exhibit a high capacity to detect and bind renalase in a complex mixture of salts, compounds and other polypeptides, e.g., as assessed by any one of several in vitro and in vivo assays known in the art. The skilled artisan will understand that the renalase binding molecules (e.g., antibodies, etc.) described herein as useful in the methods of diagnosis and treatment and prevention of disease, are also useful in procedures and methods of the invention that include, but are not limited to, an immunochromatography assay, an immunodot assay, a Luminex assay, an ELISA assay, an ELISPOT assay, a protein microarray assay, a Western blot assay, a mass spectrophotometry assay, a radioimmunoassay (RIA), a radioimmunodiffusion assay, a liquid chromatography-tandem mass spectrometry assay, an ouchterlony immunodiffusion assay, reverse phase protein microarray, a rocket immunoelectrophoresis assay, an immunohistostaining assay, an immunoprecipitation assay, a complement fixation assay, FACS, a protein chip assay, separation and purification processes, and affinity chromatography (see also, 2007, Van Emon, Immunoassay and Other Bioanalytical Techniques, CRC Press; 2005, Wild, Immunoassay Handbook, Gulf Professional Publishing; 1996, Diamandis and Christopoulos, Immunoassay, Academic Press; 2005, Joos, Microarrays in Clinical Diagnosis, Humana Press; 2005, Hamdan and Righetti, Proteomics Today, John Wiley and Sons; 2007).

More preferably, the renalase binding molecules (e.g., antibodies, etc.) of the present invention, exhibit a high capacity to reduce or to neutralize renalase activity (e.g., enzymatic activity, substrate binding activity, receptor binding activity, etc.) as assessed by any one of several in vitro and in vivo assays known in the art. For example, these renalase binding molecules (e.g., antibodies, etc.) neutralize renalase-associated or renalase-mediated disease or disorder. Preferably, renalase binding molecules (e.g., antibodies, etc.) of the present invention, also exhibit a high capacity to reduce or to neutralize renalase activity. In some embodiments, the renalase is human renalase.

As used herein, a renalase binding molecule (e.g., antibody, etc.) that "specifically binds to a renalase protein" is intended to refer to a renalase binding molecule (e.g., antibody, etc.) that binds to a renalase protein of any animal. In some embodiments, that antibody binds to human renalase. Preferably, the a renalase binding molecule (e.g., antibody, etc.) binds to a renalase protein with a KD of $1\times10^{-6}$ M or less, more preferably $1\times10^{-7}$ M or less, more preferably $1\times10^{-8}$ M or less, more preferably $5\times10_{-9}$ M or less, more preferably $1\times10^{-9}$ M or less or even more preferably $3\times10^{-10}$ M or less. The term "does not substantially bind" to a protein or cells, as used herein, means does not bind or does not bind with a high affinity to the protein or cells, i.e., binds to the protein or cells with a KD of greater than $1\times10^6$M or more, more preferably $1\times10^{-10}$ M or more, more preferably $1\times10^4$ M or more, more preferably $1\times10^3$ M or more, even more preferably $1\times10^2$ M or more. The term "KD", as used herein, is intended to refer to the dissociation constant, which is obtained from the ratio of Kd to Ka (i.e., Kd/Ka) and is expressed as a molar concentration (M). KD values for a renalase binding molecule (e.g., antibody, etc.) can be determined using methods well established in the art. A preferred method for determining the KD of a binding molecule (e.g., antibody, etc.) is by using surface plasmon resonance, preferably using a biosensor system such as a Biacore® system.

As used herein, the term "high affinity" for an IgG antibody refers to an antibody having a KD of $1\times10^{-7}$ M or less, more preferably $5\times10^{-8}$ M or less, even more preferably $1\times10^{-8}$ M or less, even more preferably $5\times10^{-9}$M or less and even more preferably $1\times10^{-9}$ M or less for a target binding partner molecule. However, "high affinity" binding can vary for other antibody isotypes. For example, "high affinity" binding for an IgM isotype refers to an antibody having a KD of $10^{-6}$ M or less, more preferably $10^{-7}$ M or less, even more preferably $10^{-8}$ M or less.

In certain embodiments, the antibody comprises a heavy chain constant region, such as an IgG1, IgG2, IgG3, IgG4, IgA, IgE, IgM or IgD constant region. Preferably, the heavy chain constant region is an IgG1 heavy chain constant region or an IgG4 heavy chain constant region. Furthermore, the antibody can comprise a light chain constant region, either a kappa light chain constant region or a lambda light chain constant region. Preferably, the antibody comprises a kappa light chain constant region. Alternatively, the antibody portion can be, for example, a Fab fragment or a single chain Fv fragment.

Generation of Anti-Renalase Antibodies

The invention provides compositions that bind to renalase. The renalase molecules disclosed herein are a class of molecules that include those having high and/or significant sequence identity with other polypeptides disclosed herein. More specifically, the putative renalase will share at least about 40% sequence identity with a nucleic acid having the sequence SEQ ID NO: 49 or 51. More preferably, a nucleic acid encoding renalase has at least about 45% identity, or at least about 50% identity, or at least about 55% identity, or at least about 60% identity, or at least about 65% identity, or at least about 70% identity, or at least about 75% identity, or at least about 80% identity, or at least about 85% identity, or at least about 90% identity, or at least about 95% identity, or at least about 98%, or at least about 99% sequence identity with SEQ ID NO: 49 or 51 disclosed herein. Even more preferably, the nucleic acid is SEQ ID NO: 49 or 51 or 93 or 95. The term "renalase" also includes renalase isoforms.

The renalase gene contains 9 exons spanning 310188 bp in chromosome 10 of human genome. The renalase clone (SEQ ID NO: 49, GenBank accession number: BC005364) disclosed herein is the gene containing exons 1, 2, 3, 4, 5, 6, 8. There are at least two additional alternatively-spliced forms of renalase protein as shown in the human genome database. One alternatively spliced form contains exons 1, 2, 3, 4, 5, 6, 9, identified by clones in the human genome database as GenBank accession number AK002080 and NMJ18363, the sequences of which are expressly incorporated herein by reference. The other alternatively spliced form contains exons 5, 6, 7, 8, identified by clones in the human genome database as GenBank accession number BX648154, the sequence of which is expressly incorporated herein by reference. Unless otherwise indicated, "renalase" encompasses all known renalases (e.g., rat renalase, and human renalase), and renalases to be discovered, including but not limited to, human renalase and chimpanzee renalase, having the characteristics and/or physical features of the renalase disclosed herein.

In addition, the putative renalase shares at least about 60% sequence identity with a polypeptide having the sequence SEQ ID NO: 8 or 50. More preferably, renalase has at least about 45% identity, or at least about 50% identity, or at least about 55% identity, or at least about 60% identity, or at least about 65% identity, or at least about 70% identity, or at least about 75% identity, or at least about 80% identity, or at least about 85% identity, or at least about 90% identity, or at least about 95% identity, or at least about 98%, or at least about 99% sequence identity with SEQ ID NO: 8 or 50 disclosed herein. Even more preferably, the renalase polypeptide has the amino acid sequence of SEQ ID NO: 8 or 50 or 92 or 94.

In one embodiment, the antibodies of the invention can be generated by using a peptide derived from the sequence of renalase to immunize an animal whereby the animal produces antibodies directed against the immunogen. Exemplary immunogens include peptide derived from renalase. That is, peptides having fragments of the renalase sequence can be used in the inventions. Peptides can be produced in a variety of ways, including expression as recombinant peptides, expression as larger polypeptides and cleaved enzymatically or chemically. Alternatively, they may be produced synthetically as is known in the art. Preferred peptides as used to generate affinity reagents of the present invention are found in FIG. 1 (SEQ ID NOs: 1-7).

Anti-renalase antibodies of the present invention can be optionally produced by a variety of techniques, including the standard somatic cell hybridization technique (hybridoma method) of Kohler and Milstein (1975) Nature 256:495. In the hybridoma method, a mouse or other appropriate host animal, such as a hamster or macaque monkey, is immunized as described herein to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding, Monoclonal Antibodies: Principles and Practice, pp. 59-103 (Academic Press, 1986)).

Methods for producing and screening for specific antibodies using hybridoma technology are routine and well known in the art. In one embodiment, the present invention provides methods of generating monoclonal antibodies as well as antibodies produced by the method comprising culturing a hybridoma cell secreting an antibody of the invention wherein, preferably, the hybridoma is generated by fusing splenocytes isolated from a mouse or rabbit or other species immunized with polypeptide or peptide of the invention with myeloma cells and then screening the hybridomas resulting from the fusion for hybridoma clones that secrete an antibody able to bind a polypeptide of the invention. Briefly, mice can be immunized with a renalase polypeptide or peptide thereof. In a preferred embodiment, the renalase polypeptide or peptide thereof is administered with an adjuvant to stimulate the immune response. Such adjuvants include complete or incomplete Freund's adjuvant, RIBI (muramyl dipeptides) or ISCOM (immunostimulating complexes). Such adjuvants may protect the polypeptide from rapid dispersal by sequestering it in a local deposit, or they may contain substances that stimulate the host to secrete factors that are chemotactic for macrophages and other components of the immune system. Preferably, if a polypeptide is being administered, the immunization schedule will involve two or more administrations of the polypeptide, spread out over several weeks.

Alternatively, rabbits can be immunized with a renalase polypeptide or peptide thereof. In this embodiment, either full length renalase proteins or peptides derived from renalase can be used as immunogens.

Renalase used in the invention can take a variety of forms. For example, they can include purified renalase proteins or fragments thereof, recombinantly produced renalase or fragments thereof. In some embodiments, the renalase is human renalase. When recombinant renalase is used, it can be produced in eukaryotic or prokaryotic cells as is known in the art. Additional immunogens include peptides derived from renalase. That is, peptides having fragments of the renalase sequence can be used in the inventions. Peptides can be produced in a variety of ways, including expression as recombinant peptides, expression as larger polypeptides and cleaved enzymatically or chemically. Alternatively, they may be produced synthetically as is known in the art. Preferred peptides as used to generate affinity reagents of the present invention are found in FIG. 1 (SEQ ID NOs:1-7). The full-length amino acid sequence of human renalase is depicted in SEQ ID NO:8, where a known polymorphism is possible as indicated (compare to SEQ ID NO. 92). The amino acid sequence of renalase-2 is found in SEQ ID NO:50, again where a known polymorphism is possible as indicated (compare to SEQ ID NO. 94). It is appreciated that other polymorphisms exist. These also are included in the definition of renalase. In some embodiments, the renalase binding molecules of the invention specifically bind to at least one of SEQ ID NOS:1-7, 8, 50, 92, 94, and fragments thereof.

The anti-renalase antibody can also be optionally generated by immunization of a transgenic animal (e.g., mouse, rat, hamster, non-human primate, and the like) capable of producing a repertoire of human antibodies, as described herein and/or as known in the art. Cells that produce a human anti-renalase antibody can be isolated from such animals and immortalized using suitable methods, such as the methods described herein. Alternatively, the antibody coding sequences may be cloned, introduced into a suitable vector, and used to transfect a host cell for expression and isolation of the antibody by methods taught herein and those known in the art.

The use of transgenic mice carrying human immunoglobulin (Ig) loci in their germline configuration provide for the isolation of high affinity fully human monoclonal antibodies directed against a variety of targets including human self antigens for which the normal human immune system is tolerant (Lonberg, N. et al., U.S. Pat. Nos. 5,569,825, 6,300,129 and 1994, Nature 368:856-9; Green, L. et al., 1994, Nature Genet. 7:13-21: Green, L. & Jakobovits, 1998, Exp. Med. 188:483-95; Lonberg, N. and Huszar, D., 1995, Int. Rev. Immunol. 13:65-93; Kucherlapati, et al. U.S. Pat. No. 6,713,610; Bruggemann, M. et al., 1991, Eur. J. Immunol. 21:1323-1326; Fishwild, D. et al., 1996, Nat. Biotechnol. 14:845-851; Mendez, M. et al., 1997, Nat. Genet. 15:146-156; Green, L., 1999, J. Immunol. Methods 231:11-23; Yang, X. et al., 1999, Cancer Res. 59:1236-1243; Bruggemann, M. and Taussig, M J., Curr. Opin. Biotechnol. 8:455-458, 1997; Tomizuka et al. WO02043478). The endogenous immunoglobulin loci in such mice can be disrupted or deleted to eliminate the capacity of the animal to produce antibodies encoded by endogenous genes. In addition, companies such as Abgenix, Inc. (Freemont, Calif.) and Medarex (San Jose, Calif.) can be engaged to provide human antibodies directed against a selected target binding partner molecule (e.g., antigen, etc.) using technology as described elsewhere herein.

In another embodiment, the human antibody is selected from a phage library, where that phage comprises human immunoglobulin genes and the library expresses human antibody binding domains as, for example, single chain antibodies (scFv), as Fab, or some other construct exhibiting paired or unpaired antibody variable regions (Vaughan et lo al. Nature Biotechnology 14:309-314 (1996): Sheets et al. PITAS (USA) 95:6157-6162 (1998)); Hoogenboom and Winter, J. Mol. Biol., 227:381 (1991); Marks et al. J. Mol. Biol., 222:581 (1991)). Human monoclonal antibodies of the invention can also be prepared using phage display methods for screening libraries of human immunoglobulin genes. Such phage display methods for isolating human antibodies are established in the art. See for example: U.S. Pat. Nos. 5,223,409; 5,403,484; and 5,571,698 to Ladner et al.; U.S. Pat. Nos. 5,427,908 and 5,580,717 to Dower et al.; U.S. Pat. Nos. 5,969,108 and 6,172,197 to McCafferty et al.; and U.S. Pat. Nos. 5,885,793; 6,521,404; 6,544,731; 6,555,313; 6,582,915 and 6,593,081 to Griffiths et al.

Preparation of immunogenic antigens, and monoclonal antibody production can be performed using any suitable technique such as recombinant protein production. The immunogenic antigens can be administered to an animal in the form of purified protein, or protein mixtures including whole cells or cell or tissue extracts, or the antigen can be formed de novo in the animal's body from nucleic acids encoding said antigen or a portion thereof.

The isolated nucleic acids of the present invention can be made using (a) recombinant methods, (b) synthetic techniques, (c) purification techniques, or combinations thereof, as well-known in the art. DNA encoding the monoclonal antibodies is readily isolated and sequenced using methods known in the art (e.g., by using oligonucleotide probes that are capable of binding specifically to genes encoding the heavy and light chains of murine antibodies). Where a hybridoma is produced, such cells can serve as a source of such DNA. Alternatively, using display techniques wherein the coding sequence and the translation product are linked, such as phage or ribosomal display libraries, the selection of the binder and the nucleic acid is simplified. After phage selection, the antibody coding regions from the phage can be isolated and used to generate whole antibodies, including human antibodies, or any other desired binding fragment, and expressed in any desired host, including mammalian cells, insect cells, plant cells, yeast, and bacteria.

Humanized Antibodies

The invention further provides humanized immunoglobulins (or antibodies) which bind human renalase. The humanized forms of immunoglobulins have variable framework region(s) substantially from a human immunoglobulin (termed an acceptor immunoglobulin) and CDRs substantially from a non-human mAbs which specifically binds renalase. The constant region(s), if present, are also substantially from a human immunoglobulin. The humanized antibodies exhibit $K_D$ for renalase of at least about $10^{-6}$ M (1 μM), about $10^{-7}$ M (100 nM), or less. The binding affinity of the humanized antibodies may be greater or less than that of the mouse antibody from which they were derived. To affect a change in affinity, improve affinity, of the humanized antibody for renalase substitutions in either the CDR residues or the human residues may be made.

The source for production of humanized antibody which binds to renalase is preferably the 1D-28-4, 1D-37-10, 1F-26-1, 1F-42-7 or 3A-5-2 rabbit monoclonal antibodies whose generation, isolation and characterization are described in the Examples provided herein, although other antibodies, which compete with the 1D-28-4, 1D-37-10, 1F-26-1, 1F42-7 or 3A-5-2 antibodies for binding to renalase can also be used. The identified CDRs set forth in the sequence listing can be a starting point of the humanization process. For example, any one or more of the following amino acid sequences (and corresponding nucleic acid sequences thereof) can be a starting point of the humanization process: (a) a heavy chain variable region CDR1 comprising an amino acid sequence selected from the group consisting of SEQ ID NOs: 11, 19, 27, 35, and 43; (b) a heavy chain variable region CDR2 comprising an amino acid sequence selected from the group consisting of SEQ ID NOs: 12, 20, 28, 36, and 44; (c) a heavy chain variable region CDR3 comprising an amino acid sequence selected from the group consisting of SEQ ID NOs: 13, 21, 29, 37, and 45; (d) a light chain variable region CDR comprising an amino acid sequence selected from the group consisting of SEQ ID NOs: 14, 22, 30, 38, and 46; (e) a light chain variable region CDR2 comprising an amino acid sequence selected from the group consisting of SEQ ID NOs: 15, 23, 31, 39 and 47; and (f) a light chain variable region CDR3 comprising an amino acid sequence selected from the group consisting of SEQ ID NOs: 16, 24, 32, 40 and 48.

The substitution of rabbit or mouse CDRs into a human variable domain framework is most likely to result in retention of their correct spatial orientation if the human variable domain framework adopts the same or similar conformation to the parental variable framework from which the CDRs originated. This is achieved by obtaining the human variable domains from human antibodies whose framework sequences exhibit a high degree of sequence identity with the parental variable framework domains from which the CDRs were derived. The heavy and light chain variable framework regions can be derived from the same or different human antibody sequences. The human antibody sequences can be the sequences of naturally occurring human antibodies, be derived from human germline immunoglobulin sequences, or can be consensus sequences of several human antibody and/or germline sequences.

Suitable human antibody sequences are identified by computer comparisons of the amino acid sequences of the rabbit or mouse variable regions with the sequences of known human antibodies. The comparison is performed separately for heavy and light chains but the principles are similar for each.

In one example, the amino acid sequence of anti-renalase mAb is used to query a human antibody database compiled from public antibody sequence databases. The heavy chain variable region can be used to find the human variable region with the highest sequence identity. The variable region of the light chain can, similarly, be used to find the human variable region with the highest sequence identity. A DNA construct in which the regions coding for the CDRs of one of the heavy chain variable regions from the parental mAbs donor are transferred into the selected human heavy chain variable sequence, replacing the CDRs of the human variable region is prepared for each parental variable region.

The unnatural juxtaposition of parental CDR regions with human variable framework region can result in unnatural conformational restraints, which, unless corrected by substitution of certain amino acid residues, lead to loss of binding affinity. As noted supra, the humanized antibodies of the invention comprise variable framework region(s) substantially from a human immunoglobulin and CDRs substantially from a parental (e.g., rabbit, or mouse) immunoglobulin. Having identified the CDRs of parental antibodies and appropriate human acceptor immunoglobulin sequences, the next step is to determine which, if any, residues from these components should be substituted to optimize the properties of the resulting humanized antibody. In general, substitution of human amino acid residues with parental should be minimized, because introduction of parental residues increases the risk of the antibody eliciting an immune response in humans. Amino acids are selected for substitution based on their possible influence on CDR conformation and/or binding to the target binding partner molecule. Investigation of such possible influences can be done by modeling, examination of the characteristics of the amino acids at particular locations, or empirical observation of the effects of substitution or mutagenesis of particular amino acids. With regard to the empirical method, it has been found to be particularly convenient to create a library of variant sequences that can be screened for the desired activity, binding affinity or specificity. One format for creation of such a library of variants is a phage display vector. Alternatively, variants can be generated using other methods for variation of a nucleic acid sequence encoding the targeted residues within the variable domain.

Another method of determining whether further substitutions are required, and the selection of amino acid residues for substitution, can be accomplished using computer modeling. Computer hardware and software for producing three-dimensional images of immunoglobulin molecules are widely available. In general, molecular models are produced starting from solved structures for immunoglobulin chains or domains thereof. The chains to be modeled are compared for amino acid sequence similarity with chains or domains of solved three dimensional structures, and the chains or domains showing the greatest sequence similarity is/are selected as starting points for construction of the molecular model. The solved starting structures are modified to allow for differences between the actual amino acids in the immunoglobulin chains or domains being modeled, and those in the starting structure. The modified structures are then assembled into a composite immunoglobulin. Finally, the model is refined by energy minimization and by verifying that all atoms are within appropriate distances from one another and that bond lengths and angles are within chemically acceptable limits.

Usually the CDR regions in humanized antibodies are substantially identical, and more usually, identical to the corresponding CDR regions in the parental antibody from which they were derived. Although not usually desirable, it is sometimes possible to make one or more conservative amino acid substitutions of CDR residues without appreciably affecting the binding affinity of the resulting humanized immunoglobulin. Occasionally, substitutions of CDR regions can enhance binding affinity.

Other than for the specific amino acid substitutions discussed above, the framework regions of humanized immunoglobulins are usually substantially identical, and more usually, identical to the framework regions of the human antibodies from which they were derived. Of course, many of the amino acids in the framework region make little or no direct contribution to the specificity or affinity of an antibody. Thus, many individual conservative substitutions of framework residues can be tolerated without appreciable change of the specificity or affinity of the resulting humanized immunoglobulin.

Because of the degeneracy of the code, a variety of nucleic acid sequences will encode each immunoglobulin amino acid sequence. The desired nucleic acid sequences can be produced by solid-phase DNA synthesis or by PCR mutagenesis of an earlier prepared variant of the desired polynucleotide. All nucleic acids encoding the antibodies described in this application are expressly included in the invention.

The variable segments of humanized antibodies produced as described supra are typically linked to at least a portion of a human immunoglobulin constant region. The antibody will contain both light chain and heavy chain constant regions. The heavy chain constant region usually includes CH1, hinge, CH2, CH3, and, sometimes, CH4 domains.

The humanized antibodies may comprise any type of constant domains from any class of antibody, including IgM, IgG, IgD, IgA and IgE, and any subclass (isotype), including IgG1, IgG2, IgG3 and IgG4. When it is desired that the humanized antibody exhibit cytotoxic activity, the constant domain is usually a complement-fixing constant domain and the class is typically IgG1. When such cytotoxic activity is not desirable, the constant domain may be of the IgG2 class. The humanized antibody may comprise sequences from more than one class or isotype.

Nucleic acids encoding humanized light and heavy chain variable regions, optionally linked to constant regions, are inserted into expression vectors. The light and heavy chains can be cloned in the same or different expression vectors. The DNA segments encoding immunoglobulin chains are operably linked to control sequences in the expression vector(s) that ensure the expression of immunoglobulin polypeptides. Such control sequences include a signal sequence, a promoter, an enhancer, and a transcription termination sequence (see Queen et al., Proc. Natl. Acad. Sci. USA 86, 10029 (1989); WO 90/07861; Co et al., J. Immunol. 148, 1149 (1992), which are incorporated herein by reference in their entirety for all purposes).

Methods of Using the Renalase Binding Molecules

Given the properties of the renalase binding molecules (e.g., antibodies, etc.) of the present invention, the renalase binding molecules are suitable as diagnostic, therapeutic and prophylactic agents for methods of diagnosing, treating or preventing renalase-associated conditions in humans and animals.

In general, usage involves a composition comprising an effective amount of one or more monoclonal antibodies or binding fragments of the present invention as part of a biochemical assay for measuring renalase, as part of the diagnosis, assessment, treatment, or prevention of a condition in which renalase activity is known to have pathological sequelae, such as tumor growth and metastasis. Any active form of the renalase binding molecule can be used, including antibody Fab and F(ab')2 fragments.

Treatment of individuals may comprise a method of measuring renalase of the present invention. The renalase binding molecules can be provided in a kit as described below. The renalase binding molecules can be used as a mixture, for example in equal amounts, or individually, provided in sequence, or used all at once. In providing an assay with a renalase binding molecule, the dosage of administered agent will vary depending upon such factors as the assay's limit of detection, limit of quantitation, repeatability, response characteristics, and other properties known in the analytical arts.

The renalase binding molecules of the present invention can be formulated according to known methods to prepare analytically or pharmaceutically useful compositions, whereby these materials, or their functional derivatives, are combined in admixture with an acceptable carrier vehicle. Suitable vehicles and their formulation, inclusive of other human proteins, e.g., human serum albumin, are described, for example, in Remington's Pharmaceutical Sciences (16th ed., Osol, A. ed., Mack Easton Pa. (1980)). In order to form an acceptable composition suitable for effective use, such compositions will contain an effective amount of the above-described compounds together with a suitable amount of carrier vehicle.

The present invention also provides kits which are useful for carrying out the present invention. The present kits comprise a first container containing or packaged in association with the above-described antibodies. The kit may also comprise another container containing or packaged in association solutions necessary or convenient for carrying out the invention. The containers can be made of glass, plastic or foil and can be a vial, bottle, pouch, tube, bag, etc. The kit may also contain written information, such as procedures for carrying out the present invention or analytical information, such as the amount of reagent contained in the first container means. The container may be in another container apparatus, e.g. a box or a bag, along with the written information.

Yet another aspect of the present invention is a kit for detecting renalase in a biological sample. The kit includes a container holding one or more renalase binding molecules which binds an epitope of renalase and instructions for using the renalase binding molecule for the purpose of binding to renalase to form complex and detecting the formation of the complex such that the presence or absence of the complex correlates with presence or absence of renalase in the sample. Examples of containers include multiwell plates which allow simultaneous detection of renalase in multiple samples.

Therapy

The renalase binding molecule compositions of the invention can be used in combination with a therapeutic treatment or agent to treat the disease or disorder. For example, the renalase binding molecule of the invention may be used alone, or in combination with one or more therapeutically effective agents or treatments. The therapeutically effective agent may be administered as a separate composition. The therapeutic agent or treatment may be administered prior to, during and/or after the use of the antibody of the invention or related compound.

In certain embodiments, the renalase binding molecule of the invention is used with one or more other therapeutic agents or treatments. In other embodiments, the renalase binding molecule of the invention is used independently from the administration of one or more therapeutic agents or treatments. For example, the renalase binding molecule of the invention is used first, followed by the administration of one or more therapeutic agents or treatments. Alternatively, one or more therapeutic agents are administered first, followed by the use of a renalase binding molecule of the invention. As another example, a treatment (e.g, a surgery, radiation, etc.) is carried out first, followed by the use of the renalase binding molecule of the invention.

Therapeutically effective agents or treatments include surgery, anti-neoplastics (including chemotherapeutic agents and radiation), anti-angiogenesis agents, antibodies, small molecules, photodynamic therapy, immunotherapy, immunity enhancing therapy, cytotoxic agents, cytokines, chemokines, growth inhibitory agents, anti-hormonal agents, kinase inhibitors, cardioprotectants, immunostimulatory agents, immunosuppressive agents, and agents that promote proliferation of hematological cells.

In one embodiment, the "therapeutic agent," as used herein, is distinct from the renalase binding molecule of the invention. Any therapeutic agent may be used in the therapies or combination therapies of the present invention. Also, therapeutic agents or "anti-cancer agents" may be selected with a view to achieving additive, greater than additive and potentially synergistic effects, according to the following guidance.

To practice anti-tumor therapy, one would administer to an animal or patient an anti-cancer agent. The agent would therefore be provided in amounts effective and for periods of time effective to result in their combined, or concurrent, presence within the tumor or tumor vasculature and their combined actions in the tumor environment. To achieve this goal, the anti-cancer agents may be administered to the animal substantially simultaneously, either in a single composition, or as two distinct compositions using different administration routes.

The therapeutic agents for therapies may be selected based upon certain criteria, including those discussed elsewhere herein. A preference for selecting one or more second, distinct anti-cancer agents for prior or subsequent administration does not preclude their use in substantially simultaneous administration if desired.

Anti-cancer agents selected for administration "subsequent to" the renalase measurement methods of the present invention, include a variety of agents. Accordingly, effective anti-cancer agents for administration include anti-angiogenic agents, which inhibit metastasis; agents targeting necrotic tumor cells, such as antibodies specific for intracellular binding partner molecules that become accessible from malignant cells in vivo (U.S. Pat. Nos. 5,019,368, 4,861,581 and 5,882,626, each specifically incorporated herein by reference); chemotherapeutic agents; and anti-tumor cell immunoconjugates, which attack any tumor cells.

The renalase binding molecule of the invention can also be used in combination with a cancer immunotherapy. The cancer immunotherapy can be one designed to elicit a humoral immune response against the subject's cancer cells, or a cell-mediated immune response against the subject's cancer cells, or a combination of a humoral response and a cell-mediated response against the subject's cancer cells. Non-limiting examples of cancer immunotherapy useful in combination with the renalase binding molecules of the invention include a cancer vaccine, a DNA cancer vaccine, adoptive cellular therapy, adoptive immunotherapy, CAR T-cell therapy, antibodies, immunity enhancing compounds, cytokines, interleukins (e.g., IL-2, etc.), interferons (IFN-α, etc.), and checkpoint inhibitors (e.g., PD-1 inhibitor, CTLA-4 inhibitor, etc.).

In some situations, it may be desirable to extend the time period for treatment significantly, where several days (2, 3, 4, 5, 6 or 7), several weeks (1, 2, 3, 4, 5, 6, 7 or 8) or even several months (1, 2, 3, 4, 5, 6, 7 or 8) lapse between the respective administrations. This would be advantageous in circumstances where one treatment was intended to substantially destroy the tumor, such as the primary therapeutic agent, and another treatment was intended to prevent micrometastasis or tumor re-growth, such as the administration of an anti-angiogenic agent. Anti-angiogenics should be administered at a careful time after surgery, however, to allow effective wound healing. Anti-angiogenic agents may then be administered for the lifetime of the patient.

It is also envisioned that more than one administration of an anti-cancer agent will be utilized. The anti-cancer agent may be administered interchangeably, on alternate days or weeks; or a sequence of one agent treatment may be given, followed by a sequence of another treatment. In any event, to achieve tumor regression using a combined therapy, all that is required is to deliver both agents in a combined amount effective to exert an anti-tumor effect, irrespective of the times for administration.

Chemotherapeutic drugs can be used in combination with the renalase measurement compositions and methods of the invention. Chemotherapeutic drugs can kill proliferating tumor cells, enhancing the necrotic areas created by the overall treatment.

One aspect of the invention provides a method of treating or preventing cancer. The skilled artisan will understand that treating or preventing cancer in a patient includes, by way of non-limiting examples, killing and destroying a cancer cell, as well as reducing the proliferation of or cell division rate of a cancer cell. The skilled artisan will also understand that a cancer cell can be, by way of non-limiting examples, a primary cancer cell, a cancer stem cell, a metastatic cancer cell. The following are non-limiting examples of cancers that can be treated by the disclosed methods and compositions: Acute Lymphoblastic; Acute Myeloid Leukemia; Adrenocortical Carcinoma; Adrenocortical Carcinoma, Childhood; Appendix Cancer; Basal Cell Carcinoma; Bile Duct Cancer, Extrahepatic; Bladder Cancer; Bone Cancer; Osteosarcoma and Malignant Fibrous Histiocytoma; Brain Stem Glioma, Childhood: Brain Tumor, Adult; Brain Tumor, Brain Stem Glioma, Childhood; Brain Tumor, Central Nervous System Atypical Teratoid/Rhabdoid Tumor, Childhood; Central Nervous System Embryonal Tumors; Cerebellar Astrocytoma; Cerebral Astrocytotna/Malignant Glioma; Craniopharyngioma; Ependymoblastoma; Ependymoma; Medulloblastoma; Medulloepithelioma; Pineal Parenchymal Tumors of intermediate Differentiation; Supratentorial Primitive Neuroectodermal Tumors and Pineoblastoma; Visual Pathway and Hypothalamic Glioma; Brain and Spinal Cord Tumors; Breast Cancer Bronchial Tumors; Burkitt Lymphoma; Carcinoid Tumor; Carcinoid Tumor, Gastrointestinal; Central Nervous System Atypical Teratoid/Rhabdoid Tumor; Central Nervous System Embryonal Tumors; Central Nervous System Lymphoma; Cerebellar Astrocytoma Cerebral Astrocytoma/Malignant Glioma, Childhood; Cervical Cancer; Chordoma, Childhood; Chronic Lymphocytic Leukemia; Chronic Myelogenous Leukemia; Chronic Myeloproliferative Disorders; Colon Cancer; Colorectal Cancer; Craniopharyngioma; Cutaneous T-Cell Lymphoma; Esophageal Cancer; Ewing Family of Tumors; Extragonadal Germ Cell Tumor; Extrahepatic Bile Duct Cancer; Eye Cancer, intraocular Melanoma; Eye Cancer, Retinoblastoma; Gallbladder Cancer; Gastric (Stomach) Cancer; Gastrointestinal Carcinoid Tumor; Gastrointestinal Stromal Tumor (GIST); Germ Cell Tumor, Extracranial; Germ Cell Tumor, Extragonadal; Germ Cell Tumor, Ovarian; Gestational Trophoblastic Tumor; Glioma; Glioma, Childhood Brain Stem; Glioma, Childhood Cerebral Astrocytoma; Glioma, Childhood Visual Pathway and Hypothalamic; Hairy Cell Leukemia; Head and Neck Cancer; Hepatocellular (Liver) Cancer; Histiocytosis, Langerhans Cell; Hodgkin Lymphoma; Hypopharyngeal Cancer; Hypothalamic and Visual Pathway Glioma; intraocular Melanoma; Islet Cell Tumors; Kidney (Renal Cell) Cancer; Langerhans Cell Histiocytosis; Laryngeal Cancer; Leukemia, Acute Lymphoblastic; Leukemia, Acute Myeloid; Leukemia, Chronic Lymphocytic; Leukemia, Chronic Myelogenous; Leukemia, Hairy Cell; Lip and Oral Cavity Cancer; Liver Cancer; Lung Cancer, Non-Small Cell; Lung Cancer, Small Cell; Lymphoma, AIDS-Related; Lymphoma, Burkitt; Lymphoma, Cutaneous T-Cell; Lymphoma, Hodgkin; Lymphoma, Non-Hodgkin; Lymphoma, Primary Central Nervous System; Macroglobulinemia, Waldenstrom; Malignant Fibrous Histiocytoma of Bone and Osteosarcoma; Medulloblastoma; Melanoma; Melanoma, intraocular (Eye); Merkel Cell Carcinoma; Mesothelioma; Metastatic Squamous Neck Cancer with Occult Primary; Mouth Cancer; Multiple Endocrine Neoplasia Syndrome, (Childhood); Multiple Myeloma/Plasma Cell Neoplasm; Mycosis; Fungoides; Myelodysplastic Syndromes; Myelodysplastic/Myeloproliferative Diseases; Myelogenous Leukemia, Chronic; Myeloid Leukemia, Adult Acute: Myeloid Leukemia, Childhood Acute: Myeloma, Multiple; Myeloproliferative Disorders, Chronic; Nasal Cavity and Paranasal Sinus Cancer; Nasopharyngeal Cancer; Neuroblastoma; Non-Small Cell Lung Cancer; Oral Cancer; Oral Cavity Cancer; Oropharyngeal Cancer; Osteosarcoma and Malignant Fibrous Histiocytoma of Bone; Ovarian Cancer; Ovarian Epithelial Cancer; Ovarian Germ Cell Tumor; Ovarian Low Malignant Potential Tumor; Pancreatic Cancer; Pancreatic Cancer, Islet Cell Tumors; Papillomatosis; Parathyroid Cancer; Penile Cancer; Pharyngeal Cancer; Pheochromocytoma; Paraganglioma; Pineal Parenchymal Tumors of Intermediate Differentiation; Pineoblastoma and Supratentorial Primitive Neuroectodermal Tumors; Pituitary Tumor; Plasma Celt Neoplasm/Multiple Myeloma; Pleuropulmonary Blastoma; Primary Central Nervous System Lymphoma; Prostate Cancer; Rectal Cancer; Renal Cell (Kidney) Cancer; Renal Pelvis and Ureter, Transitional Cell Cancer; Respiratory Tract Carcinoma Involving the NUT Gene on Chromosome 15; Retinoblastoma; Rhabdomyosarcoma; Salivary Gland Cancer; Sarcoma, Ewing Family of Tumors; Sarcoma, Kaposi; Sarcoma, Soft Tissue; Sarcoma, Uterine; Sezary Syndrome; Skin Cancer (Nonmelanoma); Skin Cancer (Melanoma); Skin Carcinoma, Merkel Cell; Small Cell Lung Cancer; Small Intestine Cancer; Soft Tissue Sarcoma; Squamous Cell Carcinoma, Squamous Neck Cancer with Occult Primary, Metastatic; Stomach (Gastric) Cancer; Supratentorial Primitive Neuroectodermal Tumors; T-Cell Lymphoma, Cutaneous; Testicular Cancer; Throat Cancer; Thymoma and Thymic Carcinoma; Thyroid Cancer; Transitional Cell Cancer of the Renal Pelvis and Ureter; Trophoblastic Tumor, Gestational; Urethral Cancer; Uterine Cancer, Endometrial; Uterine Sarcoma; Vaginal Cancer; Vulvar Cancer; Waldenstrom Macroglobulinemia; and Wilms Tumor.

In one embodiment, the invention provides a method to treat cancer comprising treating the subject prior to, concurrently with, or subsequently to the use of the renalase binding molecule of the invention, with a complementary therapy for the cancer, such as surgery, chemotherapy, chemotherapeutic agent, radiation therapy, or hormonal therapy or a combination thereof.

Chemotherapeutic agents include cytotoxic agents (e.g., 5-fluorouracil, cisplatin, carboplatin, methotrexate, daunorubicin, doxorubicin, vincristine, vinblastine, oxorubicin, carmustine (BCNU), lomustine (CCNU), cytarabine USP, cyclophosphamide, estramucine phosphate sodium, altretamine, hydroxyurea, ifosfamide, procarbazine, mitomycin, busulfan, cyclophosphamide, mitoxantrone, carboplatin, cisplatin, interferon alfa-2a recombinant, paclitaxel, teniposide, and streptozoci), cytotoxic alkylating agents (e.g., busulfan, chlorambucil, cyclophosphamide, melphalan, or ethylesulfonic acid), alkylating agents (e.g., asaley, AZQ, BCNU, busulfan, bisulphan, carboxyphthalatoplatinum, CBDCA, CCNU, CHIP, chlorambucil, chlorozotocin, cisplatinum, clomesone, cyanomorpholinodoxorubicin, cyclodisone, cyclophosphamide, dianhydrogalactitol, fluorodopan, hepsulfam, hycanthone, iphosphamide, melphalan, methyl CCNU, mitomycin C, mitozolamide, nitrogen mustard, PCNU, piperazine, piperazinedione, pipobroman, porfiromycin, spirohydantoin mustard, streptozotocin, teroxirone, tetraplatin, thiotepa, triethylenemelamine, uracil nitrogen mustard, and Yoshi-864), antimitotic agents (e.g., allocolchicine, Halichondrin M, colchicine, colchicine derivatives, dolastatin 10, maytansine, rhizoxin, paclitaxel derivatives, paclitaxel, thiocolchicine, trityl cysteine, vinblastine sulfate, and vincristine sulfate), plant alkaloids (e.g., actinomycin D, bleomycin, L-asparaginase, idarubicin, vinblastine sulfate, vincristine sulfate, mitramycin, mitomycin, daunorubicin, VP-16-213, VM-26, navelbine and taxotere), biologicals (e.g., alpha interferon, BCG, G-CSF, GM-CSF, and interleukin-2), topoisomerase I inhibitors (e.g., camptothecin, camptothecin derivatives, and morpholinodoxorubicin), topoisomerase II inhibitors (e.g., mitoxantron, amonafide, m-AMSA, anthrapyrazole derivatives, pyrazoloacridine, bisantrene HCL, daunorubicin, deoxydoxorubicin, menogaril, N,N-dibenzyl daunomycin, oxanthrazole, rubidazone, VM-26 and VP-16), and synthetics (e.g., hydroxyurea, procarbazine, o,p'-DDD, dacarbazine, CCNU, BCNU, cis-diamminedichloroplatimun, mitoxantrone, CBDCA, levamisole, hexamethylmelamine, all-trans retinoic acid, gliadel and porfimer sodium).

Antiproliferative agents are compounds that decrease the proliferation of cells. Antiproliferative agents include alkylating agents, antimetabolites, enzymes, biological response modifiers, miscellaneous agents, hormones and antagonists, androgen inhibitors (e.g., flutamide and leuprolide acetate), antiestrogens (e.g., tamoxifen citrate and analogs thereof, toremifene, droloxifene and roloxifene), Additional examples of specific antiproliferative agents include, but are not limited to levamisole, gallium nitrate, granisetron, sargramostim strontium-89 chloride, filgrastim, pilocarpine, dexrazoxane, and ondansetron.

The renalase binding molecule of the invention can be used alone or in combination with anti-tumor agents, including cytotoxic/antineoplastic agents and anti-angiogenic agents. Cytotoxic/anti-neoplastic agents are defined as agents which attack and kill cancer cells. Some cytotoxic/anti-neoplastic agents are alkylating agents, which alkylate the genetic material in tumor cells, e.g., cis-platin, cyclophosphamide, nitrogen mustard, trimethylene thiophosphoramide, carmustine, busulfan, chlorambucil, belustine, uracil mustard, chlomaphazin, and dacabazine. Other cytotoxic/anti-neoplastic agents are antimetabolites for tumor cells, e.g., cytosine arabinoside, fluorouracil, methotrexate, mercaptopuirine, azathioprime, and procarbazine. Other cytotoxic/anti-neoplastic agents are antibiotics, e.g., doxorubicin, bleomycin, dactinomycin, daunorubicin, mithramycin, mitomycin, mytomycin C, and daunomycin. There are numerous liposomal formulations commercially available for these compounds. Still other cytotoxic/anti-neoplastic agents are mitotic inhibitors (*vinca* alkaloids). These include vincristine, vinblastine and etoposide. Miscellaneous cytotoxic/anti-neoplastic agents include taxol and its derivatives, L-asparaginase, anti-tumor antibodies, dacarbazine, azacytidine, amsacrine, melphalan, VM-26, ifosfamide, mitoxantrone, and vindesine.

Anti-angiogenic agents are well known to those of skill in the art. Suitable anti-angiogenic agents for use in the methods and compositions of the present disclosure include anti-VEGF antibodies, including humanized and chimeric antibodies, anti-VEGF aptamers and antisense oligonucleotides. Other known inhibitors of angiogenesis include angiostatin, endostatin, interferons, interleukin 1 (including alpha and beta) interleukin 12, retinoic acid, and tissue inhibitors of metalloproteinase-1 and -2. (TIMP-1 and -2). Small molecules, including topoisomerases such as razoxane, a topoisomerase II inhibitor with anti-angiogenic activity, can also be used.

Other anti-cancer agents that can be used in combination with the disclosed compounds include, but are not limited to: acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alfa-2a; interferon alfa-2b; interferon alfa-n1; interferon alfa-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; albumin-bound paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine; vinorelbine tartrate; vinrosidine sulfate; vinzolidine sulfate; vorozole; zeniplatin; zinostatin; zorubicin hydrochloride. Other anti-cancer drugs include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex: formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+ estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; 06-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU: sarcophytol A; sargramostim; Sdi 1 mimetics; semustine; senescence derived inhibitor 1; sense oligonucleotides; signal transduction inhibitors; signal transduction modulators; single chain antigen binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; imilimumab; mirtazapine; BrUOG 278; BrUOG 292; RAD0001; CT-Ol1; folfirinox; tipifarnib; RI15777; LDE225; calcitriol; AZD6244; AMG 655; AMG 479; BKM120; mFOLFOX6; NC-6004; cetuximab; IM-C225; LGX818; MEK162; BBI608; MED14736; vemurafenib; ipilimumab; ivolumab; nivolumab; panobinostat; leflunomide; CEP-32496; alemtuzumab; bevacizumab; ofatumumab; panitumumab; pembrolizumab; rituximab; trastuzumab; STAT3 inhibitors (e.g., STA-21, LLL-3, LLL12, XZH-5, S31-201, SF-1066, SF-1087, STX-0119, cryptotanshinone, curcumin, diferuloylmethane, FLLL11, FLLL 12, FLLL32, FLLL62, C3, C30, C188, C188-9, LY5, OPB-31121, pyrimethamine, OPB-51602, AZD9150, etc.); hypoxia inducing factor 1 (HIF-1) inhibitors (e.g., LW6, digoxin, laurenditerpenol, PX-478, RX-0047, vitexin, KC7F2, YC-1, etc.) and zinostatin stimalamer. In one embodiment, the anti-cancer drug is 5-fluorouracil, taxol, or leucovorin.

Methods of Diagnosis

In some embodiments, a change (e.g., an increase) in the level of renalase, or a renalase fragment, in a subject's cell, tissue, or bodily fluid, compared with a comparator is used in the methods of the invention as marker for the diagnosis of a disease or disorder, assessing the severity of a disease or disorder, and for monitoring the effect or effectiveness of a treatment of a disease or disorder. In various embodiments, the disease or disorder is acute renal failure (i.e., acute tubular necrosis, or ATN, an ischemic condition in the kidney), a cardiovascular disease or disorder (e.g., hypertension, pulmonary hypertension, systolic hypertension, diabetic hypertension, asymptomatic left ventricular dysfunction, chronic congestive heart failure, myocardial infarction, cardiac rhythm disturbance, atherosclerosis, etc.), an inflammatory disease or disorder, cancer, heart disease or disorder, a kidney disease or disorder, a gastrointestinal disease or disorder, a liver disease or disorder, a lung disease or disorder, a pancreas disease or disorder (e.g., pancreatitis), mental disease or disorder (e.g., depression, anxiety, etc.), or a neurological disease or disorder.

In one embodiment, the invention is a method of diagnosing a disease or disorder of a subject by assessing the level of renalase, or a renalase fragment, in a biological sample of the subject. In one embodiment, the biological sample of the subject is a cell, tissue, or bodily fluid. Non-limiting examples of bodily fluids in which the level of renalase, or a renalase fragment, can be assessed include, but are not limited to, blood, serum, plasma and urine. In various embodiments, the level of renalase, or a renalase fragment, in the biological sample of the subject is compared with the renalase, or the renalase fragment, level in a comparator. Non-limiting examples of comparators include, but are not limited to, a reference standard, a negative control, a positive control, an expected normal background value of the subject, a historical normal background value of the subject, an expected normal background value of a population that the subject is a member of, or a historical normal background value of a population that the subject is a member of. In various embodiments, the reference standard comprises one selected from the group consisting of an acid-treated recombinant renalase, an acid-treated recombinant renalase fragment, RPC1, and RPC2. In various embodiments, the disease or disorder is acute renal failure (i.e., acute tubular necrosis, or ATN, an ischemic condition in the kidney), a cardiovascular disease or disorder (e.g., hypertension, pulmonary hypertension, systolic hypertension, diabetic hypertension, asymptomatic left ventricular dysfunction, chronic congestive heart failure, myocardial infarction, cardiac rhythm disturbance, atherosclerosis, etc.), an inflammatory disease or disorder, cancer, heart disease or disorder, a kidney disease or disorder, a gastrointestinal disease or disorder, a liver disease or disorder, a lung disease or disorder, a pancreas disease or disorder (e.g., pancreatitis), mental disease or disorder (e.g., depression, anxiety, etc.), or a neurological disease or disorder. In some embodiments, the method of diagnosing includes a further step of treating the patient for the diagnosed disease or disorder.

In another embodiment, the invention is a method of assessing the severity of a disease or disorder of a subject by assessing the level of renalase, or a renalase fragment, in a biological sample of the subject. In one embodiment, the biological sample of the subject is a cell, tissue, or bodily fluid. Non-limiting examples of bodily fluids in which the level of renalase, or a renalase fragment, can be assessed include, but are not limited to, blood, serum, plasma and urine. In various embodiments, the level of renalase, or a renalase fragment, in the biological sample of the subject is compared with the renalase, or a renalase fragment, level in a comparator. Non-limiting examples of comparators include, but are not limited to, a negative control, a positive control, a reference standard, an expected normal background value of the subject, a historical normal background value of the subject, an expected normal background value of a population that the subject is a member of, or a historical normal background value of a population that the subject is a member of. In various embodiments, the reference standard comprises one selected from the group consisting of an acid-treated recombinant renalase, an acid-treated recombinant renalase fragment, RPC1, and RPC2. In various embodiments, the disease or disorder is acute renal failure (i.e., acute tubular necrosis, or ATN, an ischemic condition in the kidney), a cardiovascular disease or disorder (e.g., hypertension, pulmonary hypertension, systolic hypertension, diabetic hypertension, asymptomatic left ventricular dysfunction, chronic congestive heart failure, myocardial infarction, cardiac rhythm disturbance, atherosclerosis, etc.), inflammatory disease or disorder, cancer, heart disease or disorder, a kidney disease or disorder, a gastrointestinal disease or disorder, a liver disease or disorder, a lung disease or disorder, a pancreas disease or disorder (e.g., pancreatitis), mental disease or disorder (e.g., depression, anxiety, etc.), or a neurological disease or disorder. In some embodiments, the method of assessing the severity includes a further step of treating the patient for the disease or disorder.

In another embodiment, the invention is a method of monitoring the effect of a treatment of a disease or disorder of a subject by assessing the level of renalase, or a renalase fragment, in a biological sample of the subject. In one embodiment, the biological sample of the subject is a cell, tissue, or bodily fluid. Non-limiting examples of bodily fluids in which the level of renalase, or a renalase fragment, can be assessed include, but are not limited to, blood, serum, plasma and urine. In various embodiments, the level of renalase, or a renalase fragment, in the biological sample of the subject is compared with the renalase, or a renalase fragment, level in a comparator. Non-limiting examples of comparators include, but are not limited to, a negative control, a positive control, a reference standard, an expected normal background value of the subject, a historical normal background value of the subject, an expected normal background value of a population that the subject is a member of, or a historical normal background value of a population that the subject is a member of. In various embodiments, the reference standard comprises one selected from the group consisting of an acid-treated recombinant renalase, an acid-treated recombinant renalase fragment, RPC1, and RPC2. In various embodiments, the disease or disorder is acute renal failure (i.e., acute tubular necrosis, or ATN, an ischemic condition in the kidney), a cardiovascular disease or disorder (e.g., hypertension, pulmonary hypertension, systolic hypertension, diabetic hypertension, asymptomatic left ventricular dysfunction, chronic congestive heart failure, myocardial infarction, cardiac rhythm disturbance, atherosclerosis, etc.), inflammatory disease or disorder, cancer, heart disease or disorder, a kidney disease or disorder, a gastrointestinal disease or disorder, a liver disease or disorder, a lung disease or disorder, a pancreas disease or disorder (e.g., pancreatitis), mental disease or disorder (e.g., depression, anxiety, etc.), or a neurological disease or disorder. In some embodiments, the method of monitoring the effect of a treatment includes a further step of treating the patient for the disease or disorder.

In various embodiments, the subject is a human subject, and may be of any race, sex and age. Representative subjects include those who are suspected of having experienced a disease or disorder, those who have been diagnosed as having experienced a disease or disorder, those who have been diagnosed as having a disease or disorder, and those who are at risk of developing a disease or disorder.

Information obtained from the methods of the invention described herein can be used alone, or in combination with other information (e.g., disease status, disease history, vital signs, blood chemistry, etc.) from the subject or from the biological sample obtained from the subject.

In the diagnostic methods of the invention, a biological sample obtained from a subject is assessed for the level of renalase, or a renalase fragment, contained therein. In one embodiment, the biological sample is a sample containing at least a fragment of a renalase polypeptide useful in the methods described herein.

In other various embodiments of the methods of the invention, the level of renalase is determined to be increased when the level of renalase, or a renalase fragment, is increased by at least 10%, by at least 20%, by at least 30%, by at least 40%, by at least 50%, by at least 60%, by at least 70%, by at least 80%, by at least 90%, by at least 100%, by at least 2000, by at least 300%, by at least 400%, by at least 500%, by at least 600%, by at least 700%, by at least 800%, by at least 900%, or by at least 1000%, when compared with a comparator control. In various embodiments, an increased level of renalase, or a renalase fragment, is indicative of a disease or disorder. In various embodiments, the disease or disorder is acute renal failure (i.e., acute tubular necrosis, or ATN, an ischemic condition in the kidney), inflammatory disease, cardiovascular disease, and cancer.

In other various embodiments of the methods of the invention, the level of renalase is determined to be decreased when the level of renalase, or a renalase fragment, is decreased by at least 10%, by at least 20%, by at least 30%, by at least 40%, by at least 50%, by at least 600, by at least 70%, by at least 80, by at least 90%, by at least 100%, by at least 200%, by at least 300%, by at least 400%, by at least 500%, by at least 600%, by at least 700%, by at least 800%, by at least 900%, or by at least 1000%, when compared with a comparator control.

In the methods of the invention, a biological sample from a subject is assessed for the level of renalase, or a renalase fragment, in the biological sample obtained from the patient. The level of renalase, or a renalase fragment, in the biological sample can be determined by assessing the amount of renalase polypeptide, or a fragment, in the biological sample, the amount of renalase mRNA, or a fragment, in the biological sample, the amount of renalase activity (e.g., enzymatic activity, substrate binding activity, receptor binding activity, etc.) in the biological sample, or a combination thereof. In some embodiments, the level of renalase in the biological sample is determined in an assay using at least one of the renalase binding molecules of the invention described elsewhere herein.

In various embodiments of the methods of the invention, methods of measuring renalase levels in a biological sample obtained from a patient include, but are not limited to, an immunochromatography assay, an immunodot assay, a Luminex assay, an ELISA assay, an ELISPOT assay, a protein microarray assay, a Western blot assay, a mass spectrophotometry assay, a radioimmunoassay (RIA), a radioimmunodiffusion assay, a liquid chromatography-tandem mass spectrometry assay, an ouchterlony immunodiffusion assay, reverse phase protein microarray, a rocket immunoelectrophoresis assay, an immunohistostaining assay, an immunoprecipitation assay, a complement fixation assay, FACS, an enzyme-substrate binding assay, an enzymatic assay, an enzymatic assay employing a detectable molecule, such as a chromophore, fluorophore, or radioactive substrate, a substrate binding assay employing such a substrate, a substrate displacement assay employing such a substrate, and a protein chip assay (see also, 2007, Van Emon, Immunoassay and Other Bioanalytical Techniques, CRC Press; 2005, Wild, Immunoassay Handbook, Gulf Professional Publishing; 1996, Diamandis and Christopoulos, Immunoassay, Academic Press; 2005, Joos, Microarrays in Clinical Diagnosis, Humana Press; 2005, Hamdan and Righetti, Proteomics Today, John Wiley and Sons; 2007). In some embodiments, the level of renalase in the biological sample is measure with an assay that uses at least one of the renalase binding molecules of the invention that are described elsewhere herein.

Kits

The invention also includes a kit comprising a renalase binding molecule (e.g., antibody, etc.), or combinations thereof, of the invention and an instructional material which describes, for instance, using the renalase binding molecule as described elsewhere herein. In an embodiment, this kit further comprises a (preferably sterile) analytically or pharmaceutically acceptable carrier suitable for dissolving or suspending the composition, comprising a renalase binding molecule, or combinations thereof, of the invention, for instance, prior to using the renalase binding molecule of the invention in a renalase measurement assay.

EXPERIMENTAL EXAMPLES

The invention is now described with reference to the following Examples. These Examples are provided for the purpose of illustration only and the invention should in no way be construed as being limited to these Examples, but rather should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

Example 1: Novel Compositions and Methods for Detecting Renalase

The results described herein provide data supporting the utility of novel compositions and methods for detecting renalase in biological samples.

The materials and methods employed in these experiments are now described.

Protein Sample Generation

Various protein samples were prepared for analysis by Immunoprecipitation, Western blotting or ELISA as follows.

Cell growth and maintenance: 293T human embryonic kidney cells (ATCC #CRL-11268), human HK-2 (ATCC #CRL-2190) and porcine LLC-PK1 (ATCC #CL-101proximal tubule cell lines were cultured in Dulbecco's modified Eagle's medium (DMEM) supplemented with 5% fetal bovine serum (FBS) and 2 mM Glutamine. Where indicated, 293T cells were transfected with a pCDNA3-renalase-1 construct using Lipofectamine 2000 transfection reagent (Invitrogen), according to the manufacturer's instructions.

Preparation of cell culture lysates: Culture medium was removed and the cell monolayer was washed with 5 mL magnesium- and calcium-free phosphate-buffered saline (PBS). Cells were detached from the flask by adding 4 mL 0.02% trypsin solution (Invitrogen) and incubating at 37° C. for 5 minutes. 5 mL complete cell growth medium (DMEM/5% FBS/2 mM Glutamine) was added to the cell suspension to neutralize the trypsin activity. Cells were pelleted by centrifugation at 1000 g for 5 minutes at room temperature and washed once with PBS. Cell pellets were resuspended in RIPA lysis buffer (50 mM Tris pH8.0, 1 mM EDTA, 150 mM sodium chloride, 1% (v/v) Triton X-100, 0.5% (w/v) sodium deoxycholate, 0.1% (w/v) sodium dodecyl sulfate) containing 1 mM dithiothreitol (DTT) and 1 mM phenylmethylsulfonylfluoride (PMSF) and incubated on ice for 10 minutes. Lysates were centrifuged at 15 000 g for 10 minutes at 4C to remove any cellular debris and the supernatant was removed to a fresh tube.

Preparation of cell culture supernatants: Cell culture medium containing secreted proteins were collected after 24 hours of culture and centrifuged at room temperature, first at 1000 g for 5 minutes and then at 15 000 g for 10 minutes, to remove unbroken cells and cellular debris. The cleared supernatant was then transferred to a fresh tube.

Preparation of tissue lysates: Human and rat kidney lysates were purchased from Prosci Inc. Human brain, testis, heart and adrenal gland lysates, and mouse kidney lysate were purchased from Abcam. Pig kidneys were obtained from Sierra Medical Science. Pig kidney tissue was dissected and homogenized in RIPA buffer, containing 1 mM PMSF and 1 mM DTT using an electric blender. The homogenate was cleared by centrifugation at 15 000 g for 10 minutes and the supernatant was removed to a fresh tube, taking care to avoid transferring any lipid that had accumulated at the surface of the supernatant. The kidney lysate was filtered (0.2 µM) before further use. The protein concentration of all samples was assessed by Bradford protein assay (Biorad). Reducing or non-reducing sample buffer (Fermentas) was added and samples were heated to 95° C. for 5 minutes prior to electrophoresis.

Western Blotting

Protein samples were resolved on 4-20% Tris-Glycine gradient gels (Invitrogen). Proteins were transferred from the gel to polyvinyldifluoride (PVDF) membranes using an XCell II blot module (Invitrogen). PVDF membranes were blocked with a solution of 5% non-fat powdered milk in phosphate-buffered saline containing 0.1% Tween-20 (PBST) for one hour at room temperature. The blocking buffer was then removed and the membrane was incubated with the detection antibody, diluted in 20 mL 5% milk/PBST. After incubation at room temperature for one hour, the membrane was washed three times for 10 minutes each with PBST. 20 mL anti-rabbit IgG horseradish peroxidase (HRP) conjugate (Dako, diluted to 0.25 µg/mL in 5% milk/PBST) was applied to the membrane and incubated for a further one hour at room temperature. The membrane was washed three times for 10 minutes each with PBST. Excess PBST was drained from the membrane and sufficient enhanced chemiluminescence (ECL) plus reagent (GE Lifesciences) to cover the surface of the membrane was applied, and incubated for one minute. Excess ECL plus reagent was then drained and the membrane was wrapped in plastic film. Protein bands were visualized by exposing the membrane to Hyperfilm-ECL (GE Lifesciences), which was processed using an automatic film developer (Konica).

Immunoprecipitation

Protein G-Sepharose immunoprecipitations: 2 µg of immunoprecipitating antibody was added to each protein sample (cell lysates, cell supernatants or tissue lysates) and incubated with agitation at 4° C. for 1 hour. 20 µL protein G Sepharose (Sigma) was then added to each sample and samples were incubated for a further 2 hours at 4° C. with agitation. Protein G Sepharose-antibody-protein immunoprecipitates were collected by centrifugation (10 000 g, 1 minute) and the supernatant was carefully removed. Immunoprecipitates were washed three times with 1 mL RIPA buffer, recovering the immunoprecipitates by centrifugation at 10000 g for 1 minute between each wash. 50 µL reducing SDS-PAGE sample buffer was added and the sample was heated to 95° C. for 5 minutes to release bound proteins from the ProteinG-Sepharose matrix. Proteins were analyzed by SDS-PAGE and Western blotting as described in the above western blotting protocol, except that in this case blocked membranes were incubated with biotinylated detection antibody diluted in 5% milk/PBST for one hour, and then with Neutravidin-HRP (Pierce) diluted 1:1000 in 5% milk/PBST for one hour.

Actigel immunoprecipitations: Immunoprecipitation antibodies were coupled to Actigel beads (Sterogene) at a substitution concentration of 2 µg antibody per 50 µL actigel according to the manufacturer's instructions. 50 µL actigel/2 µg antibody conjugate was added to each protein sample (cell lysates, cell supernatants or tissue lysates) and incubated with agitation at 4C for 3 hours. Actigel-antibody-protein immunoprecipitates were collected by centrifugation (10 000 g, 1 minute) and the supernatant was carefully removed. Immunoprecipitates were washed three times with 1 mL RIPA buffer and two times with 1 mL phosphate-buffered saline, recovering the immunoprecipitates by centrifugation at 10 000 g for 1 minute between each wash. Immunoprecipitated proteins were eluted from the Actigel-antibody matrix by incubation with 50 µL 0.1 M glycine, pH 2.5. for 10 minutes at room temperature. Samples were centrifuged at 10 000 g for 1 minute and the supernatants containing eluted proteins were removed to fresh tubes. 50 µL reducing SDS-PAGE sample buffer was added and the sample was heated to 95° C. for 5 minutes, before analysis by SDS-PAGE and Western blotting as described in the above western blotting protocol.

Immunofluorescence

Cell culture: Cells were plated into 4-well chamber slides (Labtek) at a density of $5\times10^4$ cells per well in a volume of 500 µL complete culture medium (Dulbecco's modified Eagle's medium containing 5% fetal bovine serum and 2 mM glutamine). After 24 hours, cell culture medium was aspirated and the cell monolayer was washed three times with phosphate-buffered saline.

Immunofluorescence staining: 500 µL ice-cold Methanol:Acetone (1:1) was added to each well of the culture chamber and incubated at −20° C. for 10 minutes to fix and permeabilize cells. The fixation buffer was removed and cell monolayers were washed four times with phosphate-buffered saline. Slides were blocked by adding 500 µL PBS containing 10% normal goat serum (Abcam) to each well, and incubating at room temperature for one hour. Blocking buffer was removed and 500 µL detection antibody diluted in fresh blocking buffer was added to each well and incubated for one hour at room temperature. Cells were washed three times with PBS and then incubated for a further one hour with Alexafluor488-conjugated goat anti-rabbit secondary antibody (Invitrogen) diluted to 2 µg/mL in blocking buffer. Cells were washed three times with PBS and incubated for 5 minutes with 500 µL of 0.5 µg/mL 4',6-diamidino-2-phenylindole (DAPI). Cells were then washed a further four times with PBS, the chamber slide housing was removed and coverslips were mounted onto the slides with Permount (Fisher). Slides were sealed with clear nail polish.

Detection: Images of stained cells were acquired using a Zeiss LSM 510 Meta confocal microscope, using the 40× objective. Data was analyzed using Zeiss LSM Image Browser software.

Sandwich ELISA Assay: Spectrophotometric Detection

Typically, 400 ng/well of capture antibody in phosphate-buffered saline (PBS) was bound to a 96 well microtiter plate by overnight incubation at 4° C. The plate was blocked with a solution of 8% non-fat dried milk (NFDM) in PBS for one hour at 33° C. The samples, containing renalase, were diluted in PBS containing Tween-20 to 0.05% (PBST), and 50 µL was added to each well. After one hour incubation at 33° C., the plate was rinsed three times with PBST. The biotinylated antibody probe was diluted to 4 µg/mL in PBST, and 50 µL was added to each well. After incubation for 1 hour at 33° C., the plate was washed 3 times with PBS-tween. For detection, 50 µL of horseradish peroxidase-conjugated (HRP) Neutravidin (NA-HRP) diluted to 0.4 µg/mL, was added to each well and the plate was incubated at room temperature for 45 minutes. After incubation the plate was washed three times with PBST and once with PBS. The HRP substrate 3, 3', 5, 5'-tetramethylbenzidine (TMB) was added to 100 µL per well, and plate was incubated for approximately 5 minutes at room temperature. To stop the reaction, 100 µL 2 N $H_2SO_4$ was added to each well. The plate was read at 450 nm in a spectrophotometer. Alterations to this method are described in the relevant sections.

The results of the experiments are now described.

The Use of Renalase Affinity Reagents for the Detection of Recombinant and Endogenous Renalase Using Western Blot Renalase is a FAD-containing protein that has been implicated in the control and maintenance of blood pressure. The lack of high-affinity, high-specificity anti-renalase antibodies has hindered the research and development of both renalase biology and potential renalase-associated therapeutics. To date, several polyclonal research-reagent antibodies have been developed, but these are low affinity and fail to robustly detect endogenous renalase in cell culture, tissue samples or bodily fluid samples. Thus, the development of a set of renalase antibodies with specificity for the different isoforms of renalase and further, different peptide sequences within the intact protein will allow for definitive detection and characterization of the renalase gene product. Further the selection of only high affinity antibodies will allow for the detection of potentially low levels of renalase and thus may lead to the development of a protein-based diagnostic for renalase levels.

Animals were immunized with either whole Human renalase-1 polypeptide (FIG. 1) or peptides corresponding to regions of either Human renalase-1 or Human renalase-2 (FIG. 1, peptide 1A-1F and 3A). Polyclonal antibodies raised against the whole protein were purified from post-immune serum using Protein A affinity chromatography and further purified on a recombinant renalase affinity column. Polyclonal antibodies raised against the peptide antigens were purified from the post-immune serum by an initial affinity purification on Protein A followed by a second purification step on an affinity column displaying the relevant peptide. The splenocytes from some animals that were immunized with the renalase peptides were used in the formation of hybridomas. These hybridomas were screened for anti-peptide and anti-renalase binding affinity. Clones with preferred renalase binding characteristics were expanded and monoclonal antibodies were produced and purified from the hybridoma cell-culture media by Protein A affinity chromatography.

Anti-renalase polyclonal and monoclonal antibodies are listed in FIG. 1 and FIG. 4 through FIG. 13. The selected polyclonal antibody raised against whole renalase polypeptide is denoted E2930. The selected polyclonal antibodies raised against the peptides are denoted by the peptide for which they are specific. The selected monoclonal antibodies, specific for the various peptide antigens are denoted as listed in FIG. 1. Polyclonal and monoclonal antibodies raised against peptide 1F are specific for renalase-1. Polyclonal and monoclonal antibodies raised against peptide 3A are specific for renalase-2. All other polyclonal and monoclonal antibodies have affinity for both isoforms of renalase.

All of the renalase antibodies are capable of detecting recombinant renalase protein by western blot. Further, some of the antibodies are capable of detecting endogenous renalase protein from a background of whole cell lysate proteins. Recombinant renalase-1 (RV11) and whole cell lysates of the human embryonic kidney cell line 293T and human (HK-2) and porcine (LLC-PK1) immortalized renal proximal tubule epithelial cells were examined by Western blotting comparing several of the anti-renalase antibodies as probes. Briefly, 10 µg total protein of lysates from HK-2, LLC-PK1 and 293T cells and 250 µg recombinant renalase-1 (RV11) positive control were resolved by SDS-PAGE and transferred to PVDF blotting membranes. Membranes were blocked with 5% Marvel/PBS-Tween20 (0.05%) and probed with renalase-specific primary antibodies (as indicated in FIG. 14) diluted to a final concentration of 1 µg/mL in blocking buffer. Blots were then washed with PBS-Tween and incubated with secondary HRP-conjugated anti-rabbit antibody (Dako) diluted 1:5000 in blocking buffer. Blots were then washed with PBS-Tween and bound antibodies detected using ECL-Plus and Hyperfilm (GE Life Sicences). As can be seen in FIG. 14, significant renalase protein could be detected in HK-2 cells, with all of the antibodies tested. Renalase was also detected in LLC-PK1 cells by the Ren 1D 28-4 antibody, but not with the Ren 1D 37-10 or Ren 1F 26-1 antibodies, most likely reflecting both lower expression levels and differences in amino acid sequence between human and porcine renalase.

Endogenous Renalase

Figure 15A:
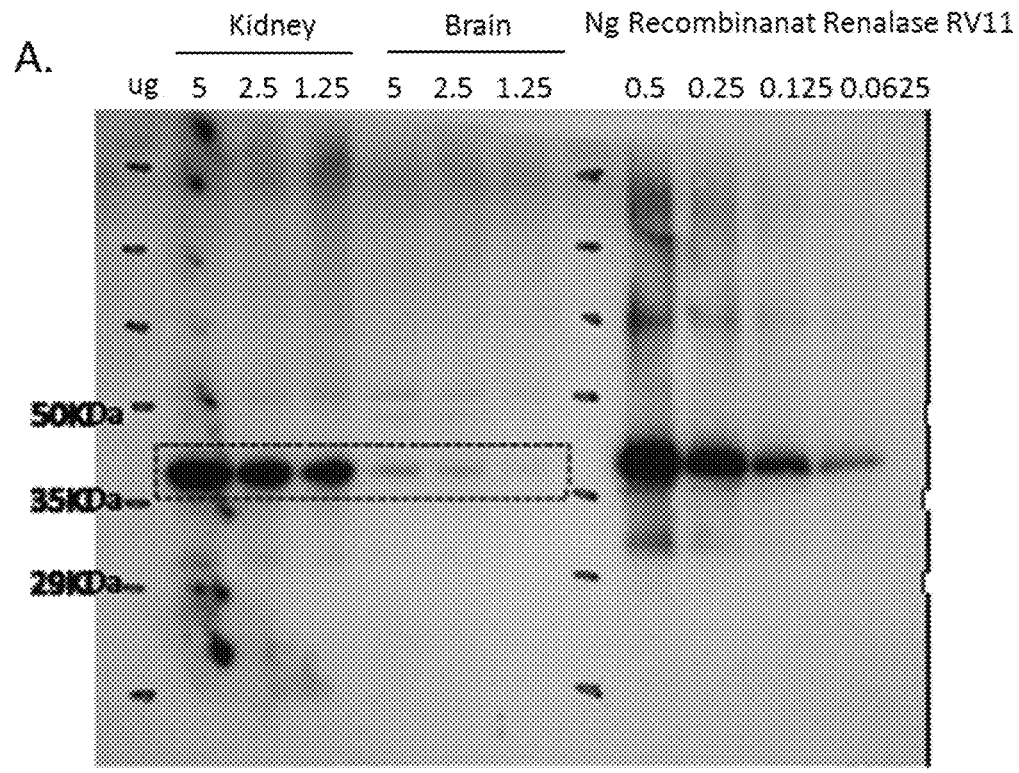
FIG. 15A through FIG. 15D, depicts the use of renalase antibodies to detect renalase in tissue lysates.
Figure 15B:
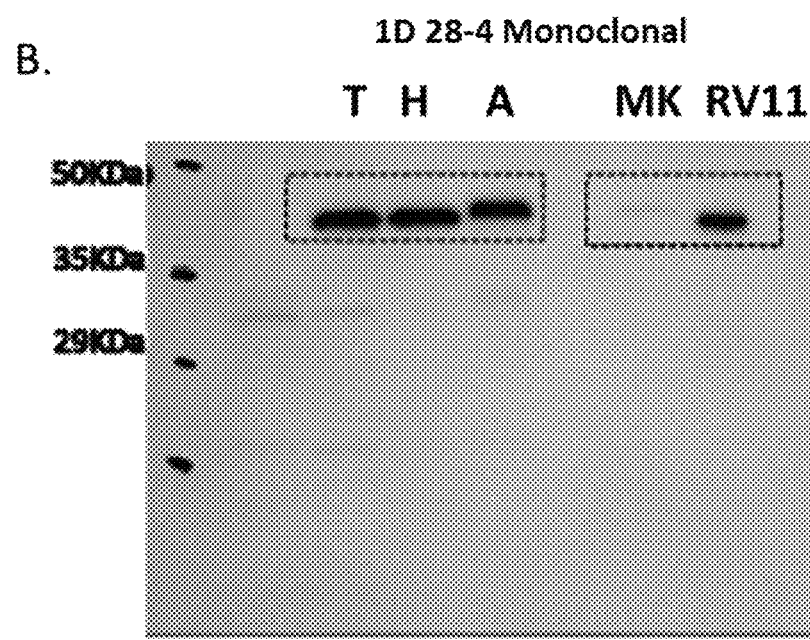
Figure 15C:
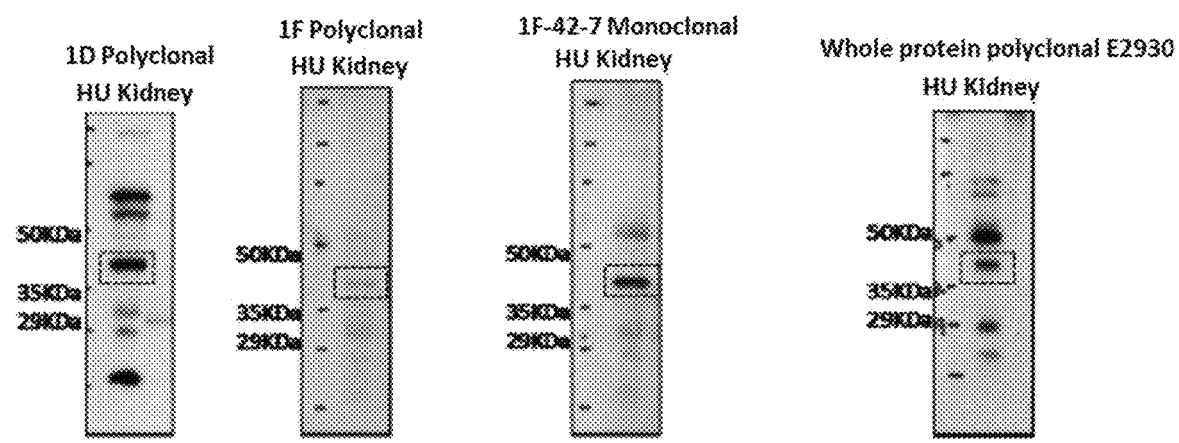
Figure 15D:
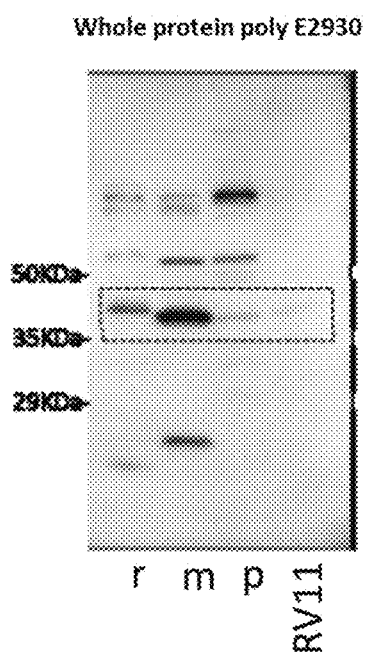

Articles have implicated Renalase in the control of mammalian blood pressure and other cardiovascular parameters. The measurement of endogenous renalase levels within a biological sample may therefore serve as a bio-marker highlighting a condition or disease. To date no method or reagent has been described to facilitate the detection of endogenous renalase in tissues. In the present example the anti-renalase antibodies of this invention detected endogenous mammalian renalase protein in whole tissue lysates from human, rat, mouse and pig tissues by Western blot analysis. The Ren 1D 28-4 antibody clearly detected renalase in human kidney, and weakly in human brain lysates (FIG. 15A). Strong detection of renalase was also seen in human testis, heart and adrenal gland (FIG. 15B), a result that correlates with published mRNA expression data. Further analysis of human kidney lysates showed that a number of other Ren antibodies could also detect human renalase in tissue lysates: Western blots with Ren1D polyclonal, Ren1F polyclonal, Ren 1F 42-7 monoclonal and the whole protein polyclonal E2930 are shown in FIG. 15C as examples. It is also shown that renalase from other species can be detected by Western blotting. Detection of rat, mouse or pig kidney renalase with the whole protein polyclonal antibody E2930 is shown in FIG. 15D.

The Detection of Endogenous Renalase in Mammalian Bodily Fluids

Figure 16:
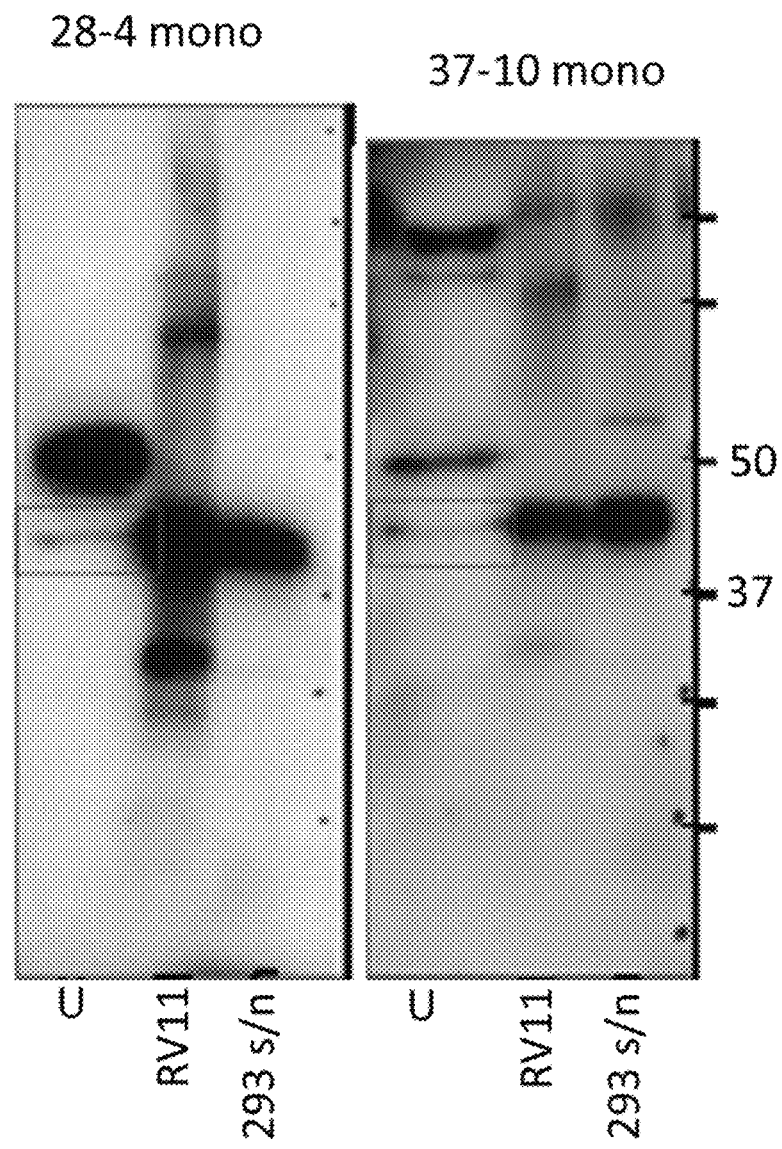
FIG. 16 depicts that the Ren 1D 28-4 and Ren 1D 37-10 monoclonal antibodies can be used to detect renalase protein in human urine samples.

Renalase has been reported to be found in urine. To assess the ability of Ren antibodies to detect urine renalase, human urine proteins were precipitated with 42% ethanol, re-solubilized and analyzed by Western blotting. FIG. 16 shows that the Ren 1D 28-4 and Ren 1D 37-10 monoclonal antibodies can be used to detect renalase protein in these samples. In this way, the detection of renalase levels within an individual could be assessed using a non-invasive test.

The Use of Anti-Renalase Affinity Reagents for the Purification of Renalase

The detection of renalase within a biological sample may require the binding of renalase protein in solution and/or purifying it away from a more complex mixture of proteins. Whilst Western blotting demonstrates the ability of an antibody to bind denatured protein, the immunoprecipitation of proteins from solution is dependent on the ability of antibodies to recognize native, folded protein. In demonstration of the renalase-specific antibody's ability to detect, bind and purify renalase from a complex mixture, bacterially expressed recombinant human renalase (RV11), mammalian cell (293T) expressed and secreted renalase, and whole pig kidney lysate were used as the input into immunoprecipitations with a variety of different antibodies. 250 µL of either pig kidney lysate, pCDNA3-renalase1-transfected 293T cell supernatant or 200 ng/mL recombinant renalase (RV11) was applied to either 50 ul Actigel beads coupled to 2 µg of various renalase-specific antibodies (RV11 and Pig kidney samples) or to 50 ul Protein G sepharose with 2 µg of renalase-specific antibodies (293T supernatant samples). All samples were incubated for 2 hours at 4° C. on a shaker. Immunoprecipitates were then washed 3 times with 1 mL RIPA buffer. 50 ul SDS-PAGE sample buffer (Fermentas) was added directly to Protein G-antibody immunoprecipitates and samples were heated to 95° C. for 5 minutes before running on SDS-PAGE. Actigel-antibody immunoprecipitates were washed a further 2 times in PBS prior to addition of 50 ul 0.1 M Glycine, pH 2.5. Samples were then agitated at room temperature for 10 minutes. Eluted proteins were recovered after centrifugation and resolved by SDS-PAGE. In all experiments 20 μL immunoprecipitate input material and 0.5 ng recombinant renalase positive control (RV11) were also loaded onto the gel.

Figure 17:
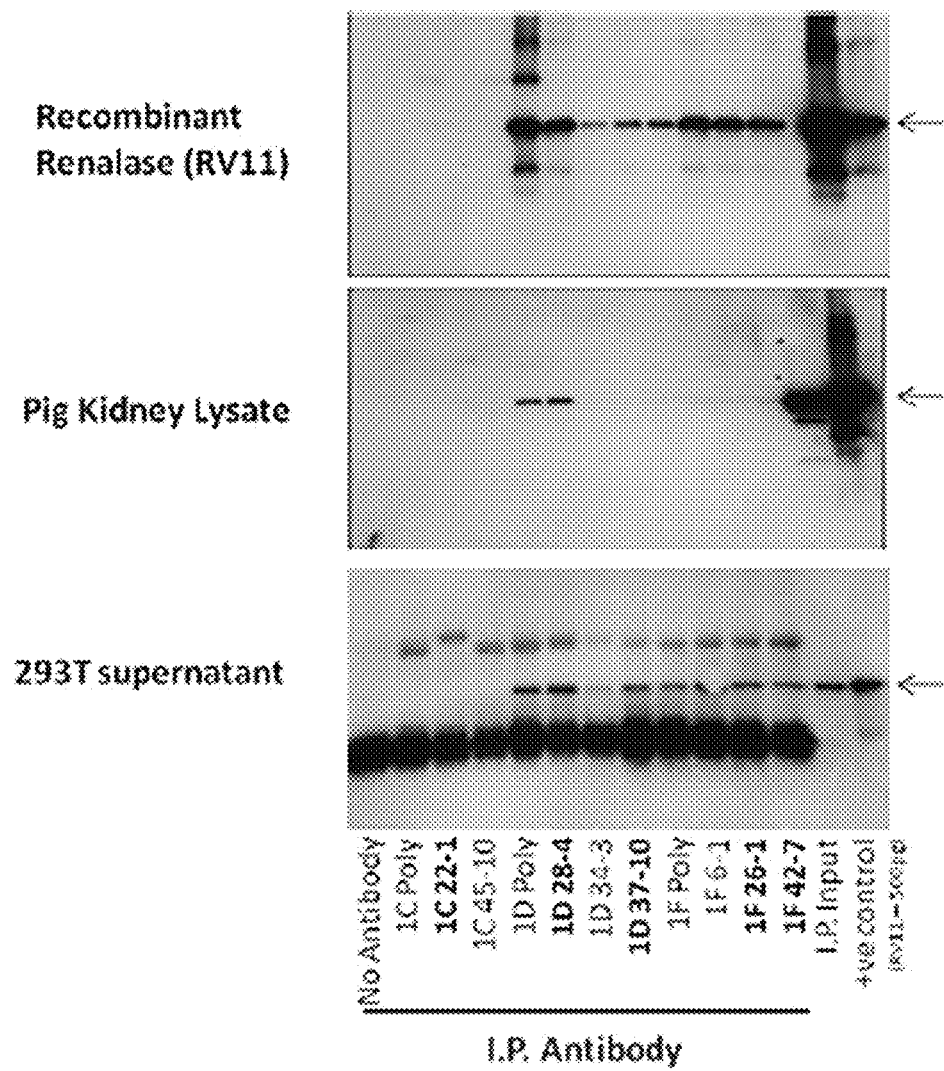
FIG. 17 depicts immunoprecipitation efficiency as assessed by Western blotting with Ren1D 28-4 monoclonal antibody, which has been shown (FIG. 14 and FIG. 15) to recognize human and porcine renalase. In the example where a Protein G-mediated immunoprecipitation was used the western primary antibody was biotinylated-Ren 28-4 followed with a neutravidin-HRP secondary probe. In all cases where no immunoprecipitating antibody was added, no renalase was detected on the Western blot. All of the 1D and 1F antibodies (monoclonal and polyclonal) were able to immunoprecipitate bacterially- or mammalian-expressed recombinant human renalase. The Ren 1D polyclonal and the Ren1D 28-4 monoclonal were also able to immunoprecipitate porcine kidney renalase. There are significant differences in the 1F antibody epitope sequence between human and porcine renalase and therefore it is unsurprising that no immunoprecipitation of renalase from pig kidney is seen with the 1F antibodies.

As can be seen in FIG. 17, immunoprecipitation efficiency was then assessed by Western blotting with Ren1D 28-4 monoclonal antibody, which has been shown (FIG. 14 and FIG. 15) to recognize human and porcine renalase. In the example where a Protein G-mediated immunoprecipitation was used the western primary antibody was biotinylated-Ren 28-4 followed with a neutravidin-HRP secondary probe. In all cases where no immunoprecipitating antibody was added, no renalase was detected on the Western blot. All of the 1D and 1F antibodies (monoclonal and polyclonal) were able to immunoprecipitate bacterially- or mammalian-expressed recombinant human renalase. The Ren 1D polyclonal and the Ren1D 28-4 monoclonal were also able to immunoprecipitate porcine kidney renalase. There are significant differences in the 1F antibody epitope sequence between human and porcine renalase and therefore it is unsurprising that no immunoprecipitation of renalase from pig kidney is seen with the 1F antibodies.

Intratissue and Intracellular Detection of Renalase Using Renalase-Specific Antibodies In situ detection of proteins within tissues or the cells from specific tissues is often used for the assessment of the expression levels of biologically important markers. Such methods are termed immunohistochemisty and immunocytochemistry. To determine whether the Ren antibodies could recognize endogenous renalase protein by this approach, HK-2 cells, shown in FIG. 14 to express significant levels of endogenous renalase, were fixed and stained with a number of different antibodies. HK-2 cells cultured in 4-well chamber slides (Labtek) were fixed and permeabilized with methanol/acetone (1:1) for 10 minutes at −20° C. Fixed cells were incubated for 1 hour in blocking buffer (PBS/10% normal goat serum) and then for 1 hour with the indicated primary antibodies (no primary antibody in control sample) diluted to 2 μg/mL in blocking buffer. Cells were then washed with PBS and incubated with AlexaFluor488-conjugated goat anti-rabbit secondary antibody (Invitrogen) diluted 1:400 in blocking buffer for 1 hour. Cells were washed with PBS and incubated for 5 minutes in 0.5 μg/mL DAPI (Invitrogen) in PBS. After rinsing in PBS the chamber slide housing was removed and coverslips were mounted onto the slides in Permount (Fisher Scientific).

Figure 18:
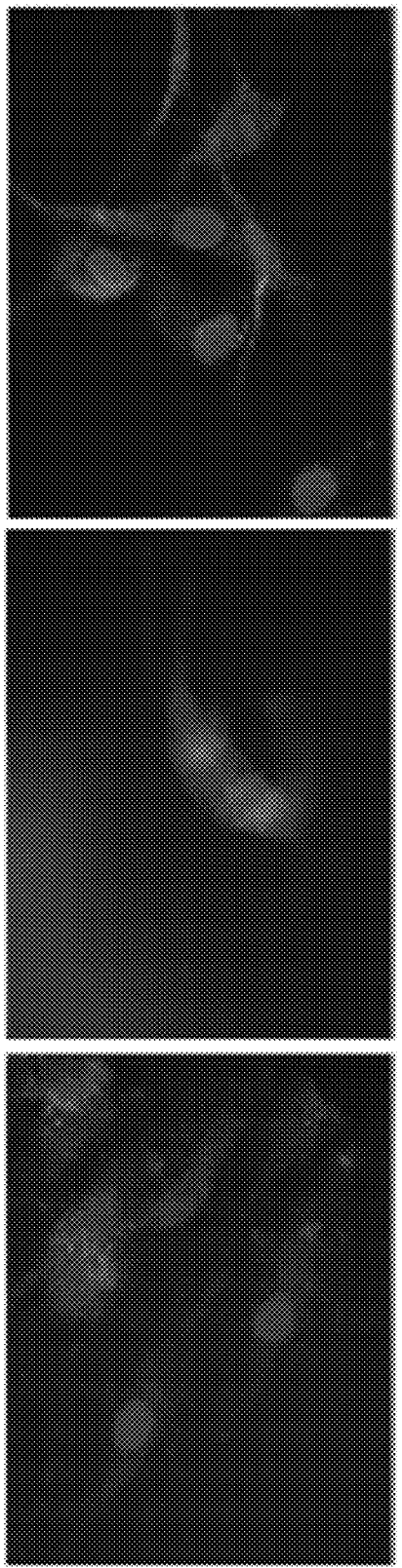
FIG. 18 depicts the use of renalase antibodies to detect renalase in cells by immunocytochemistry. An identical renalase staining pattern was observed with Ren1D 28-4 monoclonal, Ren 1F 26-1 monoclonal and Ren1b (#3009) polyclonal antibodies. Since these antibodies all recognize different epitopes of the renalase protein, the observed staining pattern is shown to be specific for renalase.

Images were acquired using a Zeiss Axioplan 2 microscope using the 63×/1.40 objective and processed using Zeiss Axiovision software. As can be seen in FIG. 18, an identical renalase staining pattern (green) was observed with Ren1D 28-4 monoclonal, Ren 1F 26-1 monoclonal and Ren1b (#3009) polyclonal antibodies. Since these antibodies all recognize different epitopes of the renalase protein, the observed staining pattern is shown to be specific for renalase.

The Capture and Detection of Renalase from Complex Biologic Samples

Figure 19:
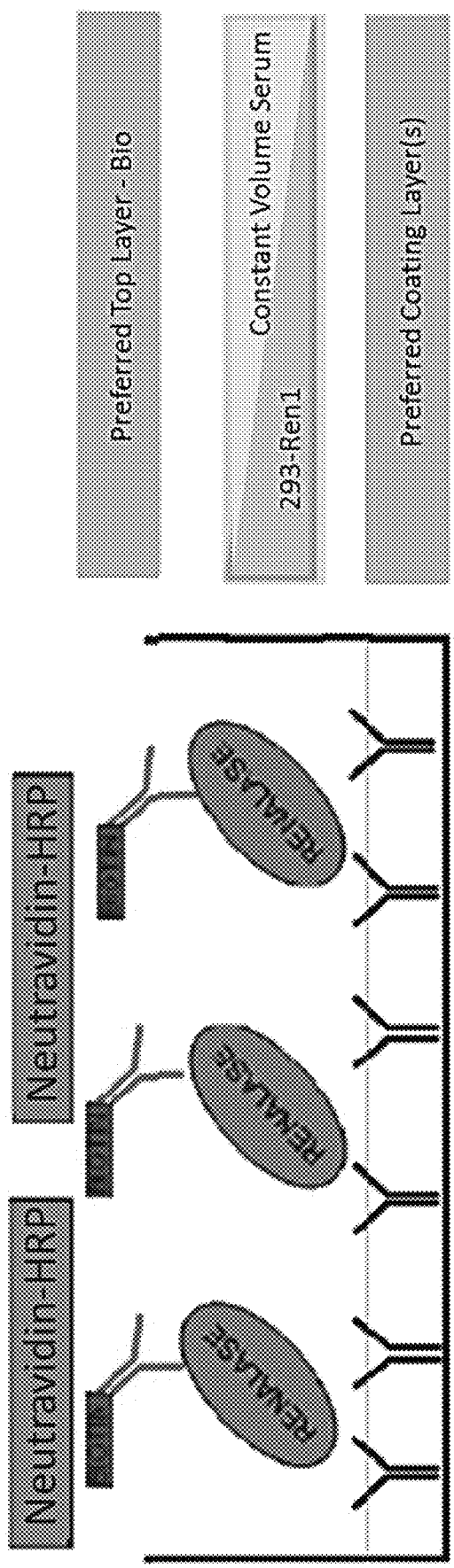
FIG. 19 depicts a schematic example of the sandwich ELISA method where an ELISA plate well is coated with an anti-renalase antibody (the capture antibody). The capture antibody specifically binds renalase from solution. The bound renalase can then be detected with a second antibody (the detection antibody) that is specific for a renalase epitope that differs from the capture antibody. The detection antibody can be visualized is numerous ways, including, the depicted conjugation to Biotin and visualization by binding a neutravidin-HRP conjugate and use of a TMB-like substrate. In this way renalase can be detected in complex solutions such as serum, plasma, cell and tissue lysates etc.

Enzyme-linked immunosorbent assay formats are often used in the detection of specific proteins from cell culture, cell lysate, blood products and other biologic samples. The preferred methodology for such detection is a sandwich ELISA assay. This format requires two affinity reagents, both specific for the target protein of interest but with differing epitope specificities. This format allows for both affinity reagents to bind to the target protein simultaneously. The two affinity reagents can be termed the 'capture reagent' and the 'detection reagent'. The capture reagent is coated onto solid surface and the sample is applied to that surface such that the target protein is bound to it and specifically captured. The target protein is then detected through the application of the detection reagent. The detection reagent can be visualized by many methods. Preferably the detection reagent is conjugated to a label that can be easily visualized and/or measures such as an enzyme, fluorescent label or radioactive label. A schematic example of the sandwich ELISA method can be seen in FIG. 19 where an ELISA plate well is coated with an anti-renalase antibody (the capture antibody). The capture antibody specifically binds renalase from solution. The bound renalase can then be detected with a second antibody (the detection antibody) that is specific for a renalase epitope that differs from the capture antibody. The detection antibody can be visualized is numerous ways, including, the depicted conjugation to Biotin and visualization by binding a neutravidin-HRP conjugate and use of a TMB-like substrate. In this way renalase can be detected in complex solutions such as serum, plasma, cell and tissue lysates etc.

The key to such a detection system is the characterization of affinity reagents that bind specifically and with high affinity to the target protein and that have non-overlapping epitopes so that simultaneous binding is possible. Such reagents have, to this point, not been described for renalase. In the current examples the anti-renalase monoclonal antibodies raised against various non-overlapping peptide epitopes on renalase are used for the specific capture and detection of renalase in complex biological samples. In some examples two monoclonal antibodies are used and in other examples one monoclonal antibody is used along with the polyclonal raised against whole renalase polypeptide.

Figure 20A:
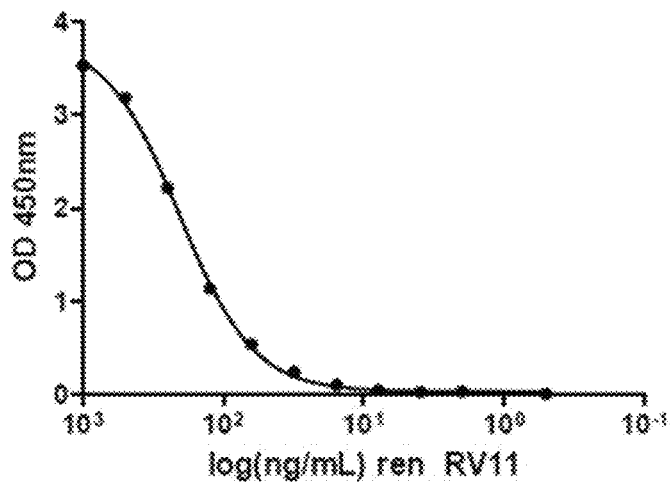
FIG. 20A and FIG. 20B, depicts the capture and detection of bacterially expressed recombinant renalase using a sandwich-ELISA format.
Figure 20B:
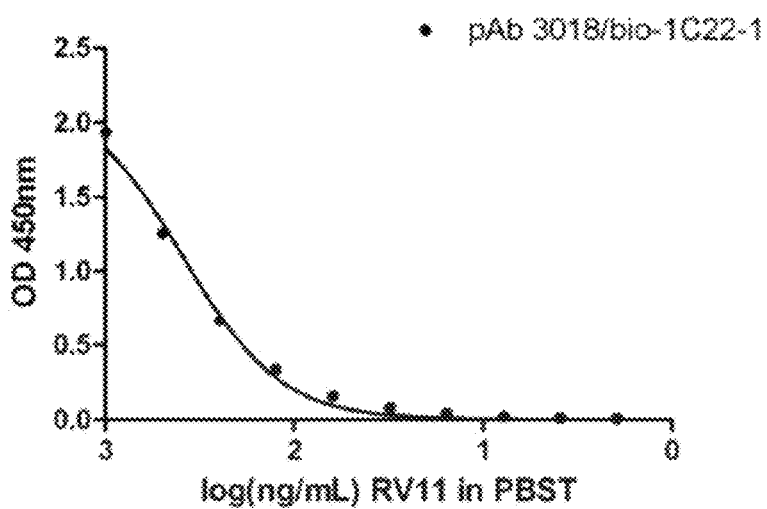

FIG. 20A shows the capture and detection of purified recombinant renalase expressed from bacterial cells. In this example the capture antibody Ren 1D 28-4 was bound to a 96 well microtiter plate by overnight incubation at 4° C. in PBS. After blocking with non-fat dried milk (NFDM), a dilution series of bacterially expressed renalase, diluted in PBST was applied to each well. After a one hour incubation at 33° C., the plate was washed with PBST. The biotinylated detection antibody Ren 1F 26-1 was diluted to 4 μg/mL in PBST, and 50 μL was added to each well. After incubation for 1 hour at 33° C., the plate was washed 3 times with PBST. For visualization, 50 μL of a 0.4 ug/mL neutravidin-HRP was added to each well and the plate was incubated at room temperature for 40 minutes. After incubation, the plate was thoroughly washed with PBST and once with PBS. The HRP substrate TMB was then added for color production. The reaction was stopped and the plate read with a spectrophotometer set at an absorbance of 450 nm. In a second example using the same protocol, the polyclonal antibody #3018, raised against the Id epitope was used as the capture antibody and the biotinylated monoclonal antibody Ren 1C 22-1 was used as the detection antibody (FIG. 20B). The experiment demonstrates renalase can be detected in a dose/dilution dependent manner using this sandwich ELISA method. Purified renalase protein of known concentration can then be used as a standard for the subsequent quantification of renalase from other complex biological sample sources.

Figure 21:
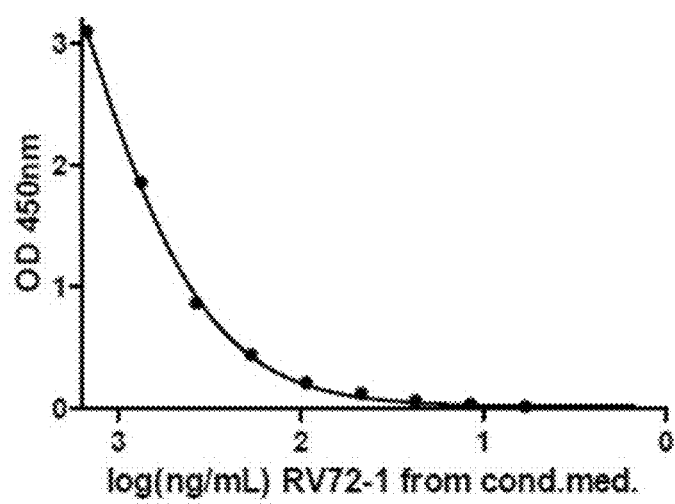
FIG. 21 depicts the capture and detection of renalase in mammalian tissue culture growth media. Renalase expressed into mammalian tissue culture growth media is captured and detected: 800 ng/well capture antibody Ren 1D 28-4 was incubated with a dilution series of growth media from HEK 293 cultured cells expressing recombinant renalase (RV72). The captured renalase was detected with biotinylated Ren 1F 26-1, and visualized with neutravidin-HRP and TMB.

In second example renalase expressed into mammalian tissue culture growth media is captured and detected: 800 ng/well capture antibody Ren 1D 28-4 was incubated with a dilution series of growth media from HEK 293 cultured cells expressing recombinant renalase (RV72). The captured renalase was detected with biotinylated Ren 1F 26-1, and visualized with neutravidin-HRP and TMB (FIG. 21). The capture and detection of renalase was seen to be dose/dilution dependent with no non-specific background signal seen with any of the antibody pairs tested. This assay format thus allows for the comparison of a tissue culture lysate, or growth media or combination thereof with a known concentration renalase dilution standard resulting the quantification of renalase in a tissue culture.

Figure 22A:
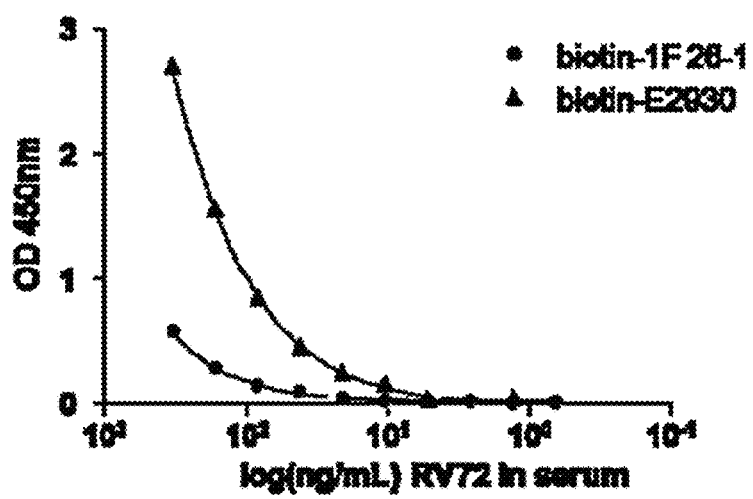
FIG. 22A and FIG. 22B, depicts the use of a sandwich-ELISA for the capture and detection of renalase in serum. The sandwich ELISA format is used for the capture and detection of renalase in a bodily fluid. 800 ng/mL Ren 1D 28-4 monoclonal (FIG. 22A) or the 1b peptide-specific polyclonal #3009 (FIG. 22B) was coated on an ELISA plate as the capture antibody. A dilution series of renalase (RV72) expressed and secreted in HEK293 cell culture medium and then spiked into human serum. Either biotinylated 1F 26-1 or biotinylated E2930, at 4 µg/mL each, was used to probe the captured RV72. Neutravidin-HRP and TMB was used for visualization. The assay shows the ability to visualize and quantify renalase in complex bodily fluids such as serum.
Figure 22B:
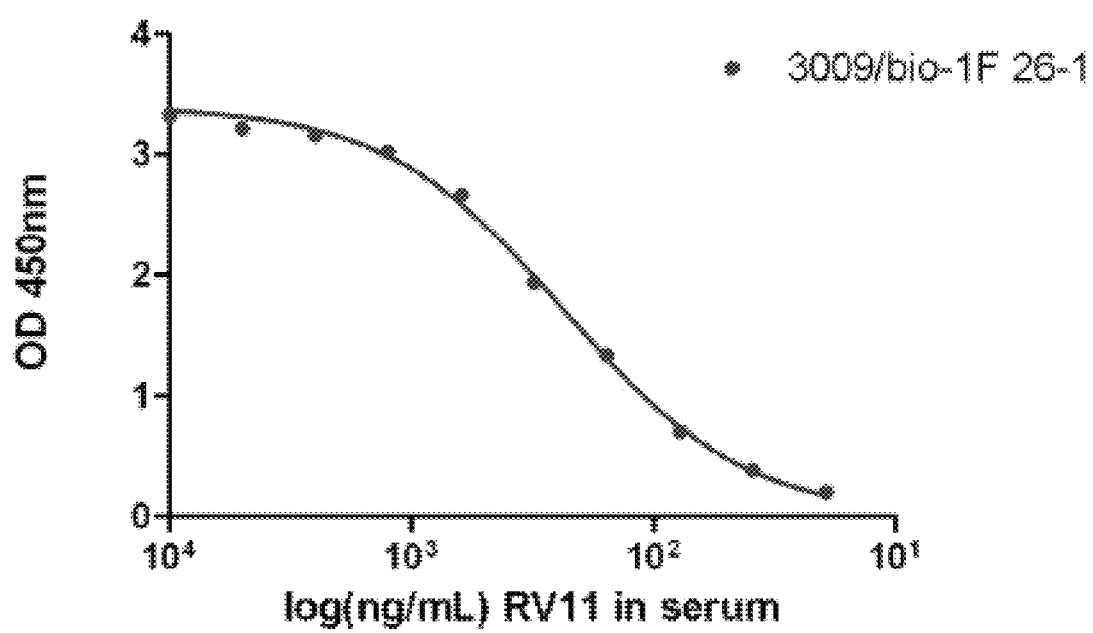

In a further example the sandwich ELISA format is used for the capture and detection of renalase in a bodily fluid. 800 ng/mL Ren 1D 28-4 monoclonal (FIG. 22A) or the 1b peptide-specific polyclonal #3009 (FIG. 22B) was coated on an ELISA plate as the capture antibody. A dilution series of renalase (RV72) expressed and secreted in HEK293 cell culture medium and then spiked into human serum. Either biotinylated 1F 26-1 or biotinylated E2930, at 4 µg/mL each, was used to probe the captured RV72. Neutravidin-HRP and TMB was used for visualization. The assay shows the ability to visualize and quantify renalase in complex bodily fluids such as serum.

Figure 23:
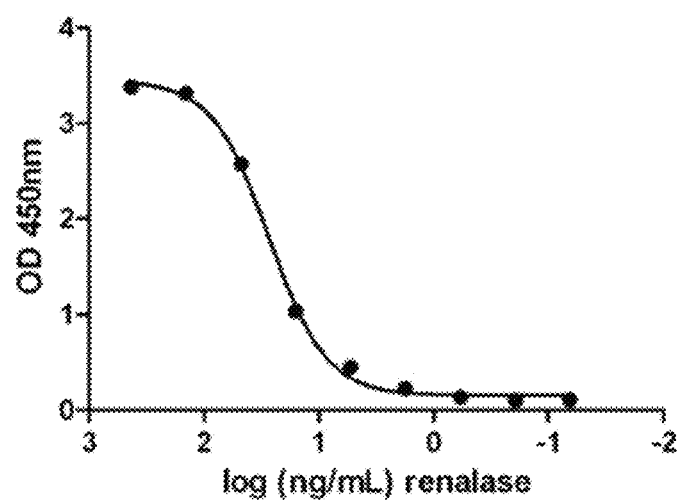
FIG. 23 depicts that endogenous renalase expressed endogenously can be detected in a tissue lysate matrix using this sandwich ELISA method.

In another example (FIG. 23), renalase specific affinity reagents were used in the detection and quantification of renalase a sandwich ELISA was used to detect endogenous renalase in mammalian tissue lysate. 200 ng/well of capture antibody, renalase affinity-purified polyclonal E2930, was bound to a 96 well microtiter plate by overnight incubation at 4° C. After blocking with non-fat dried milk, a dilution curve of tissue lysate from pig kidney was added to each well. After one hour incubation at 33° C., the plate was washed with PBST. Biotinylated antibody probe Ren 1D 28-4 was diluted to 4 µg/mL in PBST, and 50 µL was added to each well. After incubation for 1 hour at 33° C., the plate was washed 3 times with PBST. For detection, 0.4 ug/mL neutravidin-HRP was added to each well and the plate was incubated at room temperature for 40 minutes. After incubation, the plate was thoroughly washed with PBST and once with PBS. The HRP substrate TMB was then added for reaction. The reaction was stopped and the plate read with a spectrophotometer set at an absorbance of 450 nm. FIG. 23 shows that endogenous renalase expressed endogenously can be detected in a tissue lysate matrix using this sandwich ELISA method.

The use of preferred antibody pairs in the sandwich ELISA assay results in an extremely sensitive, reproducible and user friendly method for the detection and quantification of either endogenous or recombinant renalase protein in a variety of complex biological samples. The present invention demonstrates the use of affinity reagents specific for peptide epitopes seen in SEQ ID NOs. 1-7 for the detection of renalase using this approach. Such an assay kit with preferred antibody pairs would be of great benefit for diagnosing a potential renalase deficiency or over production and therefore could act as a disease biomarker detection kit.

Quantification of Plasma Renalase Levels in Humans Using Electro-Chemiluminescence Detection In this example, an ELISA method that incorporates sample pre-treatment, m42-RNLS as the capture antibody, and electro-chemiluminescence detection, is described, this method is used to measure total and free renalase levels in human plasma.

Figure 24:
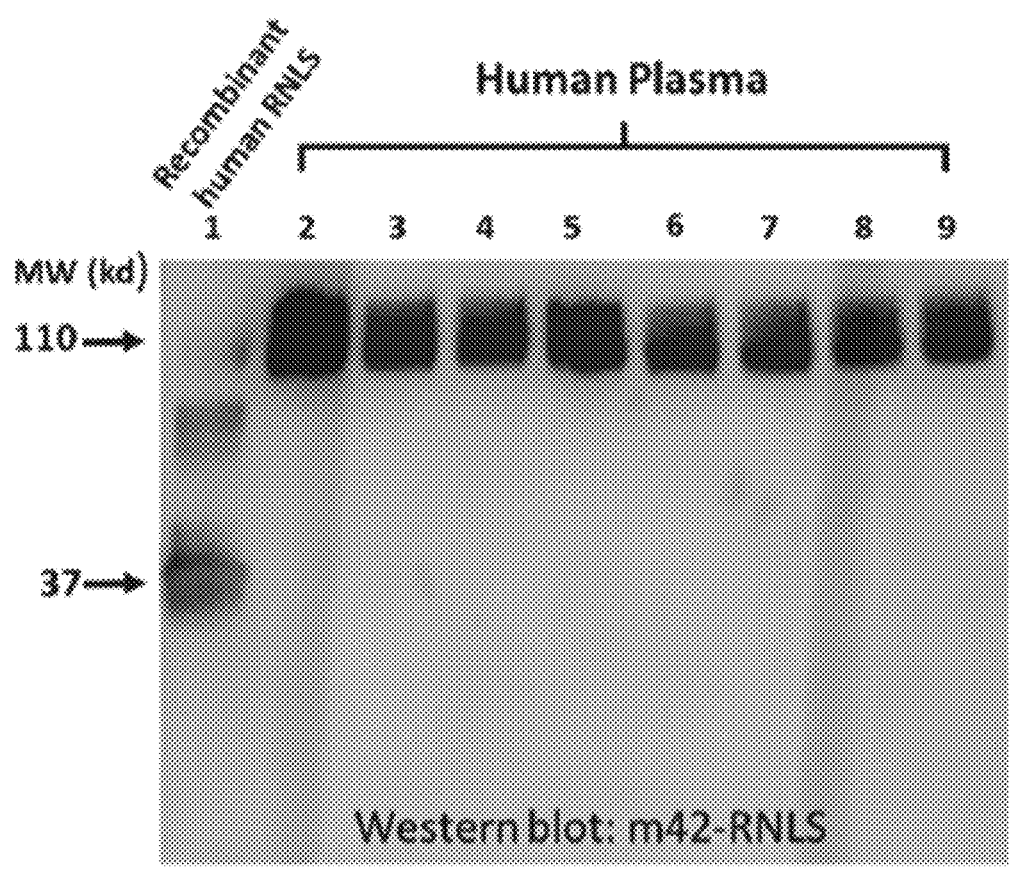
FIG. 24 depicts that western blot analysis using m42-RNLS carried under native (non-denaturing, non-reduced) conditions consistently yields an average value of ~4 µg/mL (Desir, G V et al., 2012, J Am Soc Hypertens, 6(6):417-26).
Figure 25:
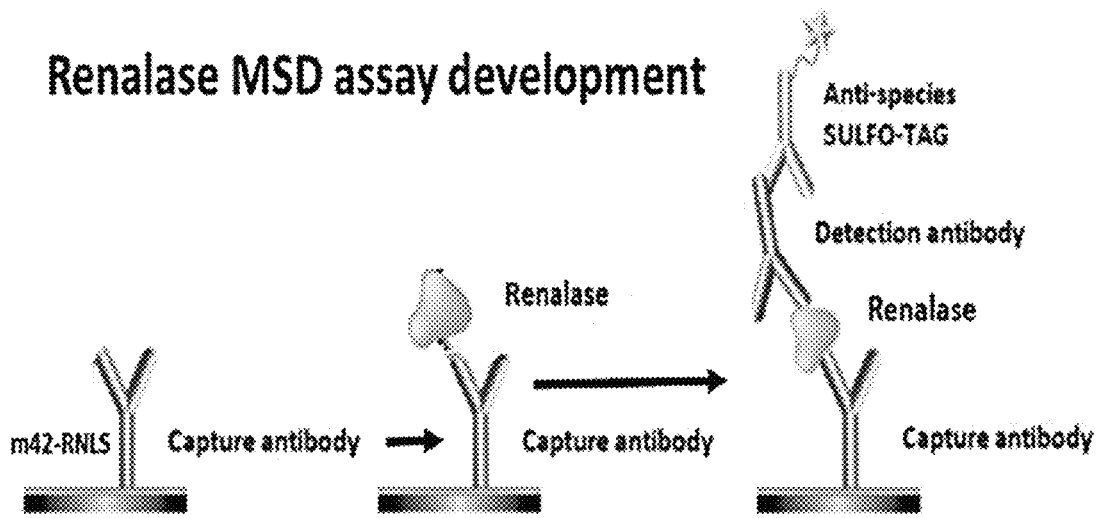
FIG. 25 depicts a schematic illustrating a sandwich ELISA assay using electro-chemiluminescence detection.
Figure 26:
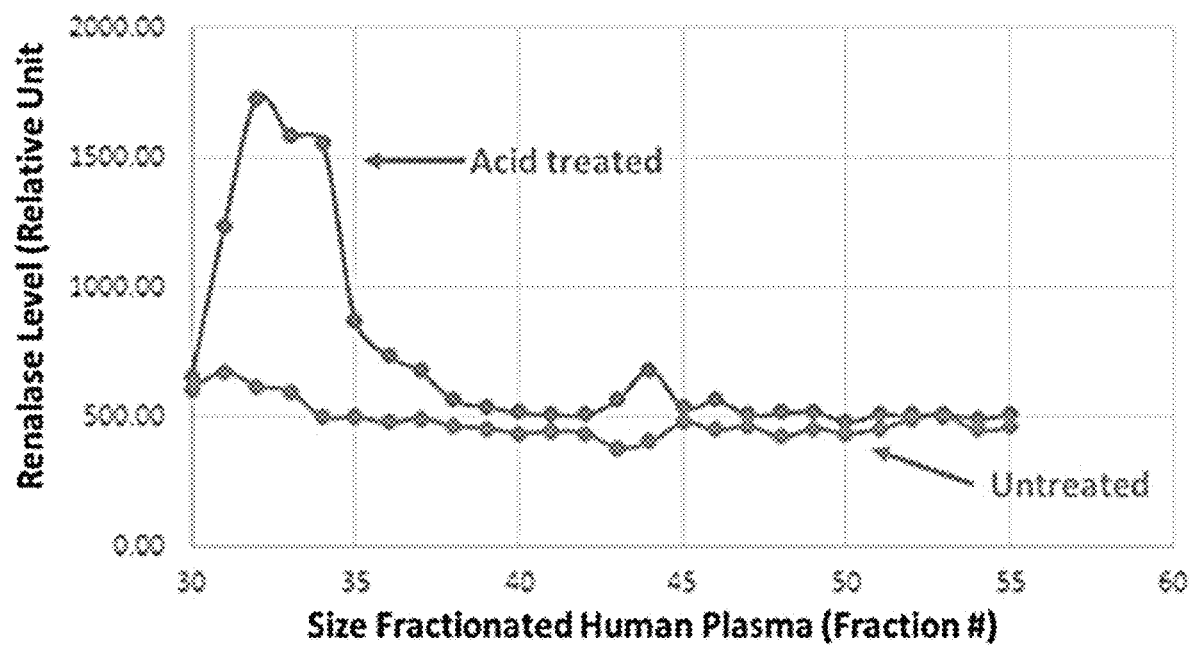
FIG. 26 depicts that different methods were tested to disrupt the renalase complex in human plasma, and it was found that acidification of the plasma samples for 10 minutes with either HCl or citric acid unmasked the antigenic site, thus enabling m42-RNLS to serve as the capture antibody in a sandwich ELISA assay using electro-chemiluminescence detection.

Measurements of plasma renalase levels in normal subjects using commercially available ELISA kits have yielded values ranging from 0.16 to 5 µg/mL for normal subjects, suggesting baseline values that vary over a 40 fold range between normal cohorts. In contrast, western blot analysis using m42-RNLS carried under native (non-denaturing, non-reduced) conditions consistently yields an average value of ~4 µg/mL (Desir, G V et al., 2012, J Am Soc Hypertens, 6(6):417-26) and FIG. 24. Size fractionation of human plasma using a Sephadex column indicated that renalase eluted as a high molecular weight complex (Fraction #30-35, FIG. 26, >250 kd). It was possible to detect renalase in fractions 30-35 by Western blotting, but not by ELISA using m42-RNLS as the capture antibody, and it was hypothesized the antigenic site was masked in human plasma. Different methods were tested to disrupt the renalase complex in human plasma, and it was found that acidification of the plasma samples for 10 minutes with either HCl or citric acid unmasked the antigenic site, thus enabling m42-RNLS to serve as the capture antibody in a Sandwich ELISA assay using electro-chemiluminescence detection (FIG. 25, FIG. 26, FIG. 27).

In this example, human plasma samples were pretreated as follows: To 40 µL of plasma, 20 µL of 1N Citric acid was added and the samples were incubated on a shaker for 15 min at RT. The reaction solution was neutralized by adding 40 µL of 1M $Na_2HPO_4$. The samples were then stored on ice and further diluted with Diluent 100 to obtain readings in linear range. Assay protocol: Renalase levels in plasma was measured using the prototype assay on the Mesoscale platform (Meso Scale diagnostics, Gaithersburg, Maryland, USA) which employs proprietary electro-chemiluminescence detection methods combined with patterned arrays. Standard 96-well assay plate from Mesoscale Diagnostics were coated with 40 µL of Ren 1F 42-7 (m42-RNLS) capture antibody (2 µg/mL) and incubated for 2 hours on a shaker at room temperature. Following this, 150 µL of 3% Blocker A was added and the plate incubated on a shaker for 1 hour at room temperature. The plate was then washed with 150 µL of PBST (3 times); diluted acid activated samples and calibrator was added and the plate incubated for 2 hrs at RT on a shaker. After rinsing three times with PBST, 25 µL of polyclonal renalase or monoclonal RNLS specific antibody (1 µg/mL) diluted in Diluent 100 was added, and then incubated at RT for another 1 hr. After washing, labeled anti-species antibody conjugated to sulfo-tag (25 µL) was pipetted to the wells and the plate was incubated for an additional 1 h. The plate was washed and 2× read buffer was added and the plate imaged on SQ120 (Meso Scale Discovery). The raw data was analyzed using the Discovery Workbench software. 4-PL curve fitting was used to determine renalase concentration.

Figure 28:
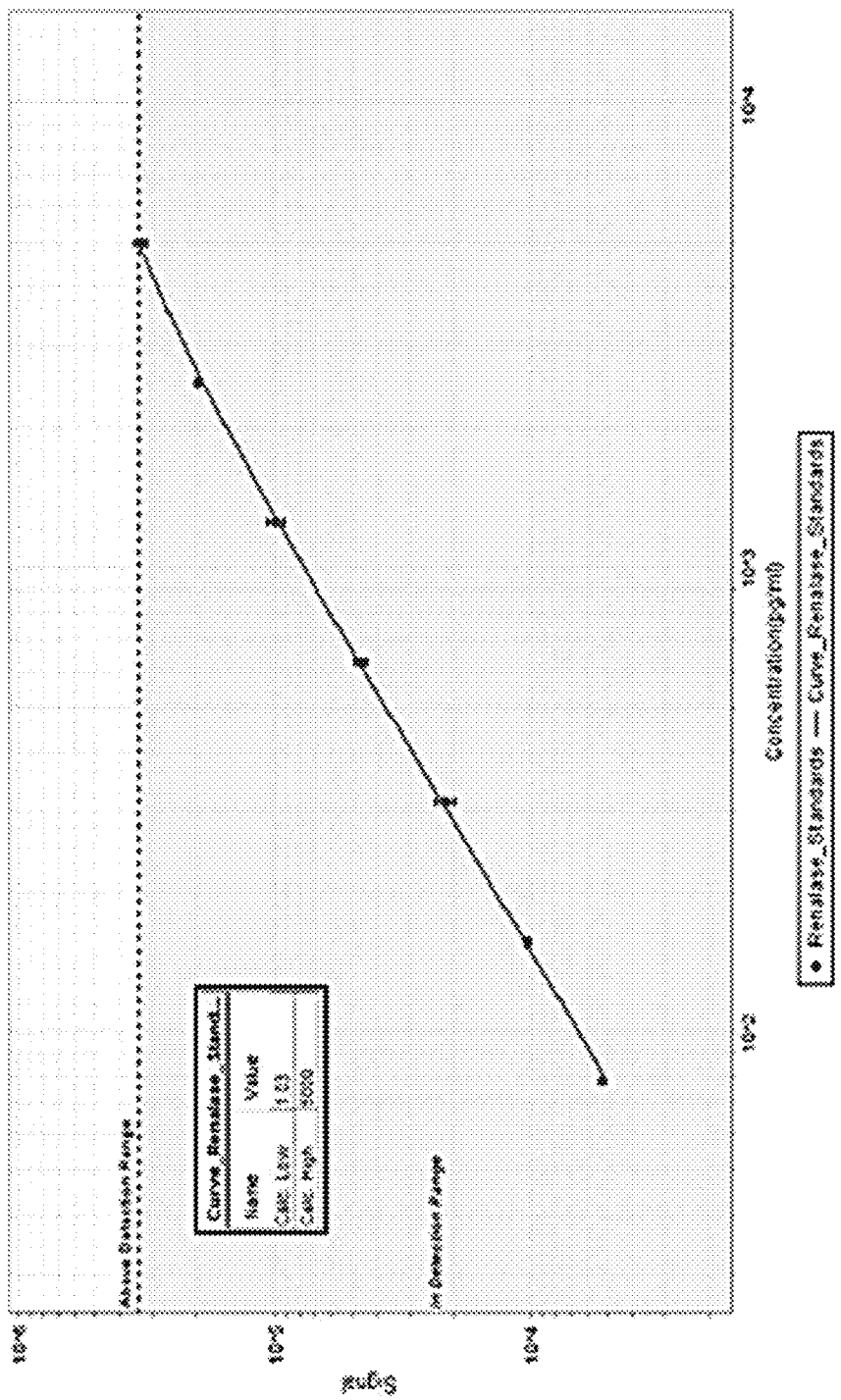
FIG. 28 depicts that due to its broad range and high sensitivity (1.03-17,000 ng/mL), the assay enabled the measurement both free renalase (~1.0 ng/mL, untreated plasma), and total renalase (0.8-17 µg/mL, acid treated) in each sample.

Due to its broad range and high sensitivity (1.03-17,000 ng/mL), (FIG. 28), the assay enabled the measurement both free renalase (~1.0 ng/mL, untreated plasma), and total renalase (0.8-17 µg/mL, acid treated) in each sample. Total and free plasma renalase levels were measured (mean standard deviation) in 15 control subjects, with acute chest pain, and 78 with heart failure (FIG. 29). Of note, free renalase concentration was below the limits of detection (<1 ng/mL) in 28% (39 of 138) of the samples tested.

Figure 30:
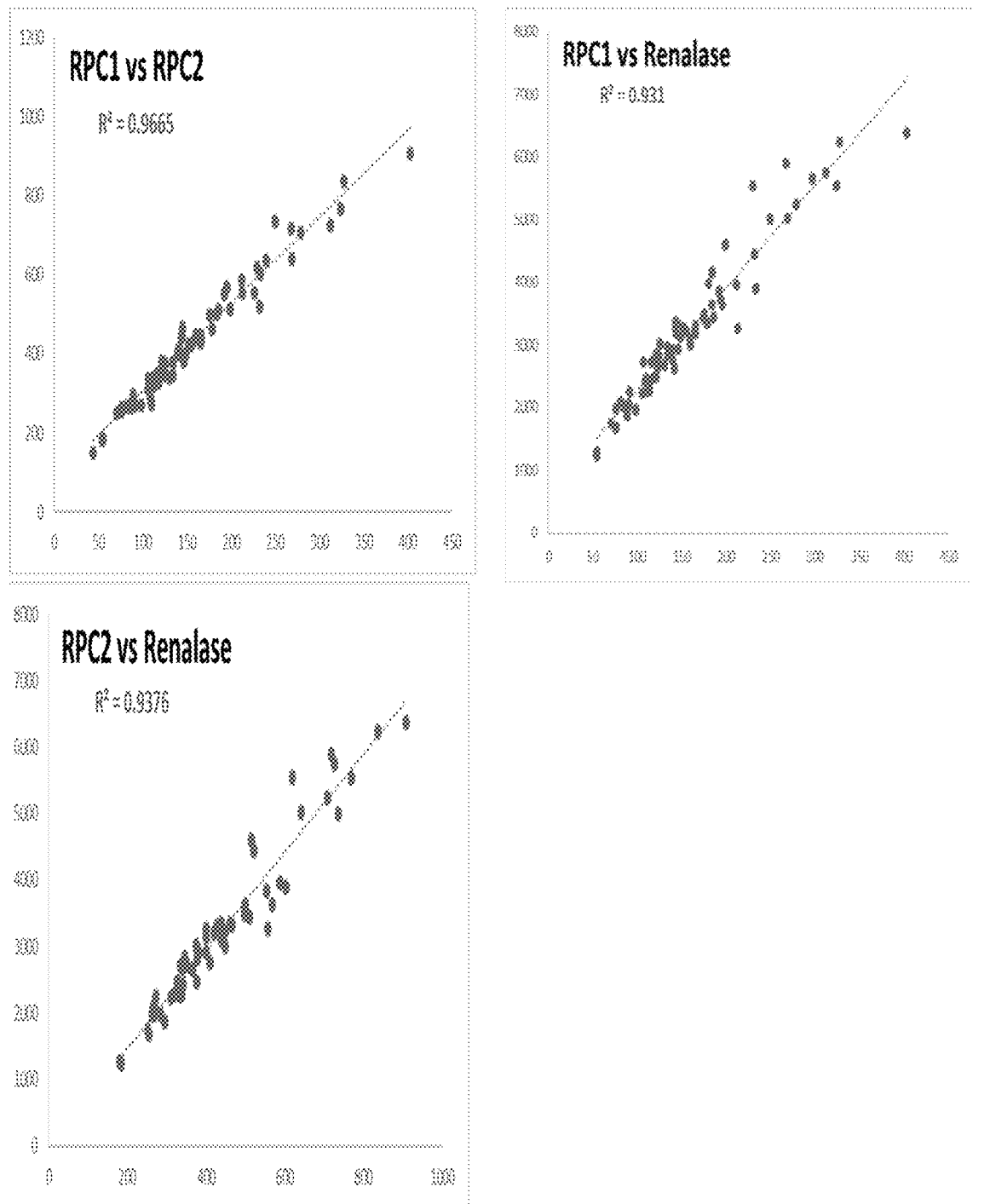
FIG. 30 depicts the results of exemplary experiments assessing RPC1 (SEQ ID NO:226), RPC2 (SEQ ID NO:227), and RPC3 (SEQ ID NO:228) as reference standards.

We also note that recombinant renalase is difficult to synthesize and is subject to dimer and multimer formation when stored even for a short period of time. This property of recombinant renalase could introduce significant errors in the establishment of standard curves, making it difficult to use as a reference standard. To improve on the reproducibility of the ELISA, we synthesized 3 novel reference standards (RPC1-3, FIG. 30) consisting of the m42 peptide antigen (VLEALKNYI: C terminus of human renalase) linked to the m28 peptide antigen (CIRFVSIDNKKRNIES-SEIGP; aa 220-240 of human renalase) using different linkage lengths (0-15).

We then compared standard curves generated using recombinant renalase, recombinant renalase with acid pretreatment (as above), RPC1 (SEQ ID NO:226) and RPC2 (SEQ ID NO:227). Recombinant renalase performed poorly as a reference standard. In contrast, acid-treated recombinant renalase, RPC1 and RPC2 performed very well with excellent correlation coefficients (Figure YYY). Due to ease of synthesis and superior stability of the peptides, excellent correlation with acid treated recombinant renalase, and with other, RPC1 and RPC2 are the preferred reference standards.

Example 2: Sequences

TABLE 1

Oligonucleotides used for humanization and affinity maturation of M28 and M42

| Oligonucleotide name | Nucleotide sequence | Amino acid sequence |
|---|---|---|
| BN452 M28 L1 | TGCCGTGCCAGTCAGA GCGTGTATGACAACAA CAACGTAGCCTGGTAT CAA (SEQ ID NO: 96) | CRASQSVYDNNNVAW YQ (SEQ ID NO: 97) |
| BN453 M42 L1 | TGCCGTGCCAGTCAGA CCGTGTATAACAACAA CTACGTAGCCTGGTAT CAA (SEQ ID NO: 98) | CRASQTVYNNNYVAW YQ (SEQ ID NO: 99) |
| BN454 M28 L2 | AAGCTTCTGATTTACG GCGCCAGCACCCTCTA CTCTGGAGTC (SEQ ID NO: 100) | KLLIYGASTLYSGV (SEQ ID NO: 101) |
| BN455 M42 L2 | AAGCTTCTGATTTACG AAACCAGCAAACTCTA CTCTGGAGTC (SEQ ID NO: 102) | KLLIYETSKLYSGV (SEQ ID NO: 103) |
| BN456 M28 L3 | GCAACTTATTACTGTC TGGGCGAATTCAGCTG CAGCAGCGCTGACTGC TTCGCCTTCGGACAGG GTACC (SEQ ID NO: 104) | ATYYCLGEFSCSSADCF AFGQGT (SEQ ID NO: 105) |
| BN457 M42 L3 | GCAACTTATTACTGTC AGGGCGGCTACAGCG GCGTGGACTTCATGGC TTTCGGACAGGGTACC (SEQ ID NO: 106) | ATYYCQGGYSGVDFM AFGQGT (SEQ ID NO: 107) |
| BN458 M28 H1 | GCTTCTGGCTTCAACC TGAGCAGCTTCGCCGT TCACTGGGTGCGTCAG (SEQ ID NO: 108) | ASGFNLSSFAVHWVRQ (SEQ ID NO: 109) |
| BN459 M42 H1 | GCTTCTGGCTTCAACC TGACCACCTACGGCGT TCACTGGGTGCGTCAG (SEQ ID NO: 110) | ASGFNLTTYGVHWVRQ (SEQ ID NO: 111) |
| BN460 M28 H2 | CTGGAATGGGTTGCAA TCATCAGCAGCGTTGG CATCACCCGCTATGCC GATAGCGTC (SEQ ID NO: 112) | LEWVAIISSVGITRYAD SV (SEQ ID NO: 113) |
| BN461 M42 H2 | CTGGAATGGGTTGCAC TGATCGGCGATCGCGG CACCACCTATTATGCC GATAGCGTC (SEQ ID NO: 114) | LEWVALIGDRGTTYYA DSV (SEQ ID NO: 115) |

TABLE 1-continued

Oligonucleotides used for humanization and affinity maturation of M28 and M42

| Oligonucleotide name | Nucleotide sequence | Amino acid sequence |
|---|---|---|
| BN462<br>M28 H3 | TATTATTGTGCTCGCT ATGGCTATAGCGG CGACGTGAACCGCCTG GACCTGTGGGGTCAAG GAACC (SEQ ID NO: 116) | YYCARYGYSGDVNRL DLWGQGT (SEQ ID NO: 117) |
| BN463<br>M42 H3 | TATTATTGTGCTCGCG GCAGCGGCTATGGCGC TCGCATCTGGGGTCAA GGAACC (SEQ ID NO: 118) | YYCARGSYGARIWGQ GT (SEQ ID NO: 119) |
| BN464<br>M28 HC71 | CGTTTCACTATAAGCA AAGACACATCCAAAA AC (SEQ ID NO: 120) | RFTISKDTSKN (SEQ ID NO: 121) |
| BN465<br>M42 HC71 | CGTTTCACTATAAGCC GCGACACATCCAAAA AC (SEQ ID NO: 122) | RFTISRDTSKN (SEQ ID NO: 123) |
| BN498<br>M28 L3 STOP | GCAACTTATTACTGTT AATGATAATTCGGACA GGGTACC (SEQ ID NO: 124) | ATYYC *** FGQGT<br>* denotes STOP<br>(SEQ ID NO: 125) |
| BN484<br>M28 H1 STOP | GCTTCTGGCTTCAATT AATGATAACACTGGGT GCGTCAG (SEQ ID NO: 126) | ASGFN *** HWVRQ<br>* denotes STOP<br>(SEQ ID NO: 127) |
| BN467<br>M28 and M42<br>H2 STOP | CTGGAATGGGTTGCAT GATAATGATATGCCGA TAGCGTC (SEQ ID NO: 128) | LEWVA *** YADSV<br>* denotes STOP<br>(SEQ ID NO: 129) |
| BN485<br>M28 and M42<br>H3 STOP | TATTATTGTGCTCGCT AATGATAATGGGGTCA AGGAACC (SEQ ID NO: 130) | YYCAR *** WGQGT<br>* denotes STOP<br>(SEQ ID NO: 131) |
| BN469<br>M42 L1 STOP | TGCCGTGCCAGTCAGT GATAATGAGTAGCCTG GTATCAA (SEQ ID NO: 132) | CRASQ *** VAWYQ<br>* denotes STOP<br>(SEQ. ID NO: 133) |
| BN466<br>M42 H1 STOP | GCTTCTGGCTTCAACT GATAATGACACTGGGT GCGTCAG (SEQ ID NO: 134) | ASGFN *** HWVRQ<br>* denotes STOP<br>(SEQ ID NO: 135) |
| BN492<br>M28 L3<br>randomization | GCAACTTATTACTGTC TGGGCGAATTCAGCTG CAGCAGCGCTGACTGC TTCGCCTTCGGACAGG GTACC<br>Nucleotides in underline are degenerate; parental = 70%, others = 10% each<br>(SEQ ID NO: 136) | ATYYCLGEFSCSSADCF AFGQGT<br>Residues in underline are randomized<br>(SEQ ID NO: 137) |
| BN488<br>M28 H1<br>randomization | GCTTCTGGCTTCAACC TGAGCAGCTTCGCCGT TCACTGGGTGCGTCAG<br>Nucleotides in underline are degenerate; parental = 70%, others = 10% each<br>(SEQ ID NO: 138) | ASGFNLSSFAVHWVRQ<br>Residues in underline are randomized (SEQ ID NO: 139) |
| BN489<br>M28 H2<br>randomization | CTGGAATGGGTTGCAA TCATCAGCAGCGTTGG CATCACCCGCTATGCC | LEWVAIISSVGITRYAD SV<br>Residues in underline are |

TABLE 1-continued

Oligonucleotides used for humanization and affinity maturation of M28 and M42

| Oligonucleotide name | Nucleotide sequence | Amino acid sequence |
|---|---|---|
| | GATAGCGTC<br>Nucleotides in underline are degenerate;<br>parental = 70%, others = 10% each<br>(SEQ ID NO: 140) | randomized<br>(SEQ ID NO: 141) |
| BN490<br>M28 H3<br>randomization | TATTATTGTGCTCGCT<br>ATGGCTATAGCGGCGA<br>CGTGAACCGCCTGGAC<br>CTGTGGGGTCAAGGA<br>ACC<br>Nucleotides in underline are degenerate;<br>parental = 70%, others = 10% each<br>(SEQ ID NO: 142) | YYCARYGYSGDVNRL<br>DLWGQGT<br>Residues in underline are randomized<br>(SE() ID NO: 143) |
| BN496<br>M42 L1<br>randomization | TGCCGTGCCAGTCAGA<br>CCGTGTATAACAA<br>CAACTACGTAGCCTGG<br>TATCAA<br>Nucleotides in underline are degenerate;<br>parental = 70%, others = 10% each<br>(SEQ ID NO: 144) | CRASQTVYNNNYVAW<br>YQ<br>Residues in underline are randomized<br>(SEQ ID NO: 145) |
| BN493<br>M42 H1<br>randomization | GCTTCTGGCTTCAACC<br>TGACCACCTACGGCGT<br>TCACTGGGTGCGTCAG<br>Nucleotides in underline are degenerate;<br>parental = 70%, others = 10% each<br>(SEQ ID NO: 146) | ASGFNLTTYGVHWVRQ<br>Residues in underline are randomized<br>(SEQ ID NO: 147) |
| BN494<br>M42 H2<br>randomization | CTGGAATGGGTTGCAC<br>TGATCGGCGATCGCGG<br>CACCACCTATTATGCC<br>GATAGCGTC<br>Nucleotides in underline are degenerate;<br>parental = 70%, others = 10% each<br>(SEQ ID NO: 148) | LEWVALIGDRGTTYYA<br>DSV<br>Residues in underline are randomized<br>(SEQ ID NO: 149) |
| BN495<br>M42 H3<br>randomization | TATTATTGTGCTCGCG<br>GCAGCGGCTATGGCGC<br>TCGCATCTGGGGTCAA<br>GGAACC<br>Nucleotides in underline are degenerate;<br>parental = 70%; others = 10% each<br>(SEQ ID NO: 150) | YYCARGSGYGARIWGQ<br>GT<br>Residues in underline are randomized<br>(SEQ ID NO: 151) |

TABLE 2

M28/M42 and variant CDRs

| | CDR-L1 | L2 | L3 | H1 | H2 | H3 |
|---|---|---|---|---|---|---|
| M28 parental | SVYDNN N (SEQ ID NO: 152) | GAST (SEQ ID NO: 153) | LGEFSC SSADCF A (SEQ ID NO: 154) | LSSFAV (SEQ ID NO: 155) | IISSVGIT R (SEQ ID NO: 156) | YGYSGD VNRLDL (SEQ ID NO: 157) |

TABLE 2-continued

| | M28/M42 and variant CDRs | | | | | |
|---|---|---|---|---|---|---|
| | CDR-L1 | L2 | L3 | H1 | H2 | H3 |
| M28-K2 | SVYDNNN (SEQ ID NO: 158) | GAST (SEQ ID NO: 159) | LGEGPCSVTDCLI (SEQ ID NO: 160) | LSSFAV (SEQ ID NO: 161) | LIGVRGSLY (SEQ ID NO: 162) | HWYSGGVVRLDA (SEQ ID NO: 163) |
| M28-K5 | SVYDNNN (SEQ ID NO: 164) | GAST (SEQ ID NO: 165) | LGEGPCSVTDCLI (SEQ ID NO: 166) | LSSFAV (SEQ ID NO: 167) | LISGRGTRF (SEQ ID NO: 168) | HWYSGGVVRLDA (SEQ ID NO: 169) |
| M28-K9 | SVYDNNN (SEQ ID NO: 170) | GAST (SEQ ID NO: 171) | LGEGPCSVTDCLI (SEQ ID NO: 172) | LSSFAV (SEQ ID NO: 173) | IISSVGITR (SEQ ID NO: 174) | HWYSGGVVRLDA (SEQ ID NO: 175) |
| M28-K13 | SVYDNNN (SEQ ID NO: 176) | GAST (SEQ ID NO: 177) | LGEFSCSSADCFA (SEQ ID NO: 178) | LSSFAV (SEQ ID NO: 179) | LIGVRGSLY (SEQ ID NO: 180) | HWYSGGVVRLDA (SEQ ID NO: 181) |
| M28-K14 | SVYDNNN (SEQ ID NO: 182) | GAST (SEQ ID NO: 183) | LGEGPCSVTDCLI (SEQ ID NO: 184) | LSSFAV (SEQ ID NO: 185) | LISGRGTRF (SEQ ID NO: 186) | YGYSGDVNRLDL (SEQ ID NO: 187) |
| M28-K16 | SVYDNNN (SEQ ID NO: 188) | GAST (SEQ ID NO: 189) | LGEFSCSSADCFA (SEQ ID NO: 190) | LSSFAV (SEQ ID NO: 191) | LISGRGTRF (SEQ ID NO: 192) | HWYSGGVVRLDA (SEQ ID NO: 193) |
| M42 parental | TVYNNNY (SEQ ID NO: 194) | ETSK (SEQ ID NO: 195) | QGGYSGVDFMA (SEQ ID NO: 196) | LTTYGVTTY (SEQ ID NO: 197) | LIGDRGTTY (SEQ ID NO: 198) | GSGYGARI (SEQ ID NO: 199) |
| M42-K31 | SVYRNNY (SEQ ID NO: 200) | ETSK (SEQ ID NO: 201) | QGGYSGVDFMA (SEQ ID NO: 202) | MSSERRWNY (SEQ ID NO: 203) | LIRDRGWNY (SEQ ID NO: 204) | GICYCARS (SEQ ID NO: 205) |
| M42-K34 | SVYRNNY (SEQ ID NO: 206) | ETSK (SEQ ID NO: 207) | QGGYSGVDFMA (SEQ ID NO: 208) | LTTYGV (SEQ ID NO: 209) | LIRDRGWNY (SEQ ID NO: 210) | GICYCARS (SEQ ID NO: 211) |
| M42-K35 | TVYNNNY (SEQ ID NO: 212) | ETSK (SEQ ID NO: 213) | QGGYSGVDFMA (SEQ ID NO: 214) | MSSERR (SEQ ID NO: 215) | LIRDRGWNY (SEQ ID NO: 216) | GICYCARS (SEQ ID NO: 217) |

SEQ ID NO: 218
M28-humanized Fv sequence Heavy chain nucleotide
GAGGTTCAGCTGGTGGAGTCTGGCGGTGGCCTGGTGCAGCCAGGGGCTC
ACTCCGTTTGTCCTGTGCAGCTTCTGGCTTCAATCTGAGCAGCTTCGCCG
TTCACTGGGTGCGTCAGGCCCCGGGTAAGGGCCTGGAATGGGTTGCAATC
ATCAGCAGCGTTGGCATCACCCGCTATGCCGATAGCGTCAAGGGCCGTTT
CACTATAAGCAAAGACACATCCAAAAACACAGCCTACCTACAAATGAACA
GCTTAAGAGCTGAGGACACTGCCGTCTATTATTGTGCTCGCTATGGCTAT
AGCGGCGACGTGAACCGCCTGGACCTGTGGGGTCAAGGAACCCTGGTCAC
CGTCTCCTCG SEQ ID NO: 219
M28-humanized Fv sequence Heavy chain Amino acid
(M28 CDR and HC71 grafts underlined)
EVQLVESGGGLVQPGGSLRLSCAASGFN<u>LSSFAV</u>HWVRQAPGKGLEWVA<u>I
ISSVGITRY</u>ADSVKGRFTIS<u>K</u>DTSKNTAYLQMNSLRAEDTAVYYCAR<u>YGY
SGDVNRLDL</u>WGQGTLVTVSS SEQ ID NO: 220
M28-humanized Fv sequence Light chain nucleotide
GATATCCAGATGACCCAGTCCCCGAGCTCCCTGTCCGCCTCTGTGGGCGA
TAGGGTCACCATCACCTGCCGTGCCAGTCAGAGCGTGTATGACAACAACA
ACGTAGCCTGGTATCAACAGAAACCAGGAAAAGCTCCGAAGCTTCTGATT
TACGGCGCCAGCACCCTCTACTCTGGAGTCCCTTCTCGCTTCTCTGGTAG
CCGTTCCGGGACGGATTTCACTCTGACCATCAGCAGTCTGCAGCCGGAAG
ACTTCGCAACTTATTACTGTCTGGGCGAATTCAGCTGCAGCAGCGCTGAC
TGCTTCGCCTTCGGACAGGGTACCAAGGTGGAGATCAAACGA SEQ ID NO: 221
M28-humanized Fv sequence Light chain Amino acid
(M28 CDR and HC71 grafts underlined)
DIQMTQSPSSLSASVGDRVTITCRAS<u>QSVYDNNN</u>VAWYQQKPGKAPKLLI
YGASTLYSGVPSRFSGSRSGTDFTLTISSLQPEDFATYYC<u>LGEFSCSSAD
CFAF</u>GQGTKVEIKR SEQ ID NO: 222
M42 humanized Fv sequence Heavy chain nucleotide
GAGGTTCAGCTGGTGGAGTCTGGCGGTGGCCTGGTGCAGCCAGGGGCTC
ACTCCGTTTGTCCTGTGCAGCTTCTGGCTTCAACCTGACCACCTACGGCG
TTCACTGGGTGCGTCAGGCCCCGGGTAAGGGCCTGGAATGGGTTGCACTG
ATCGGCGATCGCGGCACCACCTATTAIGCCGATAGCGTCAAGGGCCGTTT
CACTATAAGCCGCGACACATCCAAAAACACAGCCTACCTACAAATGAACA
GCTTAAGAGCTGAGGACACTGCCGTCTATTATTGTGCTCGCGGCAGCGGC
TATGGCGCTCGCATCTGGGGTCAAGGAACCCTGGTCACCGTCTCCTCG SEQ ID NO: 223
M42 humanized Fv sequence Heavy chain Amino acid
(M42 CDR and HC71 grafts underlined)
EVQLVESGGGLVQPGGSLRLSCAASGFN<u>LTTYGVH</u>WVRQAPGKGLEWVAL<u>
IGDRGTTYY</u>ADSVKGRFTISRDTSKNTAYLQMNSLRAEDTAVYYCAR<u>GSG
YGARI</u>WGQGTLVTVSS SEQ ID NO: 224
M42 humanized Fv sequence Light chain nucleotide
GATATCCAGATGACCCAGTCCCCGAGCTCCCTGTCCGCCTCTGTGGGCGA
TAGGGTCACCATCACCTGCCGTGCCAGTCAGACCGTGTATAACAACAACT
ACGTAGCCTGGTATCAACAGAAACCAGGAAAAGCTCCGAAGCTTCTGATT
TACGAAACCAGCAAACTCTACTCTGGAGTCCCTTCTCGCTTCTCTGGTAG
CCGTTCCGGGACGGATTTCACTCTGACCATCAGCAGTCTGCAGCCGGAAG
ACTTCGCAACTTATTACTGTCAGGGCGGCTACAGCGGCGTGGACTTCATG
GCTTTCGGACAGGGTACCAAGGTGGAGATCAAACGA SEQ ID NO: 225
M42 humanized Fv sequence Light chain Amino acid
(M42 CDR and HC71 grafts underlined)
DIQMTQSPSSLSASVGDRVTTICRAS<u>QTVYNNNY</u>VAWYQQKPGKAPKLLI
YETSKLYSGVPSRFSGSRSGTDFTLTISSLQPEDFATYYC<u>QGGYSGVDFM
AF</u>GQGTKVEIKR

SEQ ID NO: 226
RPC1;
VLEALKNYIKIDVPWAGQVITSNPCIRFVSIDNKKRNIESSEIGP

SEQ ID NO: 227
RPC2;
VLEALKNYIPWAGQYITSNPCIRFVSIDNKKRNIESSEIGP

SEQ ID NO: 228
RPC3;
VLEALKNYIRIVSIDNKKRNIESSEIGP

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A reference standard consisting of RPC1 (SEQ ID NO:226), RPC2 (SEQ ID NO:227), or RPC3 (SEQ ID NO:228).

* * * * *